(12) United States Patent
Meyers et al.

(10) Patent No.: US 7,288,392 B2
(45) Date of Patent: Oct. 30, 2007

(54) HUMAN PROTEIN KINASES AND USES THEREFOR

(75) Inventors: Rachel Meyers, Newton, MA (US); Rosana Kapeller-Libermann, Chestnut Hill, MA (US); Mark Williamson, Saugus, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 352 days.

(21) Appl. No.: 10/649,156

(22) Filed: Aug. 27, 2003

(65) Prior Publication Data

US 2004/0038346 A1 Feb. 26, 2004

Related U.S. Application Data

(60) Division of application No. 09/799,875, filed on Mar. 6, 2001, now Pat. No. 6,638,721, which is a continuation-in-part of application No. 09/659,287, filed on Sep. 12, 2000, now abandoned.

(60) Provisional application No. 60/182,059, filed on Feb. 11, 2000.

(51) Int. Cl.
C12P 21/04 (2006.01)
C12P 21/06 (2006.01)
C07H 21/04 (2006.01)
C07K 14/00 (2006.01)

(52) U.S. Cl. .............. 435/69.7; 435/69.1; 435/194; 435/320.1; 435/325; 435/6; 530/300; 530/350; 536/23.7; 536/23.5

(58) Field of Classification Search ............ 435/69.7, 435/320.1, 194, 6, 325; 530/300, 350; 536/23.7, 536/23.5
See application file for complete search history.

(56) References Cited

U.S. PATENT DOCUMENTS

2004/0005683 A1* 1/2004 Kratzsch et al. ............ 435/189

FOREIGN PATENT DOCUMENTS

WO WO0153312 * 7/2001

OTHER PUBLICATIONS

Rudinger et al, in "Peptide Hormones", edited by Parsons, J.A., University Park Press, Jun. 1976, p. 6.*
Bowie et al (Science, 1990, 257:1306-1310).*
Burgess et al ( J of Cell Bio. 111:2129-2138, 1990).*
Lazar et al (Molecular and Cellular Biology, 1988, 8:1247-1252).*
Hanks, Steven K., et al., "The Eukaryotic Protein Kinase Superfamily: Kinase (Catalytic) Domain Structure and Classification," *The FASEB Journal*, vol. 9, pp. 576-596 (May 1995).
GenBank Accession No. BAA76843.
GenBank Accession No. BAA77582.
GenBank Accession No. CAA66229.
GenBank Accession No. CAA88953.
GenBank Accession No. G01025.
GenBank Accession No. P33279.
GenBank Accession No. P54644.
GenBank Accession No. Q09298.
GenBank Accession No. Q63185.
GenBank Accession No. Q9Z2R9.
GenBank Accession No. R44008.
GenBank Accession No. R49849.
GenBank Accession No. W37158.

* cited by examiner

Primary Examiner—Susan Ungar
Assistant Examiner—Padma Baskar

(57) ABSTRACT

The invention relates to novel kinase nucleic acid sequences and proteins. Also provided are vectors, host cells, and recombinant methods for making and using the novel molecules.

8 Claims, 58 Drawing Sheets

Input File Fbh18477b1.seq; Output File 18477.trans
Sequence length 3003

```
                                                                    M   D   P   T   A   G   S      7
GGCTGCTCGCGGAGGGGCAGTGTACGCGGGGCCGCTGTAGGCTGTCCAGGG ATG GAT CCC ACC GCG GGA AGC     21
  K   K   E   P   G   G   G   A   A   T   E   E   G   V   N   R   I   A   V   P     27
AAG AAG GAG CCT GGA GGA GGC GCG GCG ACT GAG GAG GGC GTG AAT AGG ATC GCA GTG CCA     81
  K   P   P   S   I   E   E   F   S   I   V   K   P   I   S   R   G   A   F   G     47
AAA CCG CCC TCC ATT GAG GAA TTC AGC ATA GTG AAG CCC ATT AGC CGG GGC GCC TTC GGG    141
  K   V   Y   L   G   Q   K   G   G   K   L   Y   A   V   K   V   V   K   K   A     67
AAA GTG TAT CTG GGG CAG AAA GGC GGC AAA TTG TAT GCA GTA AAG GTT GTT AAA AAA GCA    201
  D   M   I   N   K   N   M   T   H   Q   V   Q   A   E   R   D   A   L   A   L     87
GAC ATG ATC AAC AAA AAT ATG ACT CAT CAG GTC CAA GCT GAG AGA GAT GCA CTG GCA CTA    261
  S   K   S   P   F   I   V   H   L   Y   Y   S   L   Q   S   A   N   N   V   Y    107
AGC AAA AGC CCA TTC ATT GTC CAT TTG TAT TAT TCA CTG CAG TCT GCA AAC AAT GTC TAC    321
  L   V   M   E   Y   L   I   G   G   D   V   K   S   L   L   H   I   Y   G   Y    127
TTG GTA ATG GAA TAT CTT ATT GGG GGA GAT GTC AAG TCT CTC CTA CAT ATA TAT GGT TAT    381
  F   D   E   E   M   A   V   K   Y   I   S   E   V   A   L   A   L   D   Y   L    147
TTT GAT GAA GAG ATG GCT GTG AAA TAT ATT TCT GAA GTA GCA CTG GCT CTA GAC TAC CTT    441
  H   R   H   G   I   I   H   R   D   L   K   P   D   N   M   L   I   S   N   E    167
CAC AGA CAT GGA ATC ATC CAC AGG GAC TTG AAA CCG GAC AAT ATG CTT ATT TCT AAT GAG    501
  G   H   I   K   L   T   D   F   G   L   S   K   V   T   L   N   R   D   I   N    187
GGT CAT ATT AAA CTG ACG GAT TTT GGC CTT TCA AAA GTT ACT TTG AAT AGA GAT ATT AAT    561
  M   M   D   I   L   T   T   P   S   M   A   K   P   R   Q   D   Y   S   R   T    207
ATG ATG GAT ATC CTT ACA ACA CCA TCA ATG GCA AAA CCT AGA CAA GAT TAT TCA AGA ACC    621
  P   G   Q   V   L   S   L   I   S   S   L   G   F   N   T   P   I   A   E   K    227
CCA GGA CAA GTG TTA TCG CTT ATC AGC TCG TTG GGA TTT AAC ACA CCA ATT GCA GAA AAA    681
  N   Q   D   P   A   N   I   L   S   A   C   L   S   E   T   S   Q   L   S   Q    247
AAT CAA GAC CCT GCA AAC ATC CTT TCA GCC TGT CTG TCT GAA ACA TCA CAG CTT TCT CAA    741
  G   L   V   C   P   M   S   V   D   Q   K   D   T   T   P   Y   S   S   K   L    267
GGA CTC GTA TGC CCT ATG TCT GTA GAT CAA AAG GAC ACT ACG CCT TAT TCT AGC AAA TTA    801
  L   K   S   C   L   E   T   V   A   S   N   P   G   M   P   V   K   C   L   T    287
CTA AAA TCA TGT CTT GAA ACA GTT GCC TCC AAC CCA GGA ATG CCT GTG AAG TGT CTA ACT    861
  S   N   L   L   Q   S   R   K   R   L   A   T   S   S   A   S   S   Q   S   H    307
TCT AAT TTA CTC CAG TCT AGG AAA AGG CTG GCC ACA TCC AGT GCC AGT AGT CAA TCC CAC    921
  T   F   I   S   S   V   E   S   E   C   H   S   S   P   K   W   E   K   D   C    327
ACC TTC ATA TCC AGT GTG GAA TCA GAA TGC CAC AGC AGT CCC AAA TGG GAA AAA GAT TGC    981
  Q   E   S   D   E   A   L   G   P   T   M   M   S   W   N   A   V   E   K   L    347
CAG GAA AGT GAT GAA GCA TTG GGC CCA ACA ATG ATG AGT TGG AAT GCA GTT GAA AAG TTA   1041
  C   A   K   S   A   N   A   I   E   T   K   G   F   N   K   K   D   L   E   L    367
TGC GCA AAA TCT GCA AAT GCC ATT GAG ACG AAA GGT TTC AAT AAA AAG GAT CTG GAG TTA   1101
  A   L   S   P   I   H   N   S   S   A   L   P   T   T   G   R   S   C   V   N       387
```

GCT CTT TCT CCC ATT CAT AAC AGC AGT GCC CTT CCC ACC ACT GGA CGC TCT TGT GTA AAC  1161
 L   A   K   K   C   F   S   G   E   V   S   W   E   A   V   E   L   D   V   N   407
CTT GCT AAA AAA TGC TTC TCT GGG GAA GTT TCT TGG GAA GCA GTA GAA CTG GAT GTA AAT 1221
 N   I   N   M   D   T   D   T   S   Q   L   G   F   H   Q   S   N   Q   W   A   427
AAT ATA AAT ATG GAC ACT GAC ACA AGT CAG TTA GGT TTC CAT CAG TCA AAT CAG TGG GCT 1281
 V   D   S   G   G   I   S   E   E   H   L   G   K   R   S   L   K   R   N   F   447
GTG GAT TCT GGT GGG ATA TCT GAA GAG CAC CTT GGG AAA AGA AGT TTA AAA AGA AAT TTT 1341
 E   L   V   D   S   S   P   C   K   K   I   I   Q   N   K   K   T   C   V   E   467
GAG TTG GTT GAC TCC AGT CCT TGT AAA AAA ATT ATA CAG AAT AAA AAA ACT TGT GTA GAG 1401
 Y   K   H   N   E   M   T   N   C   Y   T   N   Q   N   T   G   L   T   V   E   487
TAT AAG CAT AAC GAA ATG ACA AAT TGT TAT ACA AAT CAA AAT ACA GGC TTA ACA GTT GAA 1461
 V   Q   D   L   K   L   S   V   H   K   S   Q   Q   N   D   C   A   N   K   E   507
GTG CAG GAC CTT AAG CTA TCA GTG CAC AAA AGT CAA CAA AAT GAC TGT GCT AAT AAG GAG 1521
 N   I   V   N   S   F   T   D   K   Q   Q   T   P   E   K   L   P   I   P   M   527
AAC ATT GTC AAT TCT TTT ACT GAT AAA CAA CAA ACA CCA GAA AAA TTA CCT ATA CCA ATG 1581
 I   A   K   N   L   M   C   E   L   D   E   D   C   E   K   N   S   K   R   D   547
ATA GCA AAA AAC CTT ATG TGT GAA CTC GAT GAA GAC TGT GAA AAG AAT AGT AAG AGG GAC 1641
 Y   L   S   S   S   F   L   C   S   D   D   D   R   A   S   K   N   I   S   M   567
TAC TTA AGT TCT AGT TTT CTA TGT TCT GAT GAT GAT AGA GCT TCT AAA AAT ATT TCT ATG 1701
 N   S   D   S   S   F   P   G   I   S   I   M   E   S   P   L   E   S   Q   P   587
AAC TCT GAT TCA TCT TTT CCT GGA ATT TCT ATA ATG GAA AGT CCA TTA GAA AGT CAG CCC 1761
 L   D   S   D   R   S   I   K   E   S   S   F   E   E   S   N   I   E   D   P   607
TTA GAT TCA GAT AGA AGC ATT AAA GAA TCC TCT TTT GAA GAA TCA AAT ATT GAA GAT CCA 1821
 L   I   V   T   P   D   C   Q   E   K   T   S   P   K   G   V   E   N   P   A   627
CTT ATT GTA ACA CCA GAT TGC CAA GAA AAG ACC TCA CCA AAA GGT GTC GAG AAC CCT GCT 1881
 V   Q   E   S   N   Q   K   M   L   G   P   P   L   E   V   L   K   T   L   A   647
GTA CAA GAG AGT AAC CAA AAA ATG TTA GGT CCT CCT TTG GAG GTG CTG AAA ACG TTA GCC 1941
 S   K   R   N   A   V   A   F   R   S   F   N   S   H   I   N   A   S   N   N   667
TCT AAA AGA AAT GCT GTT GCT TTT CGA AGT TTT AAC AGT CAT ATT AAT GCA TCC AAT AAC 2001
 S   E   P   S   R   M   N   M   T   S   L   D   A   M   D   I   S   C   A   Y   687
TCA GAA CCA TCC AGA ATG AAC ATG ACT TCT TTA GAT GCA ATG GAT ATT TCG TGT GCC TAC 2061
 S   G   S   Y   P   M   A   I   T   P   T   Q   K   R   R   S   C   M   P   H   707
AGT GGT TCA TAT CCC ATG GCT ATA ACC CCT ACT CAA AAA AGA AGA TCC TGT ATG CCA CAT 2121
 Q   Q   T   P   N   Q   I   K   S   G   T   P   Y   R   T   P   K   S   V   R   727
CAG CAG ACC CCA AAT CAG ATC AAG TCG GGA ACT CCA TAC CGA ACT CCG AAG AGT GTG AGA 2181
 R   G   V   A   P   V   D   D   G   R   I   L   G   T   P   D   Y   L   A   P   747
AGA GGG GTG GCC CCC GTT GAT GAT GGG CGA ATT CTA GGA ACC CCA GAC TAC CTT GCA CCT 2241
 E   L   L   L   G   R   A   H   G   P   A   V   D   W   W   A   L   G   V   C   767
GAG CTG TTA CTA GGC AGG GCC CAT GGT CCT GCG GTA GAC TGG TGG GCA CTT GGA GTT TGC 2301
 L   F   E   F   L   T   G   I   P   P   F   N   D   E   T   P   Q   Q   V   F   787
TTG TTT GAA TTT CTA ACA GGA ATT CCC CCT TTC AAT GAT GAA ACA CCA CAA CAA GTA TTC 2361
```

FIGURE 1B

```
    Q   N   I   L   K   R   D   I   P   W   P   E   G   E   E   K   L   S   D   N    807
    CAG AAT ATT CTG AAA AGA GAT ATC CCT TGG CCA GAA GGT GAA GAA AAG TTA TCT GAT AAT   2421

A   Q   S   A   V   E   I   L   L   T   I   D   D   T   K   R   A   G   M   K    827
    GCT CAA AGT GCA GTA GAA ATA CTT TTA ACC ATT GAT GAT ACA AAG AGA GCT GGA ATG AAA   2481

E   L   K   R   H   P   L   F   S   D   V   D   W   E   N   L   Q   H   Q   T    847
    GAG CTA AAA CGT CAT CCT CTC TTC AGT GAT GTG GAC TGG GAA AAT CTG CAG CAT CAG ACT   2541

M   P   F   I   P   Q   P   D   D   E   T   D   T   S   Y   F   E   A   R   N    867
    ATG CCT TTC ATC CCC CAG CCA GAT GAT GAA ACA GAT ACC TCC TAT TTT GAA GCC AGG AAT   2601

T   A   Q   H   L   T   V   S   G   F   S   L   *                                880
    ACT GCT CAG CAC CTG ACC GTA TCT GGA TTT AGT CTG TAG                               2640

CACAAAAATTTTCCTTTTAGTCTAGCCTCGTGTTATAGAATGAACTTGCATAATTATATACTCCTTAATACTAGATTGA
TCTAAGGGGGAAAGATCATTATTTAACCTAGTTCAATGTGCTTTTAATGTACGTTACAGCTTTCACAGAGTTAAAAGGC
TGAAAGGAATATAGTCAGTAATTTATCTTAACCTCAAAACTGTATATAAATCTTCAAAGCTTTTTTTCATCTATTTATTT
TGTTTATTGCACTTTATGAAAACTGAAGCATCAATAAAATTAGAGGACACTATTGAAAAAAAAAAAAAAAAAAAAA
```

FIGURE 1C

Input file Fbh3695cons1.seq; Output File 3695.trans
Sequence length 5983

```
                                                                    1
GGGCCCGCGGGCCGCCTGCTGCCTCCGCCCGCGCCGGGGTCCCCAGCCGCCCCCGCTGCCGTGTCCCCTGCGGCCGGCC

M   P   A   R   I   G   Y   Y   E   I   D     11
AGCCGCGTCCCCCAGCCCCGGCCTCCCGCGGACCC            ATG CCC GCC CGT ATC GGC TAC TAC GAG ATC GAC    33

R   T   I   G   K   G   N   F   A   V   V   K   R   A   T   H   L   V   T   K     31
CGC ACC ATC GGC AAG GGC AAC TTC GCG GTG GTC AAG CGG GCC ACG CAC CTC GTC ACC AAG    93

A   K   V   A   I   K   I   I   D   K   T   Q   L   D   E   E   N   L   K   K     51
GCC AAG GTT GCT ATC AAG ATC ATA GAT AAG ACC CAG CTG GAT GAA GAA AAC TTG AAG AAG   153

I   F   R   E   V   Q   I   M   K   M   L   C   H   P   H   I   I   R   L   Y     71
ATT TTC CGG GAA GTT CAA ATT ATG AAG ATG CTT TGC CAC CCC CAT ATC ATC AGG CTC TAC   213

Q   V   M   E   T   E   R   M   I   Y   L   V   T   E   Y   A   S   G   G   E     91
CAG GTT ATG GAG ACA GAA CGG ATG ATT TAT CTG GTG ACA GAA TAT GCT AGT GGA GGG GAA   273

I   F   D   H   L   V   A   H   G   R   M   A   E   K   E   A   R   R   K   F    111
ATA TTT GAC CAC CTG GTG GCC CAT GGT AGA ATG GCA GAA AAG GAG GCA CGT CGG AAG TTC   333

K   Q   I   V   T   A   V   Y   F   C   H   C   R   N   I   V   H   R   D   L    131
AAA CAG ATC GTC ACA GCT GTC TAT TTT TGT CAC TGT CGG AAC ATT GTT CAT CGT GAT TTA   393

K   A   E   N   L   L   L   D   A   N   L   N   I   K   I   A   D   F   G   F    151
AAA GCT GAA AAT TTA CTT CTG GAT GCC AAT CTG AAT ATC AAA ATA GCA GAT TTT GGT TTC   453

S   N   L   F   T   P   G   Q   L   L   K   T   W   C   G   S   P   P   Y   A    171
AGT AAC CTC TTC ACT CCT GGG CAG CTG CTG AAG ACC TGG TGT GGC AGC CCT CCC TAT GCT   513

A   P   E   L   F   E   G   K   E   Y   D   G   P   K   V   D   I   W   S   L    191
GCA CCT GAA CTC TTT GAA GGA AAA GAA TAT GAT GGG CCC AAA GTG GAC ATC TGG AGC CTT   573

G   V   V   L   Y   V   L   V   C   G   A   L   P   F   D   G   S   T   L   Q    211
GGA GTT GTC CTC TAC GTG CTT GTG TGC GGT GCC CTG CCA TTT GAT GGA AGC ACA CTG CAG   633

N   L   R   A   R   V   L   S   G   K   F   R   I   P   F   F   M   S   T   E    231
AAT CTG CGG GCC CGC GTG CTG AGT GGA AAG TTC CGC ATC CCA TTT TTT ATG TCC ACA GAA   693

C   E   H   L   I   R   H   M   L   V   L   D   P   N   K   R   L   S   M   E    251
TGT GAG CAT TTG ATC CGC CAT ATG TTG GTG TTA GAT CCC AAT AAG CGC CTC TCC ATG GAG   753

Q   I   C   K   H   K   W   M   K   L   G   D   A   D   P   N   F   D   R   L    271
CAG ATC TGC AAG CAC AAG TGG ATG AAG CTA GGG GAC GCC GAT CCC AAC TTT GAC AGG TTA   813

I   A   E   C   Q   Q   L   K   E   E   R   Q   V   D   P   L   N   E   D   V    291
ATA GCT GAA TGC CAA CAA CTA AAG GAA GAA AGA CAG GTG GAC CCC CTG AAT GAG GAT GTC   873

L   L   A   M   E   D   M   G   L   D   K   E   Q   T   L   Q   A   E   Q   A    311
CTC TTG GCC ATG GAG GAC ATG GGA CTG GAC AAA GAA CAG ACA CTG CAG GCG GAG CAG GCA   933

G   T   A   M   N   I   S   V   P   Q   V   Q   L   I   N   P   E   N   Q   I    331
GGT ACT GCT ATG AAC ATC AGC GTT CCC CAG GTG CAG CTG ATC AAC CCA GAG AAC CAA ATT   993

V   E   P   D   G   T   L   N   L   D   S   D   E   G   E   E   P   S   P   E    351
GTG GAG CCG GAT GGG ACA CTG AAT TTG GAC AGT GAT GAG GGT GAA GAG CCT TCC CCT GAA  1053

A   L   V   R   Y   L   S   M   R   R   H   T   V   G   V   A   D   P   R   T    371
GCA TTG GTG CGC TAT TTG TCA ATG AGG AGG CAC ACA GTG GGT GTG GCT GAC CCA CGC ACG  1113
```

FIGURE 2A

```
  E   V   M   E   D   L   Q   K   L   L   P   G   F   P   G   V   N   P   Q   A    391
GAA GTT ATG GAA GAT CTG CAG AAG CTC CTA CCT GGC TTT CCT GGA GTC AAC CCC CAG GCT   1173
  P   F   L   Q   V   A   P   N   V   N   F   M   H   N   L   L   P   M   Q   N    411
CCA TTC CTG CAG GTG GCC CCT AAT GTG AAC TTC ATG CAC AAC CTG TTG CCT ATG CAA AAC   1233
  L   Q   P   T   G   Q   L   E   Y   K   E   Q   S   L   L   Q   P   P   T   L    431
TTG CAA CCA ACC GGG CAA CTT GAG TAC AAG GAG CAG TCT CTC CTA CAG CCG CCC ACG CTA   1293
  Q   L   L   N   G   M   G   P   L   G   R   R   A   S   D   G   G   A   N   I    451
CAG CTG TTG AAT GGA ATG GGC CCC CTT GGC CGG AGG GCA TCA GAT GGA GGA GCC AAC ATC   1353
  Q   L   H   A   Q   Q   L   L   K   R   P   R   G   P   S   P   L   V   T   M    471
CAA CTG CAT GCC CAG CAG CTG CTG AAG CGC CCA CGG GGA CCC TCT CCG CTT GTC ACC ATG   1413
  T   P   A   V   P   A   V   T   P   V   D   E   E   S   S   D   G   E   P   D    491
ACA CCA GCA GTG CCA GCA GTT ACC CCT GTG GAC GAG GAG AGC TCA GAC GGG GAG CCA GAC   1473
  Q   E   A   V   Q   R   Y   L   A   N   R   S   K   R   H   T   L   A   M   T    511
CAG GAA GCT GTG CAG AGG TAC TTG GCA AAT AGG TCC AAA AGA CAT ACA CTG GCC ATG ACC   1533
  N   P   T   A   E   I   P   P   D   L   Q   R   Q   L   G   Q   Q   P   F   R    531
AAC CCT ACA GCT GAG ATC CCA CCG GAC CTA CAA CGG CAG CTA GGA CAG CAG CCT TTC CGT   1593
  S   R   V   W   P   P   H   L   V   P   D   Q   H   R   S   T   Y   K   D   S    551
TCC CGG GTC TGG CCT CCT CAC CTG GTA CCT GAT CAG CAT CGC TCT ACC TAC AAG GAC TCC   1653
  N   T   L   H   L   P   T   E   R   F   S   P   V   R   R   F   S   D   G   A    571
AAC ACT CTG CAC CTC CCT ACG GAG CGT TTC TCC CCT GTG CGC CGG TTC TCA GAT GGG GCT   1713
  A   S   I   Q   A   F   K   A   H   L   E   K   M   G   N   N   S   S   I   K    591
GCG AGC ATC CAG GCC TTC AAA GCT CAC CTG GAA AAA ATG GGC AAC AAC AGC AGC ATC AAA   1773
  Q   L   Q   Q   E   C   E   Q   L   Q   K   M   Y   G   G   Q   I   D   E   R    611
CAG CTG CAG CAG GAG TGT GAG CAG CTG CAG AAG ATG TAC GGG GGG CAG ATT GAT GAA AGA   1833
  T   L   E   K   T   Q   Q   Q   H   M   L   Y   Q   Q   E   Q   H   H   Q   I    631
ACC CTG GAG AAG ACC CAG CAG CAG CAT ATG TTA TAC CAG CAG GAG CAG CAC CAT CAA ATT   1893
  L   Q   Q   Q   I   Q   D   S   I   C   P   P   Q   P   S   P   P   L   Q   A    651
CTC CAG CAA CAA ATT CAA GAC TCT ATC TGT CCT CCT CAG CCA TCT CCA CCT CTT CAG GCT   1953
  A   C   E   N   Q   P   A   L   L   T   H   Q   L   Q   R   L   R   I   Q   P    671
GCA TGT GAA AAT CAG CCA GCC CTC CTT ACC CAT CAG CTC CAG AGG TTA AGG ATT CAG CCT   2013
  S   S   P   P   P   N   H   P   N   N   H   L   F   R   Q   P   S   N   S   P    691
TCA AGC CCA CCC CCC AAC CAC CCC AAC AAC CAT CTC TTC AGG CAG CCC AGT AAT AGT CCT   2073
  P   P   M   S   S   A   M   I   Q   P   H   G   A   A   S   S   S   Q   F   Q    711
CCC CCC ATG AGC AGT GCC ATG ATC CAG CCT CAC GGG GCT GCA TCT TCT TCC CAG TTT CAA   2133
  G   L   P   S   R   S   A   I   F   Q   Q   Q   P   E   N   C   S   S   P   P    731
GGC TTA CCT TCC CGC AGT GCA ATC TTT CAG CAG CAA CCT GAG AAC TGT TCC TCT CCT CCC   2193
  N   V   A   L   T   C   L   G   M   Q   Q   P   A   Q   S   Q   Q   V   T   I    751
AAC GTG GCA CTA ACC TGC TTG GGT ATG CAG CAG CCT GCT CAG TCA CAG CAG GTC ACC ATC   2253
  Q   V   Q   E   P   V   D   M   L   S   N   M   P   G   T   A   A   G   S   S    771
CAA GTC CAA GAG CCT GTT GAC ATG CTC AGC AAC ATG CCA GGC ACA GCT GCA GGC TCC AGT   2313
```

FIGURE 2B

```
  G   R   G   I   S   I   S   P   S   A   G   Q   M   Q   M   Q   H   R   T   N    791
GGG CGC GGC ATC TCC ATC AGC CCC AGT GCT GGT CAG ATG CAG ATG CAG CAC CGT ACC AAC  2373

L   M   A   T   L   S   Y   G   H   R   P   L   S   K   Q   L   S   A   D   S    811
CTG ATG GCC ACC CTC AGC TAT GGG CAC CGT CCC TTG TCC AAG CAG CTG AGT GCT GAC AGT  2433

A   E   A   H   S   A   H   Q   Q   P   P   H   Y   T   T   S   A   L   Q   Q    831
GCA GAG GCT CAC AGT GCA CAT CAG CAG CCG CCA CAC TAT ACC ACG TCG GCA CTA CAG CAG  2493

A   L   L   S   P   T   P   P   D   Y   T   R   H   Q   Q   V   P   H   I   L    851
GCC CTG CTG TCT CCC ACG CCG CCA GAC TAT ACA AGA CAC CAG CAG GTA CCC CAC ATC CTT  2553

Q   G   L   L   S   P   R   H   S   L   T   G   H   S   D   I   R   L   P   P    871
CAA GGA CTG CTT TCT CCC CGG CAT TCG CTC ACC GGC CAC TCG GAC ATC CGG CTG CCC CCA  2613

T   E   F   A   Q   L   I   K   R   Q   Q   Q   Q   R   Q   Q   Q   Q   Q   Q    891
ACA GAG TTT GCA CAG CTC ATT AAA AGG CAG CAG CAA CAA CGG CAG CAG CAG CAG CAA CAG  2673

Q   Q   Q   Q   E   Y   Q   E   L   F   R   H   M   N   Q   G   D   A   G   S    911
CAG CAA CAG CAA GAA TAC CAG GAA CTG TTC AGG CAC ATG AAC CAA GGG GAT GCG GGG AGT  2733

L   A   P   S   L   G   G   Q   S   M   T   E   R   Q   A   L   S   Y   Q   N    931
CTG GCT CCC AGC CTT GGG GGA CAG AGC ATG ACA GAG CGC CAG GCT TTA TCT TAT CAA AAT  2793

A   D   S   Y   H   H   H   T   S   P   Q   H   L   L   Q   I   R   A   Q   E    951
GCT GAC TCT TAT CAC CAT CAC ACC AGC CCC CAG CAT CTG CTA CAA ATC AGG GCA CAA GAA  2853

C   V   S   Q   A   S   S   P   T   P   P   H   G   Y   A   H   Q   P   A   L    971
TGT GTC TCA CAG GCT TCC TCA CCC ACC CCG CCC CAC GGG TAT GCT CAC CAG CCG GCA CTG  2913

M   H   S   E   S   M   E   E   D   C   S   C   E   G   A   K   D   G   F   Q    991
ATG CAT TCA GAG AGC ATG GAG GAG GAC TGC TCG TGT GAG GGG GCC AAG GAT GGC TTC CAA  2973

D   S   K   S   S   S   T   L   T   K   G   C   H   D   S   P   L   L   L   S   1011
GAC AGT AAG AGT TCA AGT ACA TTG ACC AAA GGT TGC CAT GAC AGC CCT CTG CTC TTG AGT  3033

T   G   G   P   G   D   P   E   S   L   L   G   T   V   S   H   A   Q   E   L   1031
ACC GGT GGA CCT GGG GAC CCT GAA TCT TTG CTA GGA ACT GTG AGT CAT GCC CAA GAA TTG  3093

G   I   H   P   Y   G   H   Q   P   T   A   A   F   S   K   N   K   V   P   S   1051
GGG ATA CAT CCC TAT GGT CAT CAG CCA ACT GCT GCA TTC AGT AAA AAT AAG GTG CCC AGC  3153

R   E   P   V   I   G   N   C   M   D   R   S   S   P   G   Q   A   V   E   L   1071
AGA GAG CCT GTC ATA GGG AAC TGC ATG GAT AGA AGT TCT CCA GGA CAA GCA GTG GAG CTG  3213

P   D   H   N   G   L   G   Y   P   A   R   P   S   V   H   E   H   H   R   P   1091
CCG GAT CAC AAT GGG CTC GGG TAC CCA GCA CGC CCC TCC GTC CAT GAG CAC CAC AGG CCC  3273

R   A   L   Q   R   H   H   T   I   Q   N   S   D   D   A   Y   V   Q   L   D   1111
CGG GCC CTC CAG AGA CAC CAC ACG ATC CAG AAC AGC GAC GAT GCT TAT GTA CAG CTG GAT  3333

N   L   P   G   M   S   L   V   A   G   K   A   L   S   S   A   R   M   S   D   1131
AAC TTG CCA GGA ATG AGT CTC GTG GCT GGG AAA GCA CTT AGC TCT GCC CGG ATG TCG GAT  3393

A   V   L   S   Q   S   S   L   M   G   S   Q   Q   F   Q   D   G   E   N   E   1151
GCA GTT CTC AGT CAG TCT TCG CTC ATG GGC AGC CAG CAG TTT CAG GAT GGG GAA AAT GAG  3453

E   C   G   A   S   L   G   G   H   E   H   P   D   L   S   D   G   S   Q   H   1171
GAA TGT GGG GCA AGC CTG GGA GGT CAT GAG CAC CCA GAC CTG AGT GAT GGC AGC CAG CAT  3513

```
TTA AAC TCC TCT TGC TAT CCA TCT ACG TGT ATT ACA GAC ATT CTG CTC AGC TAC AAG CAC   3573
 P   E   V   S   F   S   M   E   Q   A   G   V   *
CCC GAA GTC TCC TTC AGC ATG GAG CAG GCA GGC GTG TAA                                1204
                                                                                   3612
```

CAAGAAACAGAGAGTTTTGTGTACAGCTTGGGAATGAAAAGGTTGATTGTAAACCCACAGTATCTAGCAGCGTTGTGCC
AAATTGCCCTTGTGTTTCTCTCCACCCAAAATATCACAGCTGCTTTCCTCACATTTGGTTCATCCGTGTGCTGTTCTTT
TGGGTTCTGAGAGGGTTTTGCCATGTTTGCTTGTATGACCAAGTCACCAAGGAAATAAACAGGAAGGAAATCCATGTTC
TCCATCTTTTGTGAAAGTATATTTGAGTTGGTGGTTTTTTGTTTTGTTTGGGGGTTTGTGTTTTGTTTTGTTTTTGGTA
TGTTTTCTTCCAGAGGTGATATACTTTCTTTTTTTTCTTCCTTTCTTTTTTTTCTTTCGTTCCTTTTTTGAAACAGGAG
AGCAAAGCAGTTAGAGTTCAGAGGCCAGCGGCCTCAGGGCCACTCCCTCCCTAGCCTTCATCAGCAGAGCACCCTCCAT
CCCCCTGCATTGCTCTTCTGTGAAAGCAAATACTAAAGGATGCCATCCTCTGGAATCCTAATGGCAGGCAAAGGGAGAG
AGGAAGGGTGACGGCTTCTGGCACTTAGAAAACAAAAAGAACAAAAAAAGAGAAACCCCCAAGCCTGGAACGCAGAGAG
GTCTTTACTGCTGGGATCCACGGAAAACATGTCTGTCCTAGCCAAGATCATATGAAGAGTTTGGCACGGAGGCTGAGAA
TGACCTGGCATAGATGGTTTGCCAGTTAGGATGTCTCAATTTGAGCCTTTGCTTTTGGTGGATAACTCAGCTCCCCTCT
TGTAACCTGGAAAGTTGGTTGCCTTTATCATCCTGCTGGTTTTATCCATGGACTGAACACCCAACAGCAGTGCACTATG
CTTTCTATGGCATCTTTCATTCTCATTTTATATTGTGCTATAAAAAGGATTGTTTCTCCATATATATATTATATATGTG
TGTATATATATAATATAATATATGTGTATATATATATTATATATATAATATATAATATATATATTATATATATATTATA
TATATAATATATATATAAAATATATATATATGCTCTCCTCTTTCAGCCTCTTTGTCACAGGGAAGAAGTGTAGGAGG
TTGCCTTGGGCCCTGCCTCTCTCCTAACCTCCTCTTCCCCACTGGGTACCCTCAGCCCCTATATTTTAATTCTTGATCA
TGTAGAAATTGTTTTTGGTAAATGTTGATATTATTGTTATTATCATTATTAATAAATAAAGAGAAAAGGAATTTTTGTT
TAAATGAGAAATGTTTAACCAGATTCTGTTCTATTTGAATTGTGACTTGCACCTTTTGTTCAAAGTATTTCCTTTAGGC
ATTGTAATTGTGAACAGCTCTTACTTGTGCCAGTGACAGATGCAGTGGTCTCCTTTCCCCAGTTGAAGCAGTGCATACG
CAGTAGCTATTATTTGTGTTATCTTTATTTCTCTTCATTGTTAGAAACCAAAGTCTTCTCTGCTGGCTGGGGCTGAGAG
AGGGTCTGGGTTATCTCCTTCTGATCTTCAAAACAAGAGAGAGACCTTGAATACACTGACTCTTCCACCCTTTTTTTT
CTGGGAAAGGAGAGCAAGAGGTCCCGAGTCCCCTCCTAGTCTTTCATCCTGAATTTGCACAGAGGAAAGCGGGTGCCCG
GCATGGCCATCCTGATGTTGCTGGCGGGATCCCCATGCACCTTGTCCTTCTCCACTGATACTGGCAGCTCGGCTCCTGG
ACCCAAGATCCCTTGAGTGGAATTCTGCAGTGCAAGAGCCCTTCGTGGGAGCTGTCCCATGTTTCCATGGTCCCCAGTC
TCCCCTCCACTTGGTGGGGTCACCAACTACTCACCAGAAGGGGGCTTACCAAGAAAGCCCTAAAAAGCTGTTGACTTAT
CTGCGCTTGTTCCAACTCTTATGCCCCCAACCTGCCCTACCACCACCACGCGCTCAGCCTGATGTGTTTACATGGTACT
GTATGTATGGGAGAGCAGACTGCACCCTCCAGCAACAACAGATGAAAGCCAGTGAGCCTACTAACCGTGCCATCTTGCA
AACTACACTTTAAAAAAAACTCATTGCTTTGTATTGTAGTAACCAATATGTGCAGTATACGTTGAATGTATATGAACAT
ACTTTCCTATTTCTGTTCTTTGAAAATGTCAGAAATATTTTTTTCTTTCTCATTTTATGTTGAACTAAAAAGGATTAAA

FIGURE 2D

AAAAAAATCTCCAGAAAAAAAAAAAAAAAAAAGGGCGGCCGCTAGA

FIGURE 2E

Input file Fbh13302FL.seq; Output File 13302.trans
Sequence length 2389

TCCGCGAGGGCATCAGACGGCGGCTGATTAGCTCCGGTTTGCATCACCCGGACCGGGGGATTAGCTCCGGTTTGCATCA

CCCGGACCGGGGGATTAGCTCCGGTTTGCATCACCCGGACCGGGGGATTAGCTCCGGTTTGCATCACCCGGACCGGGGG

ATTAGCTCCGGTTTGCATCACCCGGACCGGGGGCCGGGCGCGCACGAGACTCGCAGCGGAAGTGGAGGCGGCTCCGCGC

GCGTCCGCTGCTAGGACCCGGGCAGGGCTGGAGCTGGGCTGGGATCCCGAGCTCGGCAGCAGCGCAGCGGGCCGGCCCA

```
                                                                        M   R   A      3
CCTGCTGGTGCCCTGGAGGCTCTGAGCCCCGGCGGCGCCCGGGCCCACGCGGAACGACGGGGCGAG ATG CGA GCC      9
 T   P   L   A   A   P   A   G   S   L   S   R   K   K   R   L   E   L   D   D      23
ACC CCT CTG GCT GCT CCT GCG GGT TCC CTG TCC AGG AAG AAG CGG TTG GAG TTG GAT GAC      69
 N   L   D   T   E   R   P   V   Q   K   R   A   R   S   G   P   Q   P   R   L      43
AAC TTA GAT ACC GAG CGT CCC GTC CAG AAA CGA GCT CGA AGT GGG CCC CAG CCC AGA CTG     129
 P   P   C   L   L   P   L   S   P   P   T   A   P   D   R   A   T   A   V   A      63
CCC CCC TGC CTG TTG CCC CTG AGC CCA CCT ACT GCT CCA GAT CGT GCA ACT GCT GTG GCC     189
 T   A   S   R   L   G   P   Y   V   L   L   E   P   E   E   G   G   R   A   Y      83
ACT GCC TCC CGT CTT GGG CCC TAT GTC CTC CTG GAG CCC GAG GAG GGC GGG CGG GCC TAC     249
 Q   A   L   H   C   P   T   G   T   E   Y   T   C   K   V   Y   P   V   Q   E     103
CAG GCC CTG CAC TGC CCT ACA GGC ACT GAG TAT ACC TGC AAG GTG TAC CCC GTC CAG GAA     309
 A   L   A   V   L   E   P   Y   A   R   L   P   P   H   K   H   V   A   R   P     123
GCC CTG GCC GTG CTG GAG CCC TAC GCG CGG CTG CCC CCG CAC AAG CAT GTG GCT CGG CCC     369
 T   E   V   L   A   G   T   Q   L   L   Y   A   F   F   T   R   T   H   G   D     143
ACT GAG GTC CTG GCT GGT ACC CAG CTC CTC TAC GCC TTT TTC ACT CGG ACC CAT GGG GAC     429
 M   H   S   L   V   R   S   R   H   R   I   P   E   P   E   A   A   V   L   F     163
ATG CAC AGC CTG GTG CGA AGC CGC CAC CGT ATC CCT GAG CCT GAG GCT GCC GTG CTC TTC     489
 R   Q   M   A   T   A   L   A   H   C   H   Q   H   G   L   V   L   R   D   L     183
CGC CAG ATG GCC ACC GCC CTG GCG CAC TGT CAC CAG CAC GGT CTG GTC CTG CGT GAT CTC     549
 K   L   C   R   F   V   F   A   D   R   E   R   K   K   L   V   L   E   N   L     203
AAG CTG TGT CGC TTT GTC TTC GCT GAC CGT GAG AGG AAG AAG CTG GTG CTG GAG AAC CTG     609
 E   D   S   C   V   L   T   G   P   D   D   S   L   W   D   K   H   A   C   P     223
GAG GAC TCC TGC GTG CTG ACT GGG CCA GAT GAT TCC CTG TGG GAC AAG CAC GCG TGC CCA     669
 A   Y   V   G   P   E   I   L   S   S   R   A   S   Y   S   G   K   A   A   D     243
GCC TAC GTG GGA CCT GAG ATA CTC AGC TCA CGG GCC TCA TAC TCG GGC AAG GCA GCC GAT     729
 V   W   S   L   G   V   A   L   F   T   M   L   A   G   H   Y   P   F   Q   D     263
GTC TGG AGC CTG GGC GTG GCG CTC TTC ACC ATG CTG GCC GGC CAC TAC CCC TTC CAG GAC     789
 S   E   P   V   L   L   F   G   K   I   R   R   G   A   Y   A   L   P   A   G     283
TCG GAG CCT GTC CTG CTC TTC GGC AAG ATC CGC CGC GGG GCC TAC GCC TTG CCT GCA GGC     849
 L   S   A   P   A   R   C   L   V   R   C   L   L   R   R   E   P   A   E   R     303
CTC TCG GCC CCT GCC CGC TGT CTG GTT CGC TGC CTC CTT CGT CGG GAG CCA GCT GAA CGG     909
 L   T   A   T   G   I   L   L   H   P   W   L   R   Q   D   P   M   P   L   A     323
CTC ACA GCC ACA GGC ATC CTC CTG CAC CCC TGG CTG CGA CAG GAC CCG ATG CCC TTA GCT     969
```

FIGURE 3A

```
 P   T   R   S   H   L   W   E   A   A   Q   V   V   P   D   G   L   G   L   D     343
CCA ACC CGA TCC CAT CTC TGG GAG GCT GCC CAG GTG GTC CCT GAT GGA CTG GGG CTG GAC    1029
 E   A   R   E   E   E   G   D   R   E   V   V   L   Y   G   *                    359
GAA GCC AGG GAA GAG GAG GGA GAC AGA GAA GTG GTT CTG TAT GGC TAG                    1077
```

GACCACCCTACTACACGCTCAGCTGCCAACAGTGGATTGAGTTTGGGGGTAGCTCCAAGCCTTCTCCTGCCTCTGAACT
GAGCCAAACCTTCAGTGCCTTCCAGAAGGGAGAAAGGCAGAAGCCTGTGTGGAGTGTGCTGTGTACACATCTGCTTTGT
TCCACACACATGCAGTTCCTGCTTGGGTGCTTATCAGGTGCCAAGCCCTGTTCTCGGTGCTGGGAGTACAGCAGTGAGC
AAAGGAGACAATATTCCCTGCTCACAGAGATGACAAACTGGCATCCTTGAGCTGACAACACTTTTCCATGACCATAGGT
CACTGTCTACACTGGGTACACTTTGTACCAGTGTCGGCCTCCACTGATGCTGGTGCTCAGGCACCTCTGTCCAAGGACA
ATCCCTTTCACAAACAAACCAGCTGCCTTTGTATCTTGTACCTTTTCAGAGAAAGGGAGGTATCCCTGTGCCAAAGGCT
CCAGGCCTCTCCCCTGCAACTCAGGACCCAAGCCCAGCTCACTCTGGGAACTGTGTTCCCAGCATCTCTGTCCTCTTGA
TTAAGAGATTCTCCTTCCAGGCCTAAGCCTGGGATTTGGGCCAGAGATAAGAATCCAAACTATGAGGCTAGTTCTTGTC
TAACTCAAGACTGTTCTGGAATGAGGGTCCAGGCCTGTCAACCATGGGGCTTCTGACCTGAGCACCAAGGTTGAGGGAC
AGGATTAGGCAGGGTCTGTCCTGTGGCCACCTGGAAAGTCCCAGGTGGGACTCTTCTGGGGACACTTGGGGTCCACAAT
CCCAGGTCCATACTCTAGGTTTTGGATACCATGAGTATGTATGTTTACCTGTGCCTAATAAAGGAGAATTATGAAATAA
AAAAAAAAAAAAAAAAAAAAAAAAAAAAAAAAAAAAAAAAAAAAAAAAAAAAAAAAAA

FIGURE 3B

Input file Fbh2208FL.seq; Output File 2208.trans
Sequence length 2162

```
                                                                                    M    1
CACGCGTCCGCCCACGCGTCCGCGCCGGTGGTGGCGGCAGCGGCGGCTGCGGGGGCACCGGGCCGCGGCGCCACC ATG    3
 A   V   R   Q   A   L   G   R   G   L   Q   L   G   R   A   L   L   L   R   F    21
GCG GTG CGA CAG GCG CTG GGC CGC GGC CTG CAG CTG GGT CGA GCG CTG CTG CTG CGC TTC    63
 T   G   K   P   G   R   A   Y   G   L   G   R   P   G   P   A   A   G   C   V    41
ACG GGC AAG CCC GGC CGG GCC TAC GGC TTG GGG CGG CCG GGC CCG GCG GCG GGC TGT GTC   123
 R   G   E   R   P   G   W   A   A   G   P   G   A   E   P   R   R   V   G   L    61
CGC GGG GAG CGT CCA GGC TGG GCC GCA GGA CCG GGC GCG GAG CCT CGC AGG GTC GGG CTC   183
 G   L   P   N   R   L   R   F   F   R   Q   S   V   A   G   L   A   A   R   L    81
GGG CTC CCT AAC CGT CTC CGC TTC TTC CGC CAG TCG GTG GCC GGG CTG GCG GCG CGG TTG   243
 Q   R   Q   F   V   V   R   A   W   G   C   A   G   P   C   G   R   A   V   F   101
CAG CGG CAG TTC GTG GTG CGG GCC TGG GGC TGC GCG GGC CCT TGC GGC CGG GCA GTC TTT   303
 L   A   F   G   L   G   L   G   L   I   E   E   K   Q   A   E   S   R   R   A   121
CTG GCC TTC GGG CTA GGG CTG GGC CTC ATC GAG GAA AAA CAG GCG GAG AGC CGG CGG GCG   363
 V   S   A   C   Q   E   I   Q   A   I   F   T   Q   K   S   K   P   G   P   D   141
GTC TCG GCC TGT CAG GAG ATC CAG GCA ATT TTT ACC CAG AAA AGC AAG CCG GGG CCT GAC   423
 P   L   D   T   R   R   L   Q   G   F   R   L   E   E   Y   L   I   G   Q   S   161
CCG TTG GAC ACG AGA CGC TTG CAG GGC TTT CGG CTG GAG GAG TAT CTG ATA GGG CAG TCC   483
 I   G   K   G   C   S   A   A   V   Y   E   A   T   M   P   T   L   P   Q   N   181
ATT GGT AAG GGC TGC AGT GCT GCT GTG TAT GAA GCC ACC ATG CCT ACA TTG CCC CAG AAC   543
 L   E   V   T   K   S   T   G   L   L   P   G   R   G   P   G   T   S   A   P   201
CTG GAG GTG ACA AAG AGC ACC GGG TTG CTT CCA GGG AGA GGC CCA GGT ACC AGT GCA CCA   603
 G   E   G   Q   E   R   A   P   G   A   P   A   F   P   L   A   I   K   M   M   221
GGA GAA GGG CAG GAG CGA GCT CCG GGG GCC CCT GCC TTC CCC TTG GCC ATC AAG ATG ATG   663
 W   N   I   S   A   G   S   S   S   E   A   I   L   N   T   M   S   Q   E   L   241
TGG AAC ATC TCG GCA GGT TCC TCC AGC GAA GCC ATC TTG AAC ACA ATG AGC CAG GAG CTG   723
 V   P   A   S   R   V   A   L   A   G   E   Y   G   A   V   T   Y   R   K   S   261
GTC CCA GCG AGC CGA GTG GCC TTG GCT GGG GAG TAT GGA GCA GTC ACT TAC AGA AAA TCC   783
 K   R   G   P   K   Q   L   A   P   H   P   N   I   I   R   V   L   R   A   F   281
AAG AGA GGT CCC AAG CAA CTA GCC CCT CAC CCC AAC ATC ATC CGG GTT CTC CGC GCC TTC   843
 T   S   S   V   P   L   L   P   G   A   L   V   D   Y   P   D   V   L   P   S   301
ACC TCT TCC GTG CCG CTG CTG CCA GGG GCC CTG GTC GAC TAC CCT GAT GTG CTG CCC TCA   903
 R   L   H   P   E   G   L   G   H   G   R   T   L   F   L   V   M   K   N   Y   321
CGC CTC CAC CCT GAA GGC CTG GGC CAT GGC CGG ACG CTG TTC CTC GTT ATG AAG AAC TAT   963
 P   C   T   L   R   Q   Y   L   C   V   N   T   P   S   P   R   L   A   A   M   341
CCC TGT ACC CTG CGC CAG TAC CTT TGT GTG AAC ACA CCC AGC CCC CGC CTC GCC GCC ATG  1023
 M   L   L   Q   L   L   E   G   V   D   H   L   V   Q   Q   G   I   A   H   R   361
ATG CTG CTG CAG CTG CTG GAA GGC GTG GAC CAT CTG GTT CAA CAG GGC ATC GCG CAC AGA  1083
 D   L   K   S   D   N   I   L   V   E   L   D   P   D   G   C   P   W   L   V                              381
```

FIGURE 4A

```
                                                                                  1143
GAC CTG AAA TCC GAC AAC ATC CTT GTG GAG CTG GAC CCA GAC GGC TGC CCC TGG CTG GTG
 I   A   D   F   G   C   C   L   A   D   E   S   I   G   L   Q   L   P   F   S    401
ATC GCA GAT TTT GGC TGC TGC CTG GCT GAT GAG AGC ATC GGC CTG CAG TTG CCC TTC AGC  1203
 S   W   Y   V   D   R   G   G   N   G   C   L   M   A   P   E   V   S   T   A    421
AGC TGG TAC GTG GAT CGG GGC GGA AAC GGC TGT CTG ATG GCC CCA GAG GTG TCC ACG GCC  1263
 R   P   G   P   R   A   V   I   D   Y   S   K   A   D   A   W   A   V   G   A    441
CGT CCT GGC CCC AGG GCA GTG ATT GAC TAC AGC AAG GCT GAT GCC TGG GCA GTG GGA GCC  1323
 I   A   Y   E   I   F   G   L   V   N   P   F   Y   G   Q   G   K   A   H   L    461
ATC GCC TAT GAA ATC TTC GGG CTT GTC AAT CCC TTC TAC GGC CAG GGC AAG GCC CAC CTT  1383
 E   S   R   S   Y   Q   E   A   Q   L   P   A   L   P   E   S   V   P   P   D    481
GAA AGC CGC AGC TAC CAA GAG GCT CAG CTA CCT GCA CTG CCC GAG TCA GTG CCT CCA GAC  1443
 V   R   Q   L   V   R   A   L   L   Q   R   E   A   S   K   R   P   S   A   R    501
GTG AGA CAG TTG GTG AGG GCA CTG CTC CAG CGA GAG GCC AGC AAG AGA CCA TCT GCC CGA  1503
 V   A   A   N   V   L   H   L   S   L   W   G   E   H   I   L   A   L   K   N    521
GTA GCC GCA AAT GTG CTT CAT CTA AGC CTC TGG GGT GAA CAT ATT CTA GCC CTG AAG AAT  1563
 L   K   L   D   K   M   V   G   W   L   L   Q   Q   S   A   A   T   L   L   A    541
CTG AAG TTA GAC AAG ATG GTT GGC TGG CTC CTC CAA CAA TCG GCC GCC ACT TTG TTG GCC  1623
 N   R   L   T   E   K   C   C   V   E   T   K   M   K   M   L   F   L   A   N    561
AAC AGG CTC ACA GAG AAG TGT TGT GTG GAA ACA AAA ATG AAG ATG CTC TTT CTG GCT AAC  1683
 L   E   C   E   T   L   C   Q   A   A   L   L   L   C   S   W   R   A   A   L    581
CTG GAG TGT GAA ACG CTC TGC CAG GCA GCC CTC CTC CTC TGC TCA TGG AGG GCA GCC CTG  1743
 *                                                                                582
TGA                                                                              1746
TGTCCCTGCATGGAGCTGGTGAATTACTAAAAGAACTTGGCATCCTCTGTGTCGTGATGGTCTGTGAATGGTGAGGGTG
GGAGTCAGGAGACAAGACAGCGCAGAGAGGGCTGGTTAGCCGGAAAAGGCCTCGGGCTTGGCAAATGGAAGAACTTGAG
TGAGAGTTCAGTCTGCAGTCCTGTGCTCACAGACATCCGAAAAGTGAATGGCCAAGCTGGTCTAGTAGATGAGGCTGGA
CTGAGGAGGGGTAGGCCTGCATCCACAGAGAGGATCCAGGCCAAGGCACTGGCTGTCAGTGGCAGAGTTTGGCTGTGAC
CTTTGCCCCTAACACGAGGAACTCG
```

FIGURE 4B

Input file Fbh2193f1; Output File 2193.trans
Sequence length 1826

```
                              M   G   S   S   M   S   A   A   T   A   R   R   P   V   F      15
CCACGCGTCCGAGAGG ATG GGC TCG TCC ATG TCG GCG GCC ACC GCG CGG AGG CCG GTG TTT      45

D   D   K   E   D   V   N   F   D   H   F   Q   I   L   R   A   I   G   K   G      35
GAC GAC AAG GAG GAC GTG AAC TTC GAC CAC TTC CAG ATC CTT CGG GCC ATT GGG AAG GGC   105

S   F   G   K   V   C   I   V   Q   K   R   D   T   E   K   M   Y   A   M   K      55
AGC TTT GGC AAG GTG TGC ATT GTG CAG AAG CGG GAC ACG GAG AAG ATG TAC GCC ATG AAG   165

Y   M   N   K   Q   Q   C   I   E   R   D   E   V   R   N   V   F   R   E   L      75
TAC ATG AAC AAG CAG CAG TGC ATC GAG CGC GAC GAG GTC CGC AAC GTC TTC CGG GAG CTG   225

E   I   L   Q   E   I   E   H   V   F   L   V   N   L   W   Y   S   F   Q   D      95
GAG ATC CTG CAG GAG ATC GAG CAC GTC TTC CTG GTG AAC CTC TGG TAC TCC TTC CAG GAC   285

E   E   D   M   F   M   V   V   D   L   L   L   G   G   D   L   R   Y   H   L     115
GAG GAG GAC ATG TTC ATG GTC GTG GAC CTG CTA CTG GGC GGG GAC CTG CGC TAC CAC CTG   345

Q   Q   N   V   Q   F   S   E   D   T   V   R   L   Y   I   C   E   M   A   L     135
CAG CAG AAC GTG CAG TTC TCC GAG GAC ACG GTG AGG CTG TAC ATC TGC GAG ATG GCA CTG   405

A   L   D   Y   L   R   G   Q   H   I   I   H   R   D   V   K   P   D   N   I     155
GCT CTG GAC TAC CTG CGC GGC CAG CAC ATC ATC CAC AGA GAT GTC AAG CCT GAC AAC ATT   465

L   L   D   E   R   G   H   A   H   L   T   D   F   N   I   A   T   I   I   K     175
CTC CTG GAT GAG AGA GGA CAT GCA CAC CTG ACC GAC TTC AAC ATT GCC ACC ATC ATC AAG   525

D   G   E   R   A   T   A   L   A   G   T   K   P   Y   M   A   P   E   I   F     195
GAC GGG GAG CGG GCG ACG GCA TTA GCA GGC ACC AAG CCG TAC ATG GCT CCG GAG ATC TTC   585

H   S   F   V   N   G   G   T   G   Y   S   F   E   V   D   W   W   S   V   G     215
CAC TCT TTT GTC AAC GGC GGG ACC GGC TAC TCC TTC GAG GTG GAC TGG TGG TCG GTG GGG   645

V   M   A   Y   E   L   L   R   G   W   R   P   Y   D   I   H   S   S   N   A     235
GTG ATG GCC TAT GAG CTG CTG CGA GGA TGG AGG CCC TAT GAC ATC CAC TCC AGC AAC GCC   705

V   E   S   L   V   Q   L   F   S   T   V   S   V   Q   Y   V   P   T   W   S     255
GTG GAG TCC CTG GTG CAG CTG TTC AGC ACC GTG AGC GTC CAG TAT GTC CCC ACG TGG TCC   765

K   E   M   V   A   L   L   R   K   L   L   T   V   N   P   E   H   R   L   S     275
AAG GAG ATG GTG GCC TTG CTG CGG AAG CTC CTC ACT GTG AAC CCC GAG CAC CGG CTC TCC   825

S   L   Q   D   V   Q   A   A   P   A   L   A   G   V   L   W   D   H   L   S     295
AGC CTC CAG GAC GTG CAG GCA GCC CCG GCG CTG GCC GGC GTG CTG TGG GAC CAC CTG AGC   885

E   K   R   V   E   P   G   F   V   P   N   K   G   R   L   H   C   D   P   T     315
GAG AAG AGG GTG GAG CCG GGC TTC GTG CCC AAC AAA GGC CGT CTG CAC TGC GAC CCC ACC   945

F   E   L   E   E   M   I   L   E   S   R   P   L   H   K   K   K   K   R   L     335
TTT GAG CTG GAG GAG ATG ATC CTG GAG TCC AGG CCC CTG CAC AAG AAG AAG AAG CGT CTG  1005

A   K   N   K   S   R   D   N   S   R   D   S   S   Q   S   E   N   D   Y   L     355
GCC AAG AAC AAG TCC CGG GAC AAC AGC AGG GAC AGC TCC CAG TCC GAG AAT GAC TAT CTT  1065

Q   D   C   L   D   A   I   Q   Q   D   F   V   I   F   N   R   E   K   L   K     375
CAA GAC TGC CTC GAT GCC ATC CAG CAA GAC TTC GTG ATT TTT AAC AGA GAA AAG CTG AAG  1125

```
AGG AGC CAG GAC CTC CCG AGG GAG CCT CTC CCC GCC CCT GAG TCC AGG GAT GCT GCG GAG    1185
 P   V   E   D   E   A   E   R   S   A   L   P   M   C   G   P   I   C   P   S     415
CCT GTG GAG GAC GAG GCG GAA CGC TCC GCC CTG CCC ATG TGC GGC CCC ATT TGC CCC TCG    1245
 A   G   S   G   *                                                                  420
GCC GGG AGC GGC TAG                                                                1260
```

GCCGGGACGCCCGTGGTCCTCACCCCTTGAGCTGCTTTGGAGACTCGGCTGCCAGAGGGAGGGCCATGGGCCGAGGCCT

GGCATTCACGTTCCCACCCAGCCTGGCTGGCGGTGCCCACAGTGCCCCGGACACATTTCACACCTCAGGCTCGTGGTGG

TGCAGGGGACAAGAGGCTGTGGGTGCAGGGGACACCTGTGGAGGGCATTTCCCGTGGGCCCCCGAGACCCGCCTAGATG

GAGGAAGCGCTGCTGGGCGCCCTCTTACCGCTCACGGGGAGCTGGGGCCATGGATGGGACAGGAGTCTTTGTCCCTGCT

CAGCCCGGAGGCTGTGCACGGCCCTCGTCACAAGGTGACCCTTGCAGCACAGGCCGCGGGTGCCCCAGGCTCGGCTCAG

GTCTTGGAGGTCAAGGGCATGGGTTGGGGTAGTGGGTGGGGAGGTGAATGTTTTCTAGAGATTCAAACTGCTCCAGCAA

TTTCTGTAGTTTTCACCTCTGAGAATTACAATGTGAGAACCGCTCGGAAAAAAAAAAAAAAAAAAAAAAAAAAAAAAA

FIGURE 5B

Input file Fbh2249fl.seq; Output File 2249.trans
Sequence length 2870

GTCGACCCACGCGTCCGGGTTACTTCCGGGTCGGACGGCGCTAGCTGCAGCATCGGAGTGTGGCAGTGCTGGGCTGGCC

```
                                     M   Q   G   G   N   S   G   V   R   K   R    11
GGCGGGCTGGGCTGCGGCCCGCGCGCGGCCGGCG ATG CAG GGG GGC AAC TCC GGG GTC CGC AAG CGC     33

E   E   E   G   D   G   A   G   A   V   A   A   P   P   A   I   D   F   P   A    31
GAA GAG GAG GGC GAC GGG GCT GGG GCT GTG GCT GCG CCG CCG GCC ATC GAC TTT CCC GCC    93

E   G   P   D   P   E   Y   D   E   S   D   V   P   A   E   I   Q   V   L   K    51
GAG GGC CCG GAC CCC GAA TAT GAC GAA TCT GAT GTT CCA GCA GAA ATC CAG GTG TTA AAA   153

E   P   L   Q   Q   P   T   F   P   F   A   V   A   N   Q   L   L   L   V   S    71
GAA CCC CTA CAA CAG CCA ACC TTC CCT TTT GCA GTT GCA AAC CAA CTC TTG CTG GTT TCT   213

L   L   E   H   L   S   H   V   H   E   P   N   P   L   R   S   R   Q   V   F    91
TTG CTG GAG CAC TTG AGC CAC GTG CAT GAA CCA AAC CCA CTT CGT TCA AGA CAG GTG TTT   273

K   L   L   C   Q   T   F   I   K   M   G   L   L   S   S   F   T   C   S   D   111
AAG CTA CTT TGC CAG ACG TTT ATC AAA ATG GGG CTG CTG TCT TCT TTC ACT TGT AGT GAC   333

E   F   S   S   L   R   L   H   H   N   R   A   I   T   H   L   M   R   S   A   131
GAG TTT AGC TCA TTG AGA CTA CAT CAC AAC AGA GCT ATT ACT CAC TTA ATG AGG TCT GCT   393

K   E   R   V   R   Q   D   P   C   E   D   I   S   R   I   Q   K   I   R   S   151
AAA GAG AGA GTT CGT CAG GAT CCT TGT GAG GAT ATT TCT CGT ATC CAG AAA ATC AGA TCA   453

R   E   V   A   L   E   A   Q   T   S   R   Y   L   N   E   F   E   E   L   A   171
AGG GAA GTA GCC TTG GAA GCA CAA ACT TCA CGT TAC TTA AAT GAA TTT GAA GAA CTT GCC   513

I   L   G   K   G   G   Y   G   R   V   Y   K   V   R   N   K   L   D   G   Q   191
ATC TTA GGA AAA GGT GGA TAC GGA AGA GTA TAC AAG GTC AGG AAT AAA TTA GAT GGT CAG   573

Y   Y   A   I   K   K   I   L   I   K   G   A   T   K   T   V   C   M   K   V   211
TAT TAT GCA ATA AAA AAA ATC CTG ATT AAG GGT GCA ACT AAA ACA GTT TGC ATG AAG GTC   633

L   R   E   V   K   V   L   A   G   L   Q   H   P   N   I   V   G   Y   H   T   231
CTA CGG GAA GTG AAG GTG CTG GCA GGT CTT CAG CAC CCC AAT ATT GTT GGC TAT CAC ACC   693

A   W   I   E   H   V   H   V   I   Q   P   R   D   R   A   A   I   E   L   P   251
GCG TGG ATA GAA CAT GTT CAT GTG ATT CAG CCA CGA GAC AGA GCT GCC ATT GAG TTG CCA   753

S   L   E   V   L   S   D   Q   E   E   D   R   E   Q   C   G   V   K   N   D   271
TCT CTG GAA GTG CTC TCC GAC CAG GAA GAG GAC AGA GAG CAA TGT GGT GTT AAA AAT GAT   813

E   S   S   S   S   S   I   I   F   A   E   P   T   P   E   K   E   K   R   F   291
GAA AGT AGC AGC TCA TCC ATT ATC TTT GCT GAG CCC ACC CCA GAA AAA GAA AAA CGC TTT   873

G   E   S   D   T   E   N   Q   N   N   K   S   V   K   Y   T   T   N   L   V   311
GGA GAA TCT GAC ACT GAA AAT CAG AAT AAC AAG TCG GTG AAG TAC ACC ACC AAT TTA GTC   933

I   R   E   S   G   E   L   E   S   T   L   E   L   Q   E   N   G   L   A   G   331
ATA AGA GAA TCT GGT GAA CTT GAG TCG ACC CTG GAG CTC CAG GAA AAT GGC TTG GCT GGT   993

L   S   A   S   S   I   V   E   Q   Q   L   P   L   R   R   N   S   H   L   E   351
TTG TCT GCC AGT TCA ATT GTG GAA CAG CAG CTG CCA CTC AGG CGT AAT TCC CAC CTA GAG  1053

E   S   F   T   S   T   E   E   S   S   E   E   N   V   N   F   L   G   Q   T   371
GAG AGT TTC ACA TCC ACC GAA GAA TCT TCC GAA GAA AAT GTC AAC TTT TTG GGT CAG ACA  1113
```

FIGURE 6A

```
 E   A   Q   Y   H   L   M   L   H   I   Q   M   Q   L   C   E   L   S   L   W    391
GAG GCA CAG TAC CAC CTG ATG CTG CAC ATC CAG ATG CAG CTG TGT GAG CTC TCG CTG TGG   1173

D   W   I   V   E   R   N   K   R   G   R   E   Y   V   D   E   S   A   C   P    411
GAT TGG ATA GTC GAG AGA AAC AAG CGG GGC CGG GAG TAT GTG GAC GAG TCT GCC TGT CCT   1233

Y   V   M   A   N   V   A   T   K   I   F   Q   E   L   V   E   G   V   F   Y    431
TAT GTT ATG GCC AAT GTT GCA ACA AAA ATT TTT CAA GAA TTG GTA GAA GGT GTG TTT TAC   1293

I   H   N   M   G   I   V   H   R   D   L   K   P   R   N   I   F   L   H   G    451
ATA CAT AAC ATG GGA ATT GTG CAC CGA GAT CTG AAG CCA AGA AAT ATT TTT CTT CAT GGC   1353

P   D   Q   Q   V   K   I   G   D   F   G   L   A   C   T   D   I   L   Q   K    471
CCT GAT CAG CAA GTA AAA ATA GGA GAC TTT GGT CTG GCC TGC ACA GAC ATC CTA CAG AAG   1413

N   T   D   W   T   N   R   N   G   K   R   T   P   T   H   T   S   R   V   G    491
AAC ACA GAC TGG ACC AAC AGA AAC GGG AAG AGA ACA CCA ACA CAT ACG TCC AGA GTG GGT   1473

T   C   L   Y   A   S   P   E   Q   L   E   G   S   E   Y   D   A   K   S   D    511
ACT TGT CTG TAC GCT TCA CCC GAA CAG TTG GAA GGA TCT GAG TAT GAT GCC AAG TCA GAT   1533

M   Y   S   L   G   V   V   L   L   E   L   F   Q   P   F   G   T   E   M   E    531
ATG TAC AGC TTG GGT GTG GTC CTG CTA GAG CTC TTT CAG CCG TTT GGA ACA GAA ATG GAG   1593

R   A   E   V   L   T   G   L   R   T   G   Q   L   P   E   S   L   R   K   R    551
CGA GCA GAA GTT CTA ACA GGT TTA AGA ACT GGT CAG TTG CCG GAA TCC CTC CGT AAA AGG   1653

C   P   V   Q   A   K   Y   I   Q   H   L   T   R   R   N   S   S   Q   R   P    571
TGT CCG GTG CAA GCC AAG TAT ATC CAG CAC TTA ACG AGA AGG AAC TCA TCG CAG AGA CCA   1713

S   A   I   Q   L   L   Q   S   E   L   F   Q   N   S   G   N   V   N   L   T    591
TCT GCC ATT CAG CTG CTG CAG AGT GAA CTT TTC CAA AAT TCT GGA AAT GTT AAC CTC ACC   1773

L   Q   M   K   I   I   E   Q   E   K   E   I   A   E   L   K   K   Q   L   N    611
CTA CAG ATG AAG ATA ATA GAG CAA GAA AAA GAA ATT GCA GAA CTA AAG AAG CAG CTA AAC   1833

L   L   S   Q   D   K   G   V   R   D   D   G   K   D   G   G   V   G   *        630
CTC CTT TCT CAA GAC AAA GGG GTG AGG GAT GAC GGA AAG GAT GGG GGC GTG GGA TGA       1890
```

AAGTGGACTTAACTTTTAAGGTAGTTAACTGGAATGTAAATTTTTAATCTTTATTAGGGTATAGTTGGTACAATGCTTC
GTTGTATTTAGTAAGCCTTTACAAGACTTGTTAAAGATGTCAGAGTGCCCCAAGCTGCCGTTCCTTCCCTTCCTGCCCC
ACAAGCTCCTTTTCCTGAATTTCCTACCTAAATATTAACCATATGCCTAGTCTCTGAAACTAAAAACTTGGACCTCATC
CTCAATTATTTTCTCCTTTCAACTCTGTTGACCCTCTGTCTGGTCTTCCTCTAGAAGGTTCTACCGCAGAAATTGATGT
GTGCTCCCTGCCCTCGTCACTGCCCAAGCCCGGGCCTGCACATACTCACTGGACTGTTCCAGTTTTGACAGCTGCCAGT
CTTCCTGCCCCTTTCACACTGCAGCTGAAGTTCATTACCTGAAGGACGCCTCATCATTTCATTCCTTGGCTCCAAACCT
TCTGCTGCCTCTAAGATAAAAGCTCAACTTCTTAACAGTGTACAGTGTGCAACTTCCAACCTTTTTATCTGTTCTCTCC
ACCTTCAGTTTAGCGTCATTCCAAAACCACACCCTTGCAAAGCTTTGTACTCCGCACCCCAGATGATCTCCAGGCAGCT
CAGATCTCTTTCCTGCCTTTGCCCTGCACTGTTCCCCGGTACTTCCTCCTTTATTGTAGCACTCAGCTCCCCAGCCAAT
CTGTACATCCCTCAGAGGCAGCGATCTGATGAATTGGTTTTTGAATCCCAGAAAGGGTCTGCCATGGAGTTGGCAGTCA
TCACGGTAGATGGCGTATGATTTTGCTGAATTTTAAATAAAATGAAAACCATAAAAAAAAAAAAAAAGGGCGGCCGC

FIGURE 6B

Transmembrane Segments Predicted by MEMSAT

| Start | End | Orient | Score |
|---|---|---|---|
| 209 | 225 | out->ins | 0.4 |
| 761 | 778 | ins->out | 1.8 |

FIGURE 7A

Prosite Pattern Matches for 1847.
Prosite Version: Release 12.2 of February 1995
>PS00001-PDOC00001-ASN_GLYCOSYLATION N-glycosylation site.
Query:   73   NMTH   76
Query:  374   NSSA  377
Query:  564   NISM  567
Query:  663   NASN  666
Query:  674   NMTS  677
>PS00004-PDOC00004-CAMP_PHOSPHO_SITE cAMP- and cGMP-dependent protein kinase
Query:  700   KRRS  703                                      phosphorylation site.
>PS00005-PDOC00005-PKC_PHOSPHO_SITE Protein kinase C phosphorylation site.
Query:    7   SKK     9
Query:  264   SSK   266
Query:  293   SRK   295
Query:  320   SPK   322
Query:  381   TGR   383
Query:  442   SLK   444
Query:  514   TDK   516
Query:  544   SKR   546
Query:  590   SDR   592
Query:  593   SIK   595
Query:  619   SPK   621
Query:  648   SKR   650
Query:  698   TQK   700
Query:  722   TPK   724
Query:  725   SVR   727
Query:  821   TKR   823
>PS00006-PDOC00006-CK2_PHOSPHO_SITE Casein kinase II phosphorylation site.
Query:    7   SKKE   10
Query:   31   SIEE   34
Query:  270   SCLE  273
Query:  311   SSVE  314
Query:  464   TCVE  467
Query:  512   SFTD  515
Query:  544   SKRD  547
Query:  556   SDDD  559
Query:  577   SIME  580
Query:  581   SPLE  584
Query:  593   SIKE  596
Query:  597   SSFE  600
Query:  602   SNIE  605
Query:  676   TSLD  679
Query:  810   SAVE  813
Query:  817   TIDD  820
Query:  836   SDVD  839
Query:  861   SYFE  864
>PS00008-PDOC00008-MYRISTYL N-myristoylation site.
Query:   12   GGGAAT  17
Query:   52   GQKGGK  57
Query:  209   GQVLSL  214
>PS00009-PDOC00009-AMIDATION Amidation site.
Query:  438   LGKR  441
>PS00108-PDOC00100-PROTEIN_KINASE_ST Serine/Threonine protein kinases
Query:  152   IIHRDLKPDNMLI   164                          active-site signature.

FIGURE 7B

Transmembrane Segments Predicted by MEMSAT

| Start | End | Orient | Score |
|---|---|---|---|
| 188 | 205 | ins->out | 3.9 |
| 1172 | 1189 | out->ins | 0.1 |

FIGURE 8A

Prosite Pattern Matches for 3695.
Prosite Version: Release 12.2 of February 1995

FIGURE 8B

>PS00001-PDOC00001-ASN_GLYCOSYLATION N-glycosylation site.
Query:   316   NISV   319
Query:   501   NRSK   504
Query:   586   NMSS   589
Query:   726   NCSS   729
Query:  1173   NSSC  1176
>PS00002-PDOC00002-GLYCOSAMINOGLYCAN Glycosaminoglycan attachment site.
        RU   Additional Rules:
        RU   There must be at least two acidic amino acids (Glu or Asp) from -2 to
        RU   -4 relative to the serine.
Query:   771   SGRG   774
>PS00004-PDOC00004-CAMP_PHOSPHO_SITE cAMP- and cGMP-dependent protein kinase phosphorylation site.
Query:    23   KRAT    26
Query:   246   KRLS   249
Query:   360   RRHT   363
Query:   442   RRAS   445
Query:   504   KRHT   507
Query:   565   RRFS   568
>PS00005-PDOC00005-PKC_PHOSPHO_SITE Protein kinase C phosphorylation site.
Query:    76   TER     78
Query:   219   SGK    221
Query:   358   SMR    360
Query:   503   SKR    505
Query:   547   TYK    549
Query:   558   TER    560
Query:   589   SIK    591
Query:   771   SGR    773
Query:   856   SPR    858
Query:   922   TER    924
Query:  1126   SAR   1128
Query:  1188   SYK   1190
>PS00006-PDOC00006-CK2_PHOSPHO_SITE Casein kinase II phosphorylation site.
Query:    42   TQLD    45
Query:    88   SGGE    91
Query:   230   TECE   233
Query:   479   TPVD   482
Query:   486   SDGE   489
Query:   547   TYKD   550
Query:   837   TPPD   840
Query:   920   SMTE   923
Query:   976   SMEE   979
Query:  1084   SVHE  1087
>PS00008-PDOC00008-MYRISTYL N-myristoylation site.
Query:   312   GTAMNI  317
Query:   585   GNNSSI  590
Query:   703   GAASSS  708
Query:   765   GTAAGS  770
Query:   918   GQSMTE  923
Query:   985   GAKDGF  990
Query:  1154   GASLGG 1159
>PS00009-PDOC00009-AMIDATION Amidation site.
Query:   440   LGRR   443
>PS00108-PDOC00100-PROTEIN_KINASE_ST Serine/Threonine protein kinases active-site signature.
Query:   126   IVHRDLKAENLLL   138

Transmembrane Segments Predicted by MEMSAT

| Start | End | Orient | Score |
|---|---|---|---|
| 244 | 261 | out->in | 1.9 |

---

Prosite Pattern Matches for 13302
Prosite version: Release 12.2 of February 1995

>PS00005|PDOC00005|PKC_PHOSPHO_SITE Protein kinase C phosphorylation site.
Query: 14 SRK 16
Query: 27 TER 29
Query: 95 TCK 97
Query: 232 SSR 234
Query: 238 SGK 240

>PS00006|PDOC00006|CK2_PHOSPHO_SITE Casein kinase II phosphorylation site.
Query: 54 TAPD 57
Query: 90 TGTE 93
Query: 140 THGD 143
Query: 210 TGPD 213
Query: 215 SLWD 218

>PS00008|PDOC00008|MYRISTYL N-myristoylation site.
Query: 91 GTEYTC 96
Query: 341 GLDEAR 346

FIGURE 9

Transmembrane Segments Predicted by MEMSAT

| Start | End | Orient | Score |
|---|---|---|---|
| 89 | 111 | out->ins | 2.5 |
| 277 | 293 | ins->out | 0.7 |
| 436 | 454 | out->ins | 1.0 |

Transmembrane segments for presumed mature peptide

| Start | End | Orient | Score |
|---|---|---|---|
| 61 | 83 | out->ins | 2.5 |
| 249 | 265 | ins->out | 0.7 |
| 408 | 426 | out->ins | 1.0 |

FIGURE 10A

Prosite Pattern Matches for 2208
Prosite version: Release 12.2 of February 1995

>PS00001|PDOC00001|ASN_GLYCOSYLATION N-glycosylation site.
Query: 223 NISA 226

>PS00004|PDOC00004|CAMP_PHOSPHO_SITE cAMP- and cGMP-dependent protein kinase phosphorylation site.
Query: 496 KRPS 499

>PS00005|PDOC00005|PKC_PHOSPHO_SITE Protein kinase C phosphorylation site.
Query: 22 TGK 24
Query: 118 SRR 120
Query: 133 TQK 135
Query: 145 TRR 147
Query: 257 TYR 259
Query: 261 SKR 263
Query: 324 TLR 326
Query: 335 SPR 337
Query: 420 TAR 422
Query: 495 SKR 497
Query: 499 SAR 501
Query: 545 TEK 547
Query: 576 SWR 578

>PS00006|PDOC00006|CK2_PHOSPHO_SITE Casein kinase II phosphorylation site.
Query: 228 SSSE 231
Query: 432 SKAD 435
Query: 465 SYQE 468

>PS00007|PDOC00007|TYR_PHOSPHO_SITE Tyrosine kinase phosphorylation site.
Query: 458 KAHLESRSY 466

>PS00008|PDOC00008|MYRISTYL N-myristoylation site.
Query:  10 GLQLGR  15
Query:  39 GCVRGE  44
Query: 105 GLGLGL 110
Query: 159 GQSIGK 164
Query: 165 GCSAAV 170
Query: 189 GLLPGR 194
Query: 307 GLGHGR 312
Query: 386 GCCLAD 391
Query: 408 GGNGCL 413
Query: 455 GQGKAH 460

>PS00108|PDOC00100|PROTEIN_KINASE_ST Serine/Threonine protein kinases active-site signature.
Query: 358 IAHRDLKSDNILV 370

FIGURE 10B

Prosite Pattern Matches for 2193

Prosite version: Release 12.2 of February 1995

>PS00001|PDOC00001|ASN_GLYCOSYLATION N-glycosylation site.

Query: 338 NKSR 341

>PS00004|PDOC00004|CAMP_PHOSPHO_SITE cAMP-
and cGMP-dependent protein kinase phosphorylation site.

Query: 45 KRDT 48

>PS00005|PDOC00005|PKC_PHOSPHO_SITE Protein kinase C phosphorylation site.

Query: 9 TAR 11

Query: 48 TKK 50

Query: 125 TVR 127

Query: 295 SEK 297

>PS00006|PDOC00006|CK2_PHOSPHO_SITE Casein kinase II phosphorylation site.

Query: 92 SFQD 95

Query: 276 SLQD 279

Query: 348 SQSE 351

>PS00007|PDOC00007|TYR_PHOSPHO_SITE tyrosine kinase phosphorylation site.

Query: 45 KRDTEKMY 52

>PS00008|PDOC00008|MYRISTYL N-myristoylation site.

Query: 2 GSSMSA 7

Query: 202 GTGYSF 207

>PS00107|PDOC00100|PROTEIN_KINASE_ATP Protein kinases ATP-binding region signature.

Query: 32 IGKGSFGKV 40

>PS00108|PDOC00100|PROTEIN_KINASE_ST Serine/Threonine protein kinases active-site signature.

Query: 145 IIHRDVKPDNILL 157

FIGURE 11

Transmembrane Segments Predicted by MEMSAT

| Start | End | Orient | Score |
|---|---|---|---|
| 57 | 73 | out->in | 0.6 |

FIGURE 12A

Prosite Pattern Matches for 2249
Prosite version: Release 12.2 of February 1995
>PS00001|PDOC00001|ASN_GLYCOSYLATION N-glycosylation site.
Query: 301 NKSV 304
Query: 566 NSSQ 569
Query: 589 NLTL 592
>PS00004|PDOC00004|CAMP_PHOSPHO_SITE cAMP-and cGMP-dependent protein kinase phosphorylation site.
Query: 345 KRNS 348
Query: 564 KRNS 567
>PS00005|PDOC00005|PKC_PHOSPHO_SITE Protein kinase C phosphorylation site.
Query: 115 SLR 117
Query: 130 SAK 132
Query: 160 TSR 162
Query: 303 SVK 305
Query: 476 TNR 478
Query: 487 TSR 489
Query: 547 SLR 549
Query: 563 TRR 565
Query: 568 SQR 570

>PS00006|PDOC00006|CK2_PHOSPHO_SITE Casein kinase II phosphorylation site.
Query: 71 SLLE 74
Query: 108 TCSD 111
Query: 130 SAKE 133
Query: 257 SDQE 260
Query: 294 SDTE 297
Query: 320 STLE 323
Query: 336 SIVE 339
Query: 348 SHLE 351
Query: 355 TSTE 358
Query: 360 SSEE 363
Query: 389 SLWD 392
Query: 504 SEYD 507
Query: 528 TEME 531

>PS00007|PDOC00007|TYR_PHOSPHO_SITE tyrosine kinase phosphorylation site.
Query: 185 RNKLDGQYY 193
>PS00008|PDOC00008|MYRISTYL N-myristoylation site.
Query: 3 GGNSGV 8
Query: 102 GLLSSF 107
Query: 190 GQYYAI 195
Query: 202 GATKTV 207
Query: 331 GLSASS 336
Query: 369 GQTEAQ 374
Query: 462 GLACTD 467
Query: 538 GLRTGQ 543

>PS00009|PDOC00009|AMIDATION Amidation site.
Query: 479 NGKR 482
>PS00107|PDOC00100|PROTEIN_KINASE_ATP Protein kinases ATP-binding region signature.
Query: 173 LGKGGYGRV 181
>PS00108|PDOC00100|PROTEIN_KINASE_ST Serine/Threonine protein kinases active-site signature.
Query: 437 IVHRDLKPRNIFL 449

FIGURE 12B

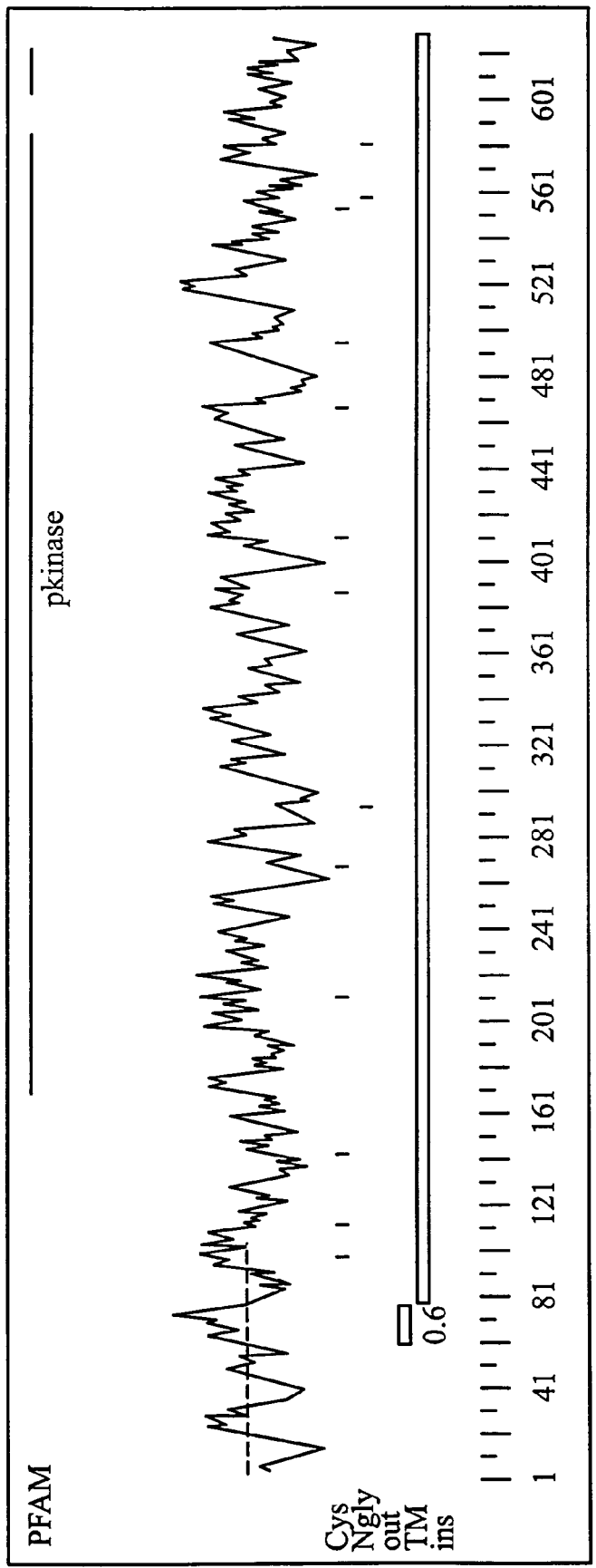

>2249
MQGGNSGVRKREEEGDGAGAVAAPPAIDFPAEGPDPEYDESDVPAEIQVLKEPLQQPTFP
FAVANQLLLVSLLEHLSHVHEPNPLRSRQVFKLLCQTFIKMGLLSSFTCSDEFSSLRLHH
NRAITHLMRSAKERVRQDPCEDISRIQKIRSREVALEAQTSRYLNEFEELAILGKGGYGR
VYKVRNKLDGQYYAIKKILIKGATKTVCMKVLREVKVLAGLQHPNIVGYHTAWIEHVHVI
QPRDRAAIELPSLEVLSDQEEDREQCGVKNDESSSSIIFAEPTPEKEKRFGESDTENQN
NKSVKYTTNLVIRESGELESTLELQENGLAGLSASSIVEQQLPLRRNSHLEESFTSTEES
SEENVNFLGQTEAQYHLMLHIQMQLCELSLWDWIVERNKRGREYVDESACPYVMANVATK
IFQELVEGVFYIHNMGIVHRDLKPRNIFLHGPDQQVKIGDFGLACTDILQKNTDWTNRNG
KRTPTHTSRVGTCLYASPEQLEGSEYDAKSDMYSLGVVLLELFQPFGTEMERAEVLTGLR
TGQLPESLRKRCPVQAKYIQHLTRRNSSQRPSAIQLLQSELFQNSGNVNLTLQMKIIEQE
KEIAELKKQLNLLSQDKGVRDDGKDGGVG

FIGURE 24

| Mapping | STS | Chr | Location |
|---|---|---|---|
| | SHGC-10502 | 1 | between D1S2732 and D1S2864 (50.4 - 52 cM) |
| | SHGC-2365 | 1 | between D1S2732 and D1S2864 (50.4 - 52 cM) |
| | TIGR-A001Z12 | 1 | between D1S483 and D1S482 (49.6 - 54 cM) |
| | WI-15835 | 1 | between D1S483 and D1S2864 (49.6 - 52 cM) |
| | stSG3718 | 1 | between D1S483 and D1S2864 (49.6 - 52 cM) |

FIGURE 28

| Mapping | STS | Chr | Location |
|---|---|---|---|
| | SGC30897 | 7 | between D7S517 and D7S481 (7.8 - 10 cM) |
| | SHGC-11260 | 7 | between D7S2563 and D7S481 (1.7 - 10 cM) |
| | stSG3095 | 7 | between D7S517 and D7S481 (7.8 - 10 cM) |

FIGURE 29

PSORT Prediction of Protein Localization

MITDISC: discrimination of mitochondrial targeting seq

R content:          0       Hyd Moment (75):   8.63
    Hyd Moment (95):   1.01    G content:        1
    D/E content:      2       S/T content:      2
    Score:       -7.17

Gavel: prediction of cleavage sites for mitochondrial preseq cleavage site motif not found NUCDISC: discrimination of nuclear localization signals pat4:  none
    pat7:  PTQKRRS (4) at 697
    bipartite:  none
    content of basic residues:  10.6%
    NLS Score:  -0.13

Final Results (k = 9/23):

91.3%:  nuclear
    8.7%:  cytoplasmic prediction for 18477 is nuc (k=23)

| Start | End | Feature | Seq |
|-------|-----|---------|-----|
| 522 | 525 | VAC:possible vacuolar targeting motif | KLPI |

FIGURE 30

PSORT Prediction of Protein Localization

MITDISC: discrimination of mitochondrial targeting seq

R content:         3        Hyd Moment (75):    4.75
    Hyd Moment (95):  7.01    G content:        1
    D/E content:      1        S/T content:     3
    Score:   -1.91

Gavel: prediction of cleavage sites for mitochondrial preseq

R-2 motif at 28   KRL|EL

NUCDISC: discrimination of nuclear localization signals pat4:   RKKR (5) at 15
    pat7:   PVQKRAR (3) at 30
    bipartite:  none
    content of basic residues:  12.3%
    NLS Score:   0.10

ER Membrane Retention Signals:

XXRR-like motif in the N-terminus:  RATP none

Final Results (k = 9/23):

39.1%:  mitochondrial
    26.1%:  cytoplasmic
    13.0%:  nuclear
     8.7%:  peroxisomal
     4.3%:  extracellular, including cell wall
     4.3%:  Golgi
     4.3%:  endoplasmic reticulum prediction for 13302 is mit (k=23)

| Start | End | Feature | Seq |
|-------|-----|---------|-----|

FIGURE 31

PSORT Prediction of Protein Localization

MITDISC: discrimination of mitochondrial targeting seq

R content:            7       Hyd Moment (75):   10.75
   Hyd Moment (95):   7.34    G content:         10
   D/E content:       1       S/T content:      1
   Score:   -2.28

Gavel: prediction of cleavage sites for mitochondrial preseq

R-2 motif at 52   VRG|ER

NUCDISC: discrimination of nuclear localization signals pat4:   none
   pat7:   none
   bipartite:   none
   content of basic residues:   11.4%
   NLS Score:   -0.47

ER Membrane Retention Signals:

XXRR-like motif in the N-terminus:   AVRQ none

Final Results (k = 9/23):

52.2%:   mitochondrial
   30.4%:   cytoplasmic
   13.0%:   nuclear
    4.3%:   peroxisomal prediction for 2208 is mit (k=23)

| Start | End | Feature | Seq |
|-------|-----|---------|-----|

FIGURE 32

PSORT Prediction of Protein Localization

MITDISC: discrimination of mitochondrial targeting seq

| | | | |
|---|---|---|---|
| R content: | 2 | Hyd Moment (75): | 1.80 |
| Hyd Moment (95): | 2.79 | G content: | 1 |
| D/E content: | 1 | S/T content: | 4 |
| Score: -3.43 | | | |

Gavel: prediction of cleavage sites for mitochondrial preseq

R-2 motif at 22 RRP|VF

NUCDISC: discrimination of nuclear localization signals pat4: HKKK (3) at 329
pat4: KKKK (5) at 330
pat4: KKKR (5) at 331
pat7: PLHKKKK (5) at 327
bipartite: none
content of basic residues: 11.9%
NLS Score: 0.77

Final Results (k = 9/23):

39.1%: nuclear
30.4%: cytoplasmic
17.4%: mitochondrial
8.7%: vesicles of secretory system
4.3%: vacuolar prediction for 2193 is nuc (k=23)

| Start | End | Feature | Seq |
|---|---|---|---|
| | | | |

FIGURE 33

PSORT Prediction of Protein Localization

MITDISC: discrimination of mitochondrial targeting seq

R content: 2        Hyd Moment (75): 2.10
   Hyd Moment (95): 4.73   G content: 3
   D/E content: 2      S/T content: 1
   Score: -7.06

Gavel: prediction of cleavage sites for mitochondrial preseq

R-2 motif at 19   VRK|RE

NUCDISC: discrimination of nuclear localization signals pat4: none
   pat7: PEKEKRF (4) at 285
   pat7: PESLRKR (3) at 545
   bipartite: none
   content of basic residues: 11.8%
   NLS Score: 0.13

Final Results (k = 9/23):

78.3%: nuclear
   13.0%: cytoplasmic
    8.7%: mitochondrial prediction for 2249 is nuc (k=23)

| Start | End | Feature | Seq |
|---|---|---|---|
| 581 | 618 | coiled coil | FQNSGNVNLT...LNLLSQDKGV |

FIGURE 34

```
Protein Family / Domain Matches, HMMer version 2
Searching for complete domains in PFAM
hmmpfam - search a single seq against HMM database HMMER 2.1.1 (Dec 1998)
Copyright (C) 1992-1998 Washington University School of Medicine
HMMER is freely distributed under the GNU General Public License (GPL).
-------------------------------
HMM file:       /prod/ddm/seqanal/PFAM/pfam4.4/Pfam
Sequence file:  /prod/ddm/wspace/orfanal/oa-script.10785.seq
-------------------------------
   Query: 18477
Scores for sequence family classification (score includes all domains):

Model       Description                                      Score     E-value    N
pkinase     Eukaryotic protein kinase domain                 241.3     1.3e-68    2
pkinase_C   Protein kinase C terminal domain                  11.6       0.027    1
wap         WAP-type (Whey Acidic Protein) four-disulf       -12.6         8.1    1
RIO1        RIO1/ZK632.3/MJ0444 family                      -109.7           2    1

Parsed for domains:
Model       Domain    seq-f   seq-t    hmm-f   hmm-t       score    E-value
pkinase     1/2          35     180 ..      1     140 [.    161.7    1.2e-44
RIO1        1/1          48     208 ..      1     222 []   -109.7          2
wap         1/1         516     551 ..      1      55 []    -12.6        8.1
pkinase     2/2         740     835 ..    149     278 .]     75.5    7.4e-20
pkinase_C   1/1         836     864 ..      1      31 [.     11.6      0.027

Alignments of top-scoring domains:
pkinase: domain 1 of 2, from 35 to 180: score 161.7, E = 1.2e-44
                  *->yelleklGeGsfGkVykakhktgkivAvKilkkesls........lr
                     +  +++++ +G+fGkVy+++   qk++AvK++kk ++ +++ +++ ++
      18477     35 FSIVKPISRGAFGKVYLGQKG-GKLYAVKVVKKADMInknmthqvQA 80

EiqilkrlsHpNIvrllgvfedtddhlylvmEymegGdLfdylrrngpls
                  E   l+   + p+Iv l+++ + + +++ylvmEy+ gGd +++l+   g+++
      18477     81 ERDALALSKSPFIVHLYYSLQ-SANNVYLVMEYLIGGDVKSLLHIYGYFD 129 ekeakkialQilrGleYLHsngivHRDLKpeNILldengtvKiaDFGLAr
                  e+ a+k+++++++ +l+YLH++gi+HRDLKp+N L++++g++K++DFGL++
      18477    130 EEMAVKYISEVALALDYLHRHGIIHRDLKPDNMLISNEGHIKLTDFGLSK 179

1<-*
                  +
      18477    180 V    180 pkinase: domain 2 of 2, from 740 to 835: score 75.5, E = 7.4e-20
                  *->GTpwYmmAPEvilegrgyysskvDvWSlGviLyElltggplfpgadlp
                     GTp+Y  APE+ l+gr ++++vD+W+lGv L+E ltg
      18477    740 GTPDYL-APEL-LLGRAHGPAVDWWALGVCLFEFLTG---------- 774 aftggdevdqliifvlklPfsdelpktridpleelfrikkr....rlplp
                               +Pf d       ++ +++f+ +++++ + ++
      18477    775 ----------------IPPFND-------ETPQQVFQNILKrdipWPEGE 801 sncSeelkdLlkkcLnkDPskRpGsatakeilnhpwf<-*
                  +  +S+++++ ++ +L+ D +kR      +ke++ hp f
      18477    802 EKLSDNAQSAVEILLTIDDTKRA---GMKELKRHPLF    835 pkinase_C: domain 1 of 1, from 836 to 864: score 11.6, E = 0.027
                  *->reIdWdkLEnkeiePPFKPkiksprDtsNFD<-*
                     +++dW+ L +  +  PF+P+ +++Dts F+
      18477    836 SDVDWENLQHQTM--PFIPQPDDETDTSYFE    864
```

FIGURE 35

Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - -
HMM file:        /prod/ddm/seqanal/PFAM/pfam4.4/Pfam
Sequence file:   /tmp/orfanal.14376.aa
- - - - - - - - - - - - - - - - - - - - - - - - - - - -
   Query: 3695

Scores for sequence family classification (score includes all domains):

| Model | Description | Score | E-value | N |
|---|---|---|---|---|
| pkinase | Eukaryotic protein kinase domain | 335.8 | 4.7e-97 | 1 |
| gla | Vitamin K-dependent carboxylation/gamma-carb | 4.7 | 8.7 | 1 |

Parsed for domains:

| Model | Domain | seq-f | seq-t | hmm-f | hmm-t | score | E-value |
|---|---|---|---|---|---|---|---|
| pkinase | 1/1 | 8 | 259 .. | 1 | 278 [] | 335.8 | 4.7e-97 |
| gla | 1/1 | 964 | 1005 .. | 1 | 42 [] | 4.7 | 8.7 |

Alignments of top-scoring domains:
pkinase: domain 1 of 1, from 8 to 259: score 335.8, E = 4.7e-97
```
                 *->yeleklGeGsfGkVykakhk.tgkivAvKilk.....kesls..lr
                    ye+ +++G+G+f++V++a+h+ t+ +vA+Ki+++++ ++e+l++ +r
        3695   8    YEIDRTIGKGNFAVVKRATHLvTKAKVAIKIIDktqldEENLKkiFR    54

EiqilkrlsHpNIvrllqvfedtddhlylvmEymegGdLfdylrrngpls
                    E+qi+k+l+Hp+I+rl+ v+e t++ +ylv+Ey+ gG+ fd+l+++g++
        3695   55   EVQIMKMLCHPHIIRLYQVME-TERMIYLVTEYASGGEIFDHLVAHGRMA  103 ekeakkialQilrGleYLHsngivHRDLKpeNILldengtvKiaDFGLAr
                    ekea++ ++Qi+ ++ ++H ++ivHRDLK+eN+Lld n ++KiaDFG++
        3695   104  EKEARRKFKQIVTAVYFCHCRNIVHRDLKAENLLLDANLNIKIADFGFSN  153 ll...eklttfvGTpwYmmAPEvileg.rgysskvDvWSlGviLyElltg
                    l+++++ l+t +G+p+Y APE+  eg+++++++kvD+WSlGv+Ly l++g
        3695   154  LFtpgQLLKTWCGSPPYA-APEL-FEGkEYDGPKVDIWSLGVVLYVLVCG  201 gplfpgadlpaftggdevdqliifvlklPfsdelpktridpleelfrikk
                                                  lPf++      ++l++l + ++
        3695   202  ------------------------ALPFDG-------STLQNLRARVL  218 r.rlplpsncSeelkdLlkkcLnkDPskRpGsatakeilnhpwf<-*
                    +++++p  S e+ +L++ +L +DP+kR+  ++++i++h+w+
        3695   219  SgKFRIPFFMSTECEHLIRHMLVLDPNKRL---SMEQICKHKWM        259
```

FIGURE 36

Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - -
HMM file:         /prod/ddm/seqanal/PFAM/pfam4.4/Pfam
Sequence file:    /prod/ddm/wspace/orfanal/oa-script.26048.seq
- - - - - - - - - - - - - - - - - - - - - - - - - - - -
    Query:  13302

Scores for sequence family classification (score includes all domains):

| Model | Description | Score | E-value | N |
|---|---|---|---|---|
| pkinase | Eukaryotic protein kinase domain | 101.0 | 6.3e-27 | 2 |

Parsed for domains:

| Model | Domain | seq-f | seq-t | hmm-f | hmm-t | score | E-value |
|---|---|---|---|---|---|---|---|
| pkinase | 1/2 | 141 | 184 .. | 75 | 118 .. | 28.9 | 6.4e-07 |
| pkinase | 2/2 | 223 | 315 .. | 151 | 278 .] | 71.8 | 7.8e-19 |

Alignments of top-scoring domains:
pkinase: domain 1 of 2, from 141 to 184: score 28.9, E = 6.4e-07
```
                  *->gGdLfdylrrngplsekeakkialQilrGleYLHsngivHRDLK<-*
                     +Gd+++++r++ +++e+ea   +++Q++ +l+++H +g v RDLK
        13302    141  HGDMHSLVRSRHRIPEPEAAVLFRQMATALAHCHQHGLVLRDLK    184
```
pkinase: domain 2 of 2, from 223 to 315: score 71.8, E = 7.8e-19
```
                  *->pwYmmAPEvileg..rgysskvDvWSlGviLyElltggplfpgadlp
                     p Y+  PE+ l+++ ++  ++++DvWSlGv L+ +l g
        13302    223  PAYV-GPEI-LSSraSYSGKAADVWSLGVALFTMLAG----------    257 aftggdevdqliifvlklPfsdelpktridppleelfrikkr.rlplpsnc
                            + Pf+d       + 1f  ++r+++ lp +
        13302    258  ---------------HYPFQD-------SEPVLLFGKIRRgAYALPAGL   284

SeelkdLlkkcLnkDPskRpGsatakeilnhpwf<-*
                     S +++ L++++L++ P++R+    ta+ il hpw+
        13302    285  SAPARCLVRCLLRREPAERL---TATGILLHPWL          315
```

FIGURE 37

Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - -
HMM file:         /prod/ddm/seqanal/PFAM/pfam4.4/Pfam
Sequence file:    /prod/ddm/wspace/orfanal/oa-script.25990.seq
- - - - - - - - - - - - - - - - - - - - - - - - -
Query:  2208

Scores for sequence family classification (score includes all domains):

| Model | Description | Score | E-value | N |
|---|---|---|---|---|
| pkinase | Eukaryotic protein kinase domain | 93.4 | 8.2e-25 | 2 |

Parsed for domains:

| Model | Domain | seq-f | seq-t | hmm-f | hmm-t | score | E-value |
|---|---|---|---|---|---|---|---|
| pkinase | 1/2 | 156 | 174 .. | 1 | 19 [. | 6.1 | 1.3 |
| pkinase | 2/2 | 266 | 501 .. | 45 | 270 .. | 87.2 | 4.4e-23 |

Alignments of top-scoring domains:
pkinase: domain 1 of 2, from 156 to 174: score 6.1, E = 1.3
```
                *->yelleklGeGsfGkVykak<-*
                   y +++ +G+G ++ Vy+a+
         2208 156   YLIGQSIGKGCSAAVYEAT    174
``` pkinase: domain 2 of 2, from 266 to 501: score 87.2, E = 4.4e-23
```
                *->krls.HpNIvrllgvfed.....................tdd
                   k+l +HpNI+r+l +f+ + +  ++  + ++   +++ ++++ ++++
         2208 266   KQLApHPNIIRVLRAFTSsvpllpgalvdypdvlpsrlhpeglgHGR 312
                hlylvmEymegGdLfdylrrngplsekeakkialQilrGleYLHsngivH
                 l lvm   ++  L++yl  n+   s++ a ++ 1Q+l+G+++L  +gi H
         2208 313   TLFLVMKNYPC-TLRQYLCVNT-PSPRLAAMMLLQLLEGVDHLVQQGIAH 360

RDLKpeNILlden....gtvKiaDFGLArll..........eklttfvGT
                RDLK++NIL++ ++++   + iaDFG +  ++ + + ++ + +++G
         2208 361   RDLKSDNILVELDpdgcPWLVIADFGCCLADesiglqlpfsSWYVDRGGN 410 pwYmmAPEvileg......rgysskvDvWSlGviLyElltggplfpgadl
                  m APEv   +++++    + sk+D W++G i yE++
         2208 411   GCLM-APEV-STArpgpraVIDYSKADAWAVGAIAYEIFGL--------- 449 paftggdevdqliifvlklPfsdelpktridpleelfrikkr...rlplp
                                   Pf++      ++ ++l +  +++ +++  lp
         2208 450   ----------------VNPFYG-------QGKAHLESRSYQeaqLPALP 475 sncSeelkdLlkkcLnkDPskRpGsatak<-*
                +++++++++L++ +L++  +skRp   +a+
         2208 476   ESVPPDVRQLVRALLQREASKRP---SAR    501
```

FIGURE 38

Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - -
HMM file:         /prod/ddm/seqanal/PFAM/pfam4.4/Pfam
Sequence file:    /prod/ddm/wspace/orfanal/oa-script.6295.seq
- - - - - - - - - - - - - - - - - - - - - - - - - - -
Query:  2193

Scores for sequence family classification (score includes all domains):

| Model | Description | Score | E-value | N |
|---|---|---|---|---|
| pkinase | Eukaryotic protein kinase domain | 240.0 | 3.3e-68 | 1 |

Parsed for domains:

| Model | Domain | seq-f | seq-t | hmm-f | hmm-t | score | E-value |
|---|---|---|---|---|---|---|---|
| pkinase | 1/1 | 26 | 278 .. | 1 | 271 [. | 240.0 | 3.3e-68 |

Alignments of top-scoring domains:
pkinase: domain 1 of 1, from 26 to 278: score 240.0, E = 3.3e-68

```
                *->yelleklGeGsfGkVykakhk.tgkivAvKilkkesls........1
                   +++l+ +G+GsfGkV ++ ++t+k +A+K ++k++ ++++ ++ +
     2193    26   FQILRAIGKGSFGKVCIVQKRdTEKMYAMKYMNKQQCIerdevrnvF  72 rEiqilkrlsHpNIvrllgvfedtddhlylvmEymegGdLfdylrrngpl
                   rE++il+++ H ++v+l+++f+ +++ + +v +++ gGdL+ +l++n ++
     2193    73   RELEILQEIEHVFLVNLWYSFQ-DEEDMFMVVDLLLGGDLRYHLQQNVQF 121 sekeakkialQilrGleYLHsngivHRDLKpeNILldengtvKiaDFGLA
                   se+ ++ ++ +++ +l+YL +++i+HRD+Kp+NILlde+g+ ++DF +A
     2193   122   SEDTVRLYICEMALALDYLRGQHIIHRDVKPDNILLDERGHAHLTDFNIA 171 rll...eklttfvGTpwYmmAPEvi...leg.rgysskvDvWSlGviLyE
                   + ++++e++t + GT +Ym APE+ ++ ++g++gys +vD+WS+Gv+ yE
     2193   172   TIIkdgERATALAGTKPYM-APEIFhsfVNGgTGYSFEVDWWSVGVMAYE 220 lltggplfpgadlpaftggdevdqliifvlklPfsdelpktridpleelf
                   ll g                         P++      i+  +++
     2193   221   LLRG------------------------WRPYD-------IHSSNAVE  237 rikkr....rlplpsncSeelkdLlkkcLnkDPskRpGsatake<-*
                   ++++  ++      +++S+e+  Ll+k+L+++P+ R+   +  +
     2193   238   SLVQLfstvSVQYVPTWSKEMVALLRKLLTVNPEHRL---SSLQ      278
```

FIGURE 39

```
Protein Family / Domain Matches, HMMer version 2
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - -
HMM file:          /prod/ddm/seqanal/PFAM/pfam4.4/Pfam
Sequence file:     /prod/ddm/wspace/orfanal/oa-script.20707.seq
- - - - - - - - - - - - - - - - - - - - - - - - - - - -
    Query: 2249

Scores for sequence family classification (score includes all domains):

Model       Description                              Score     E-value   N
pkinase     Eukaryotic protein kinase domain         186.3     4.9e-52   3
filament    Intermediate filament proteins             3.0         8.7   1

Parsed for domains:
Model       Domain     seq-f   seq-t    hmm-f   hmm-t      score    E-value
pkinase      1/3        167     239 ..      1     66 [.      60.3    1.2e-15
pkinase      2/3        379     523 ..     66    183 ..     121.9    1e-32
pkinase      3/3        564     582 ..    257    278 .]       1.9        19
filament     1/1        600     618 ..     57     75 ..       3.0       8.7

Alignments of top-scoring domains:
pkinase: domain 1 of 3, from 167 to 239: score 60.3, E = 1.2e-15
                   *->yelleklGeGsfGkVykakhk.tgkivAvKilk.kesls......1r
                      +e l +lG+G++G+Vyk+++k +g+ +A+K++  k   +++    + lr
          2249   167  FEELAILGKGGYGRVYKVRNKlDGQYYAIKKILiKGATKtvcmkvLR 213

EiqilkrlsHpNIvrllgvfedtddhl<-*
                      E+++l+ l+HpNIv ++ ++  ++ h+
          2249   214  EVKVLAGLQHPNIVGYHTAWI-EHVHV       239 pkinase: domain 2 of 3, from 379 to 523: score 121.9, E = 1e-32
                   *->lylvmEymegGdLfdylrrng.............plsekeakkialQ
                      l++ m+++e +L+d+++++++++    +++ ++   + a ki+ +
          2249   379  LHIQMQLCEL-SLWDWIVERNkrgreyvdesacpYVMANVATKIFQE  424
                      ilrGleYlHsngivHRDLKpeNILlden.gtvKiaDFGLArll.......
                      +++G+ Y+H++givHRDLKp+NI+l+ ++ +vKi+DFGLA+   +++++
          2249   425  LVEGVFYIHNMGIVHRDLKPRNIFLHGPdQQVKIGDFGLACTDilqkntd 474

.........eklttfvGTpwYmmAPEvilegrgysskvDvWSlGviLyEl
                               ++++++++++++t++vGT  Y  +PE  leg++y+  k+D++SlGv+L El
          2249   475  wtnrngkrtPTHTSRVGTCLYA-SPEQ-LEGSEYDAKSDMYSLGVVLLEL 522 l<-*
                      +
          2249   523  F       523 pkinase: domain 3 of 3, from 564 to 582: score 1.9, E = 19
                   *->nkDPskRpGsatakeilnhpwf<-*
                      +++  s+Rp  +a ++l++  f
          2249   564  RRNSSQRP---SAIQLLQSELF       582
```

FIGURE 40

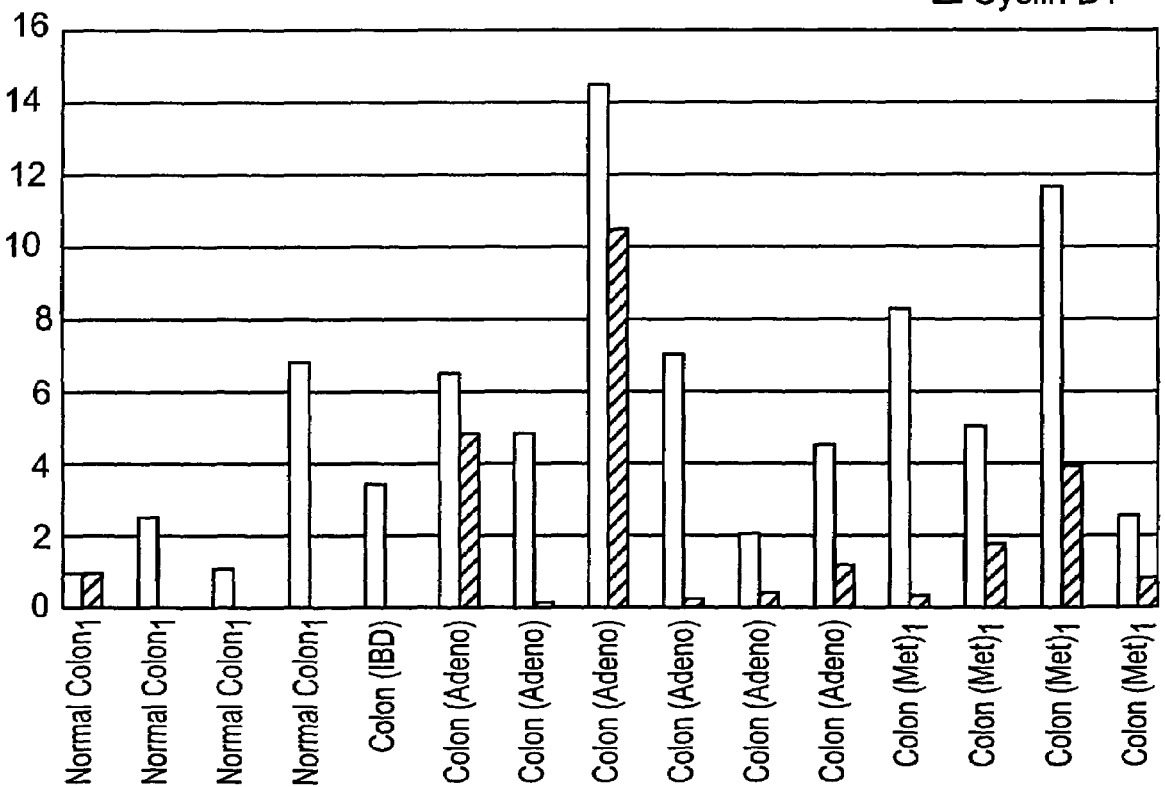
FIGURE 44

HUMAN PROTEIN KINASES AND USES THEREFOR

CROSS REFERENCE TO RELATED APPLICATIONS

This application is a divisional application of U.S. application Ser. No. 09/799,875, filed Mar. 6, 2001, now U.S. Pat. No. 6,638,721, which is a continuation-in-part of U.S. application Ser. No. 09/659,287, filed Sep. 12, 2000, now abandoned, which claims priority to U.S. Provisional Application Ser. No. 60/182,059, filed Feb. 11, 2000, all of which are hereby incorporated herein by referenced in their entirety.

FIELD OF THE INVENTION

The invention relates to novel protein kinase nucleic acid sequences and proteins. Also provided are vectors, host cells, and recombinant methods for making and using the novel molecules.

BACKGROUND OF THE INVENTION

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) *Science* 250:786-791; Birchmeier et al. (1993) *Bioessays* 15:185-189). They serve as growth factor receptors and signal transducers and have been implicated in cellular transformation and malignancy (Hunter et al. (1992) *Cell* 70:375-387; Posada et al. (1992) *Mol. Biol. Cell* 3:583-592; Hunter et al. (1994) *Cell* 79:573-582). For example, protein kinases have been shown to participate in the transmission of signals from growth-factor receptors (Sturgill et al. (1988) *Nature* 344:715-718; Gomez et al. (1991) *Nature* 353:170-173), control of entry of cells into mitosis (Nurse (1990) *Nature* 344:503-508; Maller (1991) *Curr. Opin. Cell Biol.* 3:269-275) and regulation of actin bundling (Husain-Chishti et al. (1988) *Nature* 334:718-721).

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks et al. (1988) *Science* 241:42-52).

Extracellular-signal-regulated kinases/microtubule-associated protein kinases (Erk\MAPKs) and cyclin-directed kinases (Cdks) represent two large families of serine-threonine kinases (see Songyang et al., (1996) *Mol. Cell. Biol.* 16: 6486-6493). Both types of kinases function in cell growth, cell division, and cell differentiation, in response to extracellular stimulae. The Erk\MAPK family members are critical participants in intracellular signaling pathways. Upstream activators as well as the Erk\MAPK components are phosphorylated following contact of cells with growth factors or hormones or after cellular stressors, for example, heat, ultraviolet light, and inflammatory cytokines. These kinases transport messages that have been relayed from the plasma membrane to the cytoplasm by upstream kinases into the nucleus where they phosphorylate transcription factors and effect gene transcription modulation (Karin et al., (1995) *Curr. Biol.* 5: 747-757). Substrates of the Erk\MAPK family include c-fos, c-jun, APF2, and ETS family members Elk 1, Sapla, and c-Ets-1 (cited in Brott et al., (1998) *Proc. Natl Acad. Sci. USA* 95, 963-968).

Cdks regulate transitions between successive stages of the cell cycle. The activity of these molecules is controlled by phosphorylation events and by association with cyclin. Cdk activity is negatively regulated by the association of small inhibitory molecules (Dynlacht, (1997) *Nature* 389:148-152). Cdk targets include various transcriptional activators such as p110Rb, p107 and transcription factors, such as p53, E2F and RNA polymerase II, as well as various cytoskeletal proteins and cytoplasmic signaling proteins (cited in Brott et al., above).

A protein has been isolated in *Drosophilia*, designated nemo, which has homology to Erk\MAPKs and Cdks. A mammalian homologue of nemo, designated NLK, has been reported (Brott et al., above). This protein kinase autophosphorylates and localizes to a great extent in the nucleus. This protein showed homology to both families of kinases (Erk\MAPKs and Cdks). It did not possess the characteristic MAPK phosphorylation motif TXY in the conserved kinase domain VIII. It instead exhibited the sequence TQE resembling the THE sequence found in some Cdks.

More recently, it was shown that NLK could down-regulate HMG-domain-containing proteins related to POP-1. The signaling protein Wnt regulates transcription factors containing high-mobility group (HMG) domains to direct decisions on cell fate during animal development. In *C. elegans*, the HMG-domain-containing repressor POP-1 distinguishes the fate of anterior daughter cells from posterior daughter cells throughout development. Wnt signaling down-regulates POP-1 activity in posterior daughter cells, for example, E. Meneghini et al., (1999) *Nature* 399: 793-797, show that the genes MOM-4 and LIT-1 were also required to down-regulate POP-1 not only in E but in other posterior daughter cells. MOM-4 and LIT-1 are homologous to the mammalian components of the mitogen-activated protein kinase (MAPK) pathway of TAK-1 (transforming growth factor beta activated kinase (and NLK) nemo-like kinase, respectively. MOM-4 and TAK-1 bind related proteins that promote their kinase activity. The authors of the report concluded that a MAPK-related pathway cooperates with Wnt signal transduction to down-regulate POP-1 activity.

In a further report by the same group (Ishitani et al,(1999) *Nature* 399: 798-802), it was shown that the TAK-1-NLK-MAPK-related pathway antagonizes signaling between beta-catenin and transcription factor TCF. The Wnt-signaling pathway regulates developmental processes through a complex of beta-catenin and the T-cell factor/lymphoid enhancer factor (TCF\LEF) family of high-mobility group transcription factors. Wnt stabilizes beta-catenin which then binds to TCF and activates gene transcription. This signal pathway is conserved in vertebrates, *Drosophilia* and *C. elegans*. In *C. elegans*, MOM-4 and LIT-1 regulate Wnt signaling during embryogenesis. MOM-4 is homologous to TAK-1 (a kinase activated by transforming growth factor beta). LIT-1 is homologous to mitogen-activated protein kinase kinase kinase (MAP3K) and MAP kinase (MAPK)-related NEMO-like kinase (NLK) in mammalian cells. This raised the possibility that TAK-1 and NLK were involved in Wnt signaling in mammalian cells. The authors reported that TAK-1 activation stimulates NLK activity and down-regulates transcriptional activation mediated by beta-catenin and TCF. Injection of NLK suppressed the induction of axis duplication by microinjected beta-catenin in *Xenopus* embryos. NLK was shown to phosphorylate TCF\LEF factors and inhibit the interaction of the beta-catenin-TCF complex with DNA. Accordingly, the TAK-1-NLK-MAPK-like pathway was shown to negatively regulate the Wnt signaling pathway.

Protein kinases play critical roles in cellular growth. Therefore, novel protein kinase polynucleotides and proteins are useful for modulating cellular growth, differentiation and/or development.

SUMMARY OF THE INVENTION

Isolated nucleic acid molecules corresponding to protein kinase nucleic acid sequences are provided. Additionally amino acid sequences corresponding to the polynucleotides are encompassed. In particular, the present invention provides for isolated nucleic acid molecules comprising the nucleotide sequences encoding the amino acid sequences shown in SEQ ID NOS:2, 5, 8, 11, 14 or 17. Further provided are kinase polypeptides having amino acid sequences encoded by the nucleic acid molecules described herein.

The present invention also provides vectors and host cells for recombinant expression of the nucleic acid molecules described herein, as well as methods of making such vectors and host cells and for using them for production of the polypeptides or peptides of the invention by recombinant techniques.

The kinase molecules of the present invention are useful for modulating cellular growth and/or cellular metabolic pathways particularly for regulating one or more proteins involved in growth and metabolism. Accordingly, in one aspect, this invention provides isolated nucleic acid molecules encoding kinase proteins or biologically active portions thereof, as well as nucleic acid fragments suitable as primers or hybridization probes for the detection of kinase-encoding nucleic acids.

Another aspect of this invention features an isolated or recombinant kinase protein and polypeptide. Preferred kinase proteins and polypeptides possess at least one biological activity possessed by the naturally-occurring kinase.

Variant nucleic acid molecules and polypeptides substantially homologous to the nucleotide and amino acid sequences set forth in the sequence listing are encompassed by the present invention. Additionally, fragments and substantially homologous fragments of the nucleotide and amino acid sequences are provided.

Antibodies and antibody fragments that selectively bind a kinase polypeptide and fragments are provided. Such antibodies are useful in detecting a kinase polypeptide as well as in modulating cellular growth and metabolism.

In another aspect, the present invention provides a method for detecting the presence of kinase activity or expression in a biological sample by contacting the biological sample with an agent capable of detecting an indicator of kinase activity such that the presence of kinase activity is detected in the biological sample.

In yet another aspect, the invention provides a method for modulating kinase activity comprising contacting a cell with an agent that modulates (inhibits or stimulates) kinase activity or expression such that kinase activity or expression in the cell is modulated. In one embodiment, the agent is an antibody that specifically binds to kinase protein. In another embodiment, the agent modulates expression of kinase protein by modulating transcription of a kinase gene, splicing of a kinase mRNA, or translation of a kinase mRNA. In yet another embodiment, the agent is a nucleic acid molecule having a nucleotide sequence that is antisense to the coding strand of the kinase mRNA or the kinase gene.

In one embodiment, the methods of the present invention are used to treat a subject having a disorder characterized by aberrant kinase protein activity or nucleic acid expression by administering an agent that is a kinase modulator to the subject. In one embodiment, the kinase modulator is a kinase protein. In another embodiment, the kinase modulator is a kinase nucleic acid molecule. In other embodiments, the kinase modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a kinase protein; (2) misregulation of a gene encoding a kinase protein; and (3) aberrant post-translational modification of a kinase protein, wherein a wild-type form of the gene encodes a protein with a kinase activity.

In another aspect, the invention provides a method for identifying a compound that binds to or modulates the activity of a kinase protein. In general, such methods entail measuring a biological activity of a kinase protein in the presence and absence of a test compound and identifying those compounds that alter the activity of the kinase protein.

The invention also features methods for identifying a compound that modulates the expression of the kinase gene by measuring the expression of the kinase sequence in the presence and absence of the compound.

The invention also provides compounds identified by the screening methods described herein.

Other features and advantages of the invention will be apparent from the following detailed description and claims.

BRIEF DESCRIPTION OF THE DRAWINGS

FIGS. 1A, B and C shows the 18477 nucleotide sequence (SEQ ID NO:1) and the deduced amino acid sequence (SEQ ID NO:2). The methionine-initiated open reading frame of human 18477 (without the 5' and 3' untranslated regions) extends from nucleotide position 52 to position 2688 of SEQ ID NO:1, not including the terminal codon (coding sequence shown in SEQ ID NO:3).

FIGS. 2A, B, C, D and E shows the 3695 nucleotide sequence (SEQ ID NO:4) and the deduced amino acid sequence (SEQ ID NO:5). The methionine-initiated open reading frame of human 3695 (without the 5' and 3' untranslated regions) extends from nucleotide position 115 to position 3723 of SEQ ID NO:4, not including the terminal codon (coding sequence shown in SEQ ID NO:6).

FIGS. 3A and B shows the 13302 nucleotide sequence (SEQ ID NO:7) and the deduced amino acid sequence (SEQ ID NO:8). The methionine-initiated open reading frame of human 13302 (without the 5' and 3' untranslated regions) extends from nucleotide position 383 to position 1456 of SEQ ID NO:7, not including the terminal codon (coding sequence shown in SEQ ID NO:9).

FIGS. 4A and B shows the 2208 nucleotide sequence (SEQ ID NO:10) and the deduced amino acid sequence (SEQ ID NO:11). The methionine-initiated open reading frame of human 2208 (without the 5' and 3' untranslated regions) extends from nucleotide position 76 to position 1818 of SEQ ID NO:10, not including the terminal codon (coding sequence shown in SEQ ID NO:12).

FIGS. 5A and B shows the 2193 nucleotide sequence (SEQ ID NO:13) and the deduced amino acid sequence (SEQ ID NO:14). The methionine-initiated open reading frame of human 2193 (without the 5' and 3' untranslated regions) extends from nucleotide position 17 to position 1273 of SEQ ID NO:13, not including the terminal codon (coding sequence shown in SEQ ID NO:15).

FIGS. 6A and B shows the 2249 nucleotide sequence (SEQ ID NO:16) and the deduced amino acid sequence (SEQ ID NO:17). The methionine-initiated open reading frame of human 2249 (without the 5' and 3' untranslated regions) extends from nucleotide position 114 to position 2000 of SEQ ID NO:16, not including the terminal codon (coding sequence shown in SEQ ID NO:18).

FIGS. 7A and B shows an analysis of the 18477 open reading frame for amino acids corresponding to specific functional sites and to predicted transmembrane domains of SEQ ID NO:2.

FIGS. 8A and B shows an analysis of the 3695 open reading frame for amino acids corresponding to specific functional sites and to predicted transmembrane domains of SEQ ID NO:5.

FIG. 9 shows an analysis of the 13302 open reading frame for amino acids corresponding to specific functional sites and to predicted transmembrane domains of SEQ ID NO:8.

FIGS. 10A and B shows an analysis of the 2208 open reading frame for amino acids corresponding to specific functional sites and to predicted transmembrane domains of SEQ ID NO:11.

FIG. 11 shows an analysis of the 2193 open reading frame for amino acids corresponding to specific functional sites of SEQ ID NO:14.

FIGS. 12A and B shows an analysis of the 2249 open reading frame for amino acids corresponding to specific functional sites and to predicted transmembrane domains of SEQ ID NO:17.

FIG. 24 depicts a hydropathy plot of human 2249. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:17) of human 2249 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.

FIG. 28 shows chromosome mapping information for the 2208 kinase.

FIG. 29 shows chromosome mapping information for the 2249 kinase in various cell types.

FIG. 30 shows PSORT prediction of protein localization for the 18477 protein kinase. The indicated amino acid positions correspond to positions within SEQ ID NO:2.

FIG. 31 shows PSORT prediction of protein localization for the 13302 protein kinase. The indicated amino acid positions correspond to positions within SEQ ID NO:8.

FIG. 32 shows PSORT prediction of protein localization for the 2208 protein kinase. The indicated amino acid positions correspond to positions within SEQ ID NO:11.

FIG. 33 shows PSORT prediction of protein localization for the 2193 protein kinase. The indicated amino acid positions correspond to positions within SEQ ID NO:14.

FIG. 34 shows PSORT prediction of protein localization for the 2249 protein kinase. The indicated amino acid positions correspond to positions within SEQ ID NO:17.

FIG. 35 depicts an alignment of the protein kinase domain of human 18477 with a consensus amino acid sequence derived from a hidden Markov model. The upper sequence is the consensus amino acid sequences (SEQ ID NOS:21 and 22), while the lower amino acid sequence corresponds to amino acids 35-180 and amino acids 740-835 of SEQ ID NO:2, respectfully.

FIG. 36 depicts an alignment of the protein kinase domain of human 3695 with a consensus amino acid sequence derived from a hidden Markov model. The upper sequence is the consensus amino acid sequence (SEQ ID NO:23), while the lower amino acid sequence corresponds to amino acids 8-259 of SEQ ID NO:5.

FIG. 37 depicts an alignment of the protein kinase domain of human 13302 with a consensus amino acid sequence derived from a hidden Markov model. The upper sequence is the consensus amino acid sequences (SEQ ID NOS:24 and 25), while the lower amino acid sequence corresponds to amino acids 141-184 and amino acids 223-315 of SEQ ID NO:8, respectfully.

FIG. 38 depicts an alignment of the protein kinase domain of human 2208 with a consensus amino acid sequence derived from a hidden Markov model. The upper sequence is the consensus amino acid sequences (SEQ ID NOS:26 and 27), while the lower amino acid sequence corresponds to amino acids 156-174 and amino acids 266-501 of SEQ ID NO:11, respectfully.

FIG. 39 depicts an alignment of the protein kinase domain of human 2193 with a consensus amino acid sequence derived from a hidden Markov model. The upper sequence is the consensus amino acid sequence (SEQ ID NO:28), while the lower amino acid sequence corresponds to amino acids 26-278 of SEQ ID NO:14.

FIG. 40 depicts an alignment of the protein kinase domain of human 2249 with a consensus amino acid sequence derived from a hidden Markov model. The upper sequence is the consensus amino acid sequences (SEQ ID NOS:29, 30, and 31), while the lower amino acid sequence corresponds to amino acids 167-239, 379-523 and amino acids 564-582 of SEQ ID NO:17, respectfully.

FIG. 44 shows 18477 and cyclin B1 expression in colon cell lines.

DETAILED DESCRIPTION OF THE INVENTION

Figure 13:
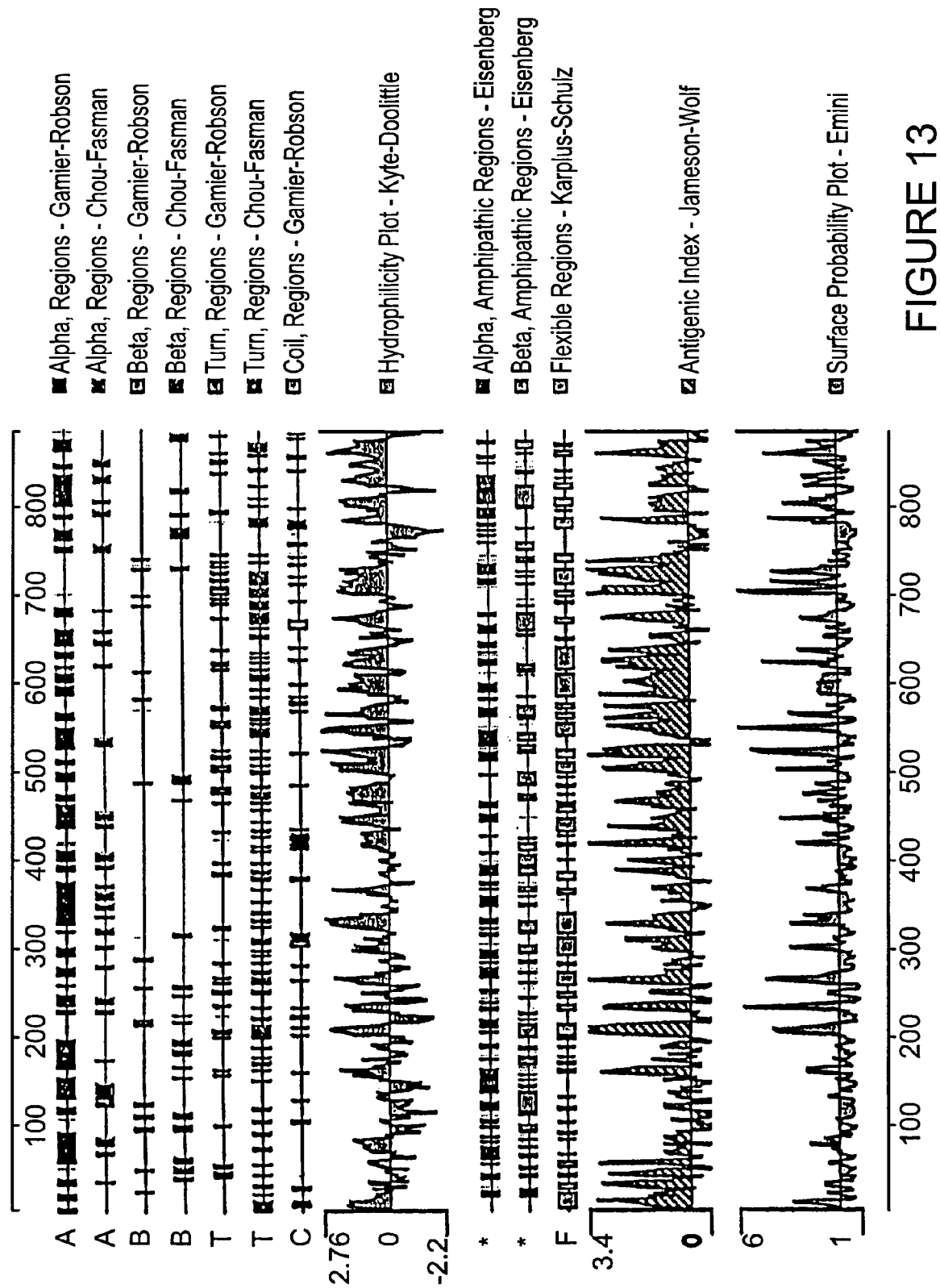
FIG. 13 shows an analysis of the 18477 amino acid sequence: α β turn and coil regions; hydrophilicity; amphipathic regions; flexible regions; antigenic index; and surface probability.
Figure 14:
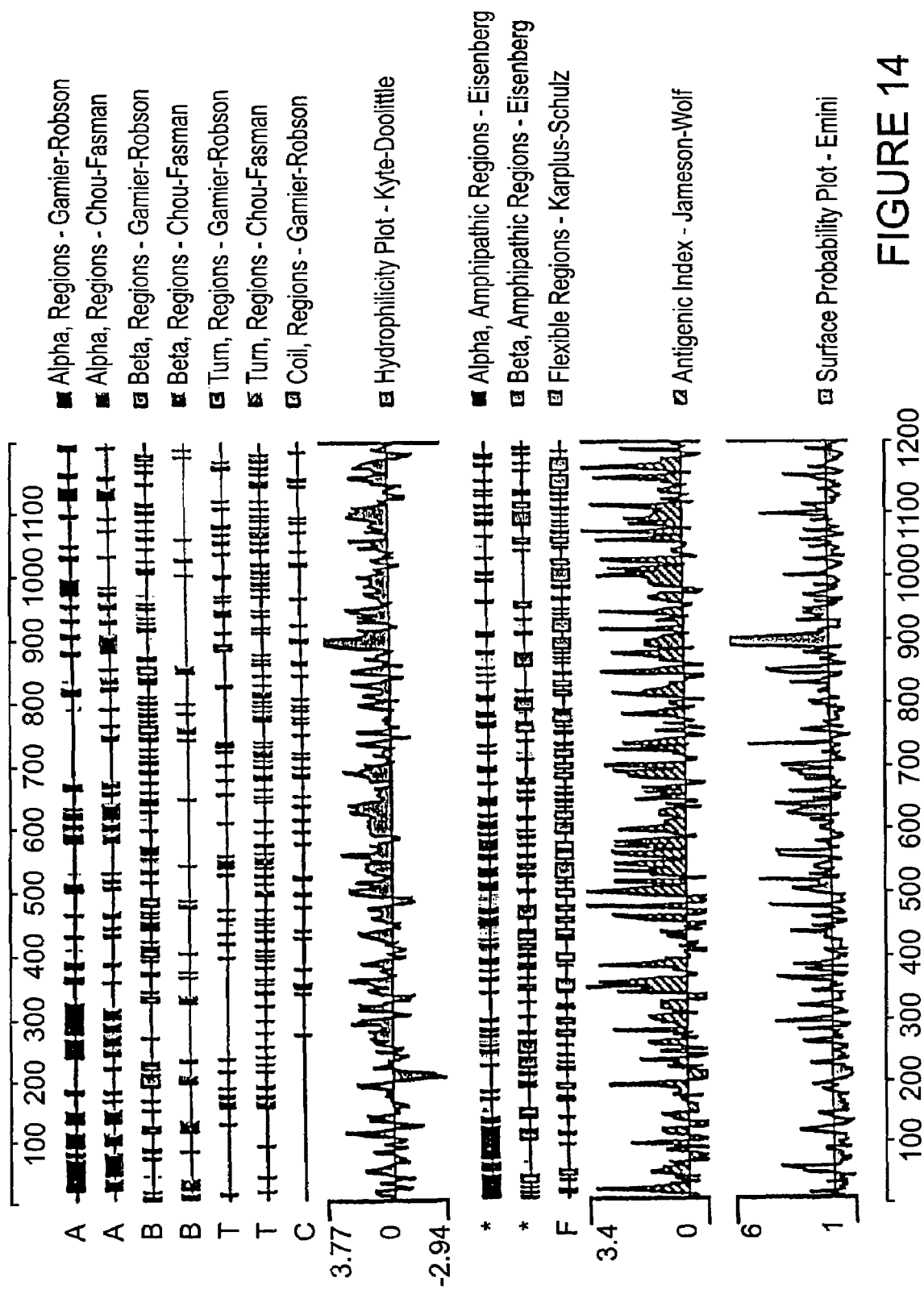
FIG. 14 shows an analysis of the 3695 amino acid sequence: α β turn and coil regions; hydrophilicity; amphipathic regions; flexible regions; antigenic index; and surface probability.
Figure 15:
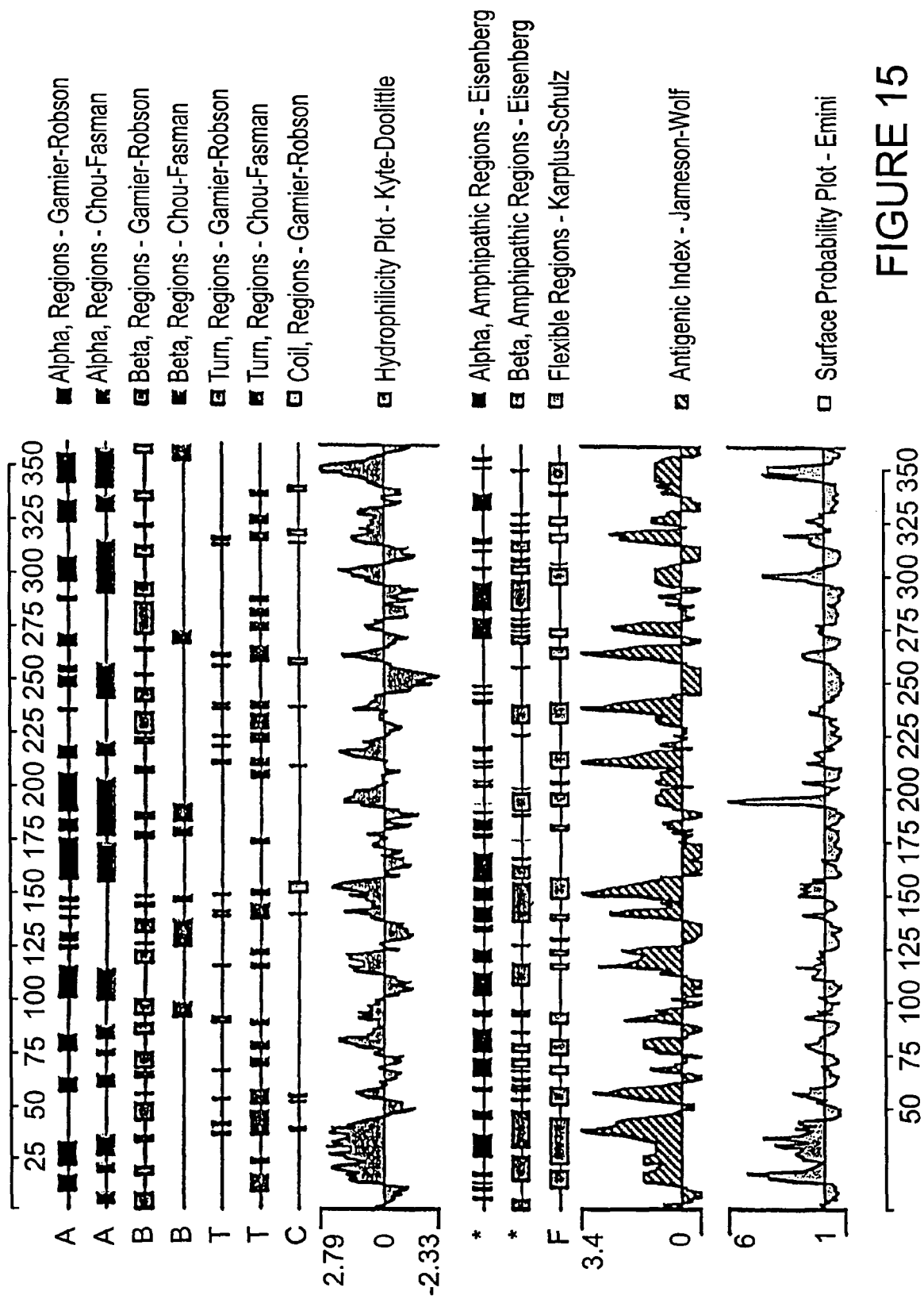
FIG. 15 shows an analysis of the 13302 amino acid sequence: α β turn and coil regions; hydrophilicity; amphipathic regions; flexible regions; antigenic index; and surface probability.
Figure 16:
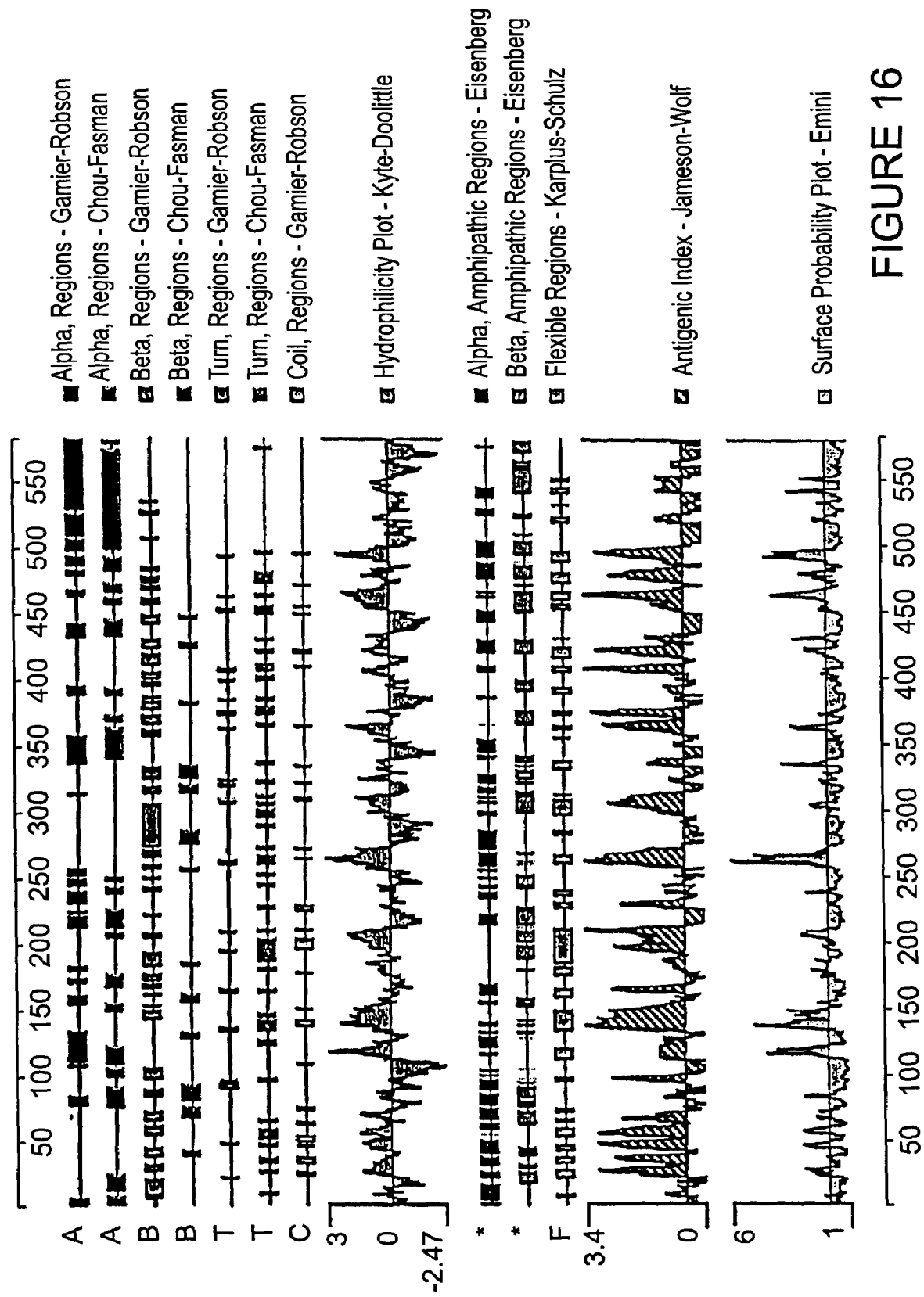
FIG. 16 shows an analysis of the 2208 amino acid sequence: α β turn and coil regions; hydrophilicity; amphipathic regions; flexible regions; antigenic index; and surface probability.
Figure 17:
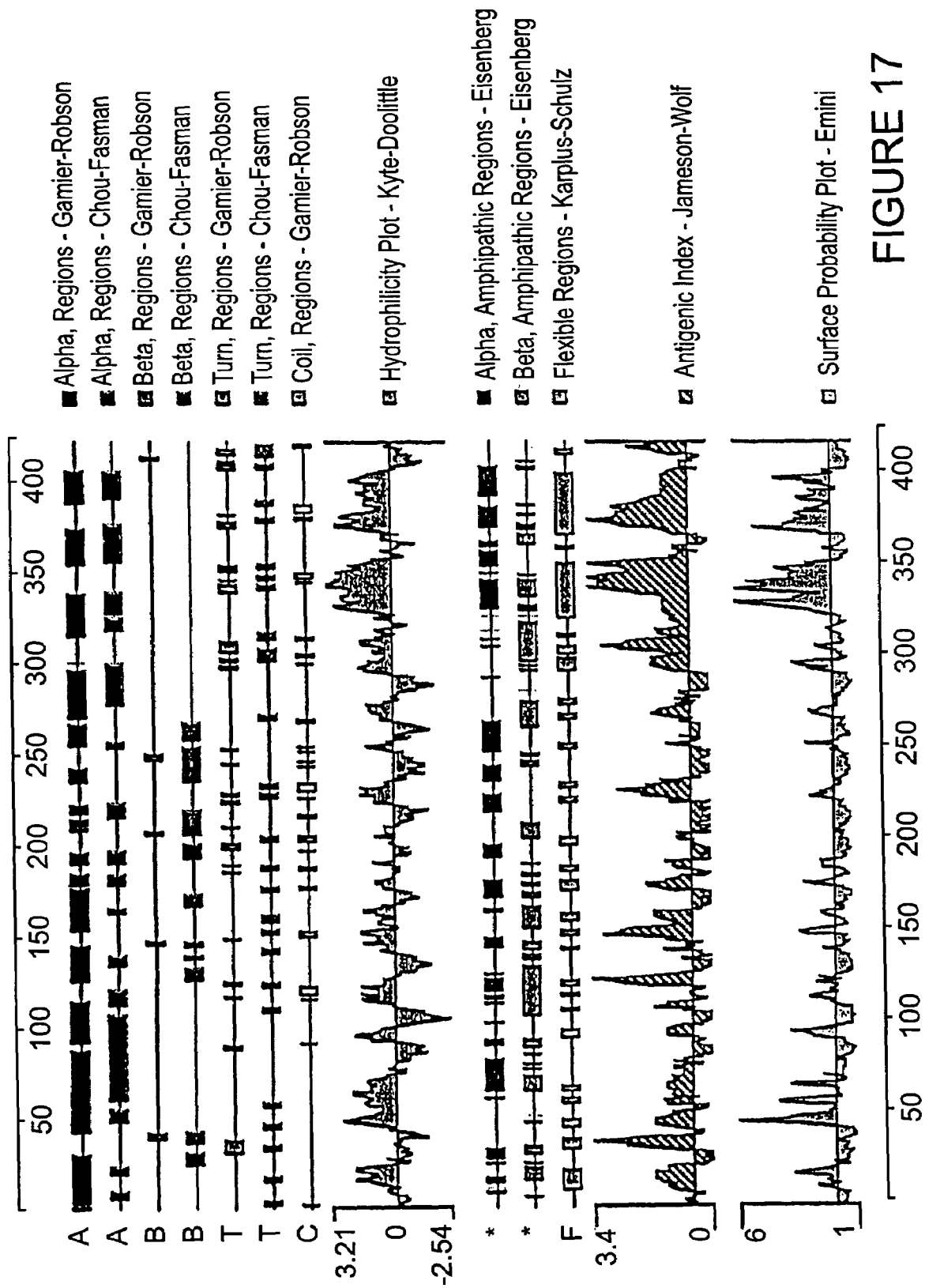
FIG. 17 shows an analysis of the 2193 amino acid sequence: α β turn and coil regions; hydrophilicity; amphipathic regions; flexible regions; antigenic index; and surface probability.
Figure 18:
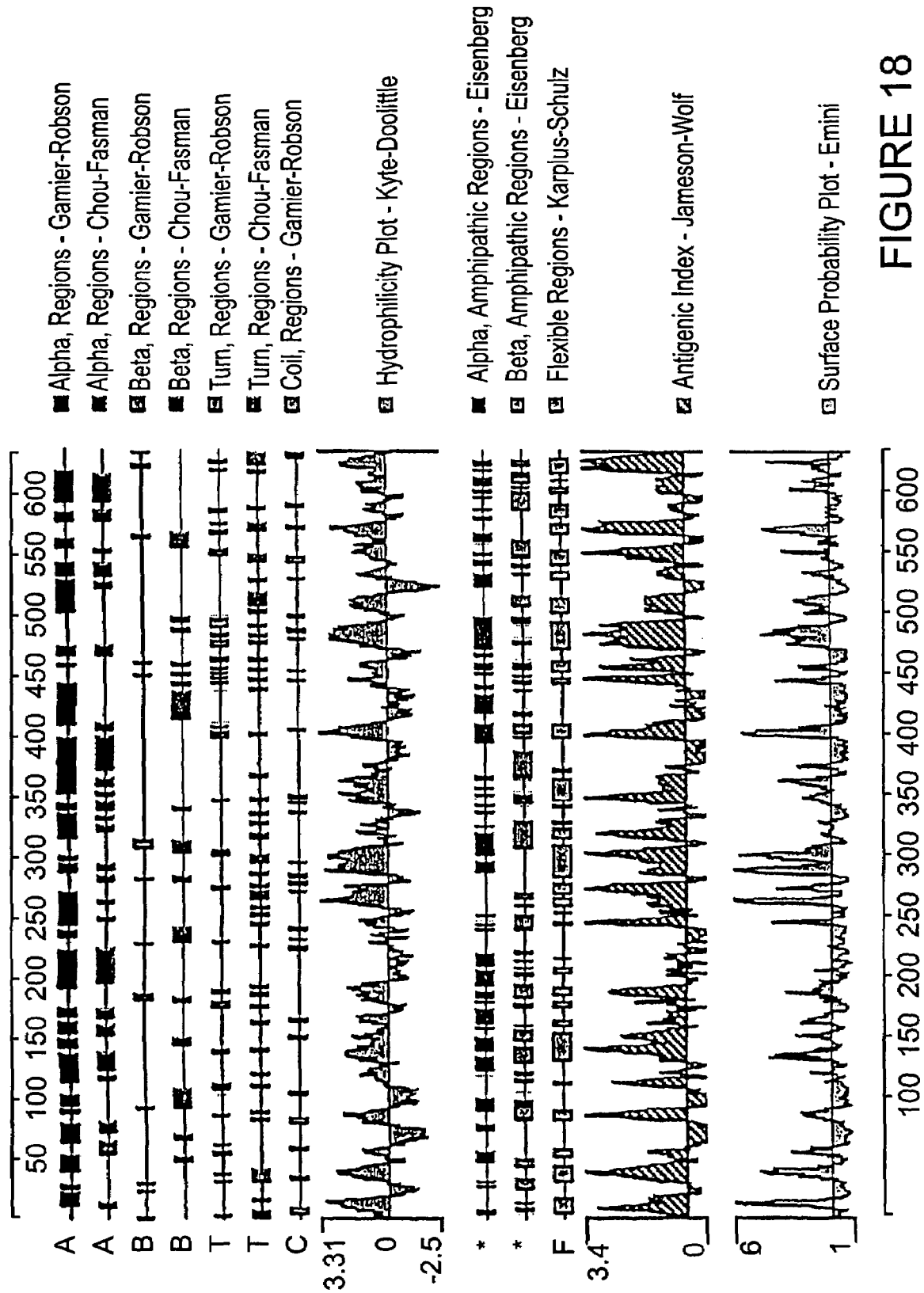
FIG. 18 shows an analysis of the 2249 amino acid sequence: α β turn and coil regions; hydrophilicity; amphipathic regions; flexible regions; antigenic index; and surface probability.
Figure 19:
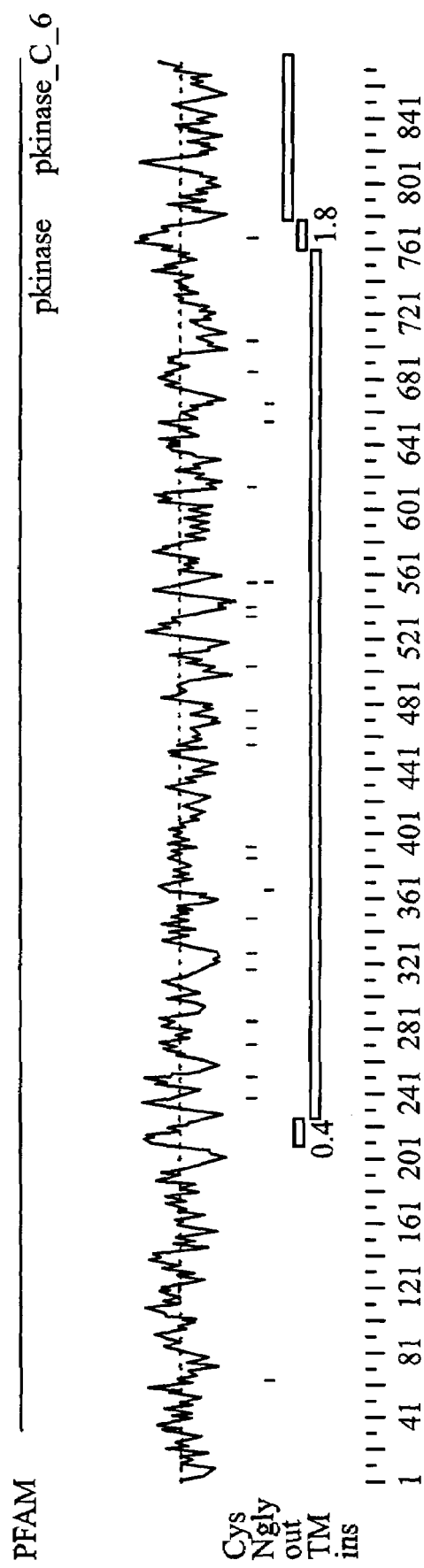
FIG. 19 depicts a hydropathy plot of human 18477. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:2) of human 18477 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 20:
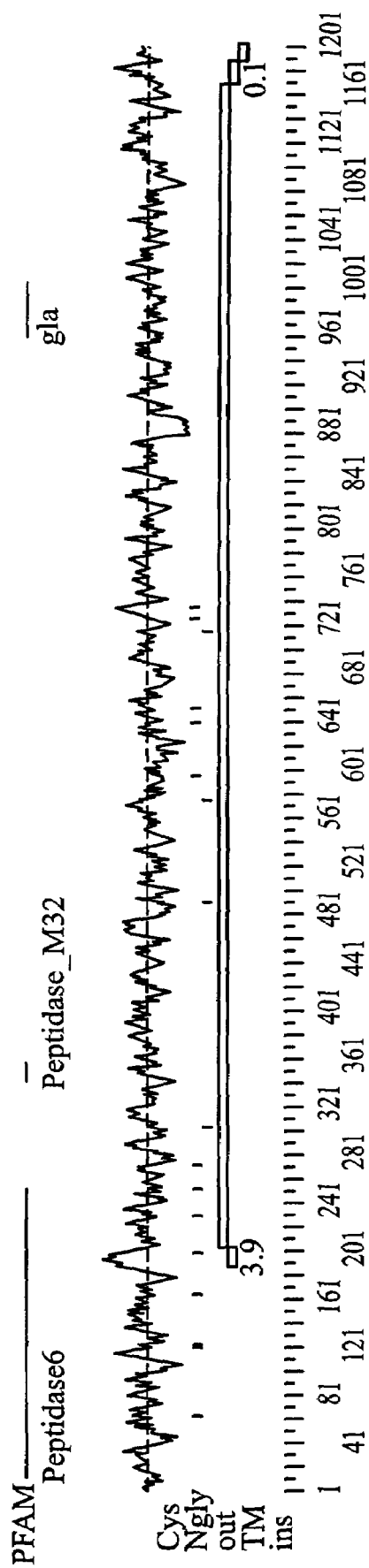
FIG. 20 depicts a hydropathy plot of human 3695. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:5) of human 3695 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 21:
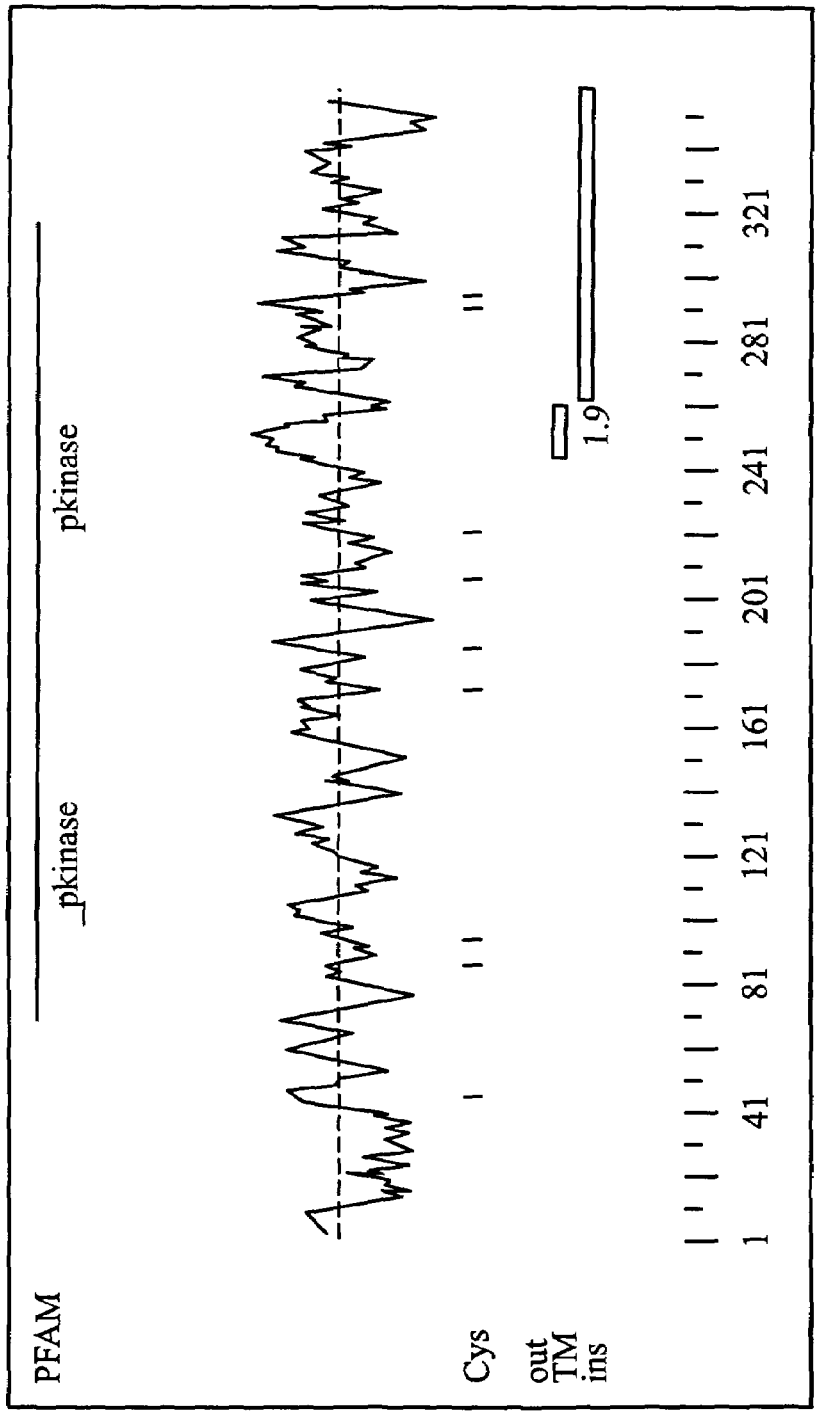
FIG. 21 depicts a hydropathy plot of human 13302. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:8) of human 13302 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 22:
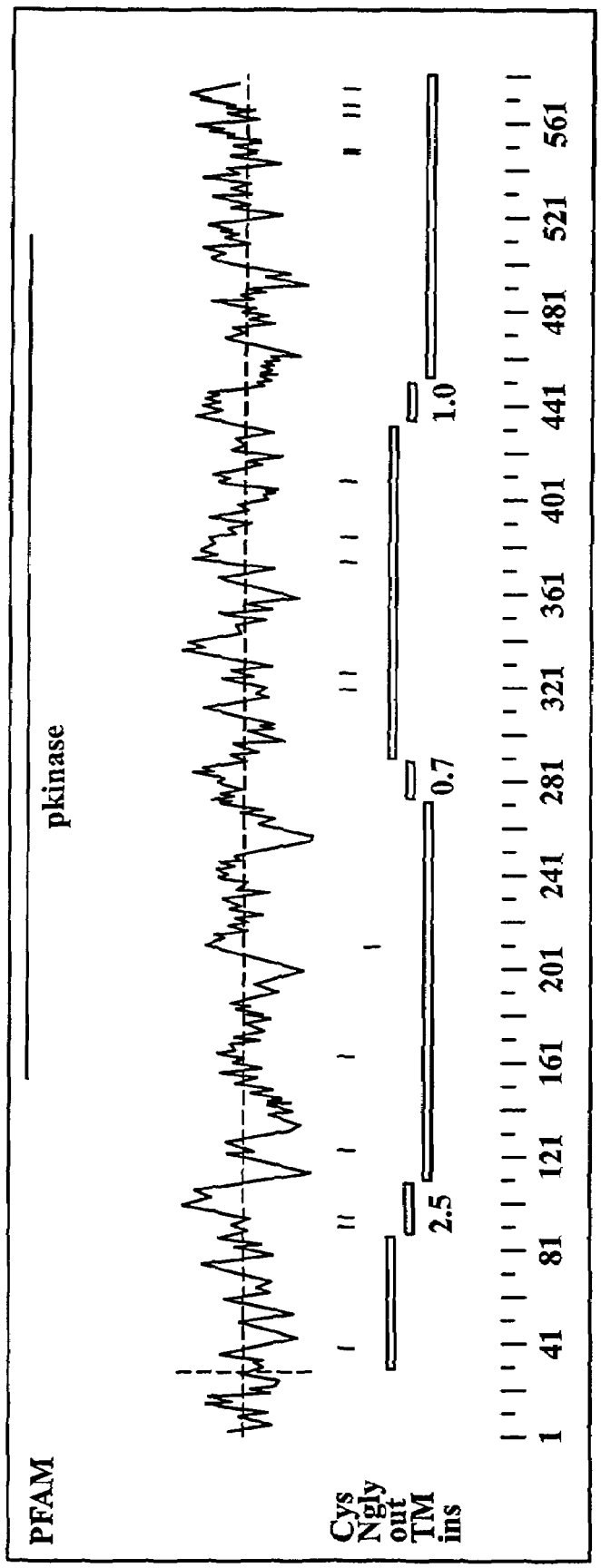
FIG. 22 depicts a hydropathy plot of human 2208. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:11) of human 2208 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 23:
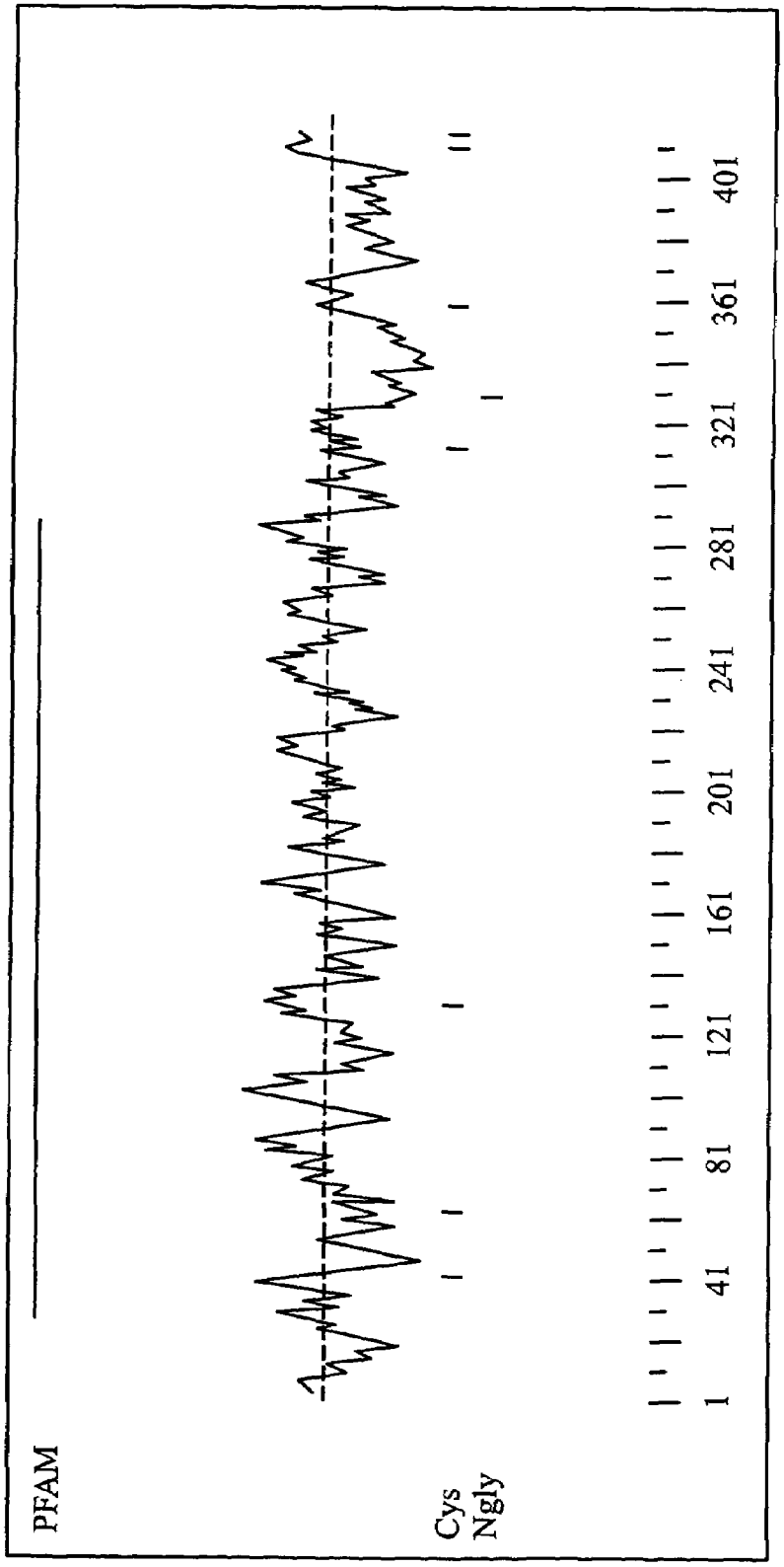
FIG. 23 depicts a hydropathy plot of human 2193. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:14) of human 2193 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.

Eukaryotic Protein Kinase Nucleic Acid and Polypeptide Molecules

The isolated nucleic acid molecules of the present invention encode a eukaryotic protein kinase polypeptide. Eukaryotic protein kinases (described in, for example, Hanks et al. (1995) *FASEB J.* 9:576-596) are enzymes that belong to an extensive family of proteins that share a conserved catalytic core common to both serine/threonine and tyrosine protein kinases. There are a number of conserved regions in the catalytic domain of protein kinases. One of these regions, located in the N-terminal extremity of the catalytic domain, is a glycine-rich stretch of residues in the vicinity of a lysine residue, which has been shown to be involved in ATP binding. Another region, located in the central part of the catalytic domain, contains a conserved aspartic acid residue which is important for the catalytic activity of the enzyme (Knighton et al. (1991) *Science* 253:407-414). Two signature patterns have been described for this region: one specific for serine/threonine kinases and one for tyrosine kinases.

Eukaryotic protein kinase polypeptides can include one of the following consensus sequences (SEQ ID NOS:19, 20, and 32, respectively):

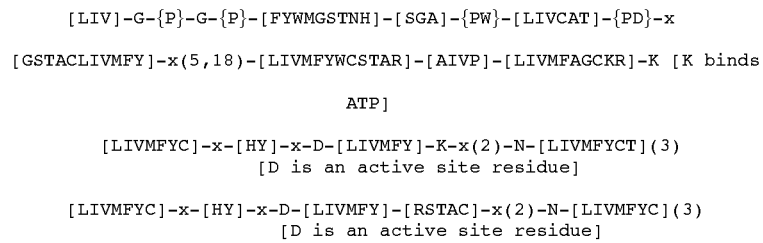

```
[LIV]-G-{P}-G-{P}-[FYWMGSTNH]-[SGA]-{PW}-[LIVCAT]-{PD}-x

[GSTACLIVMFY]-x(5,18)-[LIVMFYWCSTAR]-[AIVP]-[LIVMFAGCKR]-K  [K binds
                                                              ATP]

[LIVMFYC]-x-[HY]-x-D-[LIVMFY]-K-x(2)-N-[LIVMFYCT](3)
                     [D is an active site residue]

[LIVMFYC]-x-[HY]-x-D-[LIVMFY]-[RSTAC]-x(2)-N-[LIVMFYC](3)
                     [D is an active site residue]
```

The present invention is based, at least in part, on the identification of novel protein kinase nucleic acid and polypeptide molecules, which may play a role in, or function in, signaling pathways associated with cellular growth and/or cellular metabolic pathways, and/or a productive viral infection. These growth and metabolic pathways are described in Lodish et al. (1995) *Molecular Cell Biology* (Scientific American Books Inc., New York, N.Y.) and Stryer *Biochemistry*, (W. H. Freeman, New York), the contents of which are incorporated herein by reference.

The present invention identifies novel kinases given the following numerical designations: 18477, 3695, 13302, 2208, 2193, and 2249. A plasmid containing the nucleotide sequence encoding human 18477 was deposited with American Type Culture Collection (ATCC), 10801 University Boulevard, Manassas, Va. 20110-2209, on Apr. 19, 2000 and assigned Accession Number PTA-1775. A plasmid containing the nucleotide sequence encoding human 2193 was deposited with American Type Culture Collection (ATCC), 10801 University Boulevard, Manassas, Va. 20110-2209, on Jul. 7, 2000 and assigned Accession Number PTA-2204. A plasmid containing the nucleotide sequence encoding human 2249 was deposited with American Type Culture Collection (ATCC), 10801 University Boulevard, Manassas, Va. 20110-2209, on May 12, 2000 and assigned Accession Number PTA-1868. These deposits will be maintained under the terms of the Budapest Treaty on the International Recognition of the Deposit of Microorganisms for the Purposes of Patent Procedure. These deposits were made merely as a convenience for those of skill in the art and is not an admission that a deposit is required under 35 U.S.C. §112.

The 18477 protein kinase can modulate phosphorylation in a wide variety of tissues and cells that include, but are not limited to, islets, skin, endothelium, breast, colon, liver, brain, heart, kidney, skeletal muscle, trachea, aorta, adipose tissue, small intestine, testes, placenta, fetal liver, fetal heart, cervix, thymus, tonsil, lymph node and lung clinical tumor samples. Further, the kinase is cell-cycle regulated in WI-38 cells (G2/M). Taqman data has been used to confirm array expression data showing 18477 expression upregulated in S-G2/M phase of synchronized WI-38 cells. The gene has been shown to be similar to CEK1 (*S. pombe*) and tumor-suppressor protein, warts (*D. melanogaster*). CEK1 has been implicated in anaphase progression in fission yeast. Warts is a homolog of human myotonic distrophy kinase and is required for the control of cell shape and proliferation. The gene has been mapped to human chromosome 10 with a syntenic chromosome mo18. GAAT13D02 (5 cR) D10S593 (12.6 cR) are flanking markers. Nearby mutations/loci include human-prostate adenocarcinoma 1; SCIDA, severe combined immunodeficiency, ATHABASCAN type; IDDM10, diabetes mellitus, insulin-dependent, 10; RDPA, REFSUM disease with increased pipecolicacidemia; OB10, obesity, susceptibility to, on chromosome 10; mouse:AX, ataxia, TW, twirler; LAH, lanceolate hair; NIDD2, non-insulin dependent diabetes mellitus 2. Nearby known genes include MGA1, DNMT2, CREM, and CACNB2.

The 3695 protein kinase molecule is expressed in tissues or cells including, but not limited to, adrenal gland, blood, brain, endothelial tissue, fibroblasts, keratinocytes, kidney, liver, muscle, ovary, skin, thymus, thyroid, and osteoblasts. In addition, the gene is also expressed in lymphoma.

The 13302 protein kinase is expressed in tissues or cells including, but not limited to, adrenal gland, breast, colon, D8 dendritic cells, endothelial cells, fibroblasts, heart, keratinocytes, lung, muscle, natural killer cells, nerve cells, prostate, skin and T-cells. In addition, the gene is also expressed in colon to liver metastases and lymphoma. The gene maps to human chromosome 20 with a location between D20S199 and D20S181 (6.2-9 cM).

Figure 25:
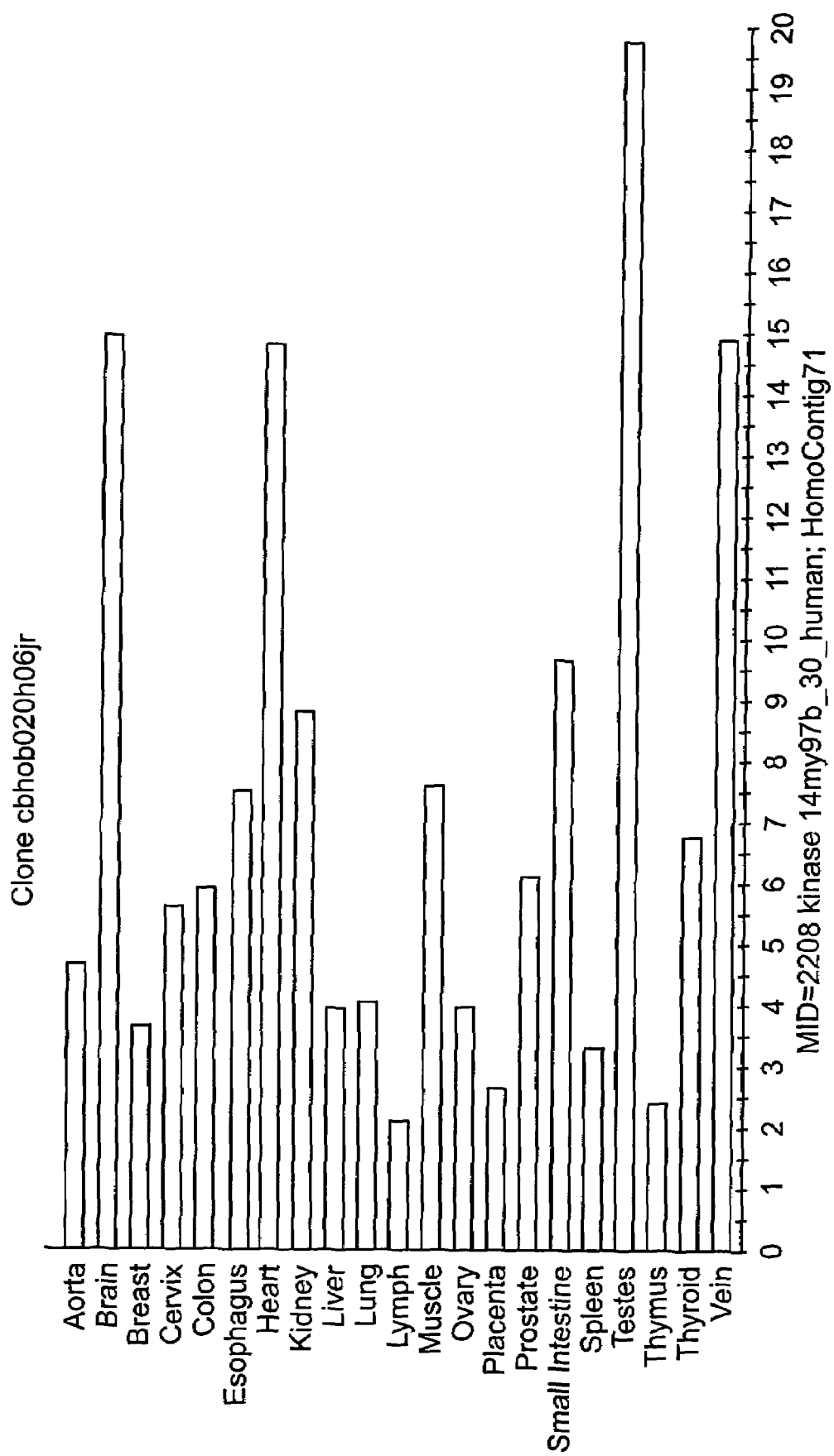
FIG. 25 shows expression of the 2208 protein kinase in various normal human tissues. Tissues in which the expression levels of the 2208 mRNA was determined include, from top to bottom, aorta, brain, breast, cervix, colon, esophagus, heart, kidney, liver, lung, lymph, muscle, ovary, placenta, prostate, small intestine, spleen, testes, thymus, thyroid, and vein.

The 2208 protein kinase is expressed in tissues or cells that include, but are not limited to, those human tissues shown in FIG. 25. Expression has also been observed in the following tissues/cells: adrenal gland, astrocyte, B-cell, brain, breast, colon, colon to liver metastases, endothelial, esophagus, heart, hypothalamus, keratinocytes, liver, lymphoma, melanocyte, muscle, nerve, osteoblast, prostate, retina, salivary gland, skin, spinal cord, spleen T-cells, testis, thymus and thyroid. The gene has been mapped in various cell types. The mapping data is shown in FIG. 28.

Figure 26:
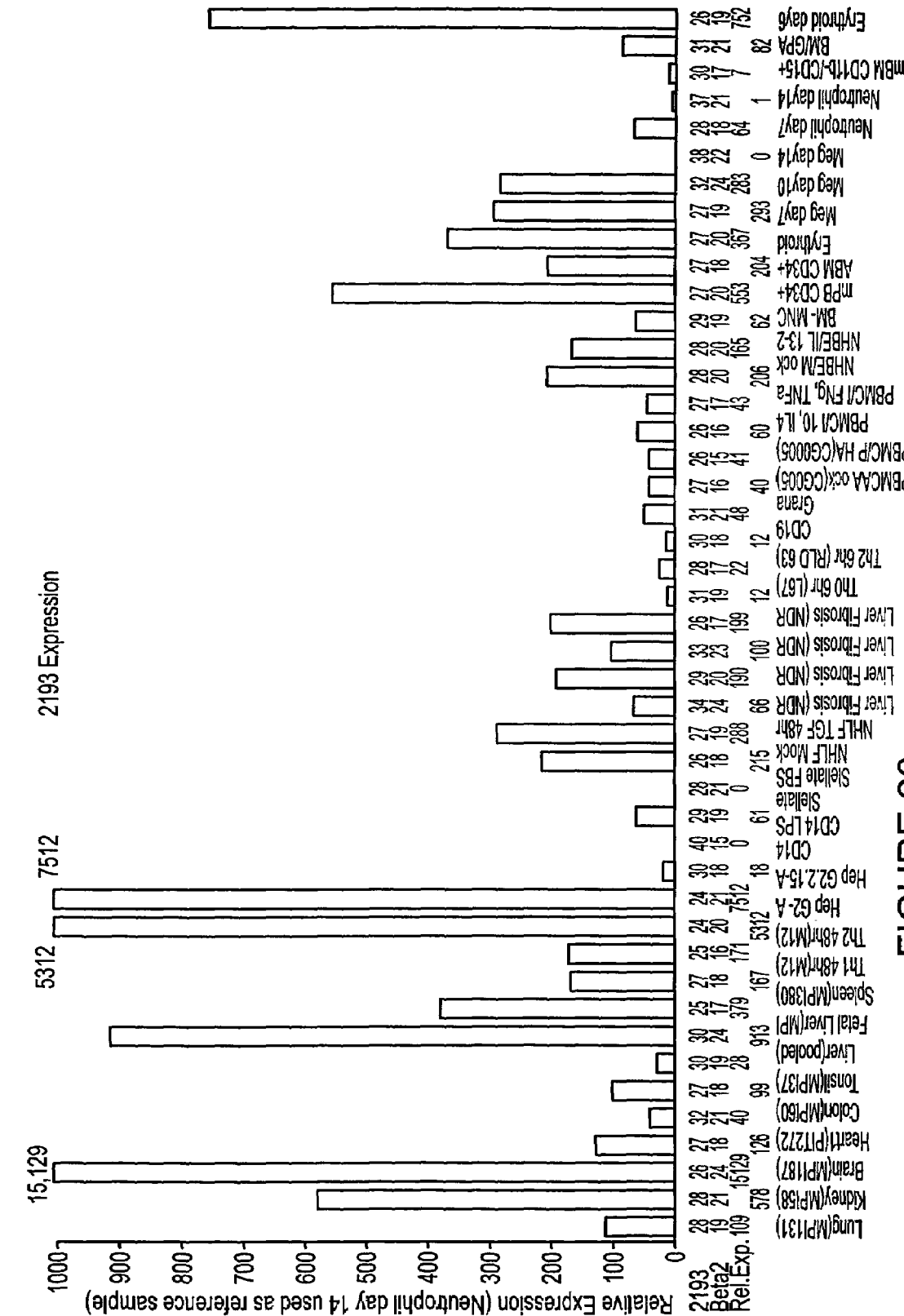
FIG. 26 shows expression of the 2193 protein kinase in various human tissues and cells. The tissues and cell lines analyzed for 2193 expression include, from left to right: lung; kidney; brain; heart; colon; tonsil; liver; fetal liver; spleen; Th1 48 hr.; Th2 48 hr.; Hep G-2-A; Hep G2.2.15-A; CD 14; CD14 LPS; stellate (resting stellate cells, deprived of serum for 72 hours); stellate/FBS (serum reactivated stellate cells); NHLF mock (normal human dermal fibroblasts); NHLF TGF 48 hr.; liver Fibrosis (NDR); (columns 20-23); Th0 6 hr.; Th2 6 hr.; CD19; Grans (normal human granulocytes); PBMC/mock (peripheral blood mononuclear cells); PBMC/PHA; PBMC/IL10, IL4; PBMC/IL FNg, TNFα; NHBE/mock (normal human bronchial epithelial); NHBE/IL 13-2; BM-MNC (bone marrow mononuclear cells); mPB CD34+; ABM CD34+ (CD34+ cells from adult bone marrow); erythroid; Meg day 7 (human megakaryocytes); Meg day 10; Meg day 14; Neutrophil day 7; Neutrophil day 14; MBM CDH b-/CD14+; BM/GPA (GPA+ cells from human bone marrow); and, erythroid day 6.
Figure 27:
FIG. 27 shows expression of the 2193 protein kinase in human tissues and virus-infected cultured hepatocytes (HepG2). In this figure, "AVE 2193" and AVE Beta2" represent averaged levels of 2193 and Beta2, respectively, while "Relative EXP" refers to relative expression.
Figure 41:
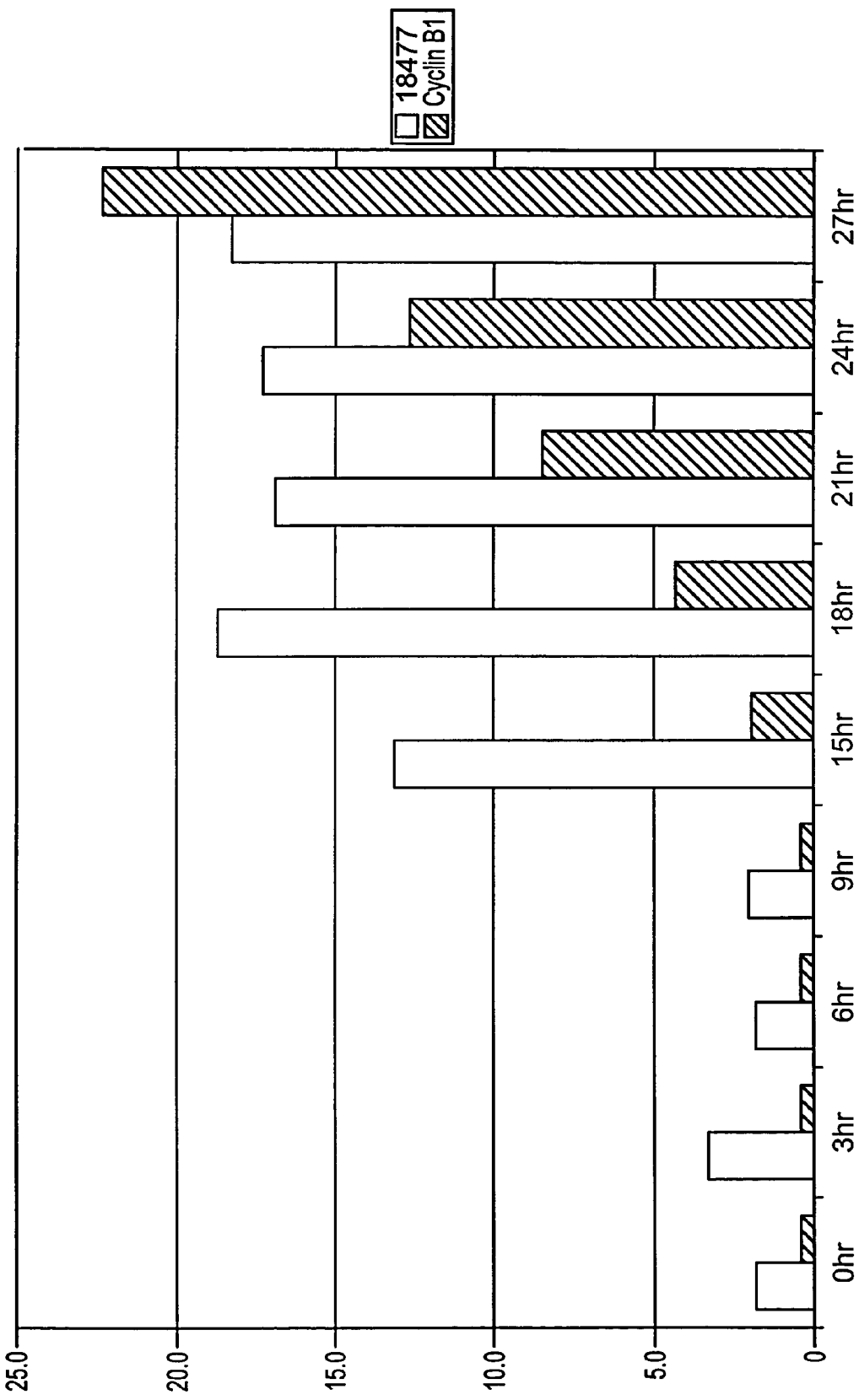
FIG. 41 shows 18477 and cyclin B1 expression in WI-38 synchronized cells over a 27 hour time course.
Figure 42:
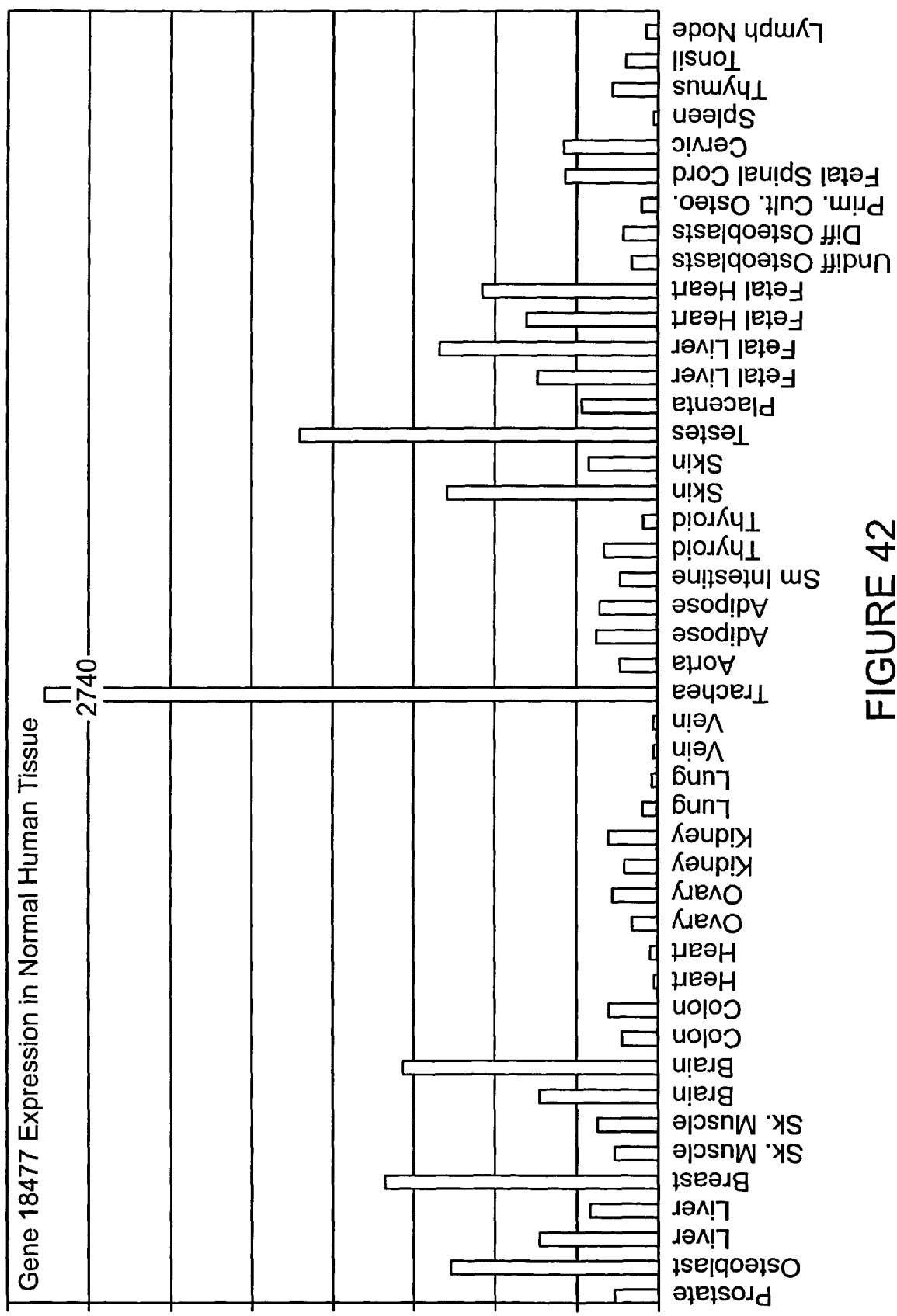
FIG. 42 shows 18477 expression in normal human tissues. Tissues analyzed for 18477 expression include, from left to right: prostate, osteoclasts; liver; breast; skeletal muscle; brain; colon; heart; ovary; kidney; lung; vein; trachea; aorta; adipose; small intestine; thyroid; skin; testes; placenta; fetal liver; fetal heart; undifferentiated osteoblasts; differentiated osteoblasts; primary cultured osteoblasts; fetal spinal cord; cervix; spleen; thymus; tonsil; and lymph node.
Figure 43:
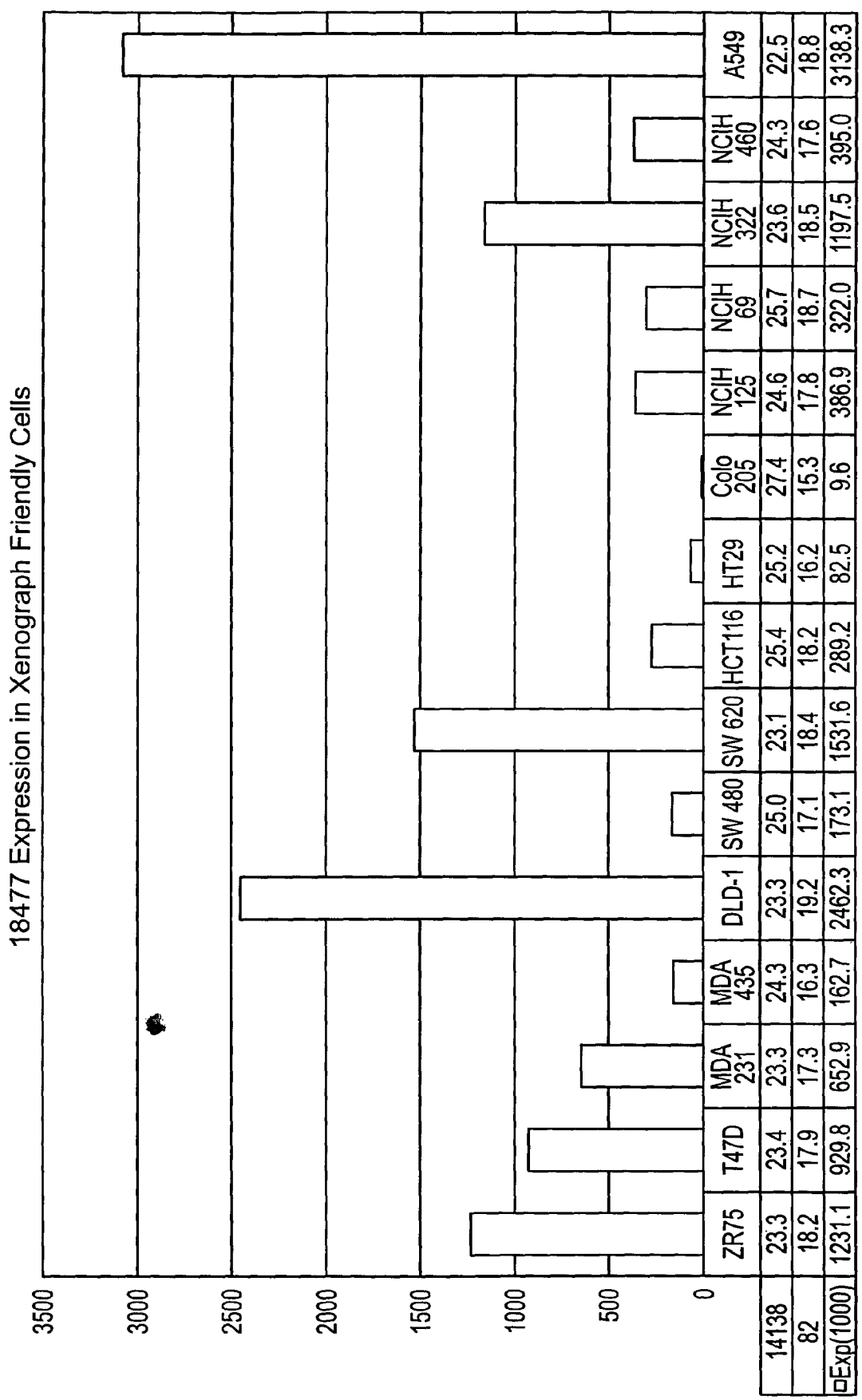
FIG. 43 shows Taqman expression data for 18477 in various Xenofriendly cell lines.

The 2193 protein kinase is expressed in tissues or cells including, but not limited to, those shown in FIGS. 26 and 27. In particular, expression of the gene is differentially regulated in virus-infected hepatocytes. The gene is also differentially expressed in fibrotic liver tissues.

As disclosed herein, 2193 protein kinase is involved in viral infection (e.g., highly expressed or differentially expressed). The protein kinase thus modulates the activity of one or more proteins involved in viral infection, cellular growth, or differentiation, e.g., HBV-infected cells. The protein kinase is capable of modulating the phosphorylation state of a kinase molecule or the phosphorylation state of one or more proteins involved in viral infection, cellular growth, or differentiation, e.g., HBV-infected cells. See also Lodish et al. and Stryer, supra. Particularly, the 2193 kinase modulates phosphorylation in HBV virus-infected tissues and cells, such as liver.

The 2249 protein kinase is expressed in tissues or cells including, but not limited to, adrenal gland, blood, bone, bone marrow, brain, breast, colon, colon to liver metastases, endothelial, heart, keratinocytes, kidney, liver, spleen, lung, lymphocyte, lymphoma, mammary gland, megakaryocytes, muscle, natural killer, nerve, osteoblast, ovary, pituitary, placenta, prostate, spinal cord, T-cell, thymus, and thyroid. Gene mapping is shown in FIG. 29.

In addition, kinases of the present invention are targets of drugs described in Goodman and Gilman (1996) *The Pharmacological Basis of Therapeutics* (9$^{th}$ed.) Hartman & Limbard Editors, the contents of which are incorporated herein by reference.

The kinases of the invention contain domains or motifs, identified by routine homology searching procedures, for example in ProDom, Pfam, Prosite, MEMSAT, and PSORT. Such analysis has identified a eukaryotic protein kinase domain for the kinases of the present invention. For general information regarding PFAM identifiers, PS prefix and PF prefix domain identification numbers, refer to Sonnhammer et al. (1997) *Protein* 28:405-420 and www.psc.edu/general/software/packages/pfam/pfam.html.

As used herein, the term "protein kinase domain" includes an amino acid sequence of about 18-252 amino acid residues in length and having a bit score for the alignment of the sequence to the protein kinase domain (HMM) of at least 8. Preferably, an protein kinase domain includes at least about 18-252 amino acids, about 95-145 amino acid residues, about 72-170 amino acids, or about 144-234 and has a bit score for the alignment of the sequence to the protein kinase domain (HMM) of at least 16 or greater. The protein kinase domain (HMM) has been assigned the PFAM Accession No. PF00069 pfam.wustl.edu/). An alignment of the protein kinase domain (amino acids 35 to 180 and amino acids 740-835 of SEQ ID NO:2; amino acids 8-259 of SEQ ID NO:5; amino acids 141-184 and 223-315 of SEQ ID NO:8; amino acids 156-174 and amino acids 266-501 of SEQ ID NO:11; amino acids 26-278 of SEQ ID NO:14; and amino acids 167-239, amino acids 379-523, and amino acids 564-582 of SEQ ID NO:17) of human kinase sequences of the invention with a consensus amino acid sequence derived from a hidden Markov model is depicted in FIGS. 35-40.

In a preferred embodiment kinase polypeptide or protein has a "protein kinase domain" or a region which includes at least about 18-252, at least about 100-250 more preferably about 130-200 or 160-200 amino acid residues and has at least about 60%, 70%, 80%, 90%, 95%, 99%, or 100% sequence identity with an "protein kinase domain," e.g., the protein kinase domain of human 18477, 3695, 13302, 2208, 2193, and 2249.

To identify the presence of an "protein kinase" domain in a kinase protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

In one embodiment, a kinase protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, pfam.wustl.edu/cgi-bin/getdesc?name=7tm-1, and Zagotta W. N. et al. (1996) *Annual Rev. Neuronsci.* 19:235-63, the contents of which are incorporated herein by reference.

In a preferred embodiment, a kinase polypeptide or protein has at least one transmembrane domain or a region which includes at least 18, 20, 22, 24, 25, 30, 35 or 40 amino acid residues and has at least about 60%, 70% 80% 90% 95%, 99%, or 100% sequence identity with a "transmembrane domain," e.g., at least one transmembrane domain of human kinase polypeptides of the invention (e.g., amino acid residues 209-225 and 761-778 of SEQ ID NO:2; amino acids 188-205 and 1172-1189 of SEQ ID NO:5; amino acids 244-261 of SEQ ID NO:8; amino acids 89-111, 277-293 and 436-454 of SEQ ID NO:11 and amino acids 61-83, 249-265, and 408-426 of the mature polypeptide of SEQ ID NO:11; and amino acids 57-73 of SEQ ID NO:17).

In another embodiment, a protein kinase of the present invention includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring protein kinase.

In a preferred embodiment, a protein kinase polypeptide or protein has a "non-transmembrane domain" or a region which includes at least about 1-350, about 200-320, about 230-300, and about 240-280 amino acid residues, and has at least about 60%, 70% 80% 90% 95%, 99% or 100% sequence identity with a "non-transmembrane domain", e.g., a non-transmembrane domain of human protein kinase (e.g., amino acids 1-208, 224-760, 779-879 of SEQ ID NO:2; amino acids 1-187, 206-1171, 1190-1203 of SEQ ID NO:5; amino acids 1-243, 244-260, 262-358 of SEQ ID NO:8;

amino acids 1-88, 112-276, 294-435, 455-581 of SEQ ID NO:11; and, amino acids 1-56 and 74-629 of SEQ ID NO: 17). In specific embodiments, a non-transmembrane domain is capable of catalytic activity (e.g., kinase activity).

A non-transmembrane domain located at the N-terminus of a protein kinase polypeptide is referred to herein as an "N-terminal non-transmembrane domain." As used herein, an "N-terminal non-transmembrane domain" includes an amino acid sequence having about 1-350, preferably about 30-325, more preferably about 50-320, or even more preferably about 80-310 amino acid residues in length and is located outside the boundaries of a membrane. For example, an N-terminal non-transmembrane domain is located at about amino acid residues 1-208 of SEQ ID NO:2; amino acids 1-187 of SEQ ID NO:5; amino acids 1-243 of SEQ ID NO:8; amino acids 1-88 of SEQ ID NO:11; and, amino acids 1-56 of SEQ ID NO:17.

Similarly, a non-transmembrane domain located at the C-terminus of a protein kinase polypeptide is referred to herein as a "C-terminal non-transmembrane domain." As used herein, an "C-terminal non-transmembrane domain" includes an amino acid sequence having about 1-300, preferably about 15-290, preferably about 20-270, more preferably about 25-255 amino acid residues in length and is located outside the boundaries of a membrane. For example, an C-terminal non-transmembrane domain is located at about amino acid residues 779-879 of SEQ ID NO:2, amino acids 1190-1203 of SEQ ID NO:5, amino acids 262-358 of SEQ ID NO:8, amino acids 455-581 of SEQ ID NO:11, amino acids 74-629 of SEQ ID NO:17.

A protein kinase molecule can further include a signal sequence. As used herein, a "signal sequence" refers to a peptide of about 20-80 amino acid residues in length which occurs at the N-terminus of secretory and integral membrane proteins and which contains a majority of hydrophobic amino acid residues. For example, a signal sequence contains at least about 12-25 amino acid residues, preferably about 30-70 amino acid residues, more preferably about 61 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a protein kinase polypeptide contains a signal sequence of about amino acids 1-29 of SEQ ID NO:11. The "signal sequence" is cleaved during processing of the mature protein. The mature protein kinase polypeptide corresponds to amino acids 30-581 of SEQ ID NO:11.

For the 18477 protein kinase, PSORT prediction of protein localization is shown in FIG. 30 and predicts nuclear localization with a potential vacuolar targeting motif. Prosite pattern analysis shows a serine/threonine protein kinase active site signature. Search for complete domains in Pfam shows a high score to eukaryotic protein kinase domains and some homology to protein kinase C terminal domain.

For the 3695 protein kinase, Prosite analysis shows a serine/threonine protein kinase active site signature. Search for complete domains in Pfam shows a high score to eukaryotic protein kinase domains.

For the 13302 protein kinase, homology searches have shown that the gene is similar to rat NIPK neuronal cell-death-inducible putative kinase. PSORT prediction of protein localization is shown in FIG. 31, with the highest localization to mitochondria. A search of complete domains in Pfam shows a high score to eukaryotic protein kinase domains.

For the 2208 protein kinase, PSORT prediction of protein localization is shown in FIG. 32. The highest score is shown for localization to mitochondria. Prosite analysis shows a serine/threonine protein kinase active site signature. A complete search of domains in Pfam shows a high score to eukaryotic protein kinase domains.

For the 2193 protein kinase, PSORT prediction of protein localization is shown in FIG. 33 with highest scores for nuclear and cytoplasmic localization. Prosite analysis shows a serine/threonine protein kinase active site signature. A search of complete domains in Pfam shows a high score with eukaryotic protein kinase domains.

For the 2249 protein kinase, PSORT prediction of protein localization is shown in FIG. 34 with the highest score to nuclear localization with the feature of having a coiled coil. Prosite analysis shows a serine/threonine protein kinase active site signature. A search of complete domains in Pfam shows the highest homology with eukaryotic protein kinase domains.

The term "kinase" includes a protein, polypeptide, or other non-proteinaceous molecule that is capable of modulating its own phosphorylation state or the phosphorylation state of a different protein, polypeptide, or other non-proteinaceous molecule. However, the term "kinase," when referring to the proteins or polypeptides of the invention, refers to a protein kinase, since the kinases of the invention are protein kinases.

Kinases can have a specificity for (i.e., a specificity to phosphorylate) serine/threonine residues, tyrosine residues, or both serine/threonine and tyrosine residues, e.g., the dual-specificity kinases. As referred to herein, kinases, such as protein kinases, preferably include a catalytic domain of about 200-400 amino acid residues in length, preferably about 200-300 amino acid residues in length, or more preferably about 250-300 amino acid residues in length, which includes preferably 5-20, more preferably 5-15, or most preferably 11 highly conserved motifs or subdomains separated by sequences of amino acids with reduced or minimal conservation. Specificity of a kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42-52, the contents of which are incorporated herein by reference). These subdomains are also described in further detail herein.

Kinases play a role in signaling pathways associated with cellular growth. For example, protein kinases are involved in the regulation of signal transmission from cellular receptors, e.g., growth-factor receptors, entry of cells into mitosis, and the regulation of cytoskeleton function, e.g., actin bundling.

Assays for measuring kinase activity are well known in the art depending on the particular kinase. Specific assay protocols are available in standard sources known to the ordinarily skilled artisan. For example, see "Kinases" in Ausubel et al., eds. (1994-1998) *Current Protocols in Molecular Biology* (3) and references cited therein; www.sdsc.edu/Kinases/pkr/pk_protocols.html; and www.sdsc.edu/Kinases/pkr/pk_protocols/tyr_synpep_assay.html Inhibition or over-stimulation of the activity of kinases involved in signaling pathways associated with cellular growth can lead to perturbed cellular growth, which can in turn lead to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma. Disorders associated with virally-infected cells or tissues are also encompassed. The compositions are useful for the treatment of viral infection, such as DNA virus infection, including but not limited to HBV.

The 18477 protein kinase is expressed in islets, skin, endothelium, breast, colon, liver, brain, heart, kidney, breast, colon, skeletal muscle, trachea, aorta, adipose tissue, small intestine, testes, placenta, fetal liver, fetal heart, cervix, thymus, tonsil, lymph node and lung clinical tumor samples as discussed above. Expression of the gene is particularly relevant in cell cycle progression and cellular differentiation, and accordingly, is particularly relevant for development, differentiation, and carcinogenesis. The gene is expressed in clinical tumor samples including, but not limited to, breast, colon and lung. 18477 is a cell cycle regulated kinase. It has been shown to be upregulated 2-5 times in 9/11 colon tumors when compared to normal colon tissues (FIG. 44). The gene is expressed in clinical tumor samples including, but not limited to, breast, colon and lung. Many cell cycle regulated genes may be considered protooncogenes. Cell cycle regulated genes control cell proliferation. Thus, modulation of these genes and their regulatory activities may permit the control of tumor cell proliferation and invasion. Accordingly, the disclosed invention relates to methods and compositions for the modulation, diagnosis and treatment of disorders associated with the tissues in which the gene is expressed, and particularly, in carcinogenesis, especially in breast, colon and lung.

The 2249 protein kinase is expressed in cells and tissues including, but not limited to, those listed hereinabove. Accordingly, the disclosed invention relates to methods and compositions for modulation, diagnosis and treatment of disorders associated with these cells and tissues. Because the gene is expressed in blood cells, in one embodiment, gene expression is relevant to treatment of immune and inflammatory disorders. Moreover, because the gene is expressed in colon to liver metastases, in one embodiment expression is important in colon cancer and in colonic metastases to the liver. The gene is also expressed in keratinocytes, and accordingly, in one embodiment expression of the gene is relevant to the development of epithelium and other structures in which keratinocytes are precursor cells. Because the gene is also expressed in lymphoma, in one embodiment, gene expression is relevant to this disorder. Further, because the gene is expressed in megakaryocytes, expression of the gene is relevant to disorders associated with platelets, including thrombocytopenia. Further, because the gene is expressed in osteoblasts, in one embodiment expression is relevant to bone disorders that include defects in development of proper bone mass, and accordingly, is relevant in osteoporosis and osteopetrosis.

The 2193 protein kinase is expressed in tissues and cells, including those shown in FIGS. 26 and 27. Accordingly, the invention relates to methods and compositions for the modulation, diagnosis and treatment of disorders associated with these cells and tissues. Particularly relevant embodiments include disorders of those tissues in which the gene is highly expressed, such as brain and erythroid cells. Moreover, because the gene is highly expressed in CD34$^+$ cells, expression of the gene is relevant to all hematopoietic lineages, and therefore to anemia, neutropenia and thrombocytopenia. In addition, some expression of the gene is found in fibrotic liver tissue and thus, expression can be relevant to tissue fibrosis and particularly liver fibrosis. In this regard, FIG. 27 shows increased expression of 2193 in Hep G2 cells that have been infected with hepatitis B virus.

RNA was isolated from HepG2 (immortalized human hepatocyte cells) and a HepG2 cell line stably transfected with the HBV genome. These cell lines can be used to screen for anti-HBV compounds. The RNA was labeled by synthesizing $^{33}$P-labeled cDNA and hybridized to a gene array containing novel human genes identified by the inventors. 2193 RNA was found to be significantly more abundant in HBV-infected HepG2 cells than in uninfected HepG2 cells.

The disclosed invention accordingly relates to methods and compositions for the modulation, diagnosis, and treatment of disorders associated with, caused by, or related to viral infection. These disorders can manifest as immune, inflammatory, respiratory, hematological, cardiovascular, and other disorders including, but not limited to, AIDS, virus associated leukemias, lymphomas, sarcomas, and carcinomas, herpetic infections and collateral symptoms, EBV infection, including mononucleosis, hepatitis virus infection, including A, B, C, and D viruses, viral induced liver cancer, and viral pneumonias.

Viruses include, but are not limited to, those identified with carcinogenesis, including hepatitis B virus (HBV) and liver cancer, Epstein-Barr virus (EBV), and lymphoma, human T-cell lymphotrophic virus Type I (HTLV-1) and leukemia, and human Herpes virus 8 (HHV-8) and Kaposi sarcoma. Virus families to which the invention pertains include but are not limited to Adenoviridae, Picornaviridae, Coronaviridae, Orthomyxoviridae, Paramyxoviridae, Reoviridae, Caliciviridae, Hepadnaviridae, Viroid-like, Flaviviridae, Norwalk-like, Togaviridae, Parvoviridae, Poxviridae, Herpesviridae, Retroviridae, Reoviridae (Orbivirus), Arenaviridae, Bunyaviridae, Filoviridae, Hantavirus, and Papovaviridae. Respiratory diseases have been associated with Adenovirus, Echovirus, Rhinovirus, Coxsackievirus, Coronavirus, Influenza viruses A, B, Parainfluenza virus 1-4, and Respiratory syncytial virus. Viral diseases of the respiratory system include, but are not limited to, lower respiratory tract infections, conjunctivitis, diarrhea; upper respiratory tract infections, pharyngitis, rash; pleurodynia, herpangina, hand-foot-and-mouth disease; influenza, croup, bronchiolitis, and pneumonia. Digestive diseases have been associated with Mumps virus, Rotavirus, Norwalk agent, Hepatitis A Virus, Hepatitis B Virus, Hepatitis D Virus, Hepatitis C Virus, and Hepatitis E Virus. These include but are not limited to mumps, pancreatitis, orchitis; childhood diarrhea; gastroenteritis; acute viral hepatitis; acute or chronic hepatitis; with HBV, acute or chronic hepatitis; and enterically transmitted hepatitis. Systemic viral pathogens associated with skin eruptions include, but are not limited to, Measles virus, Rubella virus, Parvovirus, Vaccinia virus, Varicella-zoster virus, Herpes simplex virus 1, and Herpes simplex virus 2. Disease expression includes, but is not limited to, Measles (rubeola); German measles (rubella); Erythema infectiosum, aplastic anemia; smallpox; chickenpox, shingles; "cold sore"; and genital herpes. Systemic viral pathogens associated with hematopoietic disorders include Cytomegalovirus, Epstein-Barr virus, HTLV-I, HTLV-II, HIV-1 and HIV-2. Disease expression includes, but is not limited to, Cytomegalic inclusion disease; infectious mononucleosis; adult T-cell leukemia; tropical spastic paraparesis; and AIDS. Viral pathogens associated with Arboviral and Hemorrhagic fevers include, but are not limited, Dengue virus 1-4, yellow fever virus, Colorado tick fever virus, and regional hemorrhagic fever viruses. Disease expression includes, but is not limited to, Dengue, hemorrhagic fever; yellow fever; Colorado tick fever; Bolivian, Argentinian, Lassa fever; Crimean-Congo, Hantaan, sandfly fever; Ebola, Marburg disease; Korean, U.S. pneumonia. Viral pathogens associated with warty growths include Papillomavirus and molluscum virus. Disease expression includes, but is not limited to, Condyloma; cervical carcinoma; and molluscum contagiosum. Viral pathogens associated with diseases of the central nervous system include, but are not limited to, Poliovirus, Rabiesvirus, JC virus, and Arboviral encephalitis viruses. Disease expression includes, but is not limited to, Poliomyelitis; Rabies; progressive multifocal leukoencephalopathy (opportunistic); Eastern, Western, Venezuelan, St. Louis, California group.

The 3695 protein kinase is expressed in the tissues and cells disclosed hereinabove. The invention accordingly relates to methods and compositions for the modulation, diagnosis and treatment of disorders associated with these tissues and cells. The gene is also expressed in keratinocytes, and accordingly, in one embodiment expression of the gene is relevant to the development of epithelium and other structures in which keratinocytes are precursor cells. Because the gene is also expressed in lymphoma, in one embodiment, gene expression is relevant to this disorder. Further, because the gene is expressed in osteoblasts, in one embodiment expression is relevant to bone disorders that include defects in development of proper bone mass, and accordingly, is relevant in osteoporosis and osteopetrosis.

The 13302 protein kinase is expressed in the tissues and cells described hereinabove. Accordingly, the invention relates to methods and compositions for the modulation, diagnosis and treatment of disorders associated with these tissues and cells. Moreover, because the gene is expressed in colon to liver metastases, in one embodiment expression is important in colon cancer and in colonic metastases to the liver. The gene is also expressed in keratinocytes, and accordingly, in one embodiment expression of the gene is relevant to the development of epithelium and other structures in which keratinocytes are precursor cells. Because the gene is also expressed in lymphoma, in one embodiment, gene expression is relevant to this disorder. Further, because the gene is expressed in osteoblasts, in one embodiment expression is relevant to bone disorders that include defects in development of proper bone mass, and accordingly, is relevant in osteoporosis and osteopetrosis.

The 2208 protein kinase expression is shown in the tissues and cells shown in FIG. 25. In addition, it is also expressed in tissues or cells disclosed hereinabove. Accordingly, the invention relates to methods and compositions for the modulation, diagnosis and treatment of disorders associated with these tissues and cells. In particular, expression is relevant in tissues in which the gene is highly expressed, such as brain, heart, testis and vein. Moreover, because the gene is expressed in colon to liver metastases, in one embodiment expression is important in colon cancer and in colonic metastases to the liver. The gene is also expressed in keratinocytes, and accordingly, in one embodiment expression of the gene is relevant to the development of epithelium and other structures in which keratinocytes are precursor cells. Because the gene is also expressed in lymphoma, in one embodiment, gene expression is relevant to this disorder. Further, because the gene is expressed in osteoblasts, in one embodiment expression is relevant to bone disorders that include defects in development of proper bone mass, and accordingly, is relevant in osteoporosis and osteopetrosis.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and post-menopausal changes; inflammations, such as chronic endometritis; adenomyosis; endometriosis; endometrial polyps; endometrial hyperplasia; malignant tumors, such as carcinoma of the endometrium; mixed Müllerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2-8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumor of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Novel Kinase Sequence

The present invention is based, at least in part, on the identification of novel protein kinases and nucleic acid molecules encoding them, that comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence identity as defined herein. Such family members can be naturally or non-naturally occurring and can be from either the same or different species. For example, a family can contain a first protein of human origin, as well as other, distinct proteins of human origin or alternatively, can contain homologs of non-human origin. Members of a family may also have common functional characteristics.

The invention features a protein kinase nucleic acid molecule, preferably a human protein kinase molecule, identified based on a consensus motif or protein domain characteristic of the protein kinase family of proteins.

The kinase genes of the invention were identified in human cDNA libraries. The clones to which the present invention are directed contain a mRNA transcript having a corresponding cDNA sequence set forth in SEQ ID NOS:1, 3, 4, 6, 7, 9, 10, 12, 13, 15, 16, or 18. This transcript has a nucleotide open reading frame encoding an amino acid sequence set forth in SEQ ID NOS: 2, 5, 8, 11, 14 or 17, respectively.

Preferred kinase polypeptides of the present invention have an amino acid sequence sufficiently identical to the amino acid sequence of SEQ ID NOS:2, 5, 8, 11, 14 or 17 or a domain thereof. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably about 75% identity, more preferably about 85%, 90%, 95%, or more identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. In a preferred embodiment, the percent identity between two amino acid sequences is determined using the Needleman and Wunsch (1970) *J. Mol. Biol.* 48:444-453 algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to kinase nucleic acid molecules of the invention. BLAST protein searches can be performed with the XBLAST program, score=50, wordlength=3, to obtain amino acid sequences homologous to kinase protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See www.ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated kinase proteins and polypeptides having a kinase protein activity. As used interchangeably herein, a "kinase protein activity", "biological activity of a kinase protein", or "functional activity of a kinase protein" refers to an activity exerted by a kinase protein, polypeptide, or nucleic acid molecule on a kinase-responsive cell as determined in vivo, or in vitro, according to standard assay techniques. A kinase activity can be a direct activity, such as autophosphorylation or an association with or an enzymatic activity on a second protein, such as on c-fos, c-jun, APF2, and ETS family members Elkl, Sapla, and c-Ets, or other transcription factors, targets of Cdk function or interaction, such as cyclin, the small inhibitory molecules discussed in Dynlacht, above, and Nigg, ((1995) *Bioessays* 17: 471-480), transcriptional co-activators such as p110Rb and p107 and transcription factors such as p53, E2F, and RNA polymerase II, cytoskeletal proteins and cytoplasmic signaling proteins as cited in Brott et al., above, TCF/LEF factors, POP-1 and other HMG-domain-containing proteins, or an indirect activity, such as a cellular signaling activity mediated by the Wnt or MAPK pathways, for example, as discussed hereinabove. In a preferred embodiment, a kinase activity includes at least one or more of the following activities: (1) modulating (stimulating and/or enhancing or inhibiting) cellular proliferation, growth and/or metabolism (e.g. in those cells in which the sequence is expressed, including virus infected cells); (2) the regulation of transmission of signals from cellular receptors, e.g., growth factor receptors; (3) the modulation of the entry of cells into mitosis; (4) the modulation of cellular differentiation; (5) the modulation of cell death; and (6) the regulation of cytoskeleton function, e.g., actin bundling. Functions also include, but are not limited to, those shown for the specific functional sites in FIGS. 7-12 and 35-40, including ATP binding and phosphotransferase activity.

An "isolated" or "purified" kinase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated kinase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A kinase protein that is substantially free of cellular material includes preparations of kinase protein having less than about 30%, 20%, 10%, or 5% (by dry weight) of non-kinase protein (also referred to herein as a "contaminating protein"). When the kinase protein or biologically active portion thereof is recombinantly produced, preferably, culture medium represents less than about 30%, 20%, 10%, or 5% of the volume of the protein preparation. When kinase protein is produced by chemical synthesis, preferably the protein preparations have less than about 30%, 20%, 10%, or 5% (by dry weight) of chemical precursors or non-kinase chemicals.

Various aspects of the invention are described in further detail in the following subsections.

I. Isolated Nucleic Acid Molecules

One aspect of the invention pertains to an isolated nucleic acid molecule comprising a nucleotide sequence encoding a kinase protein or biologically active portion thereof, as well as a nucleic acid molecule sufficient for use as a hybridization probe to identify kinase-encoding nucleic acids (e.g., kinase mRNA) and fragments for use as PCR primers for the amplification or mutation of kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleotide sequence encoding the kinase proteins of the present invention includes the sequence set forth in SEQ ID NO:1, 3, 4, 6, 7, 9, 10, 12, 13, 15, 16, or 18 and the complement thereof. By "complement" is intended a nucleotide sequence that is sufficiently complementary to a given nucleotide sequence such that it can hybridize to the given nucleotide sequence to thereby form a stable duplex. The corresponding amino acid sequence for the kinase protein encoded by the nucleotide sequence is set forth in SEQ ID NO: 2, 5, 8, 11, 14, or 17.

Nucleic acid molecules that are fragments of the kinase nucleotide sequence are also encompassed by the present invention. By "fragment" is intended a portion of the nucleotide sequence encoding a kinase protein of the invention. A fragment of a kinase nucleotide sequence may encode a biologically active portion of a kinase protein, or it may be a fragment that can be used as a hybridization probe or PCR primer using methods disclosed below. A biologically active portion of a kinase protein can be prepared by isolating a portion of the kinase nucleotide sequence of the invention, expressing the encoded portion of the kinase protein (e.g., by recombinant expression in vitro), and assessing the activity of the encoded portion of the kinase protein.

Generally, nucleic acid molecules that are fragments of a kinase nucleotide sequence comprise at least 15, 20, 50, 75, 100, 325, 350, 375, 400, 425, 450, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, 5000, 5200, 5400 nucleotides, or up to the number of nucleotides present in a full-length kinase nucleotide sequence disclosed herein depending upon the intended use.

Alternatively, a nucleic acid molecules that is a fragment of a 18477 nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 2000-2100, 2100-2200, 2200-2300, 2300-2400, 2400-2500, 2500-2600, 2600-2700, 2700-2900, 2900-3100, or 3100-3003 of SEQ ID NO:1 or 3.

A nucleic acid molecules that is a fragment of an 3695 nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 2000-2100, 2100-2200, 2200-2300, 2300-2400, 2400-2500, 2500-2600, 2600-2700, 2700-2900, 2900-3100, 3100-3300, 3300-3500, 3500-3700, 3700-3900, 3900-4100, 4100-4300, 4300-4500, 4500-4700, 4700-4900, 4900-5100, 5100-5300, 5300-5500, 5500-5700, or 5700-5983 of SEQ ID NO:4 or 6.

Alternatively, a nucleic acid molecules that is a fragment of an 13302 nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 2000-2100, 2100-2200, or 2200-2389 of SEQ ID NO:7 or 9.

Alternatively, a nucleic acid molecules that is a fragment of an 2208 nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2100, or 2100-2162 of SEQ ID NO:10 or 12.

Alternatively, a nucleic acid molecules that is a fragment of an 2193 nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, or 1700-1826 of SEQ ID NO:13 or 15.

Alternatively, a nucleic acid molecules that is a fragment of an 2249 nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2100, 2100-2200, 2200-2300, 2300-2400, 2400-2500, 2500-2600, 2600-2700, or 2700-2870 of SEQ ID NO:16 or 18.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences. Further, the sizes of the fragments may vary depending on the region analyzed.

Generally, a fragment of a kinase nucleotide sequence that encodes a biologically active portion of a kinase protein of the invention will encode at least 15, 25, 30, 50, 75, 100, 125, 150, 160, or 170 contiguous amino acids, or up to the total number of amino acids present in a full-length kinase protein of the invention. Fragments of a kinase nucleotide sequence that are useful as hybridization probes for PCR primers generally need not encode a biologically active portion of a kinase protein.

Nucleic acid molecules that are variants of the kinase nucleotide sequence disclosed herein are also encompassed by the present invention. "Variants" of the kinase nucleotide sequence include those sequences that encode the kinase protein disclosed herein but that differ conservatively because of the degeneracy of the genetic code. These naturally-occurring allelic variants can be identified with the use of well-known molecular biology techniques, such as polymerase chain reaction (PCR) and hybridization techniques as outlined below. Variant nucleotide sequences also include synthetically-derived nucleotide sequences that have been generated, for example, by using site-directed mutagenesis but which still encode the kinase protein disclosed in the present invention as discussed below. Generally, nucleotide sequence variants of the invention will have at least 45%, 55%, 65%, 75%, 85%, 95%, or 98% identity to the nucleotide sequence disclosed herein. A variant kinase nucleotide sequence will encode a kinase protein that has the amino acid sequence having at least 45%, 55%, 65%, 75%, 85%, 95%, or 98% identity to the amino acid sequence of the kinase protein disclosed herein.

In addition to the kinase nucleotide sequences shown in SEQ ID NO:1, 3, 4, 6, 7, 9, 10, 12, 13, 15, 16, or 18, it will be appreciated by those skilled in the art that DNA sequence polymorphisms that lead to changes in the amino acid sequences of the kinase protein may exist within a population (e.g., the human population). Such genetic polymorphism in a kinase gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a kinase protein, preferably a mammalian kinase protein. As used herein, the phrase "allelic variant" refers to a nucleotide sequence that occurs at a kinase locus or to a polypeptide encoded by the nucleotide sequence. Such natural allelic variations can typically result in 1-5% variance in the nucleotide sequence of the kinase gene. Any and all such nucleotide variations and resulting amino acid polymorphisms or variations in a kinase sequence that are the result of natural allelic variation and that do not alter the functional activity of kinase proteins are intended to be within the scope of the invention.

Moreover, nucleic acid molecules encoding kinase protein from other species (kinase homologs), which have a nucleotide sequence differing from that of the kinase sequence disclosed herein, are intended to be within the scope of the invention. Nucleic acid molecules corresponding to natural allelic variants and homologs of the kinase cDNA of the invention can be isolated based on their identity to the kinase nucleic acid disclosed herein using the cDNA, or a portion thereof, as a hybridization probe according to standard hybridization techniques under stringent hybridization conditions as disclosed below.

In addition to naturally-occurring allelic variants of the kinase sequence that may exist in the population, the skilled artisan will further appreciate that changes can be introduced by mutation into the nucleotide sequences of the invention thereby leading to changes in the amino acid sequence of the encoded kinase protein, without altering the biological activity of the kinase protein. Thus, an isolated nucleic acid molecule encoding a kinase protein having a sequence that differs from those of SEQ ID NO:1, 3, 4, 6, 7, 9, 10, 12, 13, 15, 16, or 18 can be created by introducing one or more nucleotide substitutions, additions, or deletions into the nucleotide sequences disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a kinase protein (e.g., a sequence of SEQ ID NO:2, 5, 8, 11, 14, or 17 ) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues or for amino acid residues residing within a conserved protein domain, such as the serine/threonine protein kinase domain of the disclosed clones, where such residues are essential for protein activity.

Alternatively, variant kinase nucleotide sequences can be made by introducing mutations randomly along all or part of the kinase coding sequence, such as by saturation mutagenesis, and the resultant mutants can be screened for kinase biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The kinase nucleotide sequences of the invention, and fragments and variants thereof, can be used as probes and/or primers to identify and/or clone kinase homologs in other cell types, e.g., from other tissues, as well as kinase homologs from other mammals. Such probes can be used to detect transcripts or genomic sequences encoding the same or identical proteins. These probes can be used as part of a diagnostic test kit for identifying cells or tissues that misexpress a kinase protein, such as by measuring levels of a kinase-encoding nucleic acid in a sample of cells from a subject, e.g., detecting kinase mRNA levels or determining whether a genomic kinase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Kinase nucleotide sequences isolated based on their sequence identity to the kinase nucleotide sequences set forth herein or to fragments and variants thereof are encompassed by the present invention.

In a hybridization method, all or part of a known kinase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known kinase nucleotide sequences disclosed herein. Degenerate primers designed on the basis of conserved nucleotides or amino acid residues in a known kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a kinase nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified kinase nucleic acid molecule hybridizes under stringent conditions to a probe that is a nucleic acid molecule comprising a kinase nucleotide sequence of the invention or a fragment thereof. In another embodiment, the previously unknown kinase nucleic acid molecule is at least 300, 325, 350, 375, 400, 425, 450, 500, 550, 600, 650, 700, 800, 900, 1000, 2,000, 3,000, or 4,000 nucleotides in length and hybridizes under stringent conditions to a probe that is a nucleic acid molecule comprising a kinase nucleotide sequence disclosed herein or a fragment thereof.

Accordingly, in another embodiment, an isolated previously unknown kinase nucleic acid molecule of the invention is at least 300, 325, 350, 375, 400, 425, 450, 500, 518, 550, 600, 650, 700, 800, 831, 900, 981, 1000, 1,100, 1,200, 1,300, 1,400, 1,500, 1,600, 1,700, 1,800, 1,900, 2,000, or 2,060 nucleotides in length and hybridizes under stringent conditions to a probe that is a nucleic acid molecule comprising one of the nucleotide sequences of the invention, preferably a coding sequence set forth in SEQ ID NO:1, 3, 4, 6, 7, 9, 10, 12, 13, 15, 16, 18 or a complement, fragment, or variant thereof.

As used herein, the term "hybridizes under stringent conditions" is intended to describe conditions for hybridization and washing under which nucleotide sequences typically remain hybridized to each other. Such stringent conditions are known to those skilled in the art and can be found in *Current Protocols in Molecular Biology* (John Wiley & Sons, NY (1989)), 6.3.1-6.3.6. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule that hybridizes under stringent conditions to an kinase sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the kinase nucleotide sequences disclosed herein and fragments and variants thereof, the isolated nucleic acid molecules of the invention also encompasses homologous DNA sequences identified and isolated from other cells and/or organisms by hybridization with entire or partial sequences obtained from a kinase nucleotide sequence disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire kinase coding strand, or to only a portion thereof, e.g., all or part of the protein coding region (or open reading frame). An antisense nucleic acid molecule can be antisense to a noncoding region of the coding strand of a nucleotide sequence encoding a kinase protein. The noncoding regions are the 5' and 3' sequences that flank the coding region and are not translated into amino acids.

Given the coding-strand sequence encoding a kinase protein disclosed herein (e.g., SEQ ID NOS:1, 3, 4, 6, 7, 9, 10, 12, 13, 15, 16, or 18), antisense nucleic acids of the invention can be designed according to the rules of Watson and Crick base pairing. The antisense nucleic acid molecule can be complementary to the entire coding region of kinase mRNA, but more preferably is an oligonucleotide that is antisense to only a portion of the coding or noncoding region of kinase mRNA. For example, the antisense oligonucleotide can be complementary to the region surrounding the translation start site of kinase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids, including, but not limited to, for example, phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are typically administered to a subject or generated in situ such that they hybridize with or bind to cellular mRNA and/or genomic DNA encoding a kinase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585-591)) can be used to catalytically cleave kinase mRNA transcripts to thereby inhibit translation of kinase mRNA. A ribozyme having specificity for a kinase-encoding nucleic acid can be designed based upon the nucleotide sequence of a kinase cDNA disclosed herein (e.g., SEQ ID NOS:1, 3, 4, 6, 7, 9, 10, 12, 13, 15, 16, or 18). See, e.g., Cech et al., U.S. Pat. No. 4,987,071; and Cech et al., U.S. Pat. No. 5,116,742. Alternatively, kinase mRNA can be used to select a catalytic RNA having a specific ribonuclease activity from a pool of RNA molecules. See, e.g., Bartel and Szostak (1993) *Science* 261:1411-1418.

The invention also encompasses nucleic acid molecules that form triple helical structures. For example, kinase gene expression can be inhibited by targeting nucleotide sequences complementary to the regulatory region of the kinase protein (e.g., the kinase promoter and/or enhancers) to form triple helical structures that prevent transcription of the kinase gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a kinase molecule can be used in therapeutic and diagnostic applications. For example, PNAs can be used as antisense or antigen agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping, as artificial restriction enzymes when used in combination with other enzymes, e.g., S1 nucleases (Hyrup (1996), supra, or as probes or primers for DNA sequence and hybridization (Hyrup (1996), supra; Perry-O'Keefe et al. (1996), supra).

In another embodiment, PNAs of a kinase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357-63; Mag et al. (1989) *Nucleic Acids Res.* 17:5973; and Peterser et al. (1975) *Bioorganic Med. Chem. Lett.* 5:1119.

II. Isolated Kinase Proteins and Anti-Kinase Antibodies

Kinase proteins are also encompassed within the present invention. By "kinase protein" is intended a protein having an amino acid sequence set forth in SEQ ID NO:2, 5, 8, 11, 14, or 17 as well as fragments, biologically active portions, and variants thereof.

"Fragments" or "biologically active portions" include polypeptide fragments suitable for use as immunogens to raise anti-kinase antibodies. Fragments include peptides comprising amino acid sequences sufficiently identical to or derived from the amino acid sequences of a kinase protein of the invention and exhibiting at least one activity of a kinase protein, but which include fewer amino acids than the full-length kinase protein disclosed herein. Typically, biologically active portions comprise a domain or motif with at least one activity of the kinase protein. A biologically active portion of a kinase protein can be a polypeptide which is, for example, 10, 25, 50, 100 or more amino acids in length. Such biologically active portions can be prepared by recombinant techniques and evaluated for one or more of the functional activities of a native kinase protein.

Alternatively, a fragment of a polypeptide of the present invention comprises an amino acid sequence consisting of amino acid residues 1-20, 20-40, 40-60, 60-80, 80-100, 100-120, 120-140, 140-160, 160-180, 180-200, 200-220, 220-240, 240-260, 260-280, 280-300, 300-320, 320-340, 340-360, 360-380, 380-400, 400-420, 420-440, 440-460, 460-480, 480-520, 520-560, 560-600, 600-640, 640-680, 680-720, 720-760, 760-800, 800-840, or 840-880 of SEQ ID NO:2.

Alternatively, a fragment of a polypeptide of the present invention comprises an amino acid sequence consisting of amino acid residues 1-20, 20-40, 40-60, 60-80, 80-100, 100-120, 120-140, 140-160, 160-180, 180-200, 200-220, 220-240, 240-260, 260-280, 280-300, 300-320, 320-340, 340-360, 360-380, 380-400, 400-420, 420-440, 440-460, 460-480, 480-520, 520-560, 560-600, 600-640, 640-680, 680-720, 720-760, 760-800, 800-840, 840-880, 880-920, 920-960, 960-1000, 1000-1040, 1040-1080, 1080-1120, 1120-1160, 1160-1204 of SEQ ID NO:5.

Alternatively, a fragment of a polypeptide of the present invention comprises an amino acid sequence consisting of amino acid residues 1-20, 20-40, 40-60, 60-80, 80-100, 100-120, 120-140, 140-160, 160-180, 180-200, 200-220, 220-240, 240-260, 260-280, 280-300, 300-320, 320-340, 340-359 of SEQ ID NO:8.

Alternatively, a fragment of a polypeptide of the present invention comprises an amino acid sequence consisting of amino acid residues 1-20, 20-40, 40-60, 60-80, 80-100, 100-120, 120-140, 140-160, 160-180, 180-200, 200-220, 220-240, 240-260, 260-280, 280-300, 300-320, 320-340, 340-360, 360-380, 380-400, 400-420, 420-440, 440-460, 460-480, 480-520, 520-560, 560-581 of SEQ ID NO:11.

Alternatively, a fragment of a polypeptide of the present invention comprises an amino acid sequence consisting of amino acid residues 1-20, 20-40, 40-60, 60-80, 80-100, 100-120, 120-140, 140-160, 160-180, 180-200, 200-220, 220-240, 240-260, 260-280, 280-300, 300-320, 320-340, 340-360, 360-380, 380-400, 400-419 of SEQ ID NO: 14.

Alternatively, a fragment of a polypeptide of the present invention comprises an amino acid sequence consisting of amino acid residues 1-20, 20-40, 40-60, 60-80, 80-100, 100-120, 120-140, 140-160, 160-180, 180-200, 200-220, 220-240, 240-260, 260-280, 280-300, 300-320, 320-340, 340-360, 360-380, 380-400, 400-420, 420-440, 440-460, 460-480, 480-520, 520-560, 560-600, and 600-629 of SEQ ID NO:17.

By "variants" is intended proteins or polypeptides having an amino acid sequence that is at least about 45%, 55%, 65%, preferably about 75%, 85%, 95%, or 98% identical to the amino acid sequence of SEQ ID NO:2, 5, 8, 11, 14, or 17. Variants also include polypeptides encoded by the cDNA insert of the plasmid deposited with ATCC as Accession Number PTA-1775, PTA-2204, PTA-1868, or polypeptides encoded by a nucleic acid molecule that hybridizes to the nucleic acid molecule of SEQ ID NO:1, 3, 4, 6, 7, 9, 10, 12, 13, 15, 16 or 18, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:2, 5, 8, 11, 14, or 17. If alignment is needed for this comparison the sequences should be aligned for maximum identity. "Looped" out sequences from deletions or insertions, or mismatches, are considered differences. Such variants generally retain the functional activity of the kinase-like proteins of the invention. Variants include polypeptides that differ in amino acid sequence due to natural allelic variation or mutagenesis.

The invention also provides kinase chimeric or fusion proteins. As used herein, a kinase "chimeric protein" or "fusion protein" comprises a kinase polypeptide operably linked to a non-kinase polypeptide. A "kinase polypeptide" refers to a polypeptide having an amino acid sequence corresponding to a kinase protein, whereas a "non-kinase polypeptide" refers to a polypeptide having an amino acid sequence corresponding to a protein that is not substantially identical to the kinase protein, e.g., a protein that is different from the kinase protein and which is derived from the same or a different organism. Within a kinase fusion protein, the kinase polypeptide can correspond to all or a portion of a kinase protein, preferably at least one biologically active portion of a kinase protein. Within the fusion protein, the term "operably linked" is intended to indicate that the kinase polypeptide and the non-kinase polypeptide are fused in-frame to each other. The non-kinase polypeptide can be fused to the N-terminus or C-terminus of the kinase polypeptide.

One useful fusion protein is a GST-kinase fusion protein in which the kinase sequences are fused to the C-terminus of the GST sequences. Such fusion proteins can facilitate the purification of recombinant kinase proteins.

In yet another embodiment, the fusion protein is a kinase-immunoglobulin fusion protein in which all or part of a kinase protein is fused to sequences derived from a member of the immunoglobulin protein family. The kinase-immunoglobulin fusion proteins of the invention can be incorporated into pharmaceutical compositions and administered to a subject to inhibit an interaction between a kinase ligand and a kinase protein on the surface of a cell, thereby suppressing kinase-mediated signal transduction in vivo. The kinase-immunoglobulin fusion proteins can be used to affect the bioavailability of a kinase cognate ligand. Inhibition of the kinase ligand/kinase interaction may be useful therapeutically, both for treating proliferative and differentiative disorders and for modulating (e.g., promoting or inhibiting) cell survival. Moreover, the kinase-immunoglobulin fusion proteins of the invention can be used as immunogens to produce anti-kinase antibodies in a subject, to purify kinase ligands, and in screening assays to identify molecules that inhibit the interaction of a kinase protein with a kinase ligand.

Preferably, a kinase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a kinase-encoding nucleic acid can be cloned into a commercially available expression vector such that it is linked in-frame to an existing fusion moiety. Variants of the kinase proteins can function as either kinase agonists (mimetics) or as kinase antagonists. Variants of the kinase protein can be generated by mutagenesis, e.g., discrete point mutation or truncation of the kinase protein. An agonist of the kinase protein can retain substantially the same or a subset of the biological activities of the naturally-occurring form of the kinase protein. An antagonist of the kinase protein can inhibit one or more of the activities of the naturally-occurring form of the kinase protein by, for example, competitively binding to a downstream or upstream member of a cellular signaling cascade that includes the kinase protein. Thus, specific biological effects can be elicited by treatment with a variant of limited function. Treatment of a subject with a variant having a subset of the biological activities of the naturally-occurring form of the protein can have fewer side effects in a subject relative to treatment with the naturally occurring form of the kinase proteins.

Variants of the kinase protein that function as either kinase agonists or as kinase antagonists can be identified by screening combinatorial libraries of mutants, e.g., truncation mutants, of the kinase protein for kinase protein agonist or antagonist activity. In one embodiment, a variegated library of kinase variants is generated by combinatorial mutagenesis at the nucleic acid level and is encoded by a variegated gene library. A variegated library of kinase variants can be produced by, for example, enzymatically ligating a mixture of synthetic oligonucleotides into gene sequences such that a degenerate set of potential kinase sequences is expressible as individual polypeptides, or alternatively, as a set of larger fusion proteins (e.g., for phage display) containing the set of kinase sequences therein. There are a variety of methods that can be used to produce libraries of potential kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential kinase sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the kinase protein coding sequence can be used to generate a variegated population of kinase fragments for screening and subsequent selection of variants of a kinase protein. In one embodiment, a library of coding sequence fragments can be generated by treating a double-stranded PCR fragment of a kinase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the kinase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of kinase proteins. The most widely used techniques, which are amenable to high through-put analysis for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify kinase variants (Arkin and Yourvan (1992) *Proc. Natl. Acad. Sci. USA* 89:7811-7815; Delgrave et al. (1993) *Protein Engineering* 6(3):327-331).

An isolated kinase polypeptide of the invention can be used as an immunogen to generate antibodies that bind kinase proteins using standard techniques for polyclonal and monoclonal antibody preparation. The full-length kinase protein can be used or, alternatively, the invention provides antigenic peptide fragments of the kinase protein for use as immunogens. The antigenic peptide of the kinase protein comprises at least 8, preferably 10, 15, 20, or 30 amino acid residues of an amino acid sequence shown in SEQ ID NOS:2, 5, 8, 11, 14, and 17, and encompasses an epitope of a kinase protein such that an antibody raised against the peptide forms a specific immune complex with the kinase protein. Preferred epitopes encompassed by the antigenic peptide are regions of a kinase protein that are located on the surface of the protein, e.g., hydrophilic regions.

Accordingly, another aspect of the invention pertains to anti-kinase polyclonal and monoclonal antibodies that bind a kinase protein. Polyclonal anti-kinase antibodies can be prepared by immunizing a suitable subject (e.g., rabbit, goat, mouse, or other mammal) with a kinase immunogen. The anti-kinase antibody titer in the immunized subject can be monitored over time by standard techniques, such as with an enzyme linked immunosorbent assay (ELISA) using immobilized kinase protein. At an appropriate time after immunization, e.g., when the anti-kinase antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B-cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.,* 54:387-402).

Alternative to preparing monoclonal antibody-secreting hybridomas, a monoclonal anti-kinase antibody can be identified and isolated by screening a recombinant combinatorial immunoglobulin library (e.g., an antibody phage display library) with a kinase protein to thereby isolate immunoglobulin library members that bind the kinase protein. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant anti-kinase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171, 496, 125,023, and 173,494; U.S. Pat. Nos. 4,816,567 and 5,225,539; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *Bio/Techniques* 4:214; Jones et al. (1986) *Nature* 321:552-

525; Verhoeyan et al. (1988) *Science* 239:1534; and Beidler et al. (1988) *J. Immunol.* 141:4053-4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65-93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899-903).

An anti-kinase antibody (e.g., monoclonal antibody) can be used to isolate kinase proteins by standard techniques, such as affinity chromatography or immunoprecipitation. An anti-kinase antibody can facilitate the purification of natural kinase protein from cells and of recombinantly produced kinase protein expressed in host cells. Moreover, an anti-kinase antibody can be used to detect kinase protein (e.g., in a cellular lysate or cell supernatant) in order to evaluate the abundance and pattern of expression of the kinase protein. Anti-kinase antibodies can be used diagnostically to monitor protein levels in tissue as part of a clinical testing procedure to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a kinase protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication-defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., kinase proteins, mutant forms of kinase proteins, fusion proteins, etc.).

It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The recombinant expression vectors of the invention can be designed for expression of kinase protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31-40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301-315) and pET 11d (Studier et al. (1990) in *Gene Expression Technology: Methods in Enzymology* 185 (Academic Press, San Diego, Calif.), pp. 60-89). Strategies to maximize recombinant protein expression in *E. coli* can be found in Gottesman (1990) in *Gene Expression Technology: Methods in Enzymology* 185 (Academic Press, CA), pp. 119-128 and Wada et al. (1992) *Nucleic Acids Res.* 20:2111-2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39)); yeast cells (examples of vectors for expression in yeast *S. cerevisiae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) Molecular Cloning: A Laboratory Manual (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), particular promoters of T-cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Patent Publication No. 264,166). Developmentally-regulated promoters are also encompassed, for example the murine hox promoters (Kessel and Gruss (1990) *Science* 249:374-379), the α-fetoprotein promoter (Campes and Tilghman (1989) *Genes Dev.* 3:537-546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to kinase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a kinase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) kinase protein. Accordingly, the invention further provides methods for producing kinase protein using the host cells of the invention. In one embodiment, the method comprises culturing the host cell of the invention, into which a recombinant expression vector encoding a kinase protein has been introduced, in a suitable medium such that kinase protein is produced. In another embodiment, the method further comprises isolating kinase protein from the medium or the host cell.

The host cells of the invention can also be used to produce nonhuman transgenic animals. For example, in one embodiment, a host cell of the invention is a fertilized oocyte or an embryonic stem cell into which a kinase-coding sequence has been introduced. Such host cells can then be used to create nonhuman transgenic animals in which exogenous kinase sequences have been introduced into their genome or homologous recombinant animals in which endogenous kinase sequences have been altered. Such animals are useful for studying the function and/or activity of kinase genes and proteins and for identifying and/or evaluating modulators of kinase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous kinase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing kinase-encoding nucleic acid into the male pronuclei of a fertilized oocyte, e.g., by microinjection, retroviral infection, and allowing the oocyte to develop in a pseudopregnant female foster animal. The kinase cDNA sequence can be introduced as a transgene into the genome of a nonhuman animal. Alternatively, a homolog of the kinase gene can be isolated based on hybridization and used as a transgene. Intronic sequences and polyadenylation signals can also be included in the transgene to increase the efficiency of expression of the transgene. A tissue-specific regulatory sequence(s) can be operably linked to the kinase transgene to direct expression of kinase protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the kinase transgene in its genome and/or expression of kinase mRNA in tissues or cells of the animals. A transgenic founder animal can then be used to breed additional animals carrying the transgene. Moreover, transgenic animals carrying a transgene encoding kinase gene can further be bred to other transgenic animals carrying other transgenes.

To create a homologous recombinant animal, one prepares a vector containing at least a portion of a kinase gene or a homolog of the gene into which a deletion, addition, or substitution has been introduced to thereby alter, e.g., functionally disrupt, the kinase gene. In a preferred embodiment, the vector is designed such that, upon homologous recombination, the endogenous kinase gene is functionally disrupted (i.e., no longer encodes a functional protein; such vectors are also referred to as "knock out" vectors). Alternatively, the vector can be designed such that, upon homologous recombination, the endogenous kinase gene is mutated or otherwise altered but still encodes functional protein (e.g., the upstream regulatory region can be altered to thereby alter the expression of the endogenous kinase protein). In the homologous recombination vector, the altered portion of the kinase gene is flanked at its 5' and 3' ends by additional nucleic acid of the kinase gene to allow for homologous recombination to occur between the exogenous kinase gene carried by the vector and an endogenous kinase gene in an embryonic stem cell. The additional flanking kinase nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced kinase gene has homologously recombined with the endogenous kinase gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford), pp. 113-152). A chimeric embryo can then be implanted into a suitable pseudopregnant female foster animal and the embryo brought to term. Progeny harboring the homologously-recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810-813 and PCT Publication Nos. WO 97/07668 and WO 97/07669.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

IV. Pharmaceutical Compositions

The kinase nucleic acid molecules, kinase proteins, and anti-kinase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a kinase protein or antikinase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologs, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express kinase protein (e.g., via a recombinant expression vector in a host cell in gene therapy applications), to detect kinase mRNA (e.g., in a biological sample) or a genetic lesion in a kinase gene, and to modulate kinase activity. In addition, the kinase proteins can be used to screen drugs or compounds that modulate cellular growth and/or metabolism as well as to treat disorders characterized by insufficient or excessive production of kinase protein or production of kinase protein forms that have decreased or aberrant activity compared to kinase wild type protein. In addition, the anti-kinase antibodies of the invention can be used to detect and isolate kinase proteins and modulate kinase activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to kinase proteins or have a stimulatory or inhibitory effect on, for example, kinase expression or kinase activity.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). J. Med. Chem. 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865-1869), or phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310).

Determining the ability of the test compound to bind to the kinase protein can be accomplished, for example, by coupling the test compound with a radioisotope or enzymatic label such that binding of the test compound to the kinase protein or biologically active portion thereof can be determined by detecting the labeled compound in a complex. For example, test compounds can be labeled with $^{125}$I, $^{35}$S, $^{14}$C, or $^3$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the kinase protein to bind to or interact with a kinase target molecule. By "target molecule" is intended a molecule with which a kinase protein binds or interacts in nature. In a preferred embodiment, the ability of the kinase protein to bind to or interact with a kinase target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a kinase-responsive regulatory element operably linked to a nucleic acid encoding a detectable marker, e.g., luciferase), or detecting a cellular response, for example, viral infection, cellular differentiation or cell proliferation. Biochemical events, substrates, and effector molecules, include but are not limited to, those discussed above, including those functions shown in the figures and NLK related functions, including MAPK/Erk and Cdk-like functions.

In yet another embodiment, an assay of the present invention is a cell-free assay comprising contacting a kinase protein or biologically active portion thereof with a test compound and determining the ability of the test compound to bind to the kinase protein or biologically active portion thereof. Binding of the test compound to the kinase protein can be determined either directly or indirectly as described above. In a preferred embodiment, the assay includes contacting the kinase protein or biologically active portion thereof with a known compound that binds kinase protein to form an assay mixture, contacting the assay mixture with a test compound, and determining the ability of the test compound to preferentially bind to kinase protein or biologically active portion thereof as compared to the known compound.

In another embodiment, an assay is a cell-free assay comprising contacting kinase protein or biologically active portion thereof with a test compound and determining the ability of the test compound to modulate (e.g., stimulate or inhibit) the activity of the kinase protein or biologically active portion thereof. Determining the ability of the test compound to modulate the activity of a kinase protein can be accomplished, for example, by determining the ability of the kinase protein to bind to a kinase target molecule as described above for determining direct binding. In an alternative embodiment, determining the ability of the test compound to modulate the activity of a kinase protein can be accomplished by determining the ability of the kinase protein to further modulate a kinase target molecule. For example, the catalytic/enzymatic activity of the target molecule on an appropriate substrate can be determined as previously described.

In yet another embodiment, the cell-free assay comprises contacting the kinase protein or biologically active portion thereof with a known compound that binds a kinase protein to form an assay mixture, contacting the assay mixture with a test compound, and determining the ability of the test compound to preferentially bind to or modulate the activity of a kinase target molecule.

In the above-mentioned assays, it may be desirable to immobilize either a kinase protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/kinase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or kinase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of kinase binding or activity determined using standard techniques.

Other techniques for immobilizing proteins on matrices can also be used in the screening assays of the invention. For example, either kinase protein or its target molecule can be immobilized utilizing conjugation of biotin and streptavidin. Biotinylated kinase molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a kinase protein or target molecules but which do not interfere with binding of the kinase protein to its target molecule can be derivatized to the wells of the plate, and unbound target or kinase protein trapped in the wells by antibody conjugation. Methods for detecting such complexes, in addition to those described above for the GST-immobilized complexes, include immunodetection of complexes using antibodies reactive with the kinase protein or target molecule, as well as enzyme-linked assays that rely on detecting an enzymatic activity associated with the kinase protein or target molecule.

In another embodiment, modulators of kinase expression are identified in a method in which a cell is contacted with a candidate compound and the expression of kinase mRNA or protein in the cell is determined relative to expression of kinase mRNA or protein in a cell in the absence of the candidate compound. When expression is greater (statistically significantly greater) in the presence of the candidate compound than in its absence, the candidate compound is identified as a stimulator of kinase mRNA or protein expression. Alternatively, when expression is less (statistically significantly less) in the presence of the candidate compound than in its absence, the candidate compound is identified as an inhibitor of kinase mRNA or protein expression. The level of kinase mRNA or protein expression in the cells can be determined by methods described herein for detecting kinase mRNA or protein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Bio/Techniques* 14:920-924; Iwabuchi et al. (1993) *Oncogene* 8:1693-1696; and PCT Publication No. WO 94/10300), to identify other proteins, which bind to or interact with kinase protein ("kinase-binding proteins" or "kinase-bp") and modulate kinase activity. Such kinase-binding proteins are also likely to be involved in the propagation of signals by the kinase proteins as, for example, upstream or downstream elements of a signaling pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial kinase gene sequences of the invention can be used to map their respective kinase genes on a chromosome, thereby facilitating the location of gene regions associated with genetic disease. Computer analysis of kinase sequences can be used to rapidly select PCR primers (preferably 15-25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the kinase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919-924). Somatic cell hybrids containing only fragments of human chromosomes can also be produced by using human chromosomes with translocations and deletions.

Other mapping strategies that can similarly be used to map a kinase sequence to its chromosome include in situ hybridization (described in Fan et al. (1990) *Proc. Natl. Acad. Sci. USA* 87:6223-27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783-787.

Moreover, differences in the DNA sequences between individuals affected and unaffected with a disease associated with the kinase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the kinase sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The kinase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequence of SEQ ID NOS:1, 4, 7, 10, 13, or 16 can comfortably provide positive individual identification with a panel of perhaps 10 to 1,000 primers that each yield a noncoding amplified sequence of 100 bases. If predicted coding sequences, such as in SEQ ID NOS:1, 3, 4, 6, 7, 9, 10, 12, 13, 15, 16 or 18 are used, a more appropriate number of primers for positive individual identification would be 500 to 2,000.

3. Use of Partial Kinase Sequences in Forensic Biology

DNA-based identification techniques can also be used in forensic biology. In this manner, PCR technology can be used to amplify DNA sequences taken from very small biological samples such as tissues, e.g., hair, skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to a noncoding region of SEQ ID NOS:1, 4, 7, 10, 13, or 16 are particularly appropriate for this use as greater numbers of polymorphisms occur in the noncoding region, making it easier to differentiate individuals using this technique. Examples of polynucleotide reagents include the kinase sequence or portions thereof, e.g., fragments derived from a noncoding region of SEQ ID NOS:1, 4, 7, 10, 13, or 16 having a length of at least 20 or 30 bases.

The kinase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such kinase probes, can be used to identify tissue by species and/or by organ type.

In a similar fashion, these reagents, e.g., kinase primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting kinase protein and/or nucleic acid expression as well as kinase activity, in the context of a biological sample. An exemplary method for detecting the presence or absence of kinase proteins in a biological sample involves obtaining a biological sample from a test subject and contacting the biological sample with a compound or an agent capable of detecting kinase protein or nucleic acid (e.g., mRNA, genomic DNA) that encodes kinase protein such that the presence of kinase protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting kinase mRNA or genomic DNA is a labeled nucleic acid probe capable of hybridizing to kinase mRNA or genomic DNA. The nucleic acid probe can be, for example, a full-length or partial kinase nucleic acid, such as a nucleic acid of SEQ ID NOS: 1, 3, 4, 6, 7, 9, 10, 12, 13, 15, 16, 18, or a portion thereof, such as a nucleic acid molecule of at least 15, 30, 50, 100, 250, or 500 nucleotides in length and sufficient to specifically hybridize under stringent conditions to kinase mRNA or genomic DNA. Other suitable probes for use in the diagnostic assays of the invention are described herein.

A preferred agent for detecting kinase protein is an antibody capable of binding to kinase protein, preferably an antibody with a detectable label. Antibodies can be polyclonal, or more preferably, monoclonal. An intact antibody, or a fragment thereof (e.g., Fab or F(abN)$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect kinase mRNA, protein, or genomic DNA in a biological sample in vitro as well as in vivo. For example, in vitro techniques for detection of kinase mRNA include Northern hybridizations and in situ hybridizations. In vitro techniques for detection of kinase protein include enzyme linked immunosorbent assays (ELISAs), Western blots, immunoprecipitations, and immunofluorescence. In vitro techniques for detection of kinase genomic DNA include Southern hybridizations. Furthermore, in vivo techniques for detection of kinase protein include introducing into a subject a labeled anti-kinase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Biological samples may be obtained from blood, serum, cells, or tissue of a subject.

The invention also encompasses kits for detecting the presence of kinase proteins in a biological sample (a test sample). Such kits can be used to determine if a subject is suffering from or is at increased risk of developing a disorder associated with aberrant expression of kinase protein. For example, the kit can comprise a labeled compound or agent capable of detecting kinase protein or mRNA in a biological sample and means for determining the amount of a kinase protein in the sample (e.g., an anti-kinase antibody or an oligonucleotide probe that binds to DNA encoding a kinase protein, e.g., SEQ ID NOS: 1, 3, 4, 6, 7, 9, 10, 12, 13, 15, 16 or 18). Kits can also include instructions for observing that the tested subject is suffering from or is at risk of developing a disorder associated with aberrant expression of kinase sequences if the amount of kinase protein or mRNA is above or below a normal level.

For antibody-based kits, the kit can comprise, for example: (1) a first antibody (e.g., attached to a solid support) that binds to kinase protein; and, optionally, (2) a second, different antibody that binds to kinase protein or the first antibody and is conjugated to a detectable agent. For oligonucleotide-based kits, the kit can comprise, for example: (1) an oligonucleotide, e.g., a detectably labeled oligonucleotide, that hybridizes to a kinase nucleic acid sequence or (2) a pair of primers useful for amplifying a kinase nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of kinase proteins.

2. Prognostic Assays

The methods described herein can furthermore be utilized as diagnostic or prognostic assays to identify subjects having or at risk of developing a disease or disorder associated with kinase protein, kinase nucleic acid expression, or kinase activity. Prognostic assays can be used for prognostic or predictive purposes to thereby prophylactically treat an individual prior to the onset of a disorder characterized by or associated with kinase protein, kinase nucleic acid expression, or kinase activity.

Thus, the present invention provides a method in which a test sample is obtained from a subject, and kinase protein or nucleic acid (e.g., mRNA, genomic DNA) is detected, wherein the presence of kinase protein or nucleic acid is diagnostic for a subject having or at risk of developing a disease or disorder associated with aberrant kinase expression or activity. As used herein, a "test sample" refers to a biological sample obtained from a subject of interest. For example, a test sample can be a biological fluid cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease kinase activity) to effectively treat a disease or disorder associated with aberrant kinase expression or activity. In this manner, a test sample is obtained and kinase protein or nucleic acid is detected. The presence of kinase protein or nucleic acid is diagnostic for a subject that can be administered the agent to treat a disorder associated with aberrant kinase expression or activity.

The methods of the invention can also be used to detect genetic lesions or mutations in a kinase gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a kinase-protein, or the misexpression of the kinase gene. For example, such genetic lesions or mutations can be detected by ascertaining the existence of at least one of: (1) a deletion of one or more nucleotides from a kinase gene; (2) an addition of one or more nucleotides to a kinase gene; (3) a substitution of one or more nucleotides of a kinase gene; (4) a chromosomal rearrangement of a kinase gene; (5) an alteration in the level of a messenger RNA transcript of a kinase gene; (6) an aberrant modification of a kinase gene, such as of the methylation pattern of the genomic DNA; (7) the presence of a non-wild-type splicing pattern of a messenger RNA transcript of a kinase gene; (8) a non-wild-type level of a kinase-protein; (9) an allelic loss of a kinase gene; and (10) an inappropriate post-translational modification of a kinase-protein. As described herein, there are a large number of assay techniques known in the art that can be used for detecting lesions in a kinase gene. Any cell type or tissue in which kinase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the kinase-gene (see, e.g., Abravaya et al. (1995) *Nucleic Acids Res.* 23:675-682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a kinase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a kinase molecule can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). In yet another embodiment, any of a variety of sequencing reactions known in the art can be used to directly sequence the kinase gene and detect mutations by comparing the sequence of the sample kinase gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the kinase gene include methods in which protection from cleavage agents is used to detect mismatched bases in RNA/RNA or RNA/DNA heteroduplexes (Myers et al. (1985) *Science* 230: 1242). See, also Cotton et al. (1988) *Proc. Natl. Acad. Sci. USA* 85:4397; Saleeba et al. (1992) *Methods Enzymol.*

217:286-295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in kinase cDNAs obtained from samples of cells. See, e.g., Hsu et al. (1994) *Carcinogenesis* 15:1657-1662. According to an exemplary embodiment, a probe based on a kinase sequence, e.g., a wild-type kinase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in kinase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125-144; Hayashi (1992) *Genet. Anal. Tech. Appl.* 9:73-79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437-2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is antici-pated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a kinase gene.

3. Pharmacogenomics

Agents or modulators that have a stimulatory or inhibitory effect on kinase activity (e.g., kinase gene expression) as identified by a screening assay described herein, can be administered to individuals to treat (prophylactically or therapeutically) disorders associated with aberrant kinase activity as well as to modulate the cellular growth, differentiation and/or metabolism. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of kinase protein, expression of kinase nucleic acid, or mutation content of kinase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of kinase protein, expression of kinase nucleic acid, or mutation content of kinase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a kinase modulator, such as a modulator identified by one of the exemplary screening assays described herein.

4. Monitoring of Effects During Clinical Trials

Monitoring the influence of agents (e.g., drugs, compounds) on the expression or activity of kinase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease kinase gene expression, protein levels, or protein activity, can be monitored in clinical trials of subjects exhibiting decreased or increased kinase gene expression, protein levels, or protein activity. In such clinical trials, kinase expression or activity and preferably that of other genes that have been implicated in for example, a cellular proliferation disorder, can be used as a marker of cellular growth and differentiation.

For example, and not by way of limitation, genes that are modulated in cells by treatment with an agent (e.g., compound, drug, or small molecule) that modulates kinase activity (e.g., as identified in a screening assay described herein) can be identified. Thus, to study the effect of agents on cellular proliferation disorders, for example, in a clinical trial, cells can be isolated and RNA prepared and analyzed for the levels of expression of kinase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of kinase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a kinase protein, mRNA, or genomic DNA in the preadministration sample; (3) obtaining one or more postadministration samples from the subject; (4) detecting the level of expression or activity of the kinase protein, mRNA, or genomic DNA in the postadministration samples; (5) comparing the level of expression or activity of the kinase protein, mRNA, or genomic DNA in the preadministration sample with the kinase protein, mRNA, or genomic DNA in the postadministration sample or samples; and (vi) altering the administration of the agent to the subject accordingly to bring about the desired effect, i.e., for example, an increase or a decrease in the expression or activity of a kinase protein.

C. Methods of Treatment

The present invention provides for both prophylactic and therapeutic methods of treating a subject at risk of (or susceptible to) a disorder or having a disorder associated with aberrant kinase expression or activity. "Subject", as used herein, can refer to a mammal, e.g., a human, or to an experimental or animal or disease model. The subject can also be a non-human animal, e.g., a horse, cow, goat, or other domestic animal. Additionally, the compositions of the invention find use in the treatment of disorders described herein.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides.

1. Prophylactic Methods

In one aspect, the invention provides a method for preventing in a subject a disease or condition associated with an aberrant kinase expression or activity by administering to the subject an agent that modulates kinase expression or at least one kinase gene activity. Subjects at risk for a disease that is caused, or contributed to, by aberrant kinase expression or activity can be identified by, for example, any or a combination of diagnostic or prognostic assays as described herein. Administration of a prophylactic agent can occur prior to the manifestation of symptoms characteristic of the kinase aberrancy, such that a disease or disorder is prevented or, alternatively, delayed in its progression. Depending on the type of kinase aberrancy, for example, a kinase agonist or kinase antagonist agent can be used for treating the subject. The appropriate agent can be determined based on screening assays described herein.

2. Therapeutic Methods

Another aspect of the invention pertains to methods of modulating kinase expression or activity for therapeutic purposes. The modulatory method of the invention involves contacting a cell with an agent that modulates one or more of the activities of kinase protein activity associated with the cell. An agent that modulates kinase protein activity can be an agent as described herein, such as a nucleic acid or a protein, a naturally-occurring cognate ligand of a kinase protein, a peptide, a kinase peptidomimetic, or other small molecule. In one embodiment, the agent stimulates one or more of the biological activities of kinase protein. Examples of such stimulatory agents include active kinase protein and a nucleic acid molecule encoding a kinase protein that has been introduced into the cell. In another embodiment, the agent inhibits one or more of the biological activities of kinase protein. Examples of such inhibitory agents include antisense kinase nucleic acid molecules and anti-kinase antibodies.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a kinase protein or nucleic acid molecule. In one embodiment, the method involves administering an agent (e.g., an agent identified by a screening assay described herein), or a combination of agents, that modulates (e.g., upregulates or downregulates) kinase expression or activity. In another embodiment, the method involves administering a kinase protein or nucleic acid molecule as therapy to compensate for reduced or aberrant kinase expression or activity.

Stimulation of kinase activity is desirable in situations in which a kinase protein is abnormally downregulated and/or in which increased kinase activity is likely to have a beneficial effect. Conversely, inhibition of kinase activity is desirable in situations in which kinase activity is abnormally upregulated and/or in which decreased kinase activity is likely to have a beneficial effect.

EXPERIMENTAL

Example 1

Recombinant Expression of Kinase Sequences in Bacterial Cells

In this example, the kinase sequence is expressed as a recombinant glutathione-S-transferase (GST) fusion polypeptide in *E. coli* and the fusion polypeptide is isolated and characterized. Specifically, the kinase sequence is fused to GST and this fusion polypeptide is expressed in *E. coli*, e.g., strain PEB 199. Expression of the GST-kinase fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 2

Expression of Recombinant Kinase Protein in COS Cells

To express the kinase gene in COS cells, the pCDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire kinase protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the kinase DNA sequence is amplified by PCR using two primers. The 5' primer contains the restriction site of interest followed by approximately twenty nucleotides of the kinase coding sequence starting from the initiation codon; the 3' end sequence contains complementary sequences to the other restriction site of interest, a translation stop codon, the HA tag or FLAG tag and the last 20 nucleotides of the kinase coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the kinase gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the kinase-pCDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the kinase polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the kinase coding sequence is cloned directly into the polylinker of the pCDNA/Amp vector using the appropriate restriction sites. The resulting plasmid is transfected into COS cells in the manner described above, and the expression of the kinase polypeptide is detected by radiolabelling and immunoprecipitation using a kinase specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 32

<210> SEQ ID NO 1
<211> LENGTH: 3003
<212> TYPE: DNA
<213> ORGANISM: Homo sapiens
<220> FEATURE:
<221> NAME/KEY: CDS
<222> LOCATION: (52)...(2688)

<400> SEQUENCE: 1

```
ggctgctcgc ggaggggcag tgtacgcggg gccgctgtag gctgtccagc g atg gat      57
                                                          Met Asp
                                                            1 ccc acc gcg gga agc aag aag gag cct gga gga ggc gcg gcg act gag      105
Pro Thr Ala Gly Ser Lys Lys Glu Pro Gly Gly Gly Ala Ala Thr Glu
        5                  10                  15 gag ggc gtg aat agg atc gca gtg cca aaa ccg ccc tcc att gag gaa      153
Glu Gly Val Asn Arg Ile Ala Val Pro Lys Pro Pro Ser Ile Glu Glu
 20                  25                  30 ttc agc ata gtg aag ccc att agc cgg ggc gcc ttc ggg aaa gtg tat      201
Phe Ser Ile Val Lys Pro Ile Ser Arg Gly Ala Phe Gly Lys Val Tyr
 35                  40                  45                  50 ctg ggg cag aaa ggc ggc aaa ttg tat gca gta aag gtt gtt aaa aaa      249
Leu Gly Gln Lys Gly Gly Lys Leu Tyr Ala Val Lys Val Val Lys Lys
                 55                  60                  65 gca gac atg atc aac aaa aat atg act cat cag gtc caa gct gag aga      297
Ala Asp Met Ile Asn Lys Asn Met Thr His Gln Val Gln Ala Glu Arg
             70                  75                  80 gat gca ctg gca cta agc aaa agc cca ttc att gtc cat ttg tat tat      345
Asp Ala Leu Ala Leu Ser Lys Ser Pro Phe Ile Val His Leu Tyr Tyr
         85                  90                  95 tca ctg cag tct gca aac aat gtc tac ttg gta atg gaa tat ctt att      393
Ser Leu Gln Ser Ala Asn Asn Val Tyr Leu Val Met Glu Tyr Leu Ile
    100                 105                 110 ggg gga gat gtc aag tct ctc cta cat ata tat ggt tat ttt gat gaa      441
Gly Gly Asp Val Lys Ser Leu Leu His Ile Tyr Gly Tyr Phe Asp Glu
115                 120                 125                 130 gag atg gct gtg aaa tat att tct gaa gta gca ctg gct cta gac tac      489
Glu Met Ala Val Lys Tyr Ile Ser Glu Val Ala Leu Ala Leu Asp Tyr
                135                 140                 145 ctt cac aga cat gga atc atc cac agg gac ttg aaa ccg gac aat atg      537
Leu His Arg His Gly Ile Ile His Arg Asp Leu Lys Pro Asp Asn Met
            150                 155                 160 ctt att tct aat gag ggt cat att aaa ctg acg gat ttt ggc ctt tca      585
Leu Ile Ser Asn Glu Gly His Ile Lys Leu Thr Asp Phe Gly Leu Ser
        165                 170                 175 aaa gtt act ttg aat aga gat att aat atg atg gat atc ctt aca aca      633
Lys Val Thr Leu Asn Arg Asp Ile Asn Met Met Asp Ile Leu Thr Thr
    180                 185                 190 cca tca atg gca aaa cct aga caa gat tat tca aga acc cca gga caa      681
Pro Ser Met Ala Lys Pro Arg Gln Asp Tyr Ser Arg Thr Pro Gly Gln
195                 200                 205                 210 gtg tta tcg ctt atc agc tcg ttg gga ttt aac aca cca att gca gaa      729
Val Leu Ser Leu Ile Ser Ser Leu Gly Phe Asn Thr Pro Ile Ala Glu
                215                 220                 225 aaa aat caa gac cct gca aac atc ctt tca gcc tgt ctg tct gaa aca      777
Lys Asn Gln Asp Pro Ala Asn Ile Leu Ser Ala Cys Leu Ser Glu Thr
            230                 235                 240
```

```
tca cag ctt tct caa gga ctc gta tgc cct atg tct gta gat caa aag    825
Ser Gln Leu Ser Gln Gly Leu Val Cys Pro Met Ser Val Asp Gln Lys
        245             250             255 gac act acg cct tat tct agc aaa tta cta aaa tca tgt ctt gaa aca    873
Asp Thr Thr Pro Tyr Ser Ser Lys Leu Leu Lys Ser Cys Leu Glu Thr
260             265             270 gtt gcc tcc aac cca gga atg cct gtg aag tgt cta act tct aat tta    921
Val Ala Ser Asn Pro Gly Met Pro Val Lys Cys Leu Thr Ser Asn Leu
275             280             285             290 ctc cag tct agg aaa agg ctg gcc aca tcc agt gcc agt agt caa tcc    969
Leu Gln Ser Arg Lys Arg Leu Ala Thr Ser Ser Ala Ser Ser Gln Ser
            295             300             305 cac acc ttc ata tcc agt gtg gaa tca gaa tgc cac agc agt ccc aaa   1017
His Thr Phe Ile Ser Ser Val Glu Ser Glu Cys His Ser Ser Pro Lys
                310             315             320 tgg gaa aaa gat tgc cag gaa agt gat gaa gca ttg ggc cca aca atg   1065
Trp Glu Lys Asp Cys Gln Glu Ser Asp Glu Ala Leu Gly Pro Thr Met
        325             330             335 atg agt tgg aat gca gtt gaa aag tta tgc gca aaa tct gca aat gcc   1113
Met Ser Trp Asn Ala Val Glu Lys Leu Cys Ala Lys Ser Ala Asn Ala
        340             345             350 att gag acg aaa ggt ttc aat aaa aag gat ctg gag tta gct ctt tct   1161
Ile Glu Thr Lys Gly Phe Asn Lys Lys Asp Leu Glu Leu Ala Leu Ser
355             360             365             370 ccc att cat aac agc agt gcc ctt ccc acc act gga cgc tct tgt gta   1209
Pro Ile His Asn Ser Ser Ala Leu Pro Thr Thr Gly Arg Ser Cys Val
            375             380             385 aac ctt gct aaa aaa tgc ttc tct ggg gaa gtt tct tgg gaa gca gta   1257
Asn Leu Ala Lys Lys Cys Phe Ser Gly Glu Val Ser Trp Glu Ala Val
            390             395             400 gaa ctg gat gta aat aat ata aat atg gac act gac aca agt cag tta   1305
Glu Leu Asp Val Asn Asn Ile Asn Met Asp Thr Asp Thr Ser Gln Leu
        405             410             415 ggt ttc cat cag tca aat cag tgg gct gtg gat tct ggt ggg ata tct   1353
Gly Phe His Gln Ser Asn Gln Trp Ala Val Asp Ser Gly Gly Ile Ser
        420             425             430 gaa gag cac ctt ggg aaa aga agt tta aaa aga aat ttt gag ttg gtt   1401
Glu Glu His Leu Gly Lys Arg Ser Leu Lys Arg Asn Phe Glu Leu Val
435             440             445             450 gac tcc agt cct tgt aaa aaa att ata cag aat aaa aaa act tgt gta   1449
Asp Ser Ser Pro Cys Lys Lys Ile Ile Gln Asn Lys Lys Thr Cys Val
            455             460             465 gag tat aag cat aac gaa atg aca aat tgt tat aca aat caa aat aca   1497
Glu Tyr Lys His Asn Glu Met Thr Asn Cys Tyr Thr Asn Gln Asn Thr
            470             475             480 ggc tta aca gtt gaa gtg cag gac ctt aag cta tca gtg cac aaa agt   1545
Gly Leu Thr Val Glu Val Gln Asp Leu Lys Leu Ser Val His Lys Ser
        485             490             495 caa caa aat gac tgt gct aat aag gag aac att gtc aat tct ttt act   1593
Gln Gln Asn Asp Cys Ala Asn Lys Glu Asn Ile Val Asn Ser Phe Thr
500             505             510 gat aaa caa caa aca cca gaa aaa tta cct ata cca atg ata gca aaa   1641
Asp Lys Gln Gln Thr Pro Glu Lys Leu Pro Ile Pro Met Ile Ala Lys
515             520             525             530 aac ctt atg tgt gaa ctc gat gaa gac tgt gaa aag aat agt aag agg   1689
Asn Leu Met Cys Glu Leu Asp Glu Asp Cys Glu Lys Asn Ser Lys Arg
            535             540             545 gac tac tta agt tct agt ttt cta tgt tct gat gat gat aga gct tct   1737
Asp Tyr Leu Ser Ser Ser Phe Leu Cys Ser Asp Asp Asp Arg Ala Ser
        550             555             560
```

```
aaa aat att tct atg aac tct gat tca tct ttt cct gga att tct ata      1785
Lys Asn Ile Ser Met Asn Ser Asp Ser Ser Phe Pro Gly Ile Ser Ile
            565                 570                 575 atg gaa agt cca tta gaa agt cag ccc tta gat tca gat aga agc att      1833
Met Glu Ser Pro Leu Glu Ser Gln Pro Leu Asp Ser Asp Arg Ser Ile
580                 585                 590 aaa gaa tcc tct ttt gaa gaa tca aat att gaa gat cca ctt att gta      1881
Lys Glu Ser Ser Phe Glu Glu Ser Asn Ile Glu Asp Pro Leu Ile Val
595                 600                 605                 610 aca cca gat tgc caa gaa aag acc tca cca aaa ggt gtc gag aac cct      1929
Thr Pro Asp Cys Gln Glu Lys Thr Ser Pro Lys Gly Val Glu Asn Pro
                615                 620                 625 gct gta caa gag agt aac caa aaa atg tta ggt cct cct ttg gag gtg      1977
Ala Val Gln Glu Ser Asn Gln Lys Met Leu Gly Pro Pro Leu Glu Val
            630                 635                 640 ctg aaa acg tta gcc tct aaa aga aat gct gtt gct ttt cga agt ttt      2025
Leu Lys Thr Leu Ala Ser Lys Arg Asn Ala Val Ala Phe Arg Ser Phe
        645                 650                 655 aac agt cat att aat gca tcc aat aac tca gaa cca tcc aga atg aac      2073
Asn Ser His Ile Asn Ala Ser Asn Asn Ser Glu Pro Ser Arg Met Asn
    660                 665                 670 atg act tct tta gat gca atg gat att tcg tgt gcc tac agt ggt tca      2121
Met Thr Ser Leu Asp Ala Met Asp Ile Ser Cys Ala Tyr Ser Gly Ser
675                 680                 685                 690 tat ccc atg gct ata acc cct act caa aaa aga aga tcc tgt atg cca      2169
Tyr Pro Met Ala Ile Thr Pro Thr Gln Lys Arg Arg Ser Cys Met Pro
                695                 700                 705 cat cag cag acc cca aat cag atc aag tcg gga act cca tac cga act      2217
His Gln Gln Thr Pro Asn Gln Ile Lys Ser Gly Thr Pro Tyr Arg Thr
            710                 715                 720 ccg aag agt gtg aga aga ggg gtg gcc ccc gtt gat gat ggg cga att      2265
Pro Lys Ser Val Arg Arg Gly Val Ala Pro Val Asp Asp Gly Arg Ile
        725                 730                 735 cta gga acc cca gac tac ctt gca cct gag ctg tta cta ggc agg gcc      2313
Leu Gly Thr Pro Asp Tyr Leu Ala Pro Glu Leu Leu Leu Gly Arg Ala
    740                 745                 750 cat ggt cct gcg gta gac tgg tgg gca ctt gga gtt tgc ttg ttt gaa      2361
His Gly Pro Ala Val Asp Trp Trp Ala Leu Gly Val Cys Leu Phe Glu
755                 760                 765                 770 ttt cta aca gga att ccc cct ttc aat gat gaa aca cca caa caa gta      2409
Phe Leu Thr Gly Ile Pro Pro Phe Asn Asp Glu Thr Pro Gln Gln Val
                775                 780                 785 ttc cag aat att ctg aaa aga gat atc cct tgg cca gaa ggt gaa gaa      2457
Phe Gln Asn Ile Leu Lys Arg Asp Ile Pro Trp Pro Glu Gly Glu Glu
            790                 795                 800 aag tta tct gat aat gct caa agt gca gta gaa ata ctt tta acc att      2505
Lys Leu Ser Asp Asn Ala Gln Ser Ala Val Glu Ile Leu Leu Thr Ile
        805                 810                 815 gat gat aca aag aga gct gga atg aaa gag cta aaa cgt cat cct ctc      2553
Asp Asp Thr Lys Arg Ala Gly Met Lys Glu Leu Lys Arg His Pro Leu
    820                 825                 830 ttc agt gat gtg gac tgg gaa aat ctg cag cat cag act atg cct ttc      2601
Phe Ser Asp Val Asp Trp Glu Asn Leu Gln His Gln Thr Met Pro Phe
835                 840                 845                 850 atc ccc cag cca gat gat gaa aca gat acc tcc tat ttt gaa gcc agg      2649
Ile Pro Gln Pro Asp Asp Glu Thr Asp Thr Ser Tyr Phe Glu Ala Arg
                855                 860                 865 aat act gct cag cac ctg acc gta tct gga ttt agt ctg tagcacaaaa      2698
Asn Thr Ala Gln His Leu Thr Val Ser Gly Phe Ser Leu
```

```
                 870             875
attttcctttt tagtctagcc tcgtgttata gaatgaactt gcataattat atactcctta    2758
atactagatt gatctaaggg ggaaagatca ttatttaacc tagttcaatg tgcttttaat    2818
gtacgttaca gctttcacag agttaaaagg ctgaaaggaa tatagtcagt aatttatctt    2878
aacctcaaaa ctgtatataa atcttcaaag cttttttcat ctatttattt tgtttattgc    2938
actttatgaa aactgaagca tcaataaaat tagaggacac tattgaaaaa aaaaaaaaa     2998 aaaaa                                                                3003

<210> SEQ ID NO 2
<211> LENGTH: 879
<212> TYPE: PRT
<213> ORGANISM: Homo sapiens

<400> SEQUENCE: 2

Met Asp Pro Thr Ala Gly Ser Lys Lys Glu Pro Gly Gly Ala Ala
 1               5                  10                  15

Thr Glu Glu Gly Val Asn Arg Ile Ala Val Pro Lys Pro Ser Ile
                20                  25                  30

Glu Glu Phe Ser Ile Val Lys Pro Ile Ser Arg Gly Ala Phe Gly Lys
                35                  40                  45

Val Tyr Leu Gly Gln Lys Gly Gly Lys Leu Tyr Ala Val Lys Val Val
 50                  55                  60

Lys Lys Ala Asp Met Ile Asn Lys Asn Met Thr His Gln Val Gln Ala
 65                  70                  75                  80

Glu Arg Asp Ala Leu Ala Leu Ser Lys Ser Pro Phe Ile Val His Leu
                85                  90                  95

Tyr Tyr Ser Leu Gln Ser Ala Asn Asn Val Tyr Leu Val Met Glu Tyr
                100                 105                 110

Leu Ile Gly Gly Asp Val Lys Ser Leu Leu His Ile Tyr Gly Tyr Phe
                115                 120                 125

Asp Glu Glu Met Ala Val Lys Tyr Ile Ser Glu Val Ala Leu Ala Leu
 130                 135                 140

Asp Tyr Leu His Arg His Gly Ile Ile His Arg Asp Leu Lys Pro Asp
145                  150                 155                 160

Asn Met Leu Ile Ser Asn Glu Gly His Ile Lys Leu Thr Asp Phe Gly
                165                 170                 175

Leu Ser Lys Val Thr Leu Asn Arg Asp Ile Asn Met Met Asp Ile Leu
                180                 185                 190

Thr Thr Pro Ser Met Ala Lys Pro Arg Gln Asp Tyr Ser Arg Thr Pro
                195                 200                 205

Gly Gln Val Leu Ser Leu Ile Ser Ser Leu Gly Phe Asn Thr Pro Ile
 210                 215                 220

Ala Glu Lys Asn Gln Asp Pro Ala Asn Ile Leu Ser Ala Cys Leu Ser
225                  230                 235                 240

Glu Thr Ser Gln Leu Ser Gln Gly Leu Val Cys Pro Met Ser Val Asp
                245                 250                 255

Gln Lys Asp Thr Thr Pro Tyr Ser Ser Lys Leu Leu Lys Ser Cys Leu
                260                 265                 270

Glu Thr Val Ala Ser Asn Pro Gly Met Pro Val Lys Cys Leu Thr Ser
                275                 280                 285

Asn Leu Leu Gln Ser Arg Lys Arg Leu Ala Thr Ser Ser Ala Ser Ser
 290                 295                 300
```

-continued

```
Gln Ser His Thr Phe Ile Ser Ser Val Glu Ser Glu Cys His Ser Ser
305                 310                 315                 320

Pro Lys Trp Glu Lys Asp Cys Gln Glu Ser Asp Glu Ala Leu Gly Pro
            325                 330                 335

Thr Met Met Ser Trp Asn Ala Val Glu Lys Leu Cys Ala Lys Ser Ala
            340                 345                 350

Asn Ala Ile Glu Thr Lys Gly Phe Asn Lys Lys Asp Leu Glu Leu Ala
            355                 360                 365

Leu Ser Pro Ile His Asn Ser Ser Ala Leu Pro Thr Thr Gly Arg Ser
            370                 375                 380

Cys Val Asn Leu Ala Lys Lys Cys Phe Ser Gly Glu Val Ser Trp Glu
385                 390                 395                 400

Ala Val Glu Leu Asp Val Asn Asn Ile Asn Met Asp Thr Asp Thr Ser
                405                 410                 415

Gln Leu Gly Phe His Gln Ser Asn Gln Trp Ala Val Asp Ser Gly Gly
            420                 425                 430

Ile Ser Glu Glu His Leu Gly Lys Arg Ser Leu Lys Arg Asn Phe Glu
            435                 440                 445

Leu Val Asp Ser Ser Pro Cys Lys Lys Ile Ile Gln Asn Lys Lys Thr
            450                 455                 460

Cys Val Glu Tyr Lys His Asn Glu Met Thr Asn Cys Tyr Thr Asn Gln
465                 470                 475                 480

Asn Thr Gly Leu Thr Val Glu Val Gln Asp Leu Lys Leu Ser Val His
            485                 490                 495

Lys Ser Gln Gln Asn Asp Cys Ala Asn Lys Glu Asn Ile Val Asn Ser
            500                 505                 510

Phe Thr Asp Lys Gln Gln Thr Pro Glu Lys Leu Pro Ile Pro Met Ile
            515                 520                 525

Ala Lys Asn Leu Met Cys Glu Leu Asp Glu Asp Cys Glu Lys Asn Ser
            530                 535                 540

Lys Arg Asp Tyr Leu Ser Ser Phe Leu Cys Ser Asp Asp Asp Arg
545                 550                 555                 560

Ala Ser Lys Asn Ile Ser Met Asn Ser Asp Ser Ser Phe Pro Gly Ile
            565                 570                 575

Ser Ile Met Glu Ser Pro Leu Glu Ser Gln Pro Leu Asp Ser Asp Arg
            580                 585                 590

Ser Ile Lys Glu Ser Ser Phe Glu Glu Ser Asn Ile Glu Asp Pro Leu
            595                 600                 605

Ile Val Thr Pro Asp Cys Gln Glu Lys Thr Ser Pro Lys Gly Val Glu
            610                 615                 620

Asn Pro Ala Val Gln Glu Ser Asn Gln Lys Met Leu Gly Pro Pro Leu
625                 630                 635                 640

Glu Val Leu Lys Thr Leu Ala Ser Lys Arg Asn Ala Val Ala Phe Arg
            645                 650                 655

Ser Phe Asn Ser His Ile Asn Ala Ser Asn Asn Ser Glu Pro Ser Arg
            660                 665                 670

Met Asn Met Thr Ser Leu Asp Ala Met Asp Ile Ser Cys Ala Tyr Ser
            675                 680                 685

Gly Ser Tyr Pro Met Ala Ile Thr Pro Thr Gln Lys Arg Arg Ser Cys
            690                 695                 700

Met Pro His Gln Gln Thr Pro Asn Gln Ile Lys Ser Gly Thr Pro Tyr
705                 710                 715                 720

Arg Thr Pro Lys Ser Val Arg Arg Gly Val Ala Pro Val Asp Asp Gly
```

```
                725                 730                 735
Arg Ile Leu Gly Thr Pro Asp Tyr Leu Ala Pro Glu Leu Leu Gly
            740                 745                 750

Arg Ala His Gly Pro Ala Val Asp Trp Trp Ala Leu Gly Val Cys Leu
            755                 760                 765

Phe Glu Phe Leu Thr Gly Ile Pro Pro Phe Asn Asp Glu Thr Pro Gln
            770                 775                 780

Gln Val Phe Gln Asn Ile Leu Lys Arg Asp Ile Pro Trp Pro Glu Gly
785                 790                 795                 800

Glu Glu Lys Leu Ser Asp Asn Ala Gln Ser Ala Val Glu Ile Leu Leu
                805                 810                 815

Thr Ile Asp Asp Thr Lys Arg Ala Gly Met Lys Glu Leu Lys Arg His
                820                 825                 830

Pro Leu Phe Ser Asp Val Asp Trp Glu Asn Leu Gln His Gln Thr Met
            835                 840                 845

Pro Phe Ile Pro Gln Pro Asp Asp Glu Thr Asp Thr Ser Tyr Phe Glu
        850                 855                 860

Ala Arg Asn Thr Ala Gln His Leu Thr Val Ser Gly Phe Ser Leu
865                 870                 875
```

<210> SEQ ID NO 3
<211> LENGTH: 2637
<212> TYPE: DNA
<213> ORGANISM: Homo sapiens

<400> SEQUENCE: 3

```
atggatccca ccgcgggaag caagaaggag cctggaggag gcgcggcgac tgaggagggc      60
gtgaatagga tcgcagtgcc aaaaccgccc tccattgagg aattcagcat agtgaagccc     120
attagccggg gcgccttcgg gaaagtgtat ctggggcaga aggcggcaa attgtatgca      180
gtaaaggttg ttaaaaaagc agacatgatc aacaaaaata tgactcatca ggtccaagct     240
gagagagatg cactggcact aagcaaaagc ccattcattg tccatttgta ttattcactg     300
cagtctgcaa acaatgtcta cttggtaatg aatatcttg ttgggggaga tgtcaagtct      360
ctcctacata tatatggtta ttttgatgaa gagatggctg tgaaatatat tcctgaagta     420
gcactggctc tagactacct tcacagacat ggaatcatcc acagggactt gaaaccggac     480
aatatgctta tttctaatga gggtcatatt aaactgacgg attttggcct tcaaaagtt     540
actttgaata gagatattaa tatgatggat atccttacaa caccatcaat ggcaaaacct     600
agacaagatt attcaagaac cccaggacaa gtgttatcgc ttatcagctc gttgggattt     660
aacacaccaa ttgcagaaaa aaatcaagac cctgcaaaca tcctttcagc ctgtctgtct     720
gaaacatcac agctttctca aggactcgta tgccctatgt ctgtagatca aaaggacact     780
acgcctatt ctagcaaatt actaaaatca tgtcttgaaa cagttgcctc caacccagga     840
atgcctgtga agtgtctaac ttctaattta ctccagtcta ggaaaaggct ggccacatcc     900
agtgccagta gtcaatccca caccttcata tccagtgtgg aatcagaatg ccacagcagt     960
cccaaatggg aaaaagattg ccaggaaagt gatgaagcat gggcccaac aatgatgagt    1020
tggaatgcag ttgaaaagtt atgcgcaaaa tctgcaaatg ccattgagac gaaaggttc     1080
aataaaaagg atctggagtt agctctttct cccattcata cagcagtgc ccttcccacc     1140
actggacgct cttgtgtaaa ccttgctaaa aaatgcttct ctgggaagt ttcttgggaa      1200
gcagtagaac tggatgtaaa taatataaat atggacactg acacaagtca gttaggtttc    1260
```

```
catcagtcaa atcagtgggc tgtggattct ggtgggatat ctgaagagca ccttgggaaa    1320
agaagtttaa aaagaaattt tgagttggtt gactccagtc cttgtaaaaa aattatacag    1380
aataaaaaaa cttgtgtaga gtataagcat aacgaaatga caattgtta tacaaatcaa     1440 aatacaggct taacagttga agtgcaggac cttaagctat cagtgcacaa aagtcaacaa    1500
aatgactgtg ctaataagga gaacattgtc aattcttta ctgataaaca acaaacacca    1560
gaaaaattac ctataccaat gatagcaaaa accttatgt gtgaactcga tgaagactgt    1620
gaaaagaata gtaagaggga ctacttaagt tctagttttc tatgttctga tgatgataga   1680
gcttctaaaa atatttctat gaactctgat tcatcttttc ctggaatttc tataatggaa   1740
agtccattag aaagtcagcc cttagattca gatagaagca ttaaagaatc ctctttttgaa  1800 gaatcaaata ttgaagatcc acttattgta acaccagatt gccaagaaaa gacctcacca   1860
aaaggtgtcg agaaccctgc tgtacaagag agtaaccaaa aaatgttagg tcctcctttg   1920
gaggtgctga aaacgttagc ctctaaaaga aatgctgttg cttttcgaag ttttaacagt   1980
catattaatg catccaataa ctcagaacca tccagaatga acatgacttc tttagatgca   2040
atggatattt cgtgtgccta cagtggttca tatcccatgg ctataacccc tactcaaaaa   2100
agaagatcct gtatgccaca tcagcagacc ccaaatcaga tcaagtcggg aactccatac   2160
cgaactccga agagtgtgag aagaggggtg gcccccgttg atgatgggcg aattctagga   2220
accccagact accttgcacc tgagctgtta ctaggcaggg cccatggtcc tgcggtagac   2280
tggtgggcac ttggagtttg cttgtttgaa tttctaacag gaattccccc tttcaatgat   2340
gaaacaccac aacaagtatt ccagaatatt ctgaaaagag atatcccttg ccagaaggt    2400 gaagaaaagt tatctgataa tgctcaaagt gcagtagaaa acttttttaac cattgatgat   2460 acaaagagag ctggaatgaa agagctaaaa cgtcatcctc tcttcagtga tgtggactgg   2520
gaaaatctgc agcatcagac tatgcctttc atccccaagc cagatgatga acagatacc    2580 tcctattttg aagccaggaa tactgctcag cacctgaccg tatctggatt tagtctg      2637
```

<210> SEQ ID NO 4
<211> LENGTH: 5983
<212> TYPE: DNA
<213> ORGANISM: Homo sapiens
<220> FEATURE:
<221> NAME/KEY: CDS
<222> LOCATION: (115)...(3723)

<400> SEQUENCE: 4

```
gggcccgcgg gccgcctgct gcctccgccc gcgccgggt ccccagccgc cccgctgcc     60 gtgtcccctg cggccggcca gccgcgtccc ccagccccgg cctcccgcgg acc atg     117
                                                               Met
                                                                1 ccc gcc cgt atc ggc tac tac gag atc gac cgc acc atc ggc aag ggc    165
Pro Ala Arg Ile Gly Tyr Tyr Glu Ile Asp Arg Thr Ile Gly Lys Gly
                5                  10                  15 aac ttc gcg gtg gtc aag cgg gcc acg cac ctc gtc acc aag gcc aag    213
Asn Phe Ala Val Val Lys Arg Ala Thr His Leu Val Thr Lys Ala Lys
             20                  25                  30 gtt gct atc aag atc ata gat aag acc cag ctg gat gaa gaa aac ttg    261
Val Ala Ile Lys Ile Ile Asp Lys Thr Gln Leu Asp Glu Glu Asn Leu
         35                  40                  45 aag aag att ttc cgg gaa gtt caa att atg aag atg ctt tgc cac ccc    309
Lys Lys Ile Phe Arg Glu Val Gln Ile Met Lys Met Leu Cys His Pro
     50                  55                  60                  65
```

-continued

| | |
|---|---|
| cat atc atc agg ctc tac cag gtt atg gag aca gaa cgg atg att tat<br>His Ile Ile Arg Leu Tyr Gln Val Met Glu Thr Glu Arg Met Ile Tyr<br>                70                         75                        80 | 357 |
| ctg gtg aca gaa tat gct agt gga ggg gaa ata ttt gac cac ctg gtg<br>Leu Val Thr Glu Tyr Ala Ser Gly Gly Glu Ile Phe Asp His Leu Val<br>             85                         90                        95 | 405 |
| gcc cat ggt aga atg gca gaa aag gag gca cgt cgg aag ttc aaa cag<br>Ala His Gly Arg Met Ala Glu Lys Glu Ala Arg Arg Lys Phe Lys Gln<br>100                        105                      110 | 453 |
| atc gtc aca gct gtc tat ttt tgt cac tgt cgg aac att gtt cat cgt<br>Ile Val Thr Ala Val Tyr Phe Cys His Cys Arg Asn Ile Val His Arg<br>        115                      120                      125 | 501 |
| gat tta aaa gct gaa aat tta ctt ctg gat gcc aat ctg aat atc aaa<br>Asp Leu Lys Ala Glu Asn Leu Leu Leu Asp Ala Asn Leu Asn Ile Lys<br>130                        135                      140                  145 | 549 |
| ata gca gat ttt ggt ttc agt aac ctc ttc act cct ggg cag ctg ctg<br>Ile Ala Asp Phe Gly Phe Ser Asn Leu Phe Thr Pro Gly Gln Leu Leu<br>                150                      155                      160 | 597 |
| aag acc tgg tgt ggc agc cct ccc tat gct gca cct gaa ctc ttt gaa<br>Lys Thr Trp Cys Gly Ser Pro Pro Tyr Ala Ala Pro Glu Leu Phe Glu<br>              165                      170                      175 | 645 |
| gga aaa gaa tat gat ggg ccc aaa gtg gac atc tgg agc ctt gga gtt<br>Gly Lys Glu Tyr Asp Gly Pro Lys Val Asp Ile Trp Ser Leu Gly Val<br>180                        185                      190 | 693 |
| gtc ctc tac gtg ctt gtg tgc ggt gcc ctg cca ttt gat gga agc aca<br>Val Leu Tyr Val Leu Val Cys Gly Ala Leu Pro Phe Asp Gly Ser Thr<br>        195                      200                      205 | 741 |
| ctg cag aat ctg cgg gcc cgc gtg ctg agt gga aag ttc cgc atc cca<br>Leu Gln Asn Leu Arg Ala Arg Val Leu Ser Gly Lys Phe Arg Ile Pro<br>210                        215                      220                  225 | 789 |
| ttt ttt atg tcc aca gaa tgt gag cat ttg atc cgc cat atg ttg gtg<br>Phe Phe Met Ser Thr Glu Cys Glu His Leu Ile Arg His Met Leu Val<br>                230                      235                      240 | 837 |
| tta gat ccc aat aag cgc ctc tcc atg gag cag atc tgc aag cac aag<br>Leu Asp Pro Asn Lys Arg Leu Ser Met Glu Gln Ile Cys Lys His Lys<br>              245                      250                      255 | 885 |
| tgg atg aag cta ggg gac gcc gat ccc aac ttt gac agg tta ata gct<br>Trp Met Lys Leu Gly Asp Ala Asp Pro Asn Phe Asp Arg Leu Ile Ala<br>        260                      265                      270 | 933 |
| gaa tgc caa caa cta aag gaa gaa aga cag gtg gac ccc ctg aat gag<br>Glu Cys Gln Gln Leu Lys Glu Glu Arg Gln Val Asp Pro Leu Asn Glu<br>275                        280                      285 | 981 |
| gat gtc ctc ttg gcc atg gag gac atg gga ctg gac aaa gaa cag aca<br>Asp Val Leu Leu Ala Met Glu Asp Met Gly Leu Asp Lys Glu Gln Thr<br>290                        295                      300                  305 | 1029 |
| ctg cag gcg gag cag gca ggt act gct atg aac atc agc gtt ccc cag<br>Leu Gln Ala Glu Gln Ala Gly Thr Ala Met Asn Ile Ser Val Pro Gln<br>                310                      315                      320 | 1077 |
| gtg cag ctg atc aac cca gag aac caa att gtg gag ccg gat ggg aca<br>Val Gln Leu Ile Asn Pro Glu Asn Gln Ile Val Glu Pro Asp Gly Thr<br>        325                      330                      335 | 1125 |
| ctg aat ttg gac agt gat gag ggt gaa gag cct tcc cct gaa gca ttg<br>Leu Asn Leu Asp Ser Asp Glu Gly Glu Glu Pro Ser Pro Glu Ala Leu<br>340                        345                      350 | 1173 |
| gtg cgc tat ttg tca atg agg agg cac aca gtg ggt gtg gct gac cca<br>Val Arg Tyr Leu Ser Met Arg Arg His Thr Val Gly Val Ala Asp Pro<br>        355                      360                      365 | 1221 |
| cgc acg gaa gtt atg gaa gat ctg cag aag ctc cta cct ggc ttt cct<br>Arg Thr Glu Val Met Glu Asp Leu Gln Lys Leu Leu Pro Gly Phe Pro<br>370                        375                      380                  385 | 1269 |

| | | |
|---|---|---|
| gga gtc aac ccc cag gct cca ttc ctg cag gtg gcc cct aat gtg aac<br>Gly Val Asn Pro Gln Ala Pro Phe Leu Gln Val Ala Pro Asn Val Asn<br>390 395 400 | 1317 |
| ttc atg cac aac ctg ttg cct atg caa aac ttg caa cca acc ggg caa<br>Phe Met His Asn Leu Leu Pro Met Gln Asn Leu Gln Pro Thr Gly Gln<br>405 410 415 | 1365 |
| ctt gag tac aag gag cag tct ctc cta cag ccg ccc acg cta cag ctg<br>Leu Glu Tyr Lys Glu Gln Ser Leu Leu Gln Pro Pro Thr Leu Gln Leu<br>420 425 430 | 1413 |
| ttg aat gga atg ggc ccc ctt ggc cgg agg gca tca gat gga gga gcc<br>Leu Asn Gly Met Gly Pro Leu Gly Arg Arg Ala Ser Asp Gly Gly Ala<br>435 440 445 | 1461 |
| aac atc caa ctg cat gcc cag cag ctg ctg aag cgc cca cgg gga ccc<br>Asn Ile Gln Leu His Ala Gln Gln Leu Leu Lys Arg Pro Arg Gly Pro<br>450 455 460 465 | 1509 |
| tct ccg ctt gtc acc atg aca cca gca gtg cca gca gtt acc cct gtg<br>Ser Pro Leu Val Thr Met Thr Pro Ala Val Pro Ala Val Thr Pro Val<br>470 475 480 | 1557 |
| gac gag gag agc tca gac ggg gag cca gac cag gaa gct gtg cag agg<br>Asp Glu Glu Ser Ser Asp Gly Glu Pro Asp Gln Glu Ala Val Gln Arg<br>485 490 495 | 1605 |
| tac ttg gca aat agg tcc aaa aga cat aca ctg gcc atg acc aac cct<br>Tyr Leu Ala Asn Arg Ser Lys Arg His Thr Leu Ala Met Thr Asn Pro<br>500 505 510 | 1653 |
| aca gct gag atc cca ccg gac cta caa cgg cag cta gga cag cag cct<br>Thr Ala Glu Ile Pro Pro Asp Leu Gln Arg Gln Leu Gly Gln Gln Pro<br>515 520 525 | 1701 |
| ttc cgt tcc cgg gtc tgg cct cct cac ctg gta cct gat cag cat cgc<br>Phe Arg Ser Arg Val Trp Pro Pro His Leu Val Pro Asp Gln His Arg<br>530 535 540 545 | 1749 |
| tct acc tac aag gac tcc aac act ctg cac ctc cct acg gag cgt ttc<br>Ser Thr Tyr Lys Asp Ser Asn Thr Leu His Leu Pro Thr Glu Arg Phe<br>550 555 560 | 1797 |
| tcc cct gtg cgc cgg ttc tca gat ggg gct gcg agc atc cag gcc ttc<br>Ser Pro Val Arg Arg Phe Ser Asp Gly Ala Ala Ser Ile Gln Ala Phe<br>565 570 575 | 1845 |
| aaa gct cac ctg gaa aaa atg ggc aac aac agc agc atc aaa cag ctg<br>Lys Ala His Leu Glu Lys Met Gly Asn Asn Ser Ser Ile Lys Gln Leu<br>580 585 590 | 1893 |
| cag cag gag tgt gag cag ctg cag aag atg tac ggg ggg cag att gat<br>Gln Gln Glu Cys Glu Gln Leu Gln Lys Met Tyr Gly Gly Gln Ile Asp<br>595 600 605 | 1941 |
| gaa aga acc ctg gag aag acc cag cag cag cat atg tta tac cag cag<br>Glu Arg Thr Leu Glu Lys Thr Gln Gln Gln His Met Leu Tyr Gln Gln<br>610 615 620 625 | 1989 |
| gag cag cac cat caa att ctc cag caa caa att caa gac tct atc tgt<br>Glu Gln His His Gln Ile Leu Gln Gln Gln Ile Gln Asp Ser Ile Cys<br>630 635 640 | 2037 |
| cct cct cag cca tct cca cct ctt cag gct gca tgt gaa aat cag cca<br>Pro Pro Gln Pro Ser Pro Pro Leu Gln Ala Ala Cys Glu Asn Gln Pro<br>645 650 655 | 2085 |
| gcc ctc ctt acc cat cag ctc cag agg tta agg att cag cct tca agc<br>Ala Leu Leu Thr His Gln Leu Gln Arg Leu Arg Ile Gln Pro Ser Ser<br>660 665 670 | 2133 |
| cca ccc ccc aac cac ccc aac aac cat ctc ttc agg cag ccc agt aat<br>Pro Pro Pro Asn His Pro Asn Asn His Leu Phe Arg Gln Pro Ser Asn<br>675 680 685 | 2181 |
| agt cct ccc ccc atg agc agt gcc atg atc cag cct cac ggg gct gca<br>Ser Pro Pro Pro Met Ser Ser Ala Met Ile Gln Pro His Gly Ala Ala | 2229 |

-continued

```
                690                 695                 700                 705
tct tct tcc cag ttt caa ggc tta cct tcc cgc agt gca atc ttt cag         2277
Ser Ser Ser Gln Phe Gln Gly Leu Pro Ser Arg Ser Ala Ile Phe Gln
                        710                 715                 720 cag caa cct gag aac tgt tcc tct cct ccc aac gtg gca cta acc tgc         2325
Gln Gln Pro Glu Asn Cys Ser Ser Pro Pro Asn Val Ala Leu Thr Cys
                725                 730                 735 ttg ggt atg cag cag cct gct cag tca cag cag gtc acc atc caa gtc         2373
Leu Gly Met Gln Gln Pro Ala Gln Ser Gln Gln Val Thr Ile Gln Val
            740                 745                 750 caa gag cct gtt gac atg ctc agc aac atg cca ggc aca gct gca ggc         2421
Gln Glu Pro Val Asp Met Leu Ser Asn Met Pro Gly Thr Ala Ala Gly
        755                 760                 765 tcc agt ggg cgc ggc atc tcc atc agc ccc agt gct ggt cag atg cag         2469
Ser Ser Gly Arg Gly Ile Ser Ile Ser Pro Ser Ala Gly Gln Met Gln
770                 775                 780                 785 atg cag cac cgt acc aac ctg atg gcc acc ctc agc tat ggg cac cgt         2517
Met Gln His Arg Thr Asn Leu Met Ala Thr Leu Ser Tyr Gly His Arg
                790                 795                 800 ccc ttg tcc aag cag ctg agt gct gac agt gca gag gct cac agt gca         2565
Pro Leu Ser Lys Gln Leu Ser Ala Asp Ser Ala Glu Ala His Ser Ala
                805                 810                 815 cat cag cag ccg cca cac tat acc acg tcg gca cta cag cag gcc ctg         2613
His Gln Gln Pro Pro His Tyr Thr Thr Ser Ala Leu Gln Gln Ala Leu
            820                 825                 830 ctg tct ccc acg ccg cca gac tat aca aga cac cag cag gta ccc cac         2661
Leu Ser Pro Thr Pro Pro Asp Tyr Thr Arg His Gln Gln Val Pro His
        835                 840                 845 atc ctt caa gga ctg ctt tct ccc cgg cat tcg ctc acc ggc cac tcg         2709
Ile Leu Gln Gly Leu Leu Ser Pro Arg His Ser Leu Thr Gly His Ser
850                 855                 860                 865 gac atc cgg ctg ccc cca aca gag ttt gca cag ctc att aaa agg cag         2757
Asp Ile Arg Leu Pro Pro Thr Glu Phe Ala Gln Leu Ile Lys Arg Gln
                870                 875                 880 cag caa caa cgg cag cag cag cag caa cag cag caa cag caa gaa tac         2805
Gln Gln Gln Arg Gln Gln Gln Gln Gln Gln Gln Gln Gln Gln Glu Tyr
                885                 890                 895 cag gaa ctg ttc agg cac atg aac caa ggg gat gcg ggg agt ctg gct         2853
Gln Glu Leu Phe Arg His Met Asn Gln Gly Asp Ala Gly Ser Leu Ala
            900                 905                 910 ccc agc ctt ggg gga cag agc atg aca gag cgc cag gct tta tct tat         2901
Pro Ser Leu Gly Gly Gln Ser Met Thr Glu Arg Gln Ala Leu Ser Tyr
        915                 920                 925 caa aat gct gac tct tat cac cat cac acc agc ccc cag cat ctg cta         2949
Gln Asn Ala Asp Ser Tyr His His His Thr Ser Pro Gln His Leu Leu
930                 935                 940                 945 caa atc agg gca caa gaa tgt gtc tca cag gct tcc tca ccc acc ccg         2997
Gln Ile Arg Ala Gln Glu Cys Val Ser Gln Ala Ser Ser Pro Thr Pro
                950                 955                 960 ccc cac ggg tat gct cac cag ccg gca ctg atg cat tca gag agc atg         3045
Pro His Gly Tyr Ala His Gln Pro Ala Leu Met His Ser Glu Ser Met
                965                 970                 975 gag gag gac tgc tcg tgt gag ggg gcc aag gat ggc ttc caa gac agt         3093
Glu Glu Asp Cys Ser Cys Glu Gly Ala Lys Asp Gly Phe Gln Asp Ser
            980                 985                 990 aag agt tca agt aca ttg acc aaa ggt tgc cat gac agc cct ctg ctc         3141
Lys Ser Ser Ser Thr Leu Thr Lys Gly Cys His Asp Ser Pro Leu Leu
        995                 1000                1005 ttg agt acc ggt gga cct ggg gac cct gaa tct ttg cta gga act gtg         3189
```

```
Leu Ser Thr Gly Gly Pro Gly Asp Pro Glu Ser Leu Gly Thr Val
1010                1015                1020                1025 agt cat gcc caa gaa ttg ggg ata cat ccc tat ggt cat cag cca act    3237
Ser His Ala Gln Glu Leu Gly Ile His Pro Tyr Gly His Gln Pro Thr
                1030                1035                1040 gct gca ttc agt aaa aat aag gtg ccc agc aga gag cct gtc ata ggg    3285
Ala Ala Phe Ser Lys Asn Lys Val Pro Ser Arg Glu Pro Val Ile Gly
            1045                1050                1055 aac tgc atg gat aga agt tct cca gga caa gca gtg gag ctg ccg gat    3333
Asn Cys Met Asp Arg Ser Ser Pro Gly Gln Ala Val Glu Leu Pro Asp
        1060                1065                1070 cac aat ggg ctc ggg tac cca gca cgc ccc tcc gtc cat gag cac cac    3381
His Asn Gly Leu Gly Tyr Pro Ala Arg Pro Ser Val His Glu His His
    1075                1080                1085 agg ccc cgg gcc ctc cag aga cac cac acg atc cag aac agc gac gat    3429
Arg Pro Arg Ala Leu Gln Arg His His Thr Ile Gln Asn Ser Asp Asp
1090                1095                1100                1105 gct tat gta cag ctg gat aac ttg cca gga atg agt ctc gtg gct ggg    3477
Ala Tyr Val Gln Leu Asp Asn Leu Pro Gly Met Ser Leu Val Ala Gly
                1110                1115                1120 aaa gca ctt agc tct gcc cgg atg tcg gat gca gtt ctc agt cag tct    3525
Lys Ala Leu Ser Ser Ala Arg Met Ser Asp Ala Val Leu Ser Gln Ser
            1125                1130                1135 tcg ctc atg ggc agc cag cag ttt cag gat ggg gaa aat gag gaa tgt    3573
Ser Leu Met Gly Ser Gln Gln Phe Gln Asp Gly Glu Asn Glu Glu Cys
        1140                1145                1150 ggg gca agc ctg gga ggt cat gag cac cca gac ctg agt gat ggc agc    3621
Gly Ala Ser Leu Gly Gly His Glu His Pro Asp Leu Ser Asp Gly Ser
    1155                1160                1165 cag cat tta aac tcc tct tgc tat cca tct acg tgt att aca gac att    3669
Gln His Leu Asn Ser Ser Cys Tyr Pro Ser Thr Cys Ile Thr Asp Ile
1170                1175                1180                1185 ctg ctc agc tac aag cac ccc gaa gtc tcc ttc agc atg gag cag gca    3717
Leu Leu Ser Tyr Lys His Pro Glu Val Ser Phe Ser Met Glu Gln Ala
                1190                1195                1200 ggc gtg taacaagaaa cagagagttt tgtgtacagc ttgggaatga aaggttgat     3773
Gly Val tgtaaaccca cagtatctag cagcgttgtg ccaaattgcc cttgtgtttc tctccaccca  3833
aaatatcaca gctgctttcc tcacatttgg ttcatccgtg tgctgttctt ttgggttctg  3893
agagggtttt gccatgtttg cttgtatgac caagtcacca aggaaataaa caggaaggaa  3953
atccatgttc tccatctttt gtgaaagtat atttgagttg gtggtttttt gttttgtttg  4013
ggggtttgtg ttttgttttg ttttttggtat gttttcttcc agaggtgata tactttcttt  4073
tttttcttcc tttcttttttt ttctttcgtt ccttttttga aacaggagag caaagcagtt  4133
agagttcaga ggccagcggc ctcagggcca ctccctccct agccttcatc agcagagcac  4193
cctccatccc cctgcattgc tcttctgtga agcaaatac taaggatgc catcctctgg    4253 aatcctaatg gcaggcaaag ggagagagga agggtgacgg cttctggcac ttagaaaaca  4313 aaagaacaa aaaagagaa accccaagc ctggaacgca gagaggtctt tactgctggg    4373
atccacggaa aacatgtctg tcctagccaa gatcatatga agagtttggc acggaggctg  4433
agaatgacct ggcatagatg gtttgccagt taggatgtct caatttgagc ctttgctttt  4493
ggtggataac tcagctcccc tcttgtaacc tggaaagttg gttgccttta tcatcctgct  4553
ggttttatcc atggactgaa cacccaacag cagtgcacta tgctttctat ggcatctttc  4613
attctcattt tatattgtgc tataaaaagg attgtttctc catatatata ttatatatgt  4673
```

```
gtgtatatat ataatataat atatgtgtat atatatatta tatatataat atataatata    4733
tatattatat atatattata tatataaat atatataaaa tatatatata tatgctctcc     4793
tctttcagcc tctttgtcac agggaagaag tgtaggaggt tgccttgggc cctgcctctc    4853
tcctaacctc ctcttcccca ctgggtaccc tcagcccta  tattttaatt cttgatcatg    4913
tagaaattgt ttttggtaaa tgttgatatt attgttatta tcattattaa taaataaaga    4973
gaaaaggaat ttttgtttaa atgagaaatg tttaaccaga ttctgttcta tttgaattgt    5033
gacttgcacc ttttgttcaa agtatttcct ttaggcattg taattgtgaa cagctcttac    5093
ttgtgccagt gacagatgca gtggtctcct ttccccagtt gaagcagtgc atacgcagta    5153
gctattattt gtgttatctt tatttctctt cattgttaga aaccaaagtc ttctctgctg    5213 gctgggctg  agagagggtc tgggttatct ccttctgatc ttcaaaacaa gagagagacc    5273
ttgaatacac tgactcttcc acccttttt  tttctgggaa aggagagcaa gaggtcccga    5333 gtccctcct  agtctttcat cctgaatttg cacagaggaa agcgggtgcc cggcatggcc    5393
atcctgatgt tgctggcggg atccccatgc accttgtcct tctccactga tactggcagc    5453
tcggctcctg gacccaagat cccttgagtg gaattctgca gtgcaagagc ccttcgtggg    5513
agctgtccca tgtttccatg gtccccagtc tccctccac  ttggtggggt caccaactac    5573
tcaccagaag ggggcttacc aagaaagccc taaaaagctg ttgacttatc tgcgcttgtt    5633
ccaactctta tgcccccaac ctgccctacc accaccacgc gctcagcctg atgtgtttac    5693
atggtactgt atgtatggga gagcagactg caccctccag caacaacaga tgaaagccag    5753
tgagcctact aaccgtgcca tcttgcaaac tacactttaa aaaaaactca ttgctttgta    5813
ttgtagtaac caatatgtgc agtatacgtt gaatgtatat gaacatactt tcctatttct    5873
gttctttgaa aatgtcagaa atattttttt ctttctcatt ttatgttgaa ctaaaaagga    5933
ttaaaaaaaa aatctccaga aaaaaaaaaa aaaaagggc ggccgctaga              5983
```

<210> SEQ ID NO 5  
<211> LENGTH: 1203  
<212> TYPE: PRT  
<213> ORGANISM: Homo sapiens

<400> SEQUENCE: 5

```
Met Pro Ala Arg Ile Gly Tyr Tyr Glu Ile Asp Arg Thr Ile Gly Lys
  1               5                  10                  15

Gly Asn Phe Ala Val Val Lys Arg Ala Thr His Leu Val Thr Lys Ala
             20                  25                  30

Lys Val Ala Ile Lys Ile Ile Asp Lys Thr Gln Leu Asp Glu Glu Asn
         35                  40                  45

Leu Lys Lys Ile Phe Arg Glu Val Gln Ile Met Lys Met Leu Cys His
     50                  55                  60

Pro His Ile Ile Arg Leu Tyr Gln Val Met Glu Thr Glu Arg Met Ile
 65                  70                  75                  80

Tyr Leu Val Thr Glu Tyr Ala Ser Gly Gly Glu Ile Phe Asp His Leu
                 85                  90                  95

Val Ala His Gly Arg Met Ala Glu Lys Glu Ala Arg Lys Phe Lys
            100                 105                 110

Gln Ile Val Thr Ala Val Tyr Phe Cys His Cys Arg Asn Ile Val His
        115                 120                 125

Arg Asp Leu Lys Ala Glu Asn Leu Leu Leu Asp Ala Asn Leu Asn Ile
    130                 135                 140
```

-continued

```
Lys Ile Ala Asp Phe Gly Phe Ser Asn Leu Phe Thr Pro Gly Gln Leu
145                 150                 155                 160

Leu Lys Thr Trp Cys Gly Ser Pro Tyr Ala Ala Pro Glu Leu Phe
            165                 170                 175

Glu Gly Lys Glu Tyr Asp Gly Pro Lys Val Asp Ile Trp Ser Leu Gly
                180                 185                 190

Val Val Leu Tyr Val Leu Val Cys Gly Ala Leu Pro Phe Asp Gly Ser
                195                 200                 205

Thr Leu Gln Asn Leu Arg Ala Arg Val Leu Ser Gly Lys Phe Arg Ile
        210                 215                 220

Pro Phe Phe Met Ser Thr Glu Cys Glu His Leu Ile Arg His Met Leu
225                 230                 235                 240

Val Leu Asp Pro Asn Lys Arg Leu Ser Met Glu Gln Ile Cys Lys His
                    245                 250                 255

Lys Trp Met Lys Leu Gly Asp Ala Asp Pro Asn Phe Asp Arg Leu Ile
            260                 265                 270

Ala Glu Cys Gln Gln Leu Lys Glu Glu Arg Gln Val Asp Pro Leu Asn
                275                 280                 285

Glu Asp Val Leu Leu Ala Met Glu Asp Met Gly Leu Asp Lys Glu Gln
        290                 295                 300

Thr Leu Gln Ala Glu Gln Ala Gly Thr Ala Met Asn Ile Ser Val Pro
305                 310                 315                 320

Gln Val Gln Leu Ile Asn Pro Glu Asn Gln Ile Val Glu Pro Asp Gly
                    325                 330                 335

Thr Leu Asn Leu Asp Ser Asp Glu Gly Glu Glu Pro Ser Pro Glu Ala
            340                 345                 350

Leu Val Arg Tyr Leu Ser Met Arg Arg His Thr Val Gly Val Ala Asp
                355                 360                 365

Pro Arg Thr Glu Val Met Glu Asp Leu Gln Lys Leu Leu Pro Gly Phe
        370                 375                 380

Pro Gly Val Asn Pro Gln Ala Pro Phe Leu Gln Val Ala Pro Asn Val
385                 390                 395                 400

Asn Phe Met His Asn Leu Leu Pro Met Gln Asn Leu Gln Pro Thr Gly
                    405                 410                 415

Gln Leu Glu Tyr Lys Glu Gln Ser Leu Leu Gln Pro Pro Thr Leu Gln
            420                 425                 430

Leu Leu Asn Gly Met Gly Pro Leu Gly Arg Arg Ala Ser Asp Gly Gly
                435                 440                 445

Ala Asn Ile Gln Leu His Ala Gln Gln Leu Leu Lys Arg Pro Arg Gly
        450                 455                 460

Pro Ser Pro Leu Val Thr Met Thr Pro Ala Val Pro Ala Val Thr Pro
465                 470                 475                 480

Val Asp Glu Glu Ser Ser Asp Gly Glu Pro Asp Gln Glu Ala Val Gln
                    485                 490                 495

Arg Tyr Leu Ala Asn Arg Ser Lys Arg His Thr Leu Ala Met Thr Asn
            500                 505                 510

Pro Thr Ala Glu Ile Pro Pro Asp Leu Gln Arg Gln Leu Gly Gln Gln
                515                 520                 525

Pro Phe Arg Ser Arg Val Trp Pro Pro His Leu Val Pro Asp Gln His
        530                 535                 540

Arg Ser Thr Tyr Lys Asp Ser Asn Thr Leu His Leu Pro Thr Glu Arg
545                 550                 555                 560
```

-continued

```
Phe Ser Pro Val Arg Arg Phe Ser Asp Gly Ala Ala Ser Ile Gln Ala
                565                 570                 575
Phe Lys Ala His Leu Glu Lys Met Gly Asn Asn Ser Ser Ile Lys Gln
                580                 585                 590
Leu Gln Gln Glu Cys Glu Gln Leu Gln Lys Met Tyr Gly Gly Gln Ile
                595                 600                 605
Asp Glu Arg Thr Leu Glu Lys Thr Gln Gln His Met Leu Tyr Gln
610                 615                 620
Gln Glu Gln His His Gln Ile Leu Gln Gln Ile Gln Asp Ser Ile
625                 630                 635                 640
Cys Pro Pro Gln Pro Ser Pro Leu Gln Ala Ala Cys Glu Asn Gln
                645                 650                 655
Pro Ala Leu Leu Thr His Gln Leu Gln Arg Leu Arg Ile Gln Pro Ser
                660                 665                 670
Ser Pro Pro Asn His Pro Asn Asn His Leu Phe Arg Gln Pro Ser
                675                 680                 685
Asn Ser Pro Pro Pro Met Ser Ser Ala Met Ile Gln Pro His Gly Ala
                690                 695                 700
Ala Ser Ser Ser Gln Phe Gln Gly Leu Pro Ser Arg Ser Ala Ile Phe
705                 710                 715                 720
Gln Gln Gln Pro Glu Asn Cys Ser Ser Pro Pro Asn Val Ala Leu Thr
                725                 730                 735
Cys Leu Gly Met Gln Gln Pro Ala Gln Ser Gln Gln Val Thr Ile Gln
                740                 745                 750
Val Gln Glu Pro Val Asp Met Leu Ser Asn Met Pro Gly Thr Ala Ala
                755                 760                 765
Gly Ser Ser Gly Arg Gly Ile Ser Ile Ser Pro Ser Ala Gly Gln Met
                770                 775                 780
Gln Met Gln His Arg Thr Asn Leu Met Ala Thr Leu Ser Tyr Gly His
785                 790                 795                 800
Arg Pro Leu Ser Lys Gln Leu Ser Ala Asp Ser Ala Glu Ala His Ser
                805                 810                 815
Ala His Gln Gln Pro Pro His Tyr Thr Thr Ser Ala Leu Gln Gln Ala
                820                 825                 830
Leu Leu Ser Pro Thr Pro Pro Asp Tyr Thr Arg His Gln Gln Val Pro
                835                 840                 845
His Ile Leu Gln Gly Leu Leu Ser Pro Arg His Ser Leu Thr Gly His
                850                 855                 860
Ser Asp Ile Arg Leu Pro Pro Thr Glu Phe Ala Gln Leu Ile Lys Arg
865                 870                 875                 880
Gln Gln Gln Gln Arg Gln Gln Gln Gln Gln Gln Gln Gln Glu
                885                 890                 895
Tyr Gln Glu Leu Phe Arg His Met Asn Gln Gly Asp Ala Gly Ser Leu
                900                 905                 910
Ala Pro Ser Leu Gly Gly Gln Ser Met Thr Glu Arg Gln Ala Leu Ser
                915                 920                 925
Tyr Gln Asn Ala Asp Ser Tyr His His His Thr Ser Pro Gln His Leu
                930                 935                 940
Leu Gln Ile Arg Ala Gln Glu Cys Val Ser Gln Ala Ser Ser Pro Thr
945                 950                 955                 960
Pro Pro His Gly Tyr Ala His Gln Pro Ala Leu Met His Ser Glu Ser
                965                 970                 975
Met Glu Glu Asp Cys Ser Cys Glu Gly Ala Lys Asp Gly Phe Gln Asp
```

```
                 980              985              990
Ser Lys Ser Ser Ser Thr Leu Thr Lys Gly Cys His Asp Ser Pro Leu
            995              1000             1005

Leu Leu Ser Thr Gly Gly Pro Gly Asp Pro Glu Ser Leu Leu Gly Thr
        1010             1015             1020

Val Ser His Ala Gln Glu Leu Gly Ile His Pro Tyr Gly His Gln Pro
1025             1030             1035             1040

Thr Ala Ala Phe Ser Lys Asn Lys Val Pro Ser Arg Glu Pro Val Ile
            1045             1050             1055

Gly Asn Cys Met Asp Arg Ser Ser Pro Gly Gln Ala Val Glu Leu Pro
        1060             1065             1070

Asp His Asn Gly Leu Gly Tyr Pro Ala Arg Pro Ser Val His Glu His
            1075             1080             1085

His Arg Pro Arg Ala Leu Gln Arg His His Thr Ile Gln Asn Ser Asp
        1090             1095             1100

Asp Ala Tyr Val Gln Leu Asp Asn Leu Pro Gly Met Ser Leu Val Ala
1105             1110             1115             1120

Gly Lys Ala Leu Ser Ser Ala Arg Met Ser Asp Ala Val Leu Ser Gln
            1125             1130             1135

Ser Ser Leu Met Gly Ser Gln Gln Phe Gln Asp Gly Glu Asn Glu Glu
        1140             1145             1150

Cys Gly Ala Ser Leu Gly Gly His Glu His Pro Asp Leu Ser Asp Gly
            1155             1160             1165

Ser Gln His Leu Asn Ser Ser Cys Tyr Pro Ser Thr Cys Ile Thr Asp
        1170             1175             1180

Ile Leu Leu Ser Tyr Lys His Pro Glu Val Ser Phe Ser Met Glu Gln
1185             1190             1195             1200

Ala Gly Val

<210> SEQ ID NO 6
<211> LENGTH: 3609
<212> TYPE: DNA
<213> ORGANISM: Homo sapiens

<400> SEQUENCE: 6
atgcccgccc gtatcggcta ctacgagatc gaccgcacca tcggcaaggg caacttcgcg    60
gtggtcaagc gggccacgca cctcgtcacc aaggccaagg ttgctatcaa gatcatagat   120
aagacccagc tggatgaaga aaacttgaag aagattttcc gggaagttca aattatgaag   180
atgctttgcc accccatat catcaggctc taccaggtta tggagacaga acggatgatt   240
tatctggtga cagaatatgc tagtggaggg gaaatatttg accacctggt ggcccatggt   300
agaatggcag aaaaggaggc acgtcggaag ttcaaacaga tcgtcacagc tgtctatttt   360
tgtcactgtc ggaacattgt tcatcgtgat ttaaaagctg aaaatttact tctgatgcc    420
aatctgaata tcaaaatagc agattttggt ttcagtaacc tcttcactcc tgggcagctg   480
ctgaagacct ggtgtggcag ccctccctat gctgcacctg aactctttga aggaaaagaa   540
tatgatgggc caaagtgga catctggagc cttggagttg tcctctacgt gcttgtgtgc   600
ggtgccctgc catttgatgg aagcacactg cagaatctgc gggcccgcgt gctgagtgga   660
aagttccgca tcccattttt tatgtccaca gaatgtgagc atttgatccg ccatatgttg   720
gtgttagatc ccaataagcg cctctccatg gagcagatct gcaagcacaa gtggatgaag   780
ctagggacg ccgatcccaa cttgacagg ttaatagctg aatgccaaca actaaaggaa   840
```

-continued

```
gaaagacagg tggaccccct gaatgaggat gtcctcttgg ccatggagga catgggactg    900
gacaaagaac agacactgca ggcggagcag gcaggtactg ctatgaacat cagcgttccc    960
caggtgcagc tgatcaaccc agagaaccaa attgtggagc cggatgggac actgaatttg   1020
gacagtgatg agggtgaaga gccttcccct gaagcattgg tgcgctattt gtcaatgagg   1080
aggcacacag tgggtgtggc tgacccacgc acggaagtta tggaagatct gcagaagctc   1140
ctacctggct ttcctggagt caacccccag gctccattcc tgcaggtggc ccctaatgtg   1200
aacttcatgc acaacctgtt gcctatgcaa aacttgcaac caaccgggca acttgagtac   1260
aaggagcagt ctctcctaca gccgcccacg ctacagctgt tgaatggaat gggccccctt   1320
ggccggaggg catcagatgg aggagccaac atccaactgc atgcccagca gctgctgaag   1380
cgcccacggg gaccctctcc gcttgtcacc atgacaccag cagtgccagc agttacccct   1440
gtggacgagg agagctcaga cggggagcca gaccaggaag ctgtgcagag gtacttggca   1500
aataggtcca aaagacatac actggccatg accaacccta cagctgagat cccaccggac   1560
ctacaacggc agctaggaca gcagcctttc cgttcccggg tctggcctcc tcacctggta   1620
cctgatcagc atcgctctac ctacaaggac tccaacactc tgcacctccc tacggagcgt   1680
ttctcccctg tgcgccggtt ctcagatggg gctgcgagca tccaggcctt caaagctcac   1740
ctggaaaaaa tgggcaacaa cagcagcatc aaacagctgc agcaggagtg tgagcagctg   1800
cagaagatgt acgggggggca gattgatgaa agaaccctgg agaagaccca gcagcagcat   1860
atgttatacc agcaggagca gcaccatcaa attctccagc aacaaattca agactctatc   1920
tgtcctcctc agccatctcc acctcttcag gctgcatgtg aaaatcagcc agccctcctt   1980
acccatcagc tccagaggtt aaggattcag ccttcaagcc accccccaa ccaccccaac   2040
aaccatctct tcaggcagcc cagtaatagt cctcccccca tgagcagtgc catgatccag   2100
cctcacgggg ctgcatcttc ttcccagttt caaggcttac cttcccgcag tgcaatcttt   2160
cagcagcaac ctgagaactg ttcctctcct cccaacgtgg cactaacctg cttgggtatg   2220
cagcagcctg ctcagtcaca gcaggtcacc atccaagtcc aagagcctgt tgacatgctc   2280
agcaacatgc caggcacagc tgcaggctcc agtgggcgcg gcatctccat cagccccagt   2340
gctggtcaga tgcagatgca gcaccgtacc aacctgatgg ccaccctcag ctatgggcac   2400
cgtcccttgt ccaagcagct gagtgctgac agtgcagagg ctcacagtgc acatcagcag   2460
ccgccacact ataccacgtc ggcactacag caggccctgc tgtctcccac gccgccagac   2520
tatacaagac accagcaggt accccacatc cttcaaggac tgctttctcc ccggcattcg   2580
ctcaccggcc actcggacat ccggctgccc caacagagt ttgcacagct cattaaaagg   2640
cagcagcaac aacggcagca gcagcagcaa cagcagcaac agcaagaata ccaggaactg   2700
ttcaggcaca tgaaccaagg ggatgcgggg agtctggctc ccagccttgg gggacagagc   2760
atgacagagc gccaggcttt atcttatcaa aatgctgact cttatcacca tcacaccagc   2820
ccccagcatc tgctacaaat cagggcacaa gaatgtgtct cacaggcttc ctcacccacc   2880
ccgccccacg ggtatgctca ccagccggca ctgatgcatt cagagagcat ggaggaggac   2940
tgctcgtgtg aggggggccaa ggatggcttc caagacagta agagttcaag tacattgacc   3000
aaaggttgcc atgacagccc tctgctcttg agtaccggtg gacctgggga ccctgaatct   3060
ttgctaggaa ctgtgagtca tgcccaagaa ttggggatac atccctatgg tcatcagcca   3120
actgctgcat tcagtaaaaa taaggtgccc agcagagagc tgtcatagg gaactgcatg   3180
gatagaagtt ctccaggaca agcagtggag ctgccggatc acaatgggct cgggtaccca   3240
```

-continued

```
gcacgcccct ccgtccatga gcaccacagg ccccgggccc tccagagaca ccacacgatc    3300
cagaacagcg acgatgctta tgtacagctg gataacttgc caggaatgag tctcgtggct    3360
gggaaagcac ttagctctgc ccggatgtcg gatgcagttc tcagtcagtc ttcgctcatg    3420
ggcagccagc agtttcagga tggggaaaat gaggaatgtg gggcaagcct gggaggtcat    3480
gagcacccag acctgagtga tggcagccag catttaaact cctcttgcta tccatctacg    3540
tgtattacag acattctgct cagctacaag caccccgaag tctccttcag catggagcag    3600
gcaggcgtg                                                            3609
```

<210> SEQ ID NO 7
<211> LENGTH: 2389
<212> TYPE: DNA
<213> ORGANISM: Homo sapiens
<220> FEATURE:
<221> NAME/KEY: CDS
<222> LOCATION: (383)...(1456)

<400> SEQUENCE: 7

```
tccgcgaggg catcagacgg cggctgatta gctccggttt gcatcacccg gaccggggga     60
ttagctccgg tttgcatcac ccggaccggg ggattagctc cggtttgcat cacccggacc    120
gggggattag ctccggtttg catcacccgg accgggggat tagctccggt ttgcatcacc    180
cggaccgggg gccgggcgcg cacgagactc gcagcggaag tggaggcggc tccgcgcgcg    240
tccgctgcta ggacccgggc agggctggag ctgggctggg atcccgagct cggcagcagc    300
gcagcgggcc ggcccacctg ctggtgccct ggaggctctg agccccggcg gcgcccgggc    360
ccacgcggaa cgacggggcg ag atg cga gcc acc cct ctg gct gct cct gcg      412
                         Met Arg Ala Thr Pro Leu Ala Ala Pro Ala
                           1               5                  10 ggt tcc ctg tcc agg aag aag cgg ttg gag ttg gat gac aac tta gat      460
Gly Ser Leu Ser Arg Lys Lys Arg Leu Glu Leu Asp Asp Asn Leu Asp
               15                  20                  25 acc gag cgt ccc gtc cag aaa cga gct cga agt ggg ccc cag ccc aga      508
Thr Glu Arg Pro Val Gln Lys Arg Ala Arg Ser Gly Pro Gln Pro Arg
           30                  35                  40 ctg ccc ccc tgc ctg ttg ccc ctg agc cca cct act gct cca gat cgt      556
Leu Pro Pro Cys Leu Leu Pro Leu Ser Pro Pro Thr Ala Pro Asp Arg
       45                  50                  55 gca act gct gtg gcc act gcc tcc cgt ctt ggg ccc tat gtc ctc ctg      604
Ala Thr Ala Val Ala Thr Ala Ser Arg Leu Gly Pro Tyr Val Leu Leu
   60                  65                  70 gag ccc gag gag ggc ggg cgg gcc tac cag gcc ctg cac tgc cct aca      652
Glu Pro Glu Glu Gly Gly Arg Ala Tyr Gln Ala Leu His Cys Pro Thr
75                  80                  85                  90 ggc act gag tat acc tgc aag gtg tac ccc gtc cag gaa gcc ctg gcc      700
Gly Thr Glu Tyr Thr Cys Lys Val Tyr Pro Val Gln Glu Ala Leu Ala
               95                 100                 105 gtg ctg gag ccc tac gcg cgg ctg ccc ccg cac aag cat gtg gct cgg      748
Val Leu Glu Pro Tyr Ala Arg Leu Pro Pro His Lys His Val Ala Arg
           110                 115                 120 ccc act gag gtc ctg gct ggt acc cag ctc ctc tac gcc ttt ttc act      796
Pro Thr Glu Val Leu Ala Gly Thr Gln Leu Leu Tyr Ala Phe Phe Thr
       125                 130                 135 cgg acc cat ggg gac atg cac agc ctg gtg cga agc cgc cac cgt atc      844
Arg Thr His Gly Asp Met His Ser Leu Val Arg Ser Arg His Arg Ile
   140                 145                 150 cct gag cct gag gct gcc gtg ctc ttc cgc cag atg gcc acc gcc ctg      892
```

```
                                                                           -continued Pro Glu Pro Glu Ala Ala Val Leu Phe Arg Gln Met Ala Thr Ala Leu
155                 160                 165                 170 gcg cac tgt cac cag cac ggt ctg gtc ctg cgt gat ctc aag ctg tgt        940
Ala His Cys His Gln His Gly Leu Val Leu Arg Asp Leu Lys Leu Cys
                175                 180                 185 cgc ttt gtc ttc gct gac cgt gag agg aag aag ctg gtg ctg gag aac        988
Arg Phe Val Phe Ala Asp Arg Glu Arg Lys Lys Leu Val Leu Glu Asn
            190                 195                 200 ctg gag gac tcc tgc gtg ctg act ggg cca gat gat tcc ctg tgg gac       1036
Leu Glu Asp Ser Cys Val Leu Thr Gly Pro Asp Asp Ser Leu Trp Asp
        205                 210                 215 aag cac gcg tgc cca gcc tac gtg gga cct gag ata ctc agc tca cgg       1084
Lys His Ala Cys Pro Ala Tyr Val Gly Pro Glu Ile Leu Ser Ser Arg
    220                 225                 230 gcc tca tac tcg ggc aag gca gcc gat gtc tgg agc ctg ggc gtg gcg       1132
Ala Ser Tyr Ser Gly Lys Ala Ala Asp Val Trp Ser Leu Gly Val Ala
235                 240                 245                 250 ctc ttc acc atg ctg gcc ggc cac tac ccc ttc cag gac tcg gag cct       1180
Leu Phe Thr Met Leu Ala Gly His Tyr Pro Phe Gln Asp Ser Glu Pro
                255                 260                 265 gtc ctg ctc ttc ggc aag atc cgc cgc ggg gcc tac gcc ttg cct gca       1228
Val Leu Leu Phe Gly Lys Ile Arg Arg Gly Ala Tyr Ala Leu Pro Ala
            270                 275                 280 ggc ctc tcg gcc cct gcc cgc tgt ctg gtt cgc tgc ctc ctt cgt cgg       1276
Gly Leu Ser Ala Pro Ala Arg Cys Leu Val Arg Cys Leu Leu Arg Arg
        285                 290                 295 gag cca gct gaa cgg ctc aca gcc aca ggc atc ctc ctg cac ccc tgg       1324
Glu Pro Ala Glu Arg Leu Thr Ala Thr Gly Ile Leu Leu His Pro Trp
    300                 305                 310 ctg cga cag gac ccg atg ccc tta gct cca acc cga tcc cat ctc tgg       1372
Leu Arg Gln Asp Pro Met Pro Leu Ala Pro Thr Arg Ser His Leu Trp
315                 320                 325                 330 gag gct gcc cag gtg gtc cct gat gga ctg ggg ctg gac gaa gcc agg       1420
Glu Ala Ala Gln Val Val Pro Asp Gly Leu Gly Leu Asp Glu Ala Arg
                335                 340                 345 gaa gag gag gga gac aga gaa gtg gtt ctg tat ggc taggaccacc            1466
Glu Glu Glu Gly Asp Arg Glu Val Val Leu Tyr Gly
            350                 355 ctactacacg ctcagctgcc aacagtggat tgagtttggg ggtagctcca agccttctcc     1526
tgcctctgaa ctgagccaaa ccttcagtgc cttccagaag ggagaaaggc agaagcctgt     1586
gtggagtgtg ctgtgtacac atctgctttg ttccacacac atgcagttcc tgcttgggtg     1646
cttatcaggt gccaagccct gttctcggtg ctgggagtac agcagtgagc aaaggagaca     1706
atattccctg ctcacagaga tgacaaactg catccttga gctgacaaca cttttccatg      1766
accataggtc actgtctaca ctgggtacac tttgtaccag tgtcggcctc cactgatgct     1826
ggtgctcagg cacctctgtc caaggacaat ccctttcaca aacaaaccag ctgcctttgt     1886
atcttgtacc ttttcagaga aagggaggta tccctgtgcc aaaggctcca ggcctctccc     1946
ctgcaactca ggacccaagc ccagctcact ctgggaactg tgttcccagc atctctgtcc     2006
tcttgattaa gagattctcc ttccaggcct aagcctggga tttgggccag agataagaat     2066
ccaaactatg aggctagttc ttgtctaact caagactgtt ctggaatgag ggtccaggcc     2126
tgtcaaccat ggggcttctg acctgagcac caaggttgag ggacaggatt aggcagggtc     2186
tgtcctgtgg ccacctggaa agtcccaggt gggactcttc tggggacact tggggtccac     2246
aatcccaggt ccatactcta ggttttggat accatgagta tgtatgttta cctgtgccta     2306
```

```
ataaaggaga attatgaaat aaaaaaaaaa aaaaaaaaaa aaaaaaaaaa aaaaaaaaaa    2366
aaaaaaaaaa aaaaaaaaaa aaa                                            2389
```

<210> SEQ ID NO 8
<211> LENGTH: 358
<212> TYPE: PRT
<213> ORGANISM: Homo sapiens

<400> SEQUENCE: 8

```
Met Arg Ala Thr Pro Leu Ala Ala Pro Ala Gly Ser Leu Ser Arg Lys
 1               5                  10                  15

Lys Arg Leu Glu Leu Asp Asp Asn Leu Asp Thr Glu Arg Pro Val Gln
                20                  25                  30

Lys Arg Ala Arg Ser Gly Pro Gln Pro Arg Leu Pro Pro Cys Leu Leu
            35                  40                  45

Pro Leu Ser Pro Pro Thr Ala Pro Asp Arg Ala Thr Ala Val Ala Thr
        50                  55                  60

Ala Ser Arg Leu Gly Pro Tyr Val Leu Leu Glu Pro Glu Glu Gly Gly
 65                  70                  75                  80

Arg Ala Tyr Gln Ala Leu His Cys Pro Thr Gly Thr Glu Tyr Thr Cys
                85                  90                  95

Lys Val Tyr Pro Val Gln Glu Ala Leu Ala Val Leu Glu Pro Tyr Ala
                100                 105                 110

Arg Leu Pro Pro His Lys His Val Ala Arg Pro Thr Glu Val Leu Ala
            115                 120                 125

Gly Thr Gln Leu Leu Tyr Ala Phe Phe Thr Arg Thr His Gly Asp Met
        130                 135                 140

His Ser Leu Val Arg Ser Arg His Arg Ile Pro Glu Pro Glu Ala Ala
145                 150                 155                 160

Val Leu Phe Arg Gln Met Ala Thr Ala Leu Ala His Cys His Gln His
                165                 170                 175

Gly Leu Val Leu Arg Asp Leu Lys Leu Cys Arg Phe Val Phe Ala Asp
                180                 185                 190

Arg Glu Arg Lys Lys Leu Val Leu Glu Asn Leu Glu Asp Ser Cys Val
            195                 200                 205

Leu Thr Gly Pro Asp Asp Ser Leu Trp Asp Lys His Ala Cys Pro Ala
        210                 215                 220

Tyr Val Gly Pro Glu Ile Leu Ser Ser Arg Ala Ser Tyr Ser Gly Lys
225                 230                 235                 240

Ala Ala Asp Val Trp Ser Leu Gly Val Ala Leu Phe Thr Met Leu Ala
                245                 250                 255

Gly His Tyr Pro Phe Gln Asp Ser Glu Pro Val Leu Leu Phe Gly Lys
                260                 265                 270

Ile Arg Arg Gly Ala Tyr Ala Leu Pro Ala Gly Leu Ser Ala Pro Ala
            275                 280                 285

Arg Cys Leu Val Arg Cys Leu Leu Arg Arg Glu Pro Ala Glu Arg Leu
        290                 295                 300

Thr Ala Thr Gly Ile Leu Leu His Pro Trp Leu Arg Gln Asp Pro Met
305                 310                 315                 320

Pro Leu Ala Pro Thr Arg Ser His Leu Trp Glu Ala Ala Gln Val Val
                325                 330                 335

Pro Asp Gly Leu Gly Leu Asp Glu Ala Arg Glu Glu Gly Asp Arg
                340                 345                 350

Glu Val Val Leu Tyr Gly
```

<210> SEQ ID NO 9
<211> LENGTH: 1074
<212> TYPE: DNA
<213> ORGANISM: Homo sapiens

<400> SEQUENCE: 9

| | |
|---|---|
| atgcgagcca cccctctggc tgctcctgcg ggttccctgt ccaggaagaa gcggttggag | 60 |
| ttggatgaca acttagatac cgagcgtccc gtccagaaac gagctcgaag tgggccccag | 120 |
| cccagactgc ccccctgcct gttgcccctg agcccaccta ctgctccaga tcgtgcaact | 180 |
| gctgtggcca ctgcctcccg tcttgggccc tatgtcctcc tggagcccga ggagggcggg | 240 |
| cgggcctacc aggccctgca ctgccctaca ggcactgagt atacctgcaa ggtgtacccc | 300 |
| gtccaggaag ccctggccgt gctggagccc tacgcgcggc tgccccgca caagcatgtg | 360 |
| gctcggccca ctgaggtcct ggctggtacc cagctcctct acgccttttt cactcggacc | 420 |
| catggggaca tgcacagcct ggtgcgaagc cgccaccgta tccctgagcc tgaggctgcc | 480 |
| gtgctcttcc gccagatggc caccgccctg gcgcactgtc accagcacgg tctggtcctg | 540 |
| cgtgatctca agctgtgtcg ctttgtcttc gctgaccgtg agaggaagaa gctggtgctg | 600 |
| gagaacctgg aggactcctg cgtgctgact gggccagatg attccctgtg ggacaagcac | 660 |
| gcgtgcccag cctacgtggg acctgagata tcagctcac gggcctcata tcgggcaag | 720 |
| gcagccgatg tctggagcct gggcgtggcg ctcttcacca tgctggccgg ccactacccc | 780 |
| ttccaggact cggagcctgt cctgctcttc ggcaagatcc gccgcgggc ctacgccttg | 840 |
| cctgcaggcc tctcggcccc tgcccgctgt ctggttcgct gcctccttcg tcgggagcca | 900 |
| gctgaacggc tcacagccac aggcatcctc ctgcacccct ggctgcgaca ggacccgatg | 960 |
| cccttagctc caacccgatc ccatctctgg gaggctgccc aggtggtccc tgatggactg | 1020 |
| gggctggacg aagccaggga agaggaggga gacagagaag tggttctgta tggc | 1074 |

<210> SEQ ID NO 10
<211> LENGTH: 2162
<212> TYPE: DNA
<213> ORGANISM: Homo sapiens
<220> FEATURE:
<221> NAME/KEY: CDS
<222> LOCATION: (76)...(1818)

<400> SEQUENCE: 10

| | |
|---|---|
| cacgcgtccg cccacgcgtc cgcgccggtg gtggcggcag cggcggctgc gggggcaccg | 60 |
| ggccgcggcg ccacc atg gcg gtg cga cag gcg ctg ggc cgc ggc ctg cag | 111 |
|              Met Ala Val Arg Gln Ala Leu Gly Arg Gly Leu Gln |  |
|                1               5                  10 |  |
| ctg ggt cga gcg ctg ctg ctg cgc ttc acg ggc aag ccc ggc cgg gcc | 159 |
| Leu Gly Arg Ala Leu Leu Leu Arg Phe Thr Gly Lys Pro Gly Arg Ala |  |
|         15                  20                  25 |  |
| tac ggc ttg ggg cgg ccg ggc ccg gcg gcg ggc tgt gtc cgc ggg gag | 207 |
| Tyr Gly Leu Gly Arg Pro Gly Pro Ala Ala Gly Cys Val Arg Gly Glu |  |
|     30                  35                  40 |  |
| cgt cca ggc tgg gcc gca gga ccg ggc gcg gag cct cgc agg gtc ggg | 255 |
| Arg Pro Gly Trp Ala Ala Gly Pro Gly Ala Glu Pro Arg Arg Val Gly |  |
| 45                  50                  55                  60 |  |
| ctc ggg ctc cct aac cgt ctc cgc ttc ttc cgc cag tcg gtg gcc ggg | 303 |
| Leu Gly Leu Pro Asn Arg Leu Arg Phe Phe Arg Gln Ser Val Ala Gly |  |
|             65                  70                  75 |  |

-continued

| | |
|---|---|
| ctg gcg gcg cgg ttg cag cgg cag ttc gtg gtg cgg gcc tgg ggc tgc<br>Leu Ala Ala Arg Leu Gln Arg Gln Phe Val Val Arg Ala Trp Gly Cys<br>80 85 90 | 351 |
| gcg ggc cct tgc ggc cgg gca gtc ttt ctg gcc ttc ggg cta ggg ctg<br>Ala Gly Pro Cys Gly Arg Ala Val Phe Leu Ala Phe Gly Leu Gly Leu<br>95 100 105 | 399 |
| ggc ctc atc gag gaa aaa cag gcg gag agc cgg cgg gcg gtc tcg gcc<br>Gly Leu Ile Glu Glu Lys Gln Ala Glu Ser Arg Arg Ala Val Ser Ala<br>110 115 120 | 447 |
| tgt cag gag atc cag gca att ttt acc cag aaa agc aag ccg ggg cct<br>Cys Gln Glu Ile Gln Ala Ile Phe Thr Gln Lys Ser Lys Pro Gly Pro<br>125 130 135 140 | 495 |
| gac ccg ttg gac acg aga cgc ttg cag ggc ttt cgg ctg gag gag tat<br>Asp Pro Leu Asp Thr Arg Arg Leu Gln Gly Phe Arg Leu Glu Glu Tyr<br>145 150 155 | 543 |
| cta ata ggg cag tcc att ggt aag ggc tgc agt gct gct gtg tat gaa<br>Leu Ile Gly Gln Ser Ile Gly Lys Gly Cys Ser Ala Ala Val Tyr Glu<br>160 165 170 | 591 |
| gcc acc atg cct aca ttg ccc cag aac ctg gag gtg aca aag agc acc<br>Ala Thr Met Pro Thr Leu Pro Gln Asn Leu Glu Val Thr Lys Ser Thr<br>175 180 185 | 639 |
| ggg ttg ctt cca ggg aga ggc cca ggt acc agt gca cca gga gaa ggg<br>Gly Leu Leu Pro Gly Arg Gly Pro Gly Thr Ser Ala Pro Gly Glu Gly<br>190 195 200 | 687 |
| cag gag cga gct ccg ggg gcc cct gcc ttc ccc ttg gcc atc aag atg<br>Gln Glu Arg Ala Pro Gly Ala Pro Ala Phe Pro Leu Ala Ile Lys Met<br>205 210 215 220 | 735 |
| atg tgg aac atc tcg gca ggt tcc tcc agc gaa gcc atc ttg aac aca<br>Met Trp Asn Ile Ser Ala Gly Ser Ser Ser Glu Ala Ile Leu Asn Thr<br>225 230 235 | 783 |
| atg agc cag gag ctg gtc cca gcg agc cga gtg gcc ttg gct ggg gag<br>Met Ser Gln Glu Leu Val Pro Ala Ser Arg Val Ala Leu Ala Gly Glu<br>240 245 250 | 831 |
| tat gga gca gtc act tac aga aaa tcc aag aga ggt ccc aag caa cta<br>Tyr Gly Ala Val Thr Tyr Arg Lys Ser Lys Arg Gly Pro Lys Gln Leu<br>255 260 265 | 879 |
| gcc cct cac ccc aac atc atc cgg gtt ctc cgc gcc ttc acc tct tcc<br>Ala Pro His Pro Asn Ile Ile Arg Val Leu Arg Ala Phe Thr Ser Ser<br>270 275 280 | 927 |
| gtg ccg ctg ctg cca ggg gcc ctg gtc gac tac cct gat gtg ctg ccc<br>Val Pro Leu Leu Pro Gly Ala Leu Val Asp Tyr Pro Asp Val Leu Pro<br>285 290 295 300 | 975 |
| tca cgc ctc cac cct gaa ggc ctg ggc cat ggc cgg acg ctg ttc ctc<br>Ser Arg Leu His Pro Glu Gly Leu Gly His Gly Arg Thr Leu Phe Leu<br>305 310 315 | 1023 |
| gtt atg aag aac tat ccc tgt acc ctg cgc cag tac ctt tgt gtg aac<br>Val Met Lys Asn Tyr Pro Cys Thr Leu Arg Gln Tyr Leu Cys Val Asn<br>320 325 330 | 1071 |
| aca ccc agc ccc cgc ctc gcc gcc atg atg ctg ctg cag ctg ctg gaa<br>Thr Pro Ser Pro Arg Leu Ala Ala Met Met Leu Leu Gln Leu Leu Glu<br>335 340 345 | 1119 |
| ggc gtg gac cat ctg gtt caa cag ggc atc gcg cac aga gac ctg aaa<br>Gly Val Asp His Leu Val Gln Gln Gly Ile Ala His Arg Asp Leu Lys<br>350 355 360 | 1167 |
| tcc gac aac atc ctt gtg gag ctg gac cca gac ggc tgc ccc tgg ctg<br>Ser Asp Asn Ile Leu Val Glu Leu Asp Pro Asp Gly Cys Pro Trp Leu<br>365 370 375 380 | 1215 |
| gtg atc gca gat ttt ggc tgc tgc ctg gct gat gag agc atc ggc ctg<br>Val Ile Ala Asp Phe Gly Cys Cys Leu Ala Asp Glu Ser Ile Gly Leu<br>385 390 395 | 1263 |

```
cag ttg ccc ttc agc agc tgg tac gtg gat cgg ggc gga aac ggc tgt    1311
Gln Leu Pro Phe Ser Ser Trp Tyr Val Asp Arg Gly Gly Asn Gly Cys
            400                 405                 410 ctg atg gcc cca gag gtg tcc acg gcc cgt cct ggc ccc agg gca gtg    1359
Leu Met Ala Pro Glu Val Ser Thr Ala Arg Pro Gly Pro Arg Ala Val
        415                 420                 425 att gac tac agc aag gct gat gcc tgg gca gtg gga gcc atc gcc tat    1407
Ile Asp Tyr Ser Lys Ala Asp Ala Trp Ala Val Gly Ala Ile Ala Tyr
    430                 435                 440 gaa atc ttc ggg ctt gtc aat ccc ttc tac ggc cag ggc aag gcc cac    1455
Glu Ile Phe Gly Leu Val Asn Pro Phe Tyr Gly Gln Gly Lys Ala His
445                 450                 455                 460 ctt gaa agc cgc agc tac caa gag gct cag cta cct gca ctg ccc gag    1503
Leu Glu Ser Arg Ser Tyr Gln Glu Ala Gln Leu Pro Ala Leu Pro Glu
                465                 470                 475 tca gtg cct cca gac gtg aga cag ttg gtg agg gca ctg ctc cag cga    1551
Ser Val Pro Pro Asp Val Arg Gln Leu Val Arg Ala Leu Leu Gln Arg
            480                 485                 490 gag gcc agc aag aga cca tct gcc cga gta gcc gca aat gtg ctt cat    1599
Glu Ala Ser Lys Arg Pro Ser Ala Arg Val Ala Ala Asn Val Leu His
        495                 500                 505 cta agc ctc tgg ggt gaa cat att cta gcc ctg aag aat ctg aag tta    1647
Leu Ser Leu Trp Gly Glu His Ile Leu Ala Leu Lys Asn Leu Lys Leu
    510                 515                 520 gac aag atg gtt ggc tgg ctc ctc caa caa tcg gcc gcc act ttg ttg    1695
Asp Lys Met Val Gly Trp Leu Leu Gln Gln Ser Ala Ala Thr Leu Leu
525                 530                 535                 540 gcc aac agg ctc aca gag aag tgt tgt gtg gaa aca aaa atg aag atg    1743
Ala Asn Arg Leu Thr Glu Lys Cys Cys Val Glu Thr Lys Met Lys Met
                545                 550                 555 ctc ttt ctg gct aac ctg gag tgt gaa acg ctc tgc cag gca gcc ctc    1791
Leu Phe Leu Ala Asn Leu Glu Cys Glu Thr Leu Cys Gln Ala Ala Leu
            560                 565                 570 ctc ctc tgc tca tgg agg gca gcc ctg tgatgtccct gcatggagct          1838
Leu Leu Cys Ser Trp Arg Ala Ala Leu
        575                 580 ggtgaattac taaaagaact tggcatcctc tgtgtcgtga tggtctgtga atggtgaggg   1898
tgggagtcag gagacaagac agcgcagaga gggctggtta gccggaaaag gcctcgggct   1958
tggcaaatgg aagaacttga gtgagagttc agtctgcagt cctgtgctca cagacatccg   2018
aaaagtgaat ggccaagctg gtctagtaga tgaggctgga ctgaggaggg gtaggcctgc   2078
atccacagag aggatccagg ccaaggcact ggctgtcagt ggcagagttt ggctgtgacc   2138
tttgccccta acacgaggaa ctcg                                         2162

<210> SEQ ID NO 11
<211> LENGTH: 581
<212> TYPE: PRT
<213> ORGANISM: Homo sapiens

<400> SEQUENCE: 11

Met Ala Val Arg Gln Ala Leu Gly Arg Gly Leu Gln Leu Gly Arg Ala
1               5                   10                  15

Leu Leu Leu Arg Phe Thr Gly Lys Pro Gly Arg Ala Tyr Gly Leu Gly
            20                  25                  30

Arg Pro Gly Pro Ala Ala Gly Cys Val Arg Gly Glu Arg Pro Gly Trp
        35                  40                  45

Ala Ala Gly Pro Gly Ala Glu Pro Arg Arg Val Gly Leu Gly Leu Pro
```

-continued

```
                50                  55                  60
Asn Arg Leu Arg Phe Phe Arg Gln Ser Val Ala Gly Leu Ala Ala Arg
 65                  70                  75                  80

Leu Gln Arg Gln Phe Val Val Arg Ala Trp Gly Cys Ala Gly Pro Cys
                     85                  90                  95

Gly Arg Ala Val Phe Leu Ala Phe Gly Leu Gly Leu Gly Leu Ile Glu
                    100                 105                 110

Glu Lys Gln Ala Glu Ser Arg Arg Ala Val Ser Ala Cys Gln Glu Ile
                115                 120                 125

Gln Ala Ile Phe Thr Gln Lys Ser Lys Pro Gly Pro Asp Pro Leu Asp
130                 135                 140

Thr Arg Arg Leu Gln Gly Phe Arg Leu Glu Glu Tyr Leu Ile Gly Gln
145                 150                 155                 160

Ser Ile Gly Lys Gly Cys Ser Ala Ala Val Tyr Glu Ala Thr Met Pro
                165                 170                 175

Thr Leu Pro Gln Asn Leu Glu Val Thr Lys Ser Thr Gly Leu Leu Pro
                180                 185                 190

Gly Arg Gly Pro Gly Thr Ser Ala Pro Gly Glu Gly Gln Glu Arg Ala
                195                 200                 205

Pro Gly Ala Pro Ala Phe Pro Leu Ala Ile Lys Met Met Trp Asn Ile
210                 215                 220

Ser Ala Gly Ser Ser Ser Glu Ala Ile Leu Asn Thr Met Ser Gln Glu
225                 230                 235                 240

Leu Val Pro Ala Ser Arg Val Ala Leu Ala Gly Glu Tyr Gly Ala Val
                245                 250                 255

Thr Tyr Arg Lys Ser Lys Arg Gly Pro Lys Gln Leu Ala Pro His Pro
                260                 265                 270

Asn Ile Ile Arg Val Leu Arg Ala Phe Thr Ser Ser Val Pro Leu Leu
                275                 280                 285

Pro Gly Ala Leu Val Asp Tyr Pro Asp Val Leu Pro Ser Arg Leu His
                290                 295                 300

Pro Glu Gly Leu Gly His Gly Arg Thr Leu Phe Leu Val Met Lys Asn
305                 310                 315                 320

Tyr Pro Cys Thr Leu Arg Gln Tyr Leu Cys Val Asn Thr Pro Ser Pro
                325                 330                 335

Arg Leu Ala Ala Met Met Leu Leu Gln Leu Leu Glu Gly Val Asp His
                340                 345                 350

Leu Val Gln Gln Gly Ile Ala His Arg Asp Leu Lys Ser Asp Asn Ile
                355                 360                 365

Leu Val Glu Leu Asp Pro Asp Gly Cys Pro Trp Leu Val Ile Ala Asp
                370                 375                 380

Phe Gly Cys Cys Leu Ala Asp Glu Ser Ile Gly Leu Gln Leu Pro Phe
385                 390                 395                 400

Ser Ser Trp Tyr Val Asp Arg Gly Gly Asn Gly Cys Leu Met Ala Pro
                405                 410                 415

Glu Val Ser Thr Ala Arg Pro Gly Pro Arg Ala Val Ile Asp Tyr Ser
                420                 425                 430

Lys Ala Asp Ala Trp Ala Val Gly Ala Ile Ala Tyr Glu Ile Phe Gly
                435                 440                 445

Leu Val Asn Pro Phe Tyr Gly Gln Gly Lys Ala His Leu Glu Ser Arg
                450                 455                 460

Ser Tyr Gln Glu Ala Gln Leu Pro Ala Leu Pro Glu Ser Val Pro Pro
465                 470                 475                 480
```

```
Asp Val Arg Gln Leu Val Arg Ala Leu Leu Gln Arg Glu Ala Ser Lys
                485                 490                 495
Arg Pro Ser Ala Arg Val Ala Ala Asn Val Leu His Leu Ser Leu Trp
            500                 505                 510
Gly Glu His Ile Leu Ala Leu Lys Asn Leu Lys Leu Asp Lys Met Val
        515                 520                 525
Gly Trp Leu Leu Gln Gln Ser Ala Ala Thr Leu Ala Asn Arg Leu
    530                 535                 540
Thr Glu Lys Cys Cys Val Glu Thr Lys Met Lys Met Leu Phe Leu Ala
545                 550                 555                 560
Asn Leu Glu Cys Glu Thr Leu Cys Gln Ala Ala Leu Leu Leu Cys Ser
                565                 570                 575
Trp Arg Ala Ala Leu
            580

<210> SEQ ID NO 12
<211> LENGTH: 1743
<212> TYPE: DNA
<213> ORGANISM: Homo sapiens

<400> SEQUENCE: 12
atggcggtgc gacaggcgct gggccgcggc ctgcagctgg gtcgagcgct gctgctgcgc      60
ttcacgggca gcccggccgg gcctacggc ttggggcggc cgggcccggc ggcgggctgt     120
gtccgcgggg agcgtccagg ctgggccgca ggaccgggcg cggagcctcg cagggtcggg     180
ctcgggctcc ctaaccgtct ccgcttcttc cgccagtcgg tggccgggct ggcggcgcgg     240
ttgcagcggc agttcgtggt gcgggcctgg ggctgcgcgg gcccttgcgg ccgggcagtc     300
tttctggcct tcgggctagg gctgggcctc atcgaggaaa acaggcggga gagccggcgg     360
gcggtctcgg cctgtcagga gatccaggca attttttaccc agaaaagcaa gccgggggcct     420
gacccgttgg acacgagacg cttgcaggcc tttcggctgg aggagtatct gatagggcag     480
tccattggta agggctgcag tgctgctgtg tatgaagcca ccatgcctac attgccccag     540
aacctggagg tgacaaagag caccgggttg cttccaggga gaggcccagg taccagtgca     600
ccaggagaag ggcaggagcg agctccgggg gccctgcct tcccttggc catcaagatg     660
atgtggaaca tctcggcagg ttcctccagc gaagccatct tgaacacaat gagccaggag     720
ctggtcccag cgagccgagt ggccttggct ggggagtatg gagcagtcac ttacagaaaa     780
tccaagagag gtcccaagca actagcccct caccccaaca tcatccgggt tctccgcgcc     840
ttcacctctt ccgtgccgct gctgccaggg gccctggtcg actaccctga tgtgctgccc     900
tcacgcctcc accctgaagg cctgggccat ggccggacgc tgttcctcgt tatgaagaac     960
tatccctgta ccctgcgcca gtacctttgt gtgaacacac ccagccccg cctcgccgcc    1020
atgatgctgc tgcagctgct ggaaggcgtg accatctgg ttcaacaggg catcgcgcac    1080
agagacctga atccgacaa catccttgtg gagctggacc agacggctg ccctggctg    1140
gtgatcgcag attttggctg ctgcctggct gatgagagca tcggcctgca gttgcccttc    1200
agcagctggt acgtggatcg gggcggaaac ggctgtctga tggccccaga ggtgtccacg    1260
gcccgtcctg gccccagggc agtgattgac tacagcaagg ctgatgcctg gcagtgggga    1320
gccatcgcct atgaaatctt cgggcttgtc aatcccttct acggccaggg caaggcccac    1380
cttgaaagcc gcagctacca agaggctcag ctacctgcac tgcccgagtc agtgcctcca    1440
gacgtgagac agttggtgag ggcactgctc cagcgagagg ccagcaagag accatctgcc    1500
```

-continued

```
cgagtagccg caaatgtgct tcatctaagc ctctggggtg aacatattct agccctgaag    1560
aatctgaagt tagacaagat ggttggctgg ctcctccaac aatcggccgc cactttgttg    1620
gccaacaggc tcacagagaa gtgttgtgtg gaaacaaaaa tgaagatgct ctttctggct    1680
aacctggagt gtgaaacgct ctgccaggca gccctcctcc tctgctcatg gagggcagcc    1740
ctg                                                                  1743
```

<210> SEQ ID NO 13
<211> LENGTH: 1826
<212> TYPE: DNA
<213> ORGANISM: Homo sapiens
<220> FEATURE:
<221> NAME/KEY: CDS
<222> LOCATION: (17)...(1273)

<400> SEQUENCE: 13

| | | |
|---|---|---|
| ccacgcgtcc gagagg atg ggc tcg tcc atg tcg gcg gcc acc gcg cgg agg<br>        Met Gly Ser Ser Met Ser Ala Ala Thr Ala Arg Arg<br>         1     5        10 | | 52 |
| ccg gtg ttt gac gac aag gag gac gtg aac ttc gac cac ttc cag atc<br>Pro Val Phe Asp Asp Lys Glu Asp Val Asn Phe Asp His Phe Gln Ile<br>    15        20        25 | | 100 |
| ctt cgg gcc att ggg aag ggc agc ttt ggc aag gtg tgc att gtg cag<br>Leu Arg Ala Ile Gly Lys Gly Ser Phe Gly Lys Val Cys Ile Val Gln<br>30        35        40 | | 148 |
| aag cgg gac acg gag aag atg tac gcc atg aag tac atg aac aag cag<br>Lys Arg Asp Thr Glu Lys Met Tyr Ala Met Lys Tyr Met Asn Lys Gln<br>45        50        55        60 | | 196 |
| cag tgc atc gag cgc gac gag gtc cgc aac gtc ttc cgg gag ctg gag<br>Gln Cys Ile Glu Arg Asp Glu Val Arg Asn Val Phe Arg Glu Leu Glu<br>        65        70        75 | | 244 |
| atc ctg cag gag atc gag cac gtc ttc ctg gtg aac ctc tgg tac tcc<br>Ile Leu Gln Glu Ile Glu His Val Phe Leu Val Asn Leu Trp Tyr Ser<br>    80        85        90 | | 292 |
| ttc cag gac gag gag gac atg ttc atg gtc gtg gac ctg cta ctg ggc<br>Phe Gln Asp Glu Glu Asp Met Phe Met Val Val Asp Leu Leu Leu Gly<br>        95        100       105 | | 340 |
| ggg gac ctg cgc tac cac ctg cag cag aac gtg cag ttc tcc gag gac<br>Gly Asp Leu Arg Tyr His Leu Gln Gln Asn Val Gln Phe Ser Glu Asp<br>110       115       120 | | 388 |
| acg gtg agg ctg tac atc tgc gag atg gca ctg gct ctg gac tac ctg<br>Thr Val Arg Leu Tyr Ile Cys Glu Met Ala Leu Ala Leu Asp Tyr Leu<br>125       130       135       140 | | 436 |
| cgc ggc cag cac atc atc cac aga gat gtc aag cct gac aac att ctc<br>Arg Gly Gln His Ile Ile His Arg Asp Val Lys Pro Asp Asn Ile Leu<br>        145       150       155 | | 484 |
| ctg gat gag aga gga cat gca cac ctg acc gac ttc aac att gcc acc<br>Leu Asp Glu Arg Gly His Ala His Leu Thr Asp Phe Asn Ile Ala Thr<br>    160        165        170 | | 532 |
| atc atc aag gac ggg gag cgg gcg acg gca tta gca ggc acc aag ccg<br>Ile Ile Lys Asp Gly Glu Arg Ala Thr Ala Leu Ala Gly Thr Lys Pro<br>        175       180       185 | | 580 |
| tac atg gct ccg gag atc ttc cac tct ttt gtc aac ggc ggg acc ggc<br>Tyr Met Ala Pro Glu Ile Phe His Ser Phe Val Asn Gly Gly Thr Gly<br>190       195       200 | | 628 |
| tac tcc ttc gag gtg gac tgg tgg tcg gtg ggg gtg atg gcc tat gag<br>Tyr Ser Phe Glu Val Asp Trp Trp Ser Val Gly Val Met Ala Tyr Glu<br>205       210       215       220 | | 676 |
| ctg ctg cga gga tgg agg ccc tat gac atc cac tcc agc aac gcc gtg | | 724 |

-continued

```
                Leu Leu Arg Gly Trp Arg Pro Tyr Asp Ile His Ser Ser Asn Ala Val
                            225                 230                 235 gag tcc ctg gtg cag ctg ttc agc acc gtg agc gtc cag tat gtc ccc          772
Glu Ser Leu Val Gln Leu Phe Ser Thr Val Ser Val Gln Tyr Val Pro
            240                 245                 250 acg tgg tcc aag gag atg gtg gcc ttg ctg cgg aag ctc ctc act gtg          820
Thr Trp Ser Lys Glu Met Val Ala Leu Leu Arg Lys Leu Leu Thr Val
            255                 260                 265 aac ccc gag cac cgg ctc tcc agc ctc cag gac gtg cag gca gcc ccg          868
Asn Pro Glu His Arg Leu Ser Ser Leu Gln Asp Val Gln Ala Ala Pro
        270                 275                 280 gcg ctg gcc ggc gtg ctg tgg gac cac ctg agc gag aag agg gtg gag          916
Ala Leu Ala Gly Val Leu Trp Asp His Leu Ser Glu Lys Arg Val Glu
285                 290                 295                 300 ccg ggc ttc gtg ccc aac aaa ggc cgt ctg cac tgc gac ccc acc ttt          964
Pro Gly Phe Val Pro Asn Lys Gly Arg Leu His Cys Asp Pro Thr Phe
                305                 310                 315 gag ctg gag gag atg atc ctg gag tcc agg ccc ctg cac aag aag aag         1012
Glu Leu Glu Glu Met Ile Leu Glu Ser Arg Pro Leu His Lys Lys Lys
            320                 325                 330 aag cgt ctg gcc aag aac aag tcc cgg gac aac agc agg gac agc tcc         1060
Lys Arg Leu Ala Lys Asn Lys Ser Arg Asp Asn Ser Arg Asp Ser Ser
        335                 340                 345 cag tcc gag aat gac tat ctt caa gac tgc ctc gat gcc atc cag caa         1108
Gln Ser Glu Asn Asp Tyr Leu Gln Asp Cys Leu Asp Ala Ile Gln Gln
    350                 355                 360 gac ttc gtg att ttt aac aga gaa aag ctg aag agg agc cag gac ctc         1156
Asp Phe Val Ile Phe Asn Arg Glu Lys Leu Lys Arg Ser Gln Asp Leu
365                 370                 375                 380 ccg agg gag cct ctc ccc gcc cct gag tcc agg gat gct gcg gag cct         1204
Pro Arg Glu Pro Leu Pro Ala Pro Glu Ser Arg Asp Ala Ala Glu Pro
                385                 390                 395 gtg gag gac gag gcg gaa cgc tcc gcc ctg ccc atg tgc ggc ccc att         1252
Val Glu Asp Glu Ala Glu Arg Ser Ala Leu Pro Met Cys Gly Pro Ile
            400                 405                 410 tgc ccc tcg gcc ggg agc ggc taggccggga cgcccgtggt cctcacccct            1303
Cys Pro Ser Ala Gly Ser Gly
        415 tgagctgctt tggagactcg gctgccagag ggagggccat gggccgaggc ctggcattca      1363 cgttcccacc cagcctggct ggcggtgccc acagtgcccc ggacacattt cacacctcag      1423 gctcgtggtg gtgcagggga caagaggctg tgggtgcagg ggacacctgt ggagggcatt     1483 tcccgtgggc ccccgagacc cgcctagatg gaggaagcgc tgctgggcgc cctcttaccg      1543 ctcacgggga gctggggcca tggatgggac aggagtcttt gtccctgctc agcccggagg      1603 ctgtgcacgg ccctcgtcac aaggtgaccc ttgcagcaca ggccgcgggt gccccaggct      1663 cggctcaggt cttggaggtc aagggcatgg gttggggtag tgggtgggga ggtgaatgtt      1723 ttctagagat tcaaactgct ccagcaattt ctgtagtttt cacctctgag aattacaatg     1783 tgagaaccgc tcggaaaaaa aaaaaaaaaa aaaaaaaaa aaa                         1826
```

<210> SEQ ID NO 14
<211> LENGTH: 419
<212> TYPE: PRT
<213> ORGANISM: Homo sapiens

<400> SEQUENCE: 14

```
Met Gly Ser Ser Met Ser Ala Ala Thr Ala Arg Arg Pro Val Phe Asp
1               5                   10                  15
```

-continued

Asp Lys Glu Asp Val Asn Phe Asp His Phe Gln Ile Leu Arg Ala Ile
            20                  25                  30

Gly Lys Gly Ser Phe Gly Lys Val Cys Ile Val Gln Lys Arg Asp Thr
            35                  40                  45

Glu Lys Met Tyr Ala Met Lys Tyr Met Asn Lys Gln Gln Cys Ile Glu
        50                  55                  60

Arg Asp Glu Val Arg Asn Val Phe Arg Glu Leu Glu Ile Leu Gln Glu
65                  70                  75                  80

Ile Glu His Val Phe Leu Val Asn Leu Trp Tyr Ser Phe Gln Asp Glu
                    85                  90                  95

Glu Asp Met Phe Met Val Val Asp Leu Leu Leu Gly Gly Asp Leu Arg
                100                 105                 110

Tyr His Leu Gln Gln Asn Val Gln Phe Ser Glu Asp Thr Val Arg Leu
            115                 120                 125

Tyr Ile Cys Glu Met Ala Leu Ala Leu Asp Tyr Leu Arg Gly Gln His
            130                 135                 140

Ile Ile His Arg Asp Val Lys Pro Asp Asn Ile Leu Leu Asp Glu Arg
145                 150                 155                 160

Gly His Ala His Leu Thr Asp Phe Asn Ile Ala Thr Ile Ile Lys Asp
                165                 170                 175

Gly Glu Arg Ala Thr Ala Leu Ala Gly Thr Lys Pro Tyr Met Ala Pro
                180                 185                 190

Glu Ile Phe His Ser Phe Val Asn Gly Gly Thr Gly Tyr Ser Phe Glu
            195                 200                 205

Val Asp Trp Trp Ser Val Gly Val Met Ala Tyr Glu Leu Leu Arg Gly
            210                 215                 220

Trp Arg Pro Tyr Asp Ile His Ser Ser Asn Ala Val Glu Ser Leu Val
225                 230                 235                 240

Gln Leu Phe Ser Thr Val Ser Val Gln Tyr Val Pro Thr Trp Ser Lys
                245                 250                 255

Glu Met Val Ala Leu Leu Arg Lys Leu Leu Thr Val Asn Pro Glu His
            260                 265                 270

Arg Leu Ser Ser Leu Gln Asp Val Gln Ala Ala Pro Ala Leu Ala Gly
            275                 280                 285

Val Leu Trp Asp His Leu Ser Glu Lys Arg Val Glu Pro Gly Phe Val
            290                 295                 300

Pro Asn Lys Gly Arg Leu His Cys Asp Pro Thr Phe Glu Leu Glu Glu
305                 310                 315                 320

Met Ile Leu Glu Ser Arg Pro Leu His Lys Lys Lys Arg Leu Ala
                325                 330                 335

Lys Asn Lys Ser Arg Asp Asn Ser Arg Asp Ser Ser Gln Ser Glu Asn
            340                 345                 350

Asp Tyr Leu Gln Asp Cys Leu Asp Ala Ile Gln Gln Asp Phe Val Ile
            355                 360                 365

Phe Asn Arg Glu Lys Leu Lys Arg Ser Gln Asp Leu Pro Arg Glu Pro
    370                 375                 380

Leu Pro Ala Pro Glu Ser Arg Asp Ala Ala Glu Pro Val Glu Asp Glu
385                 390                 395                 400

Ala Glu Arg Ser Ala Leu Pro Met Cys Gly Pro Ile Cys Pro Ser Ala
                405                 410                 415

Gly Ser Gly

<210> SEQ ID NO 15
<211> LENGTH: 1257
<212> TYPE: DNA
<213> ORGANISM: Homo sapiens

<400> SEQUENCE: 15

| | | |
|---|---|---|
| atgggctcgt ccatgtcggc ggccaccgcg cggaggccgg tgtttgacga caaggaggac | 60 |
| gtgaacttcg accacttcca gatccttcgg gccattggga agggcagctt tggcaaggtg | 120 |
| tgcattgtgc agaagcggga cacggagaag atgtacgcca tgaagtacat gaacaagcag | 180 |
| cagtgcatcg agcgcgacga ggtccgcaac gtcttccggg agctggagat cctgcaggag | 240 |
| atcgagcacg tcttcctggt gaacctctgg tactccttcc aggacgagga ggacatgttc | 300 |
| atggtcgtgg acctgctact gggcggggac ctgcgctacc acctgcagca gaacgtgcag | 360 |
| ttctccgagg acacggtgag gctgtacatc tgcgagatgg cactggctct ggactacctg | 420 |
| cgcggccagc acatcatcca cagagatgtc aagcctgaca acattctcct ggatgagaga | 480 |
| ggacatgcac acctgaccga cttcaacatt gccaccatca tcaaggacgg ggagcgggcg | 540 |
| acggcattag caggcaccaa gccgtacatg gctccggaga tcttccactc ttttgtcaac | 600 |
| ggcgggaccg gctactcctt cgaggtggac tggtggtcgg tgggggtgat ggcctatgag | 660 |
| ctgctgcgag gatggaggcc ctatgacatc cactccagca acgccgtgga gtccctggtg | 720 |
| cagctgttca gcaccgtgag cgtccagtat gtccccacgt ggtccaagga gatggtggcc | 780 |
| ttgctgcgga gctcctcac tgtgaacccc gagcaccggc tctccagcct ccaggacgtg | 840 |
| caggcagccc ggcgctggc cggcgtgctg tgggaccacc tgagcgagaa gagggtggag | 900 |
| ccgggcttcg tgcccaacaa aggccgtctg cactgcgacc ccacctttga gctggaggag | 960 |
| atgatcctgg agtccaggcc cctgcacaag aagaagaagc gtctggccaa gaacaagtcc | 1020 |
| cgggacaaca gcagggacag ctcccagtcc gagaatgact atcttcaaga ctgcctcgat | 1080 |
| gccatccagc aagacttcgt gatttttaac agagaaaagc tgaagaggag ccaggacctc | 1140 |
| ccgagggagc ctctcccgc ccctgagtcc agggatgctg cggagcctgt ggaggacgag | 1200 |
| gcggaacgct ccgccctgcc catgtgcggc cccatttgcc cctcggccgg gagcggc | 1257 |

<210> SEQ ID NO 16
<211> LENGTH: 2870
<212> TYPE: DNA
<213> ORGANISM: Homo sapiens
<220> FEATURE:
<221> NAME/KEY: CDS
<222> LOCATION: (114)...(2000)

<400> SEQUENCE: 16

| | |
|---|---|
| gtcgacccac gcgtccgggt tacttccggg tcggacggcg ctagctgcag catcggagtg | 60 |
| tggcagtgct gggctggccg gcgggctggg ctgcggcccg cgcgcggccg gcg atg | 116 |
|                                                                                                                                                    Met<br>                                                                                                                                                     1 |
| cag ggg ggc aac tcc ggg gtc cgc aag cgc gaa gag gag ggc gac ggg<br>Gln Gly Gly Asn Ser Gly Val Arg Lys Arg Glu Glu Glu Gly Asp Gly<br>            5                            10                              15 | 164 |
| gct ggg gct gtg gct gcg ccg ccg gcc atc gac ttt ccc gcc gag ggc<br>Ala Gly Ala Val Ala Ala Pro Pro Ala Ile Asp Phe Pro Ala Glu Gly<br>        20                            25                                30 | 212 |
| ccg gac ccc gaa tat gac gaa tct gat gtt cca gca gaa atc cag gtg<br>Pro Asp Pro Glu Tyr Asp Glu Ser Asp Val Pro Ala Glu Ile Gln Val<br>  35                              40                              45 | 260 |
| tta aaa gaa ccc cta caa cag cca acc ttc cct ttt gca gtt gca aac | 308 |

```
Leu Lys Glu Pro Leu Gln Gln Pro Thr Phe Pro Phe Ala Val Ala Asn
 50              55                  60                  65 caa ctc ttg ctg gtt tct ttg ctg gag cac ttg agc cac gtg cat gaa        356
Gln Leu Leu Leu Val Ser Leu Leu Glu His Leu Ser His Val His Glu
                 70                  75                  80 cca aac cca ctt cgt tca aga cag gtg ttt aag cta ctt tgc cag acg        404
Pro Asn Pro Leu Arg Ser Arg Gln Val Phe Lys Leu Leu Cys Gln Thr
                     85                  90                  95 ttt atc aaa atg ggg ctg ctg tct tct ttc act tgt agt gac gag ttt        452
Phe Ile Lys Met Gly Leu Leu Ser Ser Phe Thr Cys Ser Asp Glu Phe
            100                 105                 110 agc tca ttg aga cta cat cac aac aga gct att act cac tta atg agg        500
Ser Ser Leu Arg Leu His His Asn Arg Ala Ile Thr His Leu Met Arg
    115                 120                 125 tct gct aaa gag aga gtt cgt cag gat cct tgt gag gat att tct cgt        548
Ser Ala Lys Glu Arg Val Arg Gln Asp Pro Cys Glu Asp Ile Ser Arg
130                 135                 140                 145 atc cag aaa atc aga tca agg gaa gta gcc ttg gaa gca caa act tca        596
Ile Gln Lys Ile Arg Ser Arg Glu Val Ala Leu Glu Ala Gln Thr Ser
                150                 155                 160 cgt tac tta aat gaa ttt gaa gaa ctt gcc atc tta gga aaa ggt gga        644
Arg Tyr Leu Asn Glu Phe Glu Glu Leu Ala Ile Leu Gly Lys Gly Gly
                    165                 170                 175 tac gga aga gta tac aag gtc agg aat aaa tta gat ggt cag tat tat        692
Tyr Gly Arg Val Tyr Lys Val Arg Asn Lys Leu Asp Gly Gln Tyr Tyr
                180                 185                 190 gca ata aaa aaa atc ctg att aag ggt gca act aaa aca gtt tgc atg        740
Ala Ile Lys Lys Ile Leu Ile Lys Gly Ala Thr Lys Thr Val Cys Met
    195                 200                 205 aag gtc cta cgg gaa gtg aag gtg ctg gca ggt ctt cag cac ccc aat        788
Lys Val Leu Arg Glu Val Lys Val Leu Ala Gly Leu Gln His Pro Asn
210                 215                 220                 225 att gtt ggc tat cac acc gcg tgg ata gaa cat gtt cat gtg att cag        836
Ile Val Gly Tyr His Thr Ala Trp Ile Glu His Val His Val Ile Gln
                    230                 235                 240 cca cga gac aga gct gcc att gag ttg cca tct ctg gaa gtg ctc tcc        884
Pro Arg Asp Arg Ala Ala Ile Glu Leu Pro Ser Leu Glu Val Leu Ser
                245                 250                 255 gac cag gaa gag gac aga gag caa tgt ggt gtt aaa aat gat gaa agt        932
Asp Gln Glu Glu Asp Arg Glu Gln Cys Gly Val Lys Asn Asp Glu Ser
            260                 265                 270 agc agc tca tcc att atc ttt gct gag ccc acc cca gaa aaa gaa aaa        980
Ser Ser Ser Ser Ile Ile Phe Ala Glu Pro Thr Pro Glu Lys Glu Lys
    275                 280                 285 cgc ttt gga gaa tct gac act gaa aat cag aat aac aag tcg gtg aag       1028
Arg Phe Gly Glu Ser Asp Thr Glu Asn Gln Asn Asn Lys Ser Val Lys
290                 295                 300                 305 tac acc acc aat tta gtc ata aga gaa tct ggt gaa ctt gag tcg acc       1076
Tyr Thr Thr Asn Leu Val Ile Arg Glu Ser Gly Glu Leu Glu Ser Thr
                    310                 315                 320 ctg gag ctc cag gaa aat ggc ttg gct ggt ttg tct gcc agt tca att       1124
Leu Glu Leu Gln Glu Asn Gly Leu Ala Gly Leu Ser Ala Ser Ser Ile
                325                 330                 335 gtg gaa cag cag ctg cca ctc agg cgt aat tcc cac cta gag gag agt       1172
Val Glu Gln Gln Leu Pro Leu Arg Arg Asn Ser His Leu Glu Glu Ser
            340                 345                 350 ttc aca tcc acc gaa gaa tct tcc gaa gaa aat gtc aac ttt ttg ggt       1220
Phe Thr Ser Thr Glu Glu Ser Ser Glu Glu Asn Val Asn Phe Leu Gly
    355                 360                 365
```

```
cag aca gag gca cag tac cac ctg atg ctg cac atc cag atg cag ctg      1268
Gln Thr Glu Ala Gln Tyr His Leu Met Leu His Ile Gln Met Gln Leu
370                 375                 380                 385 tgt gag ctc tcg ctg tgg gat tgg ata gtc gag aga aac aag cgg ggc      1316
Cys Glu Leu Ser Leu Trp Asp Trp Ile Val Glu Arg Asn Lys Arg Gly
                390                 395                 400 cgg gag tat gtg gac gag tct gcc tgt cct tat gtt atg gcc aat gtt      1364
Arg Glu Tyr Val Asp Glu Ser Ala Cys Pro Tyr Val Met Ala Asn Val
            405                 410                 415 gca aca aaa att ttt caa gaa ttg gta gaa ggt gtg ttt tac ata cat      1412
Ala Thr Lys Ile Phe Gln Glu Leu Val Glu Gly Val Phe Tyr Ile His
        420                 425                 430 aac atg gga att gtg cac cga gat ctg aag cca aga aat att ttt ctt      1460
Asn Met Gly Ile Val His Arg Asp Leu Lys Pro Arg Asn Ile Phe Leu
435                 440                 445 cat ggc cct gat cag caa gta aaa ata gga gac ttt ggt ctg gcc tgc      1508
His Gly Pro Asp Gln Gln Val Lys Ile Gly Asp Phe Gly Leu Ala Cys
450                 455                 460                 465 aca gac atc cta cag aag aac aca gac tgg acc aac aga aac ggg aag      1556
Thr Asp Ile Leu Gln Lys Asn Thr Asp Trp Thr Asn Arg Asn Gly Lys
                470                 475                 480 aga aca cca aca cat acg tcc aga gtg ggt act tgt ctg tac gct tca      1604
Arg Thr Pro Thr His Thr Ser Arg Val Gly Thr Cys Leu Tyr Ala Ser
            485                 490                 495 ccc gaa cag ttg gaa gga tct gag tat gat gcc aag tca gat atg tac      1652
Pro Glu Gln Leu Glu Gly Ser Glu Tyr Asp Ala Lys Ser Asp Met Tyr
        500                 505                 510 agc ttg ggt gtg gtc ctg cta gag ctc ttt cag ccg ttt gga aca gaa      1700
Ser Leu Gly Val Val Leu Leu Glu Leu Phe Gln Pro Phe Gly Thr Glu
    515                 520                 525 atg gag cga gca gaa gtt cta aca ggt tta aga act ggt cag ttg ccg      1748
Met Glu Arg Ala Glu Val Leu Thr Gly Leu Arg Thr Gly Gln Leu Pro
530                 535                 540                 545 gaa tcc ctc cgt aaa agg tgt ccg gtg caa gcc aag tat atc cag cac      1796
Glu Ser Leu Arg Lys Arg Cys Pro Val Gln Ala Lys Tyr Ile Gln His
                550                 555                 560 tta acg aga agg aac tca tcg cag aga cca tct gcc att cag ctg ctg      1844
Leu Thr Arg Arg Asn Ser Ser Gln Arg Pro Ser Ala Ile Gln Leu Leu
            565                 570                 575 cag agt gaa ctt ttc caa aat tct gga aat gtt aac ctc acc cta cag      1892
Gln Ser Glu Leu Phe Gln Asn Ser Gly Asn Val Asn Leu Thr Leu Gln
        580                 585                 590 atg aag ata ata gag caa gaa aaa gaa att gca gaa cta aag aag cag      1940
Met Lys Ile Ile Glu Gln Glu Lys Glu Ile Ala Glu Leu Lys Lys Gln
    595                 600                 605 cta aac ctc ctt tct caa gac aaa ggg gtg agg gat gac gga aag gat      1988
Leu Asn Leu Leu Ser Gln Asp Lys Gly Val Arg Asp Asp Gly Lys Asp
610                 615                 620                 625 ggg ggc gtg gga tgaaagtgga cttaactttt aaggtagtta actggaatgt          2040
Gly Gly Val Gly aaatttttaa tctttattag ggtatagttg gtacaatgct tcgttgtatt tagtaagcct    2100
ttacaagact tgttaaagat gtcagagtgc cccaagctgc cgttccttcc cttcctgccc    2160
cacaagctcc ttttcctgaa tttcctacct aaatattaac catatgccta gtctctgaaa    2220
ctaaaaactt ggacctcatc ctcaattatt ttctcctttc aactctgttg accctctgtc    2280
tggtcttcct ctagaaggtt ctaccgcaga aattgatgtg tgctccctgc cctcgtcact    2340
gcccaagccc gggcctgcac atactcactg gactgttcca gttttgacag ctgccagtct    2400
```

```
tcctgcccct ttcacactgc agctgaagtt cattacctga aggacgcctc atcatttcat    2460
tccttggctc caaaccttct gctgcctcta agataaaagc tcaacttctt aacagtgtac    2520
agtgtgcaac ttccaacctt tttatctgtt ctctccacct tcagtttagc gtcattccaa    2580
aaccacaccc ttgcaaagct tgtactccg caccccagat gatctccagg cagctcagat     2640
ctctttcctg cctttgccct gcactgttcc ccggtacttc ctcctttatt gtagcactca    2700
gctccccagc caatctgtac atccctcaga ggcagcgatc tgatgaattg gttttgaat     2760 cccagaaagg gtctgccatg gagttggcag tcatcacggt agatggcgta tgattttgct    2820
gaattttaaa taaaatgaaa accataaaaa aaaaaaaaa gggcggccgc                2870
```

<210> SEQ ID NO 17
<211> LENGTH: 629
<212> TYPE: PRT
<213> ORGANISM: Homo sapiens

<400> SEQUENCE: 17

```
Met Gln Gly Gly Asn Ser Gly Val Arg Lys Arg Glu Glu Glu Gly Asp
  1               5                  10                  15

Gly Ala Gly Ala Val Ala Ala Pro Pro Ala Ile Asp Phe Pro Ala Glu
             20                  25                  30

Gly Pro Asp Pro Glu Tyr Asp Glu Ser Asp Val Pro Ala Glu Ile Gln
         35                  40                  45

Val Leu Lys Glu Pro Leu Gln Gln Pro Thr Phe Pro Phe Ala Val Ala
     50                  55                  60

Asn Gln Leu Leu Leu Val Ser Leu Leu Glu His Leu Ser His Val His
 65                  70                  75                  80

Glu Pro Asn Pro Leu Arg Ser Arg Gln Val Phe Lys Leu Leu Cys Gln
                 85                  90                  95

Thr Phe Ile Lys Met Gly Leu Leu Ser Ser Phe Thr Cys Ser Asp Glu
            100                 105                 110

Phe Ser Ser Leu Arg Leu His His Asn Arg Ala Ile Thr His Leu Met
        115                 120                 125

Arg Ser Ala Lys Glu Arg Val Arg Gln Asp Pro Cys Glu Asp Ile Ser
    130                 135                 140

Arg Ile Gln Lys Ile Arg Ser Arg Glu Val Ala Leu Glu Ala Gln Thr
145                 150                 155                 160

Ser Arg Tyr Leu Asn Glu Phe Glu Glu Leu Ala Ile Leu Gly Lys Gly
                165                 170                 175

Gly Tyr Gly Arg Val Tyr Lys Val Arg Asn Lys Leu Asp Gly Gln Tyr
            180                 185                 190

Tyr Ala Ile Lys Lys Ile Leu Ile Lys Gly Ala Thr Lys Thr Val Cys
        195                 200                 205

Met Lys Val Leu Arg Glu Val Lys Val Leu Ala Gly Leu Gln His Pro
    210                 215                 220

Asn Ile Val Gly Tyr His Thr Ala Trp Ile Glu His Val His Val Ile
225                 230                 235                 240

Gln Pro Arg Asp Arg Ala Ala Ile Glu Leu Pro Ser Leu Glu Val Leu
                245                 250                 255

Ser Asp Gln Glu Glu Asp Arg Glu Gln Cys Gly Val Lys Asn Asp Glu
            260                 265                 270

Ser Ser Ser Ser Ser Ile Ile Phe Ala Glu Pro Thr Pro Glu Lys Glu
        275                 280                 285

Lys Arg Phe Gly Glu Ser Asp Thr Glu Asn Gln Asn Asn Lys Ser Val
```

```
                    290               295               300
Lys Tyr Thr Thr Asn Leu Val Ile Arg Glu Ser Gly Glu Leu Glu Ser
305                 310               315                   320

Thr Leu Glu Leu Gln Glu Asn Gly Leu Ala Gly Leu Ser Ala Ser Ser
                325               330                   335

Ile Val Glu Gln Gln Leu Pro Leu Arg Arg Asn Ser His Leu Glu Glu
                340               345               350

Ser Phe Thr Ser Thr Glu Glu Ser Glu Glu Asn Val Asn Phe Leu
            355               360               365

Gly Gln Thr Glu Ala Gln Tyr His Leu Met Leu His Ile Gln Met Gln
370                 375               380

Leu Cys Glu Leu Ser Leu Trp Asp Trp Ile Val Glu Arg Asn Lys Arg
385                 390               395                   400

Gly Arg Glu Tyr Val Asp Glu Ser Ala Cys Pro Tyr Val Met Ala Asn
                405               410               415

Val Ala Thr Lys Ile Phe Gln Glu Leu Val Glu Gly Val Phe Tyr Ile
                420               425               430

His Asn Met Gly Ile Val His Arg Asp Leu Lys Pro Arg Asn Ile Phe
                435               440               445

Leu His Gly Pro Asp Gln Gln Val Lys Ile Gly Asp Phe Gly Leu Ala
450                 455               460

Cys Thr Asp Ile Leu Gln Lys Asn Thr Asp Trp Thr Asn Arg Asn Gly
465                 470               475                   480

Lys Arg Thr Pro Thr His Thr Ser Arg Val Gly Thr Cys Leu Tyr Ala
                485               490               495

Ser Pro Glu Gln Leu Glu Gly Ser Glu Tyr Asp Ala Lys Ser Asp Met
                500               505               510

Tyr Ser Leu Gly Val Val Leu Leu Glu Leu Phe Gln Pro Phe Gly Thr
                515               520               525

Glu Met Glu Arg Ala Glu Val Leu Thr Gly Leu Arg Thr Gly Gln Leu
                530               535               540

Pro Glu Ser Leu Arg Lys Arg Cys Pro Val Gln Ala Lys Tyr Ile Gln
545                 550               555                   560

His Leu Thr Arg Arg Asn Ser Ser Gln Arg Pro Ser Ala Ile Gln Leu
                565               570               575

Leu Gln Ser Glu Leu Phe Gln Asn Ser Gly Asn Val Asn Leu Thr Leu
                580               585               590

Gln Met Lys Ile Ile Glu Gln Glu Lys Glu Ile Ala Glu Leu Lys Lys
                595               600               605

Gln Leu Asn Leu Leu Ser Gln Asp Lys Gly Val Arg Asp Asp Gly Lys
                610               615               620

Asp Gly Gly Val Gly
625

<210> SEQ ID NO 18
<211> LENGTH: 1887
<212> TYPE: DNA
<213> ORGANISM: Homo sapiens

<400> SEQUENCE: 18
atgcaggggg gcaactccgg ggtccgcaag cgcgaagagg agggcgacgg ggctggggct     60
gtggctgcgc cgccggccat cgactttccc gccgagggcc cggaccccga atatgacgaa    120
tctgatgttc agcagaaat  ccaggtgtta aagaacccc  tacaacagcc aaccttccct    180
```

```
tttgcagttg caaaccaact cttgctggtt tctttgctgg agcacttgag ccacgtgcat    240
gaaccaaacc cacttcgttc aagacaggtg tttaagctac tttgccagac gtttatcaaa    300
atggggctgc tgtcttcttt cacttgtagt gacgagttta gctcattgag actacatcac    360
aacagagcta ttactcactt aatgaggtct gctaaagaga gagttcgtca ggatccttgt    420
gaggatattt ctcgtatcca gaaaatcaga tcaaggaag tagccttgga agcacaaact     480
tcacgttact taaatgaatt tgaagaactt gccatcttag gaaaaggtgg atacggaaga    540
gtatacaagg tcaggaataa attagatggt cagtattatg caataaaaaa aatcctgatt    600
aagggtgcaa ctaaaacagt ttgcatgaag gtcctacggg aagtgaaggt gctggcaggt    660
cttcagcacc ccaatattgt tggctatcac accgcgtgga tagaacatgt tcatgtgatt    720
cagccacgag acagagctgc cattgagttg ccatctctgg aagtgctctc cgaccaggaa    780
gaggacagag agcaatgtgg tgttaaaaat gatgaaagta gcagctcatc cattatcttt    840
gctgagccca cccagaaaaa agaaaaacgc tttggagaat ctgacactga aaatcagaat    900
aacaagtcgg tgaagtacac caccaattta gtcataagag aatctggtga acttgagtcg    960
accctggagc tccaggaaaa tggcttggct ggtttgtctg ccagttcaat tgtggaacag   1020
cagctgccac tcaggcgtaa ttcccaccta gaggagagtt tcacatccac cgaagaatct   1080
tccgaagaaa atgtcaactt tttgggtcag acagaggcac agtaccacct gatgctgcac   1140
atccagatgc agctgtgtga gctctcgctg tgggattgga tagtcgagag aaacaagcgg   1200
ggccgggagt atgtggacga tctgcctgt ccttatgtta tggccaatgt tgcaacaaaa    1260 attttttcaag aattggtaga aggtgtgttt tacatacata acatgggaat tgtgcaccga   1320
gatctgaagc aagaaatat tttttcttcat ggccctgatc agcaagtaaa aataggagac    1380
tttggtctgg cctgcacaga catcctacag aagaacacag actggaccaa cagaaacggg   1440
aagagaacac caaacatac gtccagagtg ggtacttgtc tgtacgcttc acccgaacag    1500
ttggaaggat ctgagtatga tgccaagtca gatatgtaca gcttgggtgt ggtcctgcta   1560
gagctctttc agccgtttgg aacagaaatg gagcgagcag aagttctaac aggtttaaga   1620
actggtcagt tgccggaatc cctccgtaaa aggtgtccgg tgcaagccaa gtatatccag   1680
cacttaacga gaaggaactc atcgcagaga ccatctgcca ttcagctgct gcagagtgaa   1740
cttttccaaa attctggaaa tgttaacctc accctacaga tgaagataat agagcaagaa   1800
aaagaaattg cagaactaaa gaagcagcta aacctccttt ctcaagacaa aggggtgagg   1860
gatgacggaa aggatggggg cgtggga                                        1887
```

<210> SEQ ID NO 19
<211> LENGTH: 17
<212> TYPE: PRT
<213> ORGANISM: Unknown
<220> FEATURE:
<223> OTHER INFORMATION: Consensus sequence for Eukaryotic protein
      kinase
<220> FEATURE:
<221> NAME/KEY: VARIANT
<222> LOCATION: (1)...(1)
<223> OTHER INFORMATION: Residue 1 could also be Isoleucine or Valine
<220> FEATURE:
<221> NAME/KEY: VARIANT
<222> LOCATION: (3)...(3)
<223> OTHER INFORMATION: Residue 3 is any amino acid except Proline
<220> FEATURE:
<221> NAME/KEY: VARIANT
<222> LOCATION: (5)...(5)
<223> OTHER INFORMATION: Residue 5 is any amino acid except Proline
<220> FEATURE:

```
<221> NAME/KEY: VARIANT
<222> LOCATION: (6)...(6)
<223> OTHER INFORMATION: Residue 6 could also be Tyrosine, Tryptophan,
      Methionine, Glycine, Serine, Threonine, Asparagine
      or Histidine
<220> FEATURE:
<221> NAME/KEY: VARIANT
<222> LOCATION: (7)...(7)
<223> OTHER INFORMATION: Residue 7 could also be Glycine or Alanine
<220> FEATURE:
<221> NAME/KEY: VARIANT
<222> LOCATION: (8)...(8)
<223> OTHER INFORMATION: Residue 8 is any amino acid except for Proline
      or Tryptophan
<220> FEATURE:
<221> NAME/KEY: VARIANT
<222> LOCATION: (9)...(9)
<223> OTHER INFORMATION: Residue 9 could also be Isoleucine, Valine,
      Cysteine, Alanine or Threonine
<220> FEATURE:
<221> NAME/KEY: VARIANT
<222> LOCATION: (10)...(10)
<223> OTHER INFORMATION: Residue 10 is any amino acid except for Proline
      or Aspartic Acid
<220> FEATURE:
<221> NAME/KEY: VARIANT
<222> LOCATION: (12)...(12)
<223> OTHER INFORMATION: Residue 12 could also be Serine, Threonine,
      Alanine, Cysteine, Leucine, Isoleucine, Valine,
      Methionine, Phenylalanine or Tyrosine
<220> FEATURE:
<221> NAME/KEY: VARIANT
<222> LOCATION: (13)...(13)
<223> OTHER INFORMATION: Position 13 "Xaa" means anywhere between 5 and
      18 residues (any amino acid)
<220> FEATURE:
<221> NAME/KEY: VARIANT
<222> LOCATION: (14)...(14)
<223> OTHER INFORMATION: Residue 14 could also be Isoleucine, Valine,
      Methionine, Phenylalanine, Tyrosine, Tryptophan,
      Cysteine, Threonine, Alanine or Arginine
<220> FEATURE:
<221> NAME/KEY: VARIANT
<222> LOCATION: (15)...(15)
<223> OTHER INFORMATION: Residue 15 could also be Isoleucine, Valine or
      Proline
<220> FEATURE:
<221> NAME/KEY: VARIANT
<222> LOCATION: (16)...(16)
<223> OTHER INFORMATION: Residue 16 could also be Isoleucine, Valine,
      Methionine, Phenylalanine, Alanine, Glycine,
      Cysteine, Lysine or Arginine
<220> FEATURE:
<221> NAME/KEY: VARIANT
<222> LOCATION: (11)...(11)
<223> OTHER INFORMATION: Xaa = Any Amino Acid

<400> SEQUENCE: 19

Leu Gly Xaa Gly Xaa Phe Ser Xaa Leu Xaa Xaa Gly Xaa Leu Ala Leu
 1               5                  10                  15

Lys

<210> SEQ ID NO 20
<211> LENGTH: 13
<212> TYPE: PRT
<213> ORGANISM: Unknown
<220> FEATURE:
<223> OTHER INFORMATION: Consensus sequence for Eukaryotic protein
      kinase
<220> FEATURE:
<221> NAME/KEY: VARIANT
<222> LOCATION: (1)...(1)
<223> OTHER INFORMATION: Residue 1 could also be Isoleucine, Valine,
      Methionine, Phenylalanine, Tyrosine or Cysteine
<220> FEATURE:
<221> NAME/KEY: VARIANT
```

```
<222> LOCATION: (3)...(3)
<223> OTHER INFORMATION: Residue 3 could also be Tyrosine
<220> FEATURE:
<221> NAME/KEY: VARIANT
<222> LOCATION: (6)...(6)
<223> OTHER INFORMATION: Residue 6 could also be Isoleucine, Valine,
      Methionine, Phenylalanine or Tyrosine
<220> FEATURE:
<221> NAME/KEY: VARIANT
<222> LOCATION: (11)...(13)
<223> OTHER INFORMATION: Residues 11-13 could also be triple Isoleucine,
      Valine, Methionine, Phenylalanine, Tyrosine or
      Cysteine
<220> FEATURE:
<221> NAME/KEY: VARIANT
<222> LOCATION: (1)...(13)
<223> OTHER INFORMATION: Xaa = Any Amino Acid
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Any Amino Acid
<220> FEATURE:
<221> NAME/KEY: VARIANT
<222> LOCATION: (8)...(9)
<223> OTHER INFORMATION: Xaa = Any Amino Acid

<400> SEQUENCE: 20

Leu Xaa His Xaa Asp Leu Lys Xaa Xaa Asn Leu Leu Leu
  1               5                  10

<210> SEQ ID NO 21
<211> LENGTH: 139
<212> TYPE: PRT
<213> ORGANISM: Artificial Sequence
<220> FEATURE:
<223> OTHER INFORMATION: protein kinase consensus

<400> SEQUENCE: 21

Tyr Glu Leu Leu Glu Lys Leu Gly Glu Gly Ser Phe Gly Lys Val Tyr
  1               5                  10                  15

Lys Ala Lys His Lys Thr Gly Lys Ile Val Ala Val Lys Ile Leu Lys
             20                  25                  30

Lys Glu Ser Leu Ser Leu Arg Glu Ile Gln Ile Leu Lys Arg Leu Ser
         35                  40                  45

His Pro Asn Ile Val Arg Leu Leu Gly Val Phe Glu Asp Thr Asp Asp
     50                  55                  60

His Leu Tyr Leu Val Met Glu Tyr Met Glu Gly Gly Asp Leu Phe Asp
 65                  70                  75                  80

Tyr Leu Arg Arg Asn Gly Pro Leu Ser Glu Lys Glu Ala Lys Lys Ile
                 85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg
    130                 135

<210> SEQ ID NO 22
<211> LENGTH: 130
<212> TYPE: PRT
<213> ORGANISM: Artificial Sequence
<220> FEATURE:
<223> OTHER INFORMATION: protein kinase consensus sequence
```

```
<400> SEQUENCE: 22

Gly Thr Pro Trp Tyr Met Met Ala Pro Glu Val Ile Leu Glu Gly Arg
 1               5                  10                  15

Gly Tyr Ser Ser Lys Val Asp Val Trp Ser Leu Gly Val Ile Leu Tyr
                20                  25                  30

Glu Leu Leu Thr Gly Gly Pro Leu Phe Pro Gly Ala Asp Leu Pro Ala
            35                  40                  45

Phe Thr Gly Gly Asp Glu Val Asp Gln Leu Ile Ile Phe Val Leu Lys
        50                  55                  60

Leu Pro Phe Ser Asp Glu Leu Pro Lys Thr Arg Ile Asp Pro Leu Glu
65                  70                  75                  80

Glu Leu Phe Arg Ile Lys Lys Arg Leu Pro Leu Pro Ser Asn Cys
                85                  90                  95

Ser Glu Glu Leu Lys Asp Leu Leu Lys Lys Cys Leu Asn Lys Asp Pro
                100                 105                 110

Ser Lys Arg Pro Gly Ser Ala Thr Ala Lys Glu Ile Leu Asn His Pro
                115                 120                 125

Trp Phe
    130

<210> SEQ ID NO 23
<211> LENGTH: 279
<212> TYPE: PRT
<213> ORGANISM: Artificial Sequence
<220> FEATURE:
<223> OTHER INFORMATION: protein kinase consensus sequence

<400> SEQUENCE: 23

Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
                20                  25                  30

Lys Glu Ser Leu Ser Leu Arg Glu Ile Gln Ile Leu Lys Arg Leu Ser
            35                  40                  45

His Pro Asn Ile Val Arg Leu Leu Gly Val Phe Glu Asp Thr Asp Asp
        50                  55                  60

His Leu Tyr Leu Val Met Glu Glu Tyr Met Glu Gly Gly Asp Leu Phe
65                  70                  75                  80

Asp Tyr Leu Arg Arg Asn Gly Pro Leu Ser Glu Lys Glu Ala Lys Lys
                85                  90                  95

Ile Ala Leu Gln Ile Leu Arg Gly Leu Glu Tyr Leu His Ser Asn Gly
                100                 105                 110

Ile Val His Arg Asp Leu Lys Pro Glu Asn Ile Leu Leu Asp Glu Asn
                115                 120                 125

Gly Thr Val Lys Ile Ala Asp Phe Gly Leu Ala Arg Leu Leu Glu Lys
                130                 135                 140

Leu Thr Thr Phe Val Gly Thr Pro Trp Tyr Met Met Ala Pro Glu Val
145                 150                 155                 160

Ile Leu Glu Gly Arg Gly Tyr Ser Ser Lys Val Asp Val Trp Ser Leu
                165                 170                 175

Gly Val Ile Leu Tyr Glu Leu Leu Thr Gly Gly Pro Leu Phe Pro Gly
                180                 185                 190

Ala Asp Leu Pro Ala Phe Thr Gly Gly Asp Glu Val Asp Gln Leu Ile
                195                 200                 205
```

```
Ile Phe Val Leu Lys Leu Pro Phe Ser Asp Glu Leu Pro Lys Thr Arg
    210                 215                 220
Ile Asp Pro Leu Glu Glu Leu Phe Arg Ile Lys Lys Arg Arg Leu Pro
225                 230                 235                 240
Leu Pro Ser Asn Cys Ser Glu Glu Leu Lys Asp Leu Leu Lys Lys Cys
                245                 250                 255
Leu Asn Lys Asp Pro Ser Lys Arg Pro Gly Ser Ala Thr Ala Lys Glu
                260                 265                 270
Ile Leu Asn His Pro Trp Phe
                275

<210> SEQ ID NO 24
<211> LENGTH: 44
<212> TYPE: PRT
<213> ORGANISM: Artificial Sequence
<220> FEATURE:
<223> OTHER INFORMATION: protein kinase consensus sequence

<400> SEQUENCE: 24

Gly Gly Asp Leu Phe Asp Tyr Leu Arg Arg Asn Gly Pro Leu Ser Glu
1               5                   10                  15
Lys Glu Ala Lys Lys Ile Ala Leu Gln Ile Leu Arg Gly Leu Glu Tyr
                20                  25                  30
Leu His Ser Asn Gly Ile Val His Arg Asp Leu Lys
                35                  40

<210> SEQ ID NO 25
<211> LENGTH: 126
<212> TYPE: PRT
<213> ORGANISM: Artificial Sequence
<220> FEATURE:
<223> OTHER INFORMATION: protein kinase consensus sequence

<400> SEQUENCE: 25

Pro Trp Tyr Met Met Ala Pro Glu Val Ile Leu Glu Gly Arg Gly Tyr
1               5                   10                  15
Ser Ser Lys Val Asp Val Trp Leu Gly Val Ile Leu Tyr Glu Leu Leu
                20                  25                  30
Thr Gly Gly Pro Leu Phe Pro Gly Ala Asp Leu Pro Ala Phe Thr Gly
                35                  40                  45
Gly Asp Glu Val Asp Gln Leu Ile Ile Phe Val Leu Lys Pro Phe Ser
            50                  55                  60
Asp Glu Leu Pro Lys Thr Arg Ile Asp Pro Leu Glu Glu Leu Phe Arg
65                  70                  75                  80
Ile Lys Lys Arg Arg Leu Pro Leu Pro Ser Asn Cys Ser Glu Glu Leu
                85                  90                  95
Lys Asp Leu Leu Lys Lys Cys Leu Asn Lys Asp Pro Ser Lys Arg Pro
                100                 105                 110
Gly Ser Ala Thr Ala Lys Glu Ile Leu Asn His Pro Trp Phe
                115                 120                 125

<210> SEQ ID NO 26
<211> LENGTH: 19
<212> TYPE: PRT
<213> ORGANISM: Artificial Sequence
<220> FEATURE:
<223> OTHER INFORMATION: protein kinase consensus sequence

<400> SEQUENCE: 26

Tyr Glu Leu Leu Glu Lys Leu Gly Glu Gly Ser Phe Gly Lys Val Tyr
```

Lys Ala Lys

<210> SEQ ID NO 27
<211> LENGTH: 176
<212> TYPE: PRT
<213> ORGANISM: Artificial Sequence
<220> FEATURE:
<223> OTHER INFORMATION: protein kinase consensus sequence

<400> SEQUENCE: 27

```
Lys Arg Leu Ser His Pro Asn Ile Val Arg Leu Gly Val Phe Glu
 1               5                  10                  15

Asp Thr Asp Asp Arg Asp Leu Lys Pro Glu Asn Ile Leu Leu Asp Glu
            20                  25                  30

Asn Gly Thr Val Lys Ile Ala Asp Phe Gly Leu Ala Arg Leu Leu Glu
        35                  40                  45

Lys Leu Thr Thr Phe Val Gly Thr Pro Trp Tyr Met Met Ala Pro Glu
50                  55                  60

Val Ile Leu Glu Gly Arg Gly Tyr Ser Ser Lys Val Asp Val Trp Ser
65                  70                  75                  80

Leu Gly Val Ile Leu Tyr Glu Leu Leu Thr Gly Gly Pro Leu Phe Pro
                85                  90                  95

Gly Ala Asp Leu Pro Ala Phe Thr Gly Gly Asp Glu Val Asp Gln Leu
            100                 105                 110

Ile Ile Phe Val Leu Lys Leu Pro Phe Ser Asp Glu Leu Pro Lys Thr
        115                 120                 125

Arg Ile Asp Pro Leu Glu Glu Leu Phe Arg Ile Lys Lys Arg Arg Leu
    130                 135                 140

Pro Leu Pro Ser Asn Cys Ser Glu Glu Leu Lys Asp Leu Leu Lys Lys
145                 150                 155                 160

Cys Leu Asn Lys Asp Pro Ser Lys Arg Pro Gly Ser Ala Thr Ala Lys
                165                 170                 175
```

<210> SEQ ID NO 28
<211> LENGTH: 271
<212> TYPE: PRT
<213> ORGANISM: Artificial Sequence
<220> FEATURE:
<223> OTHER INFORMATION: protein kinase consensus sequence

<400> SEQUENCE: 28

```
Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu Tyr Leu Val Met Glu Tyr Met Glu Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
```

```
                115                 120                 125
Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
                180                 185                 190

Asp Leu Pro Ala Phe Thr Gly Gly Asp Glu Val Asp Gln Leu Ile Ile
                195                 200                 205

Phe Val Leu Lys Leu Pro Phe Ser Asp Glu Leu Pro Lys Thr Arg Ile
                210                 215                 220

Asp Pro Leu Glu Glu Leu Phe Arg Ile Lys Lys Arg Leu Pro Leu
225                 230                 235                 240

Pro Ser Asn Cys Ser Glu Glu Leu Lys Asp Leu Leu Lys Cys Leu
                245                 250                 255

Asn Lys Asp Pro Ser Lys Arg Pro Gly Ser Ala Thr Ala Lys Glu
                260                 265                 270
```

<210> SEQ ID NO 29
<211> LENGTH: 66
<212> TYPE: PRT
<213> ORGANISM: Artificial Sequence
<220> FEATURE:
<223> OTHER INFORMATION: protein kinase consensus sequence

<400> SEQUENCE: 29

```
Tyr Glu Leu Leu Glu Lys Leu Gly Glu Gly Ser Phe Gly Lys Val Tyr
1               5                   10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu
65
```

<210> SEQ ID NO 30
<211> LENGTH: 117
<212> TYPE: PRT
<213> ORGANISM: Artificial Sequence
<220> FEATURE:
<223> OTHER INFORMATION: protein kinase consensus

<400> SEQUENCE: 30

```
Leu Tyr Leu Val Met Glu Tyr Met Glu Gly Gly Asp Leu Phe Asp Tyr
1               5                   10                  15

Leu Arg Arg Asn Gly Pro Leu Ser Glu Lys Glu Ala Lys Lys Ile Ala
            20                  25                  30

Leu Gln Ile Leu Arg Gly Leu Glu Tyr Leu His Ser Asn Gly Ile Val
        35                  40                  45

His Arg Asp Leu Lys Pro Glu Asn Ile Leu Leu Asp Glu Asn Gly Thr
    50                  55                  60

Val Lys Ile Ala Asp Phe Gly Leu Ala Arg Leu Leu Glu Lys Leu Thr
65                  70                  75                  80
```

-continued

```
Thr Phe Val Gly Thr Pro Trp Tyr Met Met Ala Pro Glu Val Ile Leu
                 85                  90                  95

Glu Gly Arg Gly Tyr Ser Ser Lys Val Asp Val Trp Ser Leu Gly Val
            100                 105                 110

Ile Leu Tyr Glu Leu
        115

<210> SEQ ID NO 31
<211> LENGTH: 22
<212> TYPE: PRT
<213> ORGANISM: Artificial Sequence
<220> FEATURE:
<223> OTHER INFORMATION: protein kinase consensus

<400> SEQUENCE: 31

Asn Lys Asp Pro Ser Lys Arg Pro Gly Ser Ala Thr Ala Lys Glu Ile
1               5                   10                  15

Leu Asn His Pro Trp Phe
            20

<210> SEQ ID NO 32
<211> LENGTH: 13
<212> TYPE: PRT
<213> ORGANISM: Unknown
<220> FEATURE:
<223> OTHER INFORMATION: Consensus sequence for Eukaryotic protein
      kinase
<220> FEATURE:
<221> NAME/KEY: VARIANT
<222> LOCATION: (1)...(1)
<223> OTHER INFORMATION: Residue 1 could also be Isoleucine, Valine,
      Methionine, Phenylalanine, Tyrosine or Cysteine
<220> FEATURE:
<221> NAME/KEY: VARIANT
<222> LOCATION: (3)...(3)
<223> OTHER INFORMATION: Residue 3 could also be Tyrosine
<220> FEATURE:
<221> NAME/KEY: VARIANT
<222> LOCATION: (6)...(6)
<223> OTHER INFORMATION: Residue 6 could also be Isoleucine, Valine,
      Methionine, Phenylalanine or Tyrosine
<220> FEATURE:
<221> NAME/KEY: VARIANT
<222> LOCATION: (7)...(7)
<223> OTHER INFORMATION: Residue 7 could also be Serine, Threonine,
      Alanine or Cysteine
<220> FEATURE:
<221> NAME/KEY: VARIANT
<222> LOCATION: (11)...(13)
<223> OTHER INFORMATION: Residue 11-13 could also be triple Isoleucine,
      Valine, Methionine, Phenylalanine, Tyrosine or
      Cysteine
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Any Amino Acid
<220> FEATURE:
<221> NAME/KEY: VARIANT
<222> LOCATION: (8)...(9)
<223> OTHER INFORMATION: Xaa = Any Amino Acid

<400> SEQUENCE: 32

Leu Xaa His Xaa Asp Leu Arg Xaa Xaa Asn Leu Leu Leu
1               5                   10
```

That which is claimed:

1. An isolated polypeptide comprising the amino acid sequence of SEQ ID NO:14.
2. An isolated polypeptide consisting of the amino acid sequence of SEQ ID NO:14.
3. An isolated polypeptide, SEQ ID NO: 14 which is encoded by a nucleic acid molecule comprising the nucleotide sequence of SEQ ID NO: 13 or SEQ ID NO: 15.
4. An isolated polypeptide which is encoded by the nucleotide sequence of the DNA insert of the plasmid deposited with ATCC as Accession Number PTA-2204.
5. The polypeptide of claims 1, further comprising heterologous amino acid sequences.
6. The polypeptide of claims 2, further comprising heterologous amino acid sequences.
7. The polypeptide of claims 3, further comprising heterologous amino acid sequences.
8. The polypeptide of claims 4, further comprising heterologous amino acid sequences.

* * * * *